(12) United States Patent
Repetti et al.

(10) Patent No.: US 10,597,667 B2
(45) Date of Patent: Mar. 24, 2020

(54) STRESS TOLERANCE IN PLANTS

(71) Applicant: Mendel Biotechnology, Inc., Hayward, CA (US)

(72) Inventors: Peter P. Repetti, Emeryville, CA (US); T. Lynne Reuber, San Mateo, CA (US); Oliver Ratcliffe, Oakland, CA (US); Karen S. Century, Chapel Hill, NC (US); Katherine Krolikowski, Oakland, CA (US); Robert A. Creelman, Castro Valley, CA (US); Frederick D. Hempel, Albany, CA (US); Roderick W. Kumimoto, Sacramento, CA (US); Luc J. Adam, Hayward, CA (US); Neal I. Gutterson, Oakland, CA (US); Roger Canales, Redwood City, CA (US); Emily L. Queen, San Leandro, CA (US); Jennifer M. Costa, Union City, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 0 days.

(21) Appl. No.: 15/347,676

(22) Filed: Nov. 9, 2016

(65) Prior Publication Data

US 2017/0121733 A1 May 4, 2017

Related U.S. Application Data

(60) Continuation of application No. 14/480,473, filed on Sep. 8, 2014, now abandoned, which is a division of application No. 13/244,288, filed on Sep. 24, 2011, now abandoned, which is a continuation-in-part of application No. 12/077,535, filed on Mar. 17, 2008, now Pat. No. 8,030,546, which is a continuation-in-part of application No. 10/286,264, filed on Nov. 1, 2002, now abandoned, which is a division of application No. 09/533,030, filed on Mar. 22, 2000, now abandoned, said application No. 12/077,535 is a continuation-in-part of application No. 10/675,852, filed on Sep. 30, 2003, now abandoned, and a continuation-in-part of application No. 11/479,226, filed on Jun. 30, 2006, now Pat. No. 7,858,848, and a continuation-in-part of application No. 10/669,824, filed on Sep. 23, 2003, now abandoned, which is a continuation-in-part of application No. 09/823,676, filed on Mar. 30, 2001, now Pat. No. 6,717,034, said application No. 12/077,535 is a continuation-in-part of application No. 11/725,235, filed on Mar. 16, 2007, now Pat. No. 7,601,893, which is a division of application No. 10/225,068, filed on Aug. 9, 2002, now Pat. No. 7,193,129, which is a continuation-in-part of application No. 09/837,944, filed on Apr. 18, 2001, now abandoned, and a continuation-in-part of application No. 10/171,469, filed on Jun. 14, 2002, now abandoned, said application No. 12/077,535 is a continuation-in-part of application No. 11/728,567, filed on Mar. 26, 2007, now Pat. No. 7,635,800, which is a division of application No. 10/225,066, filed on Aug. 9, 2002, now Pat. No. 7,238,860, which is a continuation-in-part of application No. 09/837,944, filed on Apr. 18, 2001, now abandoned, and a continuation-in-part of application No. 10/171,468, filed on Jun. 14, 2002, now abandoned, (Continued)

(51) Int. Cl.
*C12N 15/82* (2006.01)

(52) U.S. Cl.
CPC ....... *C12N 15/8242* (2013.01); *C12N 15/827* (2013.01)

(58) Field of Classification Search
None
See application file for complete search history.

(56) References Cited

U.S. PATENT DOCUMENTS 7,196,245 B2   3/2007   Jiang et al.
7,663,025 B2   2/2010   Heard et al.
(Continued)

FOREIGN PATENT DOCUMENTS

EP   1033405   6/2000
EP   1586645   10/2005
(Continued)

OTHER PUBLICATIONS

Sagasset et al. *A. thaliana* Transparent Testa 1 is involved in seed coat development and defines the WIP subfamily of plant zinc finger proteins. Genes & Development. 2002. 16: 138-149.*

(Continued)

*Primary Examiner* — Ashley K Buran
(74) *Attorney, Agent, or Firm* — Dentons US LLP; David Lanzotti, Esq.

(57) ABSTRACT

Transcription factor polynucleotides and polypeptides incorporated into nucleic acid constructs, including expression vectors, have been introduced into plants and were ectopically expressed. Transgenic plants transformed with many of these constructs have been shown to be more resistant to disease (in some cases, to more than one pathogen), or more tolerant to an abiotic stress (in some cases, to more than one abiotic stress). The abiotic stress may include, for example, salt, hyperosmotic stress, water deficit, heat, cold, drought, or low nutrient conditions.

16 Claims, 36 Drawing Sheets
Specification includes a Sequence Listing.

Related U.S. Application Data said application No. 12/077,535 is a continuation-in-part of application No. 11/375,241, filed on Mar. 13, 2006, now Pat. No. 7,598,429, which is a continuation-in-part of application No. 10/225,067, filed on Aug. 9, 2002, now Pat. No. 7,135,616, which is a continuation-in-part of application No. 09/837,944, filed on Apr. 18, 2001, now abandoned, and a continuation-in-part of application No. 10/171,468, filed on Jun. 14, 2002, now abandoned, said application No. 12/077,535 is a continuation-in-part of application No. 11/069,255, filed on Feb. 28, 2005, now Pat. No. 8,558,059, which is a continuation-in-part of application No. 10/112,887, filed on Mar. 18, 2002, now abandoned, said application No. 12/077,535 is a continuation-in-part of application No. 10/374,780, filed on Feb. 25, 2003, now Pat. No. 7,511,190, which is a continuation-in-part of application No. 09/934,455, filed on Aug. 22, 2001, now abandoned, which is a continuation-in-part of application No. 09/713,994, filed on Nov. 16, 2000, now abandoned, which is a continuation-in-part of application No. 09/837,944, filed on Apr. 18, 2001, now abandoned, said application No. 10/374,780 is a continuation-in-part of application No. 10/225,068, filed on Aug. 9, 2002, now Pat. No. 7,193,129, which is a continuation-in-part of application No. 09/837,944, filed on Apr. 18, 2001, now abandoned, said application No. 10/374,780 is a continuation-in-part of application No. 10/225,066, filed on Aug. 9, 2002, now Pat. No. 7,238,860, which is a continuation-in-part of application No. 09/837,944, filed on Apr. 18, 2001, now abandoned, and a continuation-in-part of application No. 10/171,468, filed on Jun. 14, 2002, now abandoned, said application No. 10/374,780 is a continuation-in-part of application No. 10/225,067, filed on Aug. 9, 2002, now Pat. No. 7,135,616, which is a continuation-in-part of application No. 09/837,944, filed on Apr. 18, 2001, now abandoned, and a continuation-in-part of application No. 10/171,468, filed on Jun. 14, 2002, now abandoned, said application No. 12/077,535 is a continuation-in-part of application No. 10/546,266, filed as application No. PCT/US2004/005654 on Feb. 25, 2004, now Pat. No. 7,659,446, which is a continuation-in-part of application No. 10/374,780, filed on Feb. 25, 2003, now Pat. No. 7,511,190, and a continuation-in-part of application No. 10/675,852, filed on Sep. 30, 2003, now abandoned, said application No. 12/077,535 is a continuation-in-part of application No. 10/412,699, filed on Apr. 10, 2003, now Pat. No. 7,345,217, which is a continuation-in-part of application No. 10/295,403, filed on Nov. 15, 2002, now abandoned, which is a division of application No. 09/394,519, filed on Sep. 13, 1999, now abandoned, said application No. 10/412,699 is a continuation-in-part of application No. 09/489,376, filed on Jan. 21, 2000, now abandoned, and a continuation-in-part of application No. 10/302,267, filed on Nov. 22, 2002, now Pat. No. 7,223,904, which is a division of application No. 09/506,720, filed on Feb. 17, 2000, now abandoned, said application No. 10/412,699 is a continuation-in-part of application No. 10/278,173, filed on Oct. 21, 2002, now abandoned, which is a division of application No. 09/533,392, filed on Mar. 22, 2000, now abandoned, said application No. 10/412,699 is a continuation-in-part of application No. 09/713,994, filed on Nov. 16, 2000, now abandoned, and a continuation-in-part of application No. 09/819,142, filed on Mar. 27, 2001, now abandoned, and a continuation-in-part of application No. 09/934,455, filed on Aug. 22, 2001, now abandoned, which is a continuation-in-part of application No. 09/713,994, filed on Nov. 16, 2000, now abandoned, which is a continuation-in-part of application No. 09/837,944, filed on Apr. 18, 2001, now abandoned, said application No. 10/412,699 is a continuation-in-part of application No. 10/225,068, filed on Aug. 9, 2002, now Pat. No. 7,193,129, which is a continuation-in-part of application No. 09/837,944, filed on Apr. 18, 2001, now abandoned, and a continuation-in-part of application No. 10/171,469, filed on Jun. 14, 2002, now abandoned, said application No. 10/412,699 is a continuation-in-part of application No. 10/225,066, filed on Aug. 9, 2002, now Pat. No. 7,238,860, which is a continuation-in-part of application No. 09/837,944, filed on Apr. 18, 2001, now abandoned, and a continuation-in-part of application No. 10/171,468, filed on Jun. 14, 2002, now abandoned, said application No. 10/412,699 is a continuation-in-part of application No. 10/225,067, filed on Aug. 9, 2002, now Pat. No. 7,135,616, which is a continuation-in-part of application No. 09/837,944, filed on Apr. 18, 2001, now abandoned, and a continuation-in-part of application No. 10/171,468, filed on Jun. 14, 2002, now abandoned, said application No. 10/412,699 is a continuation-in-part of application No. 10/374,780, filed on Feb. 25, 2003, now Pat. No. 7,511,190, said application No. 12/077,535 is a continuation-in-part of application No. 10/559,441, filed as application No. PCT/US2004/017768 on Jun. 4, 2004, now abandoned, which is a continuation-in-part of application No. 10/456,882, filed on Jun. 6, 2003, now abandoned, said application No. 12/077,535 is a continuation-in-part of application No. 11/642,814, filed on Dec. 20, 2006, now Pat. No. 7,825,296, which is a division of application No. 10/666,642, filed on Sep. 18, 2003, now Pat. No. 7,196,245, said application No. 12/077,535 is a continuation-in-part of application No. 10/714,887, filed on Nov. 13, 2003, now abandoned, which is a continuation-in-part of application No. 10/456,882, filed on Jun. 6, 2003, now abandoned, and a continuation-in-part of application No. 10/666,642, filed on Sep. 18, 2003, now Pat. No. 7,196,245, said application No. 12/077,535 is a continuation-in-part of application No. 11/435,388, filed on May 15, 2006, now Pat. No. 7,663,025, which is a continuation-in-part of application No. PCT/US2004/037584, filed on Nov. 12, 2004, which is a continuation-in-part of application No. 10/714,887, filed on Nov. 13, 2003, now abandoned, said application No. 12/077,535 is a continuation-in-part of application No. 11/632,390, filed as application No. PCT/US2005/025010 on Jul. 14, 2005, now abandoned, said application No. 12/077,535 is a continuation-in-part of application No. 12/064,961, filed on Dec. 22, 2008, which is a continuation-in-part of application No. PCT/US2006/034615, filed on Aug. 31, 2006, said application No. 12/077,535 is a continuation-in-part of application No. PCT/US2006/

034615, filed on Aug. 31, 2006, and a continuation-in-part of application No. 10/903,236, filed on Jul. 30, 2004, which is a continuation-in-part of application No. 10/456,882, filed on Jun. 9, 2003, now abandoned, and a continuation-in-part of application No. 10/666,642, filed on Sep. 18, 2003, now Pat. No. 7,196,245, said application No. 12/077,535 is a continuation-in-part of application No. 11/699,973, filed on Jan. 29, 2007, now abandoned, which is a continuation-in-part of application No. PCT/US2005/027151, filed on Jul. 29, 2005, which is a continuation-in-part of application No. 10/903,236, filed on Jul. 30, 2004, said application No. 12/077,535 is a continuation-in-part of application No. 10/870,198, filed on Jun. 16, 2004, now Pat. No. 7,897,843, which is a continuation-in-part of application No. 10/669,824, filed on Sep. 23, 2003, now abandoned, which is a continuation-in-part of application No. 09/823,676, filed on Mar. 30, 2001, now Pat. No. 6,717,034, said application No. 12/077,535 is a continuation-in-part of application No. 10/838,616, filed on May 4, 2004, now Pat. No. 8,283,519, and a continuation-in-part of application No. 10/685,922, filed on Oct. 14, 2003, now abandoned, and a continuation-in-part of application No. PCT/US2007/017321, filed on Aug. 7, 2006, and a continuation-in-part of application No. 11/705,903, filed on Feb. 12, 2007, now Pat. No. 7,868,229, which is a continuation-in-part of application No. PCT/US2006/034615, filed on Aug. 31, 2006, said application No. 12/077,535 is a continuation-in-part of application No. 11/821,448, filed on Jun. 22, 2007, now Pat. No. 7,692,067, and a continuation-in-part of application No. PCT/US2007/009124, filed on Apr. 12, 2007, and a continuation-in-part of application No. 11/986,992, filed on Nov. 26, 2007, now Pat. No. 8,809,630, which is a division of application No. 10/412,699, filed on Apr. 10, 2003, now Pat. No. 7,345,217, which is a continuation-in-part of application No. 09/533,029, filed on Mar. 22, 2000, now Pat. No. 6,664,446, which is a continuation-in-part of application No. 10/278,536, filed on Oct. 22, 2002, which is a division of application No. 09/532,591, filed on Mar. 22, 2000.

(60) Provisional application No. 60/961,403, filed on Jul. 20, 2007, provisional application No. 60/125,814, filed on Mar. 23, 1999, provisional application No. 60/166,228, filed on Nov. 17, 1999, provisional application No. 60/198,899, filed on Apr. 17, 2000, provisional application No. 60/227,439, filed on Aug. 22, 2000, provisional application No. 60/310,847, filed on Aug. 9, 2001, provisional application No. 60/336,049, filed on Nov. 19, 2001, provisional application No. 60/338,692, filed on Dec. 11, 2001, provisional application No. 60/713,952, filed on Aug. 31, 2005, provisional application No. 60/101,349, filed on Sep. 22, 1998, provisional application No. 60/103,312, filed on Oct. 6, 1998, provisional application No. 60/108,734, filed on Nov. 17, 1998, provisional application No. 60/113,409, filed on Dec. 22, 1998, provisional application No. 60/116,841, filed on Jan. 22, 1999, provisional application No. 60/120,880, filed on Feb. 18, 1999, provisional application No. 60/121,037, filed on Feb. 22, 1999, provisional application No. 60/124,278, filed on Mar. 11, 1999, provisional application No. 60/129,450, filed on Apr. 15, 1999, provisional application No. 60/135,134, filed on May 20, 1999, provisional application No. 60/144,153, filed on Jul. 15, 1999, provisional application No. 60/161,143, filed on Oct. 22, 1999, provisional application No. 60/162,656, filed on Nov. 1, 1999, provisional application No. 60/162,656, filed on Nov. 1, 1999, provisional application No. 60/125,814, filed on Mar. 23, 1999, provisional application No. 60/166,228, filed on Nov. 17, 1999, provisional application No. 60/197,899, filed on Apr. 17, 2000, provisional application No. 60/411,837, filed on Sep. 18, 2002, provisional application No. 60/434,166, filed on Dec. 17, 2002, provisional application No. 60/465,809, filed on Apr. 24, 2003, provisional application No. 60/527,658, filed on Dec. 5, 2003, provisional application No. 60/542,928, filed on Feb. 5, 2004, provisional application No. 60/588,405, filed on Jul. 14, 2004, provisional application No. 60/713,952, filed on Aug. 31, 2005, provisional application No. 60/565,948, filed on Apr. 26, 2004, provisional application No. 60/836,243, filed on Aug. 7, 2006, provisional application No. 60/817,886, filed on Jun. 29, 2006, provisional application No. 60/791,663, filed on Apr. 12, 2006.

(56) References Cited

U.S. PATENT DOCUMENTS

| | | | |
|---|---|---|---|
| 7,825,296 B2 | 11/2010 | Jiang et al. | |
| 7,858,848 B2 | 12/2010 | Reuber et al. | |
| 7,956,242 B2 | 6/2011 | Zhang et al. | |
| 8,030,546 B2 | 10/2011 | Reuber et al. | |
| 8,541,665 B2 | 9/2013 | Jiang et al. | |
| 8,686,226 B2 | 4/2014 | Heard et al. | |
| 2008/0313756 A1* | 12/2008 | Zhang | C07K 14/415 800/260 |
| 2009/0138981 A1* | 5/2009 | Repetti | C07K 14/415 800/263 |
| 2009/0265815 A1 | 10/2009 | Alexandrov et al. | |
| 2011/0119789 A1 | 5/2011 | Creelman et al. | |
| 2013/0061345 A1 | 3/2013 | Reuber et al. | |

FOREIGN PATENT DOCUMENTS

| | | |
|---|---|---|
| EP | 1887081 | 2/2008 |
| WO | WO 2004-031349 | 4/2004 |
| WO | WO 2005/047516 | 5/2005 |

OTHER PUBLICATIONS

GenBank Accession No. AY037202. Published Jun. 10, 2001. pp. 1-2.*
Seo et al. Modulation of sugar metabolism by an Indeterminate Domain transcription factor contributes to photoperiodic flowering in *Arabidopsis*. The Plant Journal. 2011. 65: 418-429.*
Friedberg. Automated protein function prediction—the genomic challenge. Briefings in Bioinformatics. 2006. 7(3): 225-242.*
U.S. Appl. No. 60/527,658, filed Dec. 5, 2003, Heard et al.
U.S. Appl. No. 60/336,049, filed Nov. 19, 2001, Adam et al.
U.S. Appl. No. 60/411,837, filed Sep. 18, 2002, Creelman et al.
U.S. Appl. No. 09/713,994, filed Nov. 16, 2000, Keddie et al.
NCBI Accession No. AL021633 (GI:2827513) (Jan. 29, 1998); Bevan, M., et al.; "*Arabidopsis thaliana* DNA chromosome 4, BAC clone F8F16 (ESSAII project)".
NCBI Accession No. BE922396 (GI:10448472) (Oct. 2, 2000); Van Der Hoeven, R.S., et al; "EST426165 potato leaves and petioles *Solanum tuberosum* cDNA clone cSTB20E23 5-sequence, mRNA sequence".

(56) References Cited

OTHER PUBLICATIONS

NCBI Accession No. BE462252 (GI:9508021) (Jul. 27, 2000); Van Der Hoeven, R.S., et al.; "EST324516 tomato flower buds 0-3 mm, Cornell University Solanum lycopersicum cDNA clone cTOA12121, mRNA sequence".

NCBI Accession No. AW775770 (GI:7765583( (May 9, 2000); Fedorova, M., et al.; "EST334835 DSIL Medicago truncatula cDNA clone pDSIL-3G23, mRNA sequence".

NCBI Accession No. AW831343 (GI:7925378) (May 18, 2000); Shoemaker, R., et al.; "sm23e07.y1 GM-c1028 Glycine max cDNA clone Genome Systems Clone ID: Gm-c1028-47655—similar to TR:O49577 O49577 Hypothetical 33.1 KD Protein.; mRNA sequence".

* cited by examiner

| | | |
|---|---|---|
| G3434 | (3502) | REQDRFLPIANISRIMKKAVPAN------GKIAKDAKETLQECVSEFISFVT |
| G3395 | (3484) | REQDRFLPIANISRIMKKAVPAN------GKIAKDAKETLQECVSEFISFVT |
| G3470 | (3527) | REQDRYLPIANISRIMKKALPPN------GKIAKDAKDTMQECVSEFISFIT |
| G3471 | (3528) | REQDRYLPIANISRIMKKALPPN------GKIAKDAKDTMQECVSEFISFIT |
| G481 | (2377) | REQDRYLPIANISRIMKKALPPN------GKIGKDAKDTVQECVSEFISFIT |
| G1364 | (2941) | REQDRFLPIANISRIMKRGLPAN------GKIAKDAKEIVQECVSEFISFVT |
| G2345 | (3234) | REQDRFLPIANISRIMKRGLPLN------GKIAKDAKETMQECVSEFISFIT |
| G3876 | (3681) | REQDRFLPIANISRIMKKAIPAN------GKIAKDAKETVQECVSEFISFIT |
| G3866 | (3677) | REQDRFLPIANISRIMKKAIPANGKIAKDAKETVQECVSEFISFIT |
| G3394 | (3483) | -RQDRFLPIANISRIMKKAIPAN------GKIAKDAKETVQECVSEFISFIT |
| G3435 | (3503) | REQDRFLPIANVSRIMKKALPAN------AKISKDAKETVQECVSEFISFIT |
| G3436 | (3504) | REQDRFLPIANVSRIMKKALPAN------AKISKDAKETVQECVSEFISFIT |
| G3397 | (3486) | REQDRFLPIANVSRIMKKALPAN------AKISKDAKETVQECVSEFISFIT |
| G3398 | (3487) | REQDRFLPIANVSRIMKKALPAN------AKISKDAKETVQECVSEFISFIT |
| G3475 | (3532) | REQDRFLPIANVSRIMKKALPAN------AKISKDAKETVQECVSEFISFIT |
| G3478 | (3534) | REQDRFLPIANVSRIMKKALPAN------AKISKDAKETVQECVSEFISFIT |
| G3476 | (3533) | REQDRFLPIANVSRIMKKALPAN------AKISKDAKETMQECVSEFISFIT |
| G482 | (2378) | REQDRFLPIANVSRIMKKALPAN------AKISKDAKETVQECVSEFISFVT |
| G485 | (2616) | REQDRFLPIANVSRIMKKALPAN------AKISKDAKETVQECVSEFISFIT |
| G3474 | (3531) | REQDRFLPIANVSRIMKKALPAN------AKISKEAKETVQECVSEFISFIT |
| G3472 | (3529) | REQDRFLPIANVSRIMKKALPAN------AKISKEAKETVQECVSEFISFIT |
| G3396 | (3485) | KEQDRFLPIANIGRIMRRAVPEN------GKIAKDSKESVQECVSEFISFIT |
| G3429 | (3498) | ---TNAELPMANLVRLIKKVLPGK------AKIGGAAKGLTHDCAVEFVGFVG |

FIG. 3A

| | | |
|---|---|---|
| G3434 | (3502) | SEASDKCQKEKRKTINGDDLLWAMATLGFEEYVEPLKIYLQKYK |
| G3395 | (3484) | SEASDKCQKEKRKTINGEDLLFAMGTLGFEEYVDPLKIYLHKYR |
| G3470 | (3527) | SEASEKCQKEKRKTINGDDLLWAMATLGFEDYIEPLKVYLARYR |
| G3471 | (3528) | SEASEKCQKEKRKTINGDDLLWAMATLGFEDYIEPLKVYLARYR |
| G481  | (2377) | SEASDKCQKEKRKTVNGDDLLWAMATLGFEDYLEPLKIYLARYR |
| G1364 | (2941) | SEASDKCQREKRKTINGDDLLWAMATLGFEDYMEPLKVYLMRYR |
| G2345 | (3234) | SEASDKCQREKRKTINGDDLLWAMATLGFEDYIDPLKVYLMRYR |
| G3876 | (3681) | SEASDKCQREKRKTINGDDLLWAMATLGFEDYIEPLKVYLQKYR |
| G3866 | (3677) | SEASDKCQREKRKTINGDDLLWAMATLGFEDYIEPLKVYLQKYR |
| G3394 | (3483) | SEASDKCQREKRKTINGDDLLWAMATLGFEDYIEPLKVYLQKYR |
| G3435 | (3503) | GEASDKCQREKRKTINGDDLLWAMTTLGFEDYVEPLKHYLHKFR |
| G3436 | (3504) | GEASDKCQREKRKTINGDDLLWAMTTLGFEDYIEPLKLYLHKFR |
| G3397 | (3486) | GEASDKCQREKRKTINGDDLLWAMTTLGFEDYVDPLKHYLHKFR |
| G3398 | (3487) | GEASDKCQREKRKTINGDDLLWAMTTLGFEDYIDPLKLYLHKFR |
| G3475 | (3532) | GEASDKCQREKRKTINGDDLLWAMTTLGFEDYVEPLKGYLQRFR |
| G3478 | (3534) | GEASDKCQREKRKTINGDDLLWAMTTLGFEDYVEPLKGYLQRFR |
| G3476 | (3533) | GEASDKCQREKRKTINGDDLLWAMTTLGFEDYIEPLKIYLQRFR |
| G482  | (2378) | GEASDKCQREKRKTINGDDLLWAMTTLGFEEYVEPLKVYLQRFR |
| G485  | (2616) | GEASDKCQREKRKTINGDDLLWAMTTLGFEDYVEPLKVYLQKYR |
| G3474 | (3531) | GEASDKCQREKRKTINGDDLLWAMTTLGFEDYVDPLKIYLHKYR |
| G3472 | (3529) | GEASDKCQKEKRKTINGDDLLWAMTTLGFEEYVEPLKVYLHKYR |
| G3396 | (3485) | SEASDKCLKEKRKTINGDDLIWSMGTLGFEDYVEPLKLYLRLYR |
| G3429 | (3498) | DEASEKAKAEHRRTVAPEDYLGSFGDLGFDRYVDPMDAYIHGYR |

FIG. 3B

```
G3459 (1918)  GSKNKPKPPVIITRESA--NTLRAHILEVGSGSDVFDCVTAYARRRQRGICVLSGSGT
G3459 (1920)  GSKNKPKPPVIITRESA--NTLRAHILEVGSGSDVFDCVTAYARRRQRGICVLSGSGT
G3406 (5144)  GSKNKPKPPVIITRESA--NTLRAHILEVGSGSDVFECVSTYARRRQRGVCVLSGSGV
G3407 (1876)  GSKNKPKPPVIITRESA--NALRAHILEVAAGCDVFEALTAYARRRQRGVCVLSAAGT
G1067 (798)   GSKNKAKPPIIVTRDSP--NALRSHVLEVSPGADIVESVSTYARRRGRGVSVLGGNGT
G2156 (1424)  GSKNKPKPPVIVTRDSP--NVLRSHVLEVSSGADIVESVTTYARRRGRGVSILSGNGT
G1073 (18)    GSKNKPKPTIITRDSP--NVLRSHVLEVTSGSDISEAVSTYATRRGCGVCIISGTGA
G3399 (1870)  GSKNKPKPPIIVTRDSP--NALHSHVLEVAGGADVVDCVAEYARRRGRGVCVLSGGGA
G3400 (1872)  GSKNKPKPPIIVTRDSP--NAFHSHVLEVAAGTDIVECVCEFARRRGRGVSVLSGGGA
G2153 (1420)  GSKNKPKPPIFVTRDSP--NALKSHVMEIASGTDVIETLATFARRRGRGICILSGNGT
G1069 (802)   GSKNKPKPAPIFVTRDSP--NALRSHVLEISDGSDVADTIAHFSRRRQRGVCVLSGTGS
G3401 (1874)  GSKNKPKPPIFVTRDSP--NALRSHVMEVAGGADVAESIAHFARRRQRGVCVLSGAGT
G3456 (1916)  GSRNKPKPPIFVTRDSP--NALRSHVMEIAVGADIADCVAQFARRRQRGVSILSGSGT
G3556 (2034)  GSKNKPKPPVVVTRESP--NAMRSHVLEIASGADIVEAIAGFSRRRQRGVSVLSGSGA
G2157 (1426)  GSKNKPKSPVVVTKESP--NSLQSHVLEIATGADVAESLNAFARRRGRGVSVLSGSGL
G2789 (1694)  GSKNKPKAPIIVTRDSA--NAFRCHVMEITNACDVMESLAVFARRRQRGVCVLTGNGA
G1667 (1116)  GSKNKPKPPIIVTHDSP--NSLRANAVEISSGCDICETLSDFARRKQRGLCILSANGC
G3408 (1878)  -SKNKPKPPVVITREAEPAAAMRPHVIEIPGGRDVAEALARFSSRRNLGICVLAGTGA
```

FIG. 5A

| | | | | |
|---|---|---|---|---|
| G3459 | (1918) | VTNVSLRQP------ | ------AAAGA----- | ------VVTLHGRFEILSLSGSFLPPP------ | ------A |
| G3459 | (1920) | VTNVSLRQP------ | ------AAAGA----- | ------VVRLHGRFEILSLSGSFLPPP------ | ------A |
| G3406 | (5144) | VTNVTLRQPS----- | ------APAGA----- | ------VVSLHGRFEILSLSGSFLPPP------ | ------A |
| G3407 | (1876) | VANVTLRQPQSAQPGPASPA | ------VATLHGRFEILSLAGSFLPPP------ | ------A |
| G1067 | (798) | VSNVTLRQP------ | ------VTPGNGGVSGGGVVTLHGRFEILSLTGTVLPPP | ------A |
| G2156 | (1424) | VANVSLRQP------ | ------ATTAAHGANGGTGGVVALHGRFEILSLTGTVLPPP | ------A |
| G1073 | (18) | VTNVTIRQP------ | ------AAPAG----- | ------GGVITLHGRFDILSLTGTALPPP------ | ------A |
| G3399 | (1870) | VVNVALRQPG----- | ------ASPPG----- | ------SMVATLRGRFEILSLTGTVLPPP------ | ------A |
| G3400 | (1872) | VANVALRQPG----- | ------ASPPG----- | ------SLVATMRGQFEILSLTGTVLPPP------ | ------A |
| G2153 | (1420) | VANVTLRQPSTAAVAAAPGGAA | ------VLALQGRFEILSLTGSFLPGP------ | ------A |
| G1069 | (802) | VANVTLRQ------- | ------AAAAPGG--- | ------VVSLQGRFEILSLTGAFLPGP------ | ------S |
| G3401 | (1874) | VTDVALRQ------- | ------PAAPSA---- | ------VVALRGRFEILSLTGTFLPGP------ | ------A |
| G3456 | (1916) | VVNVNLRQ------- | ------PTAPGA---- | ------VMALHGRFDILSLTGSFLPGP------ | ------S |
| G3556 | (2034) | VTNVTLRQ------- | ------PAGTGAA--- | ------AVALRGRFEILSMSGAFLPAP------ | ------A |
| G2157 | (1426) | VTNVTLRQ------- | ------PAASGG---- | ------VVSLRGQFEILSMCGAFLPTSG----- | ------S |
| G2789 | (1694) | VTNVTVRQ------- | ------PGG------- | ------GVVSLHGRFEILSLSGSFLPPP------ | ------A |
| G1667 | (1116) | VTNVTLRQP------ | ------ASSGA----- | ------IVTLHGRYEILSLLGSILPPP------ | ------A |
| G3408 | (1878) | VANVSLRHPS----- | ------PGVPGSAP-- | ------AAIVFHGRYEILSLSATFLPPAMSSVAPQA |

FIG. 5B

G3459 (1918) PPGATSLTIYLAGGQGQVVGGNVIGELTAAGPVIVIAASFTNVAYERLPLEE-
G3459 (1920) PPGATSLTIYLAGGQGQVVGGNVVGELTAAGPVIVIAASFTNVAYERLPLEE-
G3406 (5144) PPGATSLTIFLAGGQGQVVGGNVVGALYAAGPVIVIAASFANVAYERLPL---
G3407 (1876) PPGATSLAAFLAGGQGQVVGGSVAGALIAAGPVVVAASFSNVAYERLPLED-
G1067 (798)  PPGAGGLSIFLAGGQGQVVGGSVVAPLIAASAPVILMAASFSNAVFERLPIEE-
G2156 (1424) PPGSGGLSIFLSGVQGQVIGGNVVAPLVASGPVILMAASFSNATFERLPLED-
G1073 (18)   PPGAGGLTVYLAGGQGQVVGGSVVGGSLIASGPVVLMAASFANAVYDRLPIEE-
G3399 (1870) PPGASGLTVFLSGGQGQVIGGSVVGPLVAAGPVVLMAASFANAVYERLPLEG-
G3400 (1872) PPSASGLTVFLSGGQGQVVGGSVAGQLIAAGPVFLMAASFANAVYERLPLDG-
G2153 (1420) PPGSTGLTIYLAGGQGQVVGGSVVGPLMAAGPVMLIAATFSNATFSNATYERLPLEE-
G1069 (802)  PPGSTGLTVYLAGVQGQVVGGSVVGPLLAIGSVMVIAATFSNATYERLPMEE-
G3401 (1874) PPGSTGLTVYLAGGQGQVVGGSVVGTLTAAGPVMVIASTFANATYERLPLDQ
G3456 (1916) PPGATGLTIYLAGGQGQIVGGGVVGPLVAAGPVLVMAATFSNATYERLPLED-
G3556 (2034) PPGATGLAVYLAGGQGQVVGGSVMGELIASGPVMVIAATFGNATYERLPLD--
G2157 (1426) PAAAAGLTIYLAGAQGQVVGGVAGPLIASGPVIVIAATFCNATYERLPIEE-
G2789 (1694) PPAASGLKVYLAGGQGQVIGGSVVGPLTASSPVVMAASFGNASYERLPLEE-
G1667 (1116) PLGITGLTIYLIAGPQGQVVGGVVGGLIASGPVVLMAASFMNAVFDRLPMDD-
G3408 (1878) AVAAAGLSISLAGPHGQIVGGAVAGPLYAATTVVVVAAAFTNPTFHRLPADD-

FIG. 5C

| | | |
|---|---|---|
| G3864 | (3675) | RGKHFRGVRQRPWGKFAAEIRDPAKNGARVWLGTFDSAEDAAVAYDRAA |
| G3430 | (2374) | RGKHYRGVRQRPWGKFAAEIRDPAKNGARVWLGTFDSAEEAAVAYDRAA |
| G3856 | (3672) | RGKHYRGVRQRPWGKFAAEIRDPAKNGARVWLGTYDSAEDAAVAYDRAA |
| G3661 | (3596) | RGKHYRGVRQRPWGKFAAEIRDPARNGARVWLGTYDTAEDAALAYDRAA |
| G3848 | (3670) | RGKHYRGVRQRPWGKFAAEIRDPAKNGARVWLGTFDTAEDAALAYDRAA |
| G3718 | (3614) | KGKHYRGVRQRPWGKFAAEIRDPAKNGARVWLGTFETAEDAALAYDRAA |
| G3659 | (3594) | KGKHYRGVRQRPWGKFAAEIRDPAKNGARVWLGTFETAEDAALAYDRAA |
| G3660 | (3595) | KGKHYRGVRQRPWGKFAAEIRDPAKKGAREWLGTFETAEDAALAYDRAA |
| G28 | (2373) | KGKHYRGVRQRPWGKFAAEIRDPAKNGARVWLGTFETAEDAALAYDRAA |
| G1006 | (2828) | KAKHYRGVRQRPWGKFAAEIRDPAKNGARVWLGTFETAEDAALAYDIAA |
| G3717 | (3613) | KGKHYRGVRQRPWGKFAAEIRDPAKNGARVWLGTFETAEDAALAYDRAA |
| G3841 | (3665) | KGRHYRGVRQRPWGKFAAEIRDPAKNGARVWLGTYETAEEAAIAYDKAA |
| G22 | (2406) | KGMQYRGVRRRPWGKFAAEIRDPKKNGARVWLGTYETPEDAAVAYDRAA |

FIG. 7A

| | | |
|---|---|---|
| G3864 | (3675) | YRMRGSRALLNFPLRI |
| G3430 | (2374) | YRMRGSRALLNFPLRI |
| G3856 | (3672) | YRMRGSRALLNFPLRI |
| G3661 | (3596) | YRMRGSRALLNFPLRI |
| G3848 | (3670) | YRMRGSRALLNFPLRI |
| G3718 | (3614) | YRMRGSRALLNFPLRI |
| G3659 | (3595) | FRMRGSRALLNFPLRV |
| G3660 | (3595) | FRMRGSRALLNFPLRV |
| G28   | (2373) | FRMRGSRALLNFPLRV |
| G1006 | (2828) | FRMRGSRALLNFPLRV |
| G3717 | (3613) | YRMRGSRALLNFPLRV |
| G3841 | (3665) | YRMRGSKAHLNFPHRI |
| G22   | (2406) | FQLRGSKAKLNFPHLI |

FIG. 7B

G3649 (3590) EMMRYRGVRRRRWGKWVSEIRVPGTRERLWLGSYATAEAAAVAHDAAV
G3644 (3586) ERCRYRGVRRRRWGKWVSEIRVPGTRERLWLGSYATPEAAAVAHDTAV
G3650 (3591) RRCRYRGVRRRAWGKWVSEIRVPGTRERLWLGSYAAPEAAAVAHDAAA
G47   (2375) SQSKYKGIRRRKWGKWVSEIRVPGTRDRLWLGSFSTAEGAAVAHDVAF
G2133 (2376) DQSKYKGIRRRKWGKWVSEIRVPGTRQRLWLGSFSTAEGAAVAHDVAF
G3643 (3585) TNNKLKGVRRRKWGKWVSEIRVPGTQERLWLGTYATPEAAAVAHDVAV

G3649 (3590) CLLRLGGGRRAAAGGGGGLNFPARA-
G3644 (3586) YFLRGGAG--DGGGGATLNFPERA-
G3650 (3591) CLLRGCAG--------RRLNFPGRAA
G47   (2375) FCLHQPDSL-------ESLNFPHLL-
G2133 (2376) YCLHRPSSLDD-----ESFNFPHLL-
G3643 (3585) YCLSRPSSL-------DKLNFPETL-

FIG. 9

| | | |
|---|---|---|
| G3728 | (3624) | DDGFKWRKYGKKAVKNSPNPRNYYRCSSEGCGVKKRVERDRDDPRYVI |
| G3804 | (3643) | DDGFKWRKYGKKAVKNSPNPRNYYRCSSEGCGVKKRVERDRDDPRYVI |
| G3727 | (3623) | DDGFKWRKYGKKAVKSSPNPRNYYRCSSEGCGVKKRVERDRDDPRYVI |
| G3730 | (3626) | DDGFKWRKYGKKAVKSSPNPRNYYRCSAAGCGVKKRVERDGDDPRYVV |
| G3719 | (3615) | DDGFKWRKYGKKTVKSSPNPRNYYRCSAEGCGVKKRVERDSDDPRYVV |
| G3721 | (3617) | DDGFKWRKYGKKAVKNSPNPRNYYRCSTEGCNVKKRVERDREDHRYVI |
| G3726 | (3622) | DDGYKWRKYGKKSVKNSPNPRNYYRCSTEGCNVKKRVERDKDDPSYVV |
| G3720 | (3616) | DDGYKWRKYGKKSVKNSPNPRNYYRCSTEGCNVKKRVERDKDDPSYVV |
| G3725 | (3621) | DDGYKWRKYGKKSVKNSPNPRNYYRCSTEGCNVKKRVERDKNDPRYVV |
| G3722 | (3618) | DDGYKWRKYGKKSVKMSPNPRNYYRCSSEGCRVKKRVERARDDARFVV |
| G3729 | (3625) | DDGYKWRKYGKKMVKNSPNPRNYYRCSGEGCNVKKRVERDRDDSNYVL |
| G3803 | (3642) | DDGYKWRKYGKKTVKNPNPRNYYKCSGEGCDVKKRVERDRDDSNYVL |
| G3723 | (3619) | DDGYKWRKYGKKTVKSSPNPRNYYKCSSEGCSVKKRVERDGDDAAYVI |
| G1274 | (2384) | DDGFKWRKYGKKSVKNNINKRNYYKCSSEGCSVKKRVERDGDDAAYVI |
| G3724 | (3620) | DDGYKWRKYGKKSVKSSPNLRNYYKCSSGGCSVKKRVERDDYSYVI |
| G1275 | (2908) | DDGFKWRKYGKKMVKNSPHPRNYYKCSVDGCPVKKRVERDRDDPSFVI |

FIG. 11A

| | | |
|---|---|---|
| G3728 | (3624) | TTYDGVHNH |
| G3804 | (3643) | TTYDGVHNH |
| G3727 | (3623) | TTYDGVHNH |
| G3730 | (3626) | TTYDGVHNH |
| G3719 | (3615) | TTYDGVHNH |
| G3721 | (3617) | TTYDGVHNH |
| G3726 | (3622) | TTYEGTHNH |
| G3720 | (3616) | TTYEGMHNH |
| G3725 | (3621) | TMYEGIHNH |
| G3722 | (3618) | TMYEGVHNH |
| G3729 | (3625) | TTYDGVHNH |
| G3803 | (3642) | TTYDGVHNH |
| G3723 | (3619) | TTYDGVHNH |
| G1274 | (2384) | TTYEGVHNH |
| G3724 | (3620) | TTYEGVHNH |
| G1275 | (2908) | TTYEGSHNH |

FIG. 11B

| ID | SEQ ID | Sequence |
|---|---|---|
| G3515 | (3554) | SSSSYRGVRKRPWGKFAAEIRDPERGGARVWLGTFDTAEEAARAYDRAA |
| G3516 | (3555) | KEGKYRGVRKRPWGKFAAEIRDPERGGSRVWLGTFDTAEEAARAYDRAA |
| G3737 | (3627) | AASKYRGVRRRPWGKFAAEIRDPERGGSRVWLGTFDTAEEAARAYDRAA |
| G3383 | (3475) | TATKYRGVRRRPWGKFAAEIRDPERGGARVWLGTFDTAEEAARAYDRAA |
| G3517 | (3556) | EPTKYRGVRRRPWGKYAAAEIRDSSRHGVRIWLGTFDTAEEAARAYDRSA |
| G3739 | (3628) | EPTKYRGVRRRPWGKYAAAEIRDSSRHGVRIWLGTFDTAEEAARAYDRSA |
| G3381 | (3474) | LVAKYRGVRRRPWGKFAAAEIRDSSRHGVRVWLGTFDTAEEAARAYDRSA |
| G3380 | (3473) | ETTKYRGVRRRPSGKFAAEIRDSSRQSVRVWLGTFDTAEEAARAYDRAA |
| G3794 | (3641) | EPTKYRGVRRRPSGKFAAAEIRDSSRQSVRMWLGTFDTAEEAARAYDRAA |
| G1795 | (2387) | EHGKYRGVRRRPWGKYAAEIRDSRKHGERVWLGTFDTAEEAARAYDQAA |
| G30 | (2411) | EQGKYRGVRRRPWGKFAAEIRDSRKHGERVWLGTFDTAEDAARAYDRAA |
| G1791 | (3064) | NEMKYRGVRKRPWGKYAAEIRDSARHGARVWLGTFNTAEDAARAYDRAA |
| G3519 | (3558) | CEVRYRGIRRRPWGKFAAEIRDPTRKGTRIWLGTFDTAEQAARAYDAAA |
| G3518 | (3557) | VEVRYRGIRRRPWGKFAAEIRDPTRKGTRIWLGTFDTAEQAARAYDAAA |
| G1792 | (2386) | KQARFRGVRRRPWGKFAAEIRDPSRNGARLWLGTFETAEEAARAYDRAA |
| G3520 | (3559) | EEPRYRGVRRRPWGKFAAEIRDPARHGARVWLGTFLTAEEAARAYDRAA |

FIG. 13A

| | | |
|---|---|---|
| G3515 | (3554) | FAMKGATAMLNFPGDH |
| G3516 | (3555) | FAMKGATAVLNFPASG |
| G3737 | (3627) | FAMKGAMAVLNFPGRT |
| G3383 | (3475) | YAQRGAAAVLNFPAAA |
| G3517 | (3556) | NSMRGANAVLNFPEDA |
| G3739 | (3628) | YSMRGANAVLNFPEDA |
| G3381 | (3474) | YSMRGANAVLNFPADA |
| G3380 | (3473) | YAMRGHLAVLNFPAEA |
| G3794 | (3641) | YAMRGQIAVLNFPAEA |
| G1795 | (2387) | YSMRGQAAILNFPHEY |
| G30 | (2411) | YSMRGKAAILNFPHEY |
| G1791 | (3064) | FGMRGQRAILNFPHEY |
| G3519 | (3558) | FHFRGHRAILNFPNEY |
| G3518 | (3557) | FHFRGHRAILNFPNEY |
| G1792 | (2386) | FNLRGHLAILNFPNEY |
| G3520 | (3559) | YEMRGALAVLNFPNEY |

FIG. 13B

| | | |
|---|---|---|
| G3515 | (5136) | KVELECLDDKVLEDLL |
| G3516 | (5137) | KVELECLDDRVLEELL |
| G3737 | (5135) | KVELVYLDDKVLDELL |
| G3383 | (5131) | KIEFEYLDDKVLDDLL |
| G1795 | (5129) | VFEFEYLDDSVLEELL |
| G30   | (5130) | VFEFEYLDDSVLDELL |
| G1792 | (5128) | VFEFEYLDDKVLEELL |
| G3519 | (5133) | TEELEYLDNKLLEELL |
| G3518 | (5140) | TFEELEYFDNKLLEELL |
| G1791 | (5132) | VIEFEYLDDSLLEELL |
| G3520 | (5138) | VIEFECLDDKLLEDLL |
| G3517 | (5139) | VIEFEYLDDEVLQEML |
| G3739 | (5141) | VIELEYLDDEVLQEML |
| G3380 | (5142) | VIELECLDDQVLQEML |
| G3794 | (5143) | VIELECLDDQVLQEML |
| G3381 | (5134) | PIEFEYLDDHVLQEML |

FIG. 14

| | | |
|---|---|---|
| G4297 | (3761) | CELCGGAAAAVHCAADSAFLCPRCDAKVHGANFLASRHVRRRL---- |
| G4000 | (3712) | CELCGGAAAAVHCAADSAFLCLRCDAKVHGANFLASRHVRRRL---- |
| G4012 | (3718) | CELCGGVAAAVHCAADSAFLCLVCDDKVHGANFLASRHRRRRL---- |
| G4298 | (3762) | CELCGGVAAAVHCAADSAFLCLVCDDKVHGANFLASRHRRRRL---- |
| G4011 | (3717) | CALCGAAAAVHCEADAAFLCAACDAKVHGANFLASRHHRRRV---- |
| G1988 | (2389) | CELCGAEADLHCAADSAFLCRSCDAKFHASNELFARHFRRVICPNC |
| G4005 | (3714) | CELCDQQASLYCPSDSAFLCSDCDAAVHAANFLVARHLRRLLCSKC |
| G4004 | (3713) | CELCHQLASLYCPSDSAFLCFHCDAAVHAANFLVARHLRRLLCSKC |
| G4299 | (3763) | CELCNDQAALFCPSDSAFLCFHCDAKVHQANFLVARHLRLTLCSHC |
| G4007 | (3715) | CELCSQEAALHCASDEAFLCFDCDDRVHKANFLVARHVRQTLCSQC |
| G4009 | (3716) | CELCKGEAGVYCDSDAAYLCFDCDSNVHNANFLVARHIRRVICSGC |

FIG. 16

| ID | Sequence |
|---|---|
| G1760 (2385) | GRGKIVIQRIDDSTSRQVTFSKRRKGLIKKAKELAILCDAEVGLIIFSST |
| G152 (2433) | GRGKIVIQKIDDSTSRQVTFSKRRKGLIKKAKELAILCDAEVCLIIFSNT |
| G3982 (5163) | GRGKIVIQRIDKSTSRQVTFSKRRSGLLKKAKELAILCDAEVGVIFSST |
| G3980 (3710) | GRGKIVIRRIDNSTSRQVTFSKRRNGLIKKAKELAILCDAEVGVMIFSST |
| G3981 (3711) | GRGKIVIRRIDNSTSRQVTFSKRRNGLIKKAKELAILCDAEVGVMIFSST |
| G3485 (3541) | GRGKIVIRRIDNSTSRQVTFSKRRNGLIKKAKELAILCDAEVGVMIFSST |
| G860 (2756) | GRGKIAIKRINNSTSRQVTFSKRRNGLIKKAKELAILCDAEVGVIIFSST |
| G153 (2434) | GRGKIVIRRIDNSTSRQVTFSKRRSGLLKKAKELSILCDAEVGVIIFSST |
| G3479 (3535) | GRGKIVIRRIDNSTSRQVTFSKRRNGIFKKAKELAILCDAEVGLVIFSST |
| G3489 (3544) | GRGKIVIRRIDNSTSRQVTFSKRRNGIFKKAKELAILCDAEVGLVIFSST |
| G3488 (3543) | GRGKIVIRRIDNSTSRQVTFSKRRNGIFKKARELAILCDAEVGLVIFSST |
| G3480 (3536) | GRGKIVIRRIDNSTSRQVTFSKRRNGIFKKAKELAILCDAEVGLMIFSST |
| G3487 (3542) | GRGKIEIKRIDNATSRQVTFSKRRGGLFKKAKELAILCDAEVGLVVFSST |
| G3483 (3539) | GRGKIEIKRIDNATSRQVTFSKRRSGLFKKARELSILCDAEVGLLVFSST |
| G3481 (3537) | GRGKIVIRRIDNSTSRQVTFSKRRNGLLKKAKELSILCDAEVGLVVFSST |
| G3484 (3540) | GRGKIAIRRIDNSTSRQVTFSKRRNGLLKKARELSILCDAEVGLMVFSST |

FIG. 18A

| | | |
|---|---|---|
| G1760 | (2385) | GKLYDF |
| G152 | (2433) | DKLYDF |
| G3982 | (5163) | GKLYEF |
| G3980 | (3710) | GKLYDF |
| G3981 | (3711) | GKLYDF |
| G3485 | (3541) | GKLYDF |
| G860 | (2756) | GRLYDF |
| G153 | (2434) | GKLYDY |
| G3479 | (3535) | GRLYEY |
| G3489 | (3544) | GRLYEY |
| G3488 | (3543) | GRLYEY |
| G3480 | (3536) | GRLYEY |
| G3487 | (3542) | GRLYHF |
| G3483 | (3539) | SRLYDF |
| G3481 | (3537) | GRLYEF |
| G3484 | (3540) | GKLYDY |

FIG. 18B

```
G2514 (3277)  DPVYRGIRCRSGKWVSEIREPRKTTTRIWLGTYPMAEMAAAAYDVAAMALK
G976  (2806)  NPVYRGIRCRSGKWVSEIREPKKTTRVWLGTYPTPEMAAAAYDVAALALK
G913  (2781)  HSIFRGIRLRNGKWVSEIREPRKTTRIWLGTYPVPEMAAAAYDVAALALK

G2514 (3277)  GREAVLNFPGSVGSYPV
G976  (2806)  GGDTLLNFPDSLGSYPI
G913  (2781)  GPDAVLNFPGLALTYVA
```

FIG. 20

| ID | | Sequence |
|---|---|---|
| G3510 | (3553) | PHRPKKLRLSKEQSRLLEESFRLNHTLTPKQKEALAIKLKLRPRQVEVWFQNRRARTKLKQ |
| G4370 | (17838) | PHRPKKLRLSKEQSRLLEESFRLNHTLSPKQKEALAIKLKLRPRQVEVWFQNRRARTKLKH |
| G3490 | (3545) | PHRAKKLRLSKEQSRLLEESFRLNHTLTPKQKEALAVKLKLRPRQVEVWFQNRRARTKLKQ |
| G4369 | (17834) | PHRAKKLRLSKEQSRLLEESFRLNHTLTPKQKEALAVKLKLRPRQVEVWFQNRRARTKLKQ |
| G3524 | (3560) | EPPRKKLRLTKEQSRLLEESFRQNHTLNPKQKESLAMQLKLRPRQVEVWFQNRRARSKLKQ |
| G4371 | (17830) | EPPRKKLRLTKEQSLLLEESFRQNHTLNPKQKESLAMQLKLRPRQVEVWFQNRRARSKLKQ |
| G1543 | (3004) | APPRKKLRLTREQSRLLEDSFRQNHTLNPKQKEVLAKHLMLRPQIEVWFQNRRARSKLKH |
| G2712 | (17842) | GRRRKKLRLTKEQSHLLEESFIQNHTLTPKQKKDLATFLKLSQRQVEVWFQNRRARSKLKH |
| | | **::*.::*:*::. **:. :: * * ::****:::*:* |

Figure 21

```
G3490  (17827)  -KQTELECEYLKRCFGSLTEENRRLQREVEELRAMRVAPPTVLS-
G4369  (17835)  -KQTELECEYLKRCFGSLTEENRRLQREVEELRAMRVAPPTVLS-
G3510  (17826)  -KQTEMECEYLKRCFGSLTEENRRLQREVEELRAMRVAPPTVLS-
G4370  (17839)  -KHTEMECEYLKRCFGSLTEENRRLQREVEELRAMRMAPPTVLS-
G3524  (17825)  GKQTEMECEYLKRWFGSLTEQNRRLQREVEELRAMRLAIKVGPPTVIS-
G4371  (17831)  -KQTEMECEYLKRWFGSLTEQNRRLQREVEELRAIKVGPPTVIS-
G1543  (17824)  -KQTEMECEYLKRWFGSLTEENHRLHREVEELRAIKVGPTTVNSA
G2712  (17843)  -KHTEMECEYLKRWFGSLKEQNRRLQIEVEELRALKPSSTS---
                 *  ****:*******:***: *:**  *****:*: .. .
```

Figure 22

```
G1266  (2902)   EKSYRGVRKRPWGKFAAEIRDSTRNGIRVWLGTFESAEEAALAYDQAAFSMRGSSAILNF
G5184 (17935)   EKSYRGVRKRPWGKFAAEIRDSTRNGIRVWLGTFDSAEAAALAYDQAAFSMRGSAAILNF
G1752  (3045)   ERSYRGVRKRPWGKFAAEIRDSTRHGMRVWLGTFDSAEAAALAYDQAAFATKGSLATLNF
G2512  (3275)   EKSYRGVRKRPWGKFAAEIRDSTRNGIRVWLGTFDKAEEAALAYDQAAFALKGSLAVLNF
G5183 (17934)   QQAFRGVRKRPWGKFAAEIRDSTRKGIRVWLGTFDTAEAAALAYDQAAFAMRGSAAVLNF
G5186 (17936)   KRPFRGVRKRPWGKFAAEIRDSTRNGVRVWLGTFDSAEEAALAYDQAALSTRGSMAVLNF
G5185 (17933)   PAPYIGVRKRPWGKFAAEIRDSTRKGARVWLGTFDSPEAAAMAYDQAAFSVRGAAAVLNF
G5170 (17937)   EKHYIGVRKRPWGKYASEIRDSTRNGIRVWLGTFDTAEEAALAYDQAALSMRGPWSLLNF
                    **:****** ** .******:*:*****:**:: **  .****** .*: *  ::**

G1266  (2902)   SAERVQESL
G5184 (17935)   PAEIVRESL
G1752  (3045)   PVEVVRESL
G2512  (3275)   PADVVEESL
G5183 (17934)   PMEQVRRSM
G5186 (17936)   PEEVVRESL
G5185 (17933)   PVERVQESL
G5170 (17937)   PMEHVKKSL
                  *  ::*:
```

Figure 23

| | | |
|---|---|---|
| G2933 | (17956) | PVVVKKLNHNASERDRRKKINTLFSSLRSCLPASDQSKKLSIPETVSKSLKYIPELQQQVK |
| G2932 | (17957) | PVVVKKLNHNASERDRRKKINSLFSSLRSCLPASGQSKKLSIPATVSRSLKYIPELQEQVK |
| G2928 | (17958) | PVVMKKLNHNASERERRKKINTMFSSLRSCLPPTNQTKKLSVSATVSQALKYIPELQEQVK |
| G5192 | (17961) | PTMVKKLNHNASERDRRKKINSLYSSLRSLLPAADQAKKLSIPSTVSRVLKYIPELQKQVK |
| G5191 | (17963) | ----KKLSHNASERDRRKKVNHLVSSLRSLLPGPDQTKKMSIPATVSRVLKYIPELQHQVQ |
| G5190 | (17960) | ----RKLSHNAYERDRRKQLNDLYSSLRSLLPDADHTKKLSIPTTVSRVLKYIPELQKQV- |
| G5189 | (17962) | ----RKLSHNAYERDRRKQLNELYSSLRALLPDADHTKKLSIPTTVSRVLKYIPELQKQVE |
| G5193 | (17959) | ----RKISHNAYERDRRKQLNELYSDLRSLLPDSDHTKKLSIPITVSRVLKYIPELQKQV- |
| G2936 | (17964) | VVLEKKLNHNASERDRRKKLNALYSSLRALLPLSDQKRKLSIPMTVARVVKYIPEQKQELQ |
| | | .: *.:.* *::: : :: . .. :: *:*.:*:::* |

Figure 24

```
G154   (17993)  VRGKTQMKRIENATSRQVTFSKRRNGLLKKAFELSVLCDAEVSLIIFSPKGKLYEF
G5306  (18002)  VRGKTQMKRIENATSRQVTFSKRRNGLLKKAFELSVLCDAEVSLIIFSPKGKLYEF
G5307  (18020)  VRGKTQMKRIENATSRQVTFSKRRNGLLKKAFELSVLCDAEVSLIIFSPRGKLYEF
G4062  (18001)  VRGKTQMKRIENATSRQVTFSKRRNGLLKKAFELSVLCDAEVSLIIFSPKAKLYEF
G4064  (18014)  VRGKTQMKRIENATSRQVTFSKRRNGLLKKAFELSVLCDAEVALIIFSPRGKLYEF
G5315  (18017)  VRGKTQMRRIENATSRQVTFSKRRNGLLKKAFELSVLCDAEVALIIFSPRGKLYEF
G5311  (18005)  VRGKTQMRRIENATSRQVTFSKRRNGLFKKAFELSVLCDAEVALIIFSPRGKLSEF
G5313  (18006)  VRGKTQMRRIENATSRQVTFSKRRNGLLKKAFELSVLCDAEVAVIIFSPRGKLYEF
G4063  (18013)  VRGKTQLRRIENATSRQVTFSKRRNGLLKKAFELSVLCDAEVALIIFSPRGKLYEF
G5309  (18000)  VRGKTQMRRIENATSRQVTFSKRRNGLLKKAFELSVLCDAEVGLIIFSPRGKLYEF
G5319  (18010)  VRGKTQMRRIENATSRQVTFSKRRNGLLKKAFELSVLCDAEVGLVIFSPRGKLYEF
G5310  (18018)  VRGKTQMRRIENATSRQVTFSKRRNGLLKKAFELSVLCDAQVGLVIFSPRGKQYEF
G5318  (18009)  VRGKTQMRRIENATSRQVTFSKRRNGLLKKAFELSVLCDAEVSLIIFSTRGKLYEF
G5317  (18008)  VRGKTQMRRIENATSRQVTFSKRRNGLLKKAFELSVLCDAEVALIIFSPRGKLYEF
G5314  (18064)  VRGKTQMKRIENATSRQVTFSKRRNGLLKKAFELSVLCDAEVALIVFSPRGKLYEF
G5303  (18015)  VRGKTQMKRIENATSRQVTFSKRRNGLLKKAFELSVLCDAEVALIVFSPRGRLYEF
G5312  (17994)  VRGRTELKRIENPTSRQVTFSKRRNGLLKKAFELSVLCDAEVALIVFSPRGKLYEF
G4067  (18012)  VRGKTQMKRIENPTSRQVTFSKRRNGLLKKAFELSVLCDAEVALIVFSPRGKLYEF
G4065  (18003)  VRGKTQMKRIENPTSRQVTFSKRRNGLLKKAFELSVLCDVEVALIVFSPRGKPYEF
G4066  (18011)  VRGKTQMKRIENPTSRQVTFSKRRNGLLKKAFELSVLCDVEVALIIFSPRGKPYEF
G5305  (18004)  VRGKVEMKRIENSTSRQVTFSKRRNGLLKKAFELSVLCDAEVALIIFSPRGKLYEF
G149   (17995)  VRGKTEMKRIENATSRQVTFSKRRNGLTKKAYELSVLCDAEVAFIIFSHKGRLYEF
G627   (17996)  VRGKTEMKRIENATSRQVTFSKRRNGMLKKAYELSVLCDAEVAVIIFSQKGRLYEF
G5304  (18016)  VRGKTQIKRIENATSRQVTFSKRRSGLFKKAHELSVLCDAQLSLIIFSQRGRLYEF
G4061  (18019)  VRGKIEMKKIENDTSRQVTFSKRRNGLFKKAHELSVLCDAEVAAMIFSQKGRLYEF
G5316  (18007)  VRGKIEMKKIENATSRQVTFSKRRSGLFKKAHELSVLCDAQVAAIVFSQRGRLYEF
G1011  (17997)  VRGKIEIKKIENVTSRQVTFSKRRSGLFKKAHELSVLCDAQVAAIVFSQSGRLHEY
G1797  (17998)  VRGKIEIKKIENVTSRQVTFSKRRSGLFKKAHELSVLCDAQVAAIVFSQSGRLHEY
G1798  (17999)                                                          *
                *** :    ** .***********.**:***: *******.::.::::**   ::: .
```

Figure 25

| | |
|---|---|
| G1782 (3060) | -EPIFVNAKQYHAILRRKHRAKLEAQNKLIKCRKPYLHESRHLHALKRARGSGGRFLNTK |
| G1363 (2940) | -EPIFVNAKQYQAILRRERRAKLEAQNKLIKVRKPYLHESRHLHALKRVRGSGGRFLNTK |
| G4262 (3748) | -EPIYVNAKQYHAILRRQLRAKLEAENKLVKSRKPYLHESRHLHAMKRARGTGGRFLNTK |
| G4263 (3749) | -EPIYVNAKQYHAILRRQLRAKLEAENKLVKSRKPYLHESRHLHAMKRARGTGGRFLNTK |
| G3925 (3701) | -EPIYVNAKQYHAILRRQLRAKLEAENKLVKNRKPYLHESRHQHAMKRARGTGGRFLNTK |
| G3922 (5117) | -EPIYVNAKQYHAILRRQTRAKLEAQNKMVKNRKPYLHESRHRHAMKRARGSGGRFLNTK |
| G3920 (3698) | -EPVYVNAKQYHGILRRQSRAKAEIEKKVIKNRKPYLHESRHLHAMRRARGNGGRFLNTK |
| G4270 (3755) | EAPIYVNAKQYDAIMRRCARAKAERENRLVKGRKPYLHESRHQHALRRPRGSGGRFLNTK |
| |  ******   *:.   *:**   :*::* *******:  :*:* *:***** |

Figure 26

| ID | Sequence |
|---|---|
| G5472 (17864) | -GRGRVELKRIENKINRQVTFSKRRNGLLKKAYELSVLCDAEVALIIFSSRGKLYEF |
| G5487 (17911) | -GRGRVQLRRIENKINRQVTFSKRRNGLLKKAYELSVLCDAEVALIIFSTRGKLYEF |
| G5480 (17917) | -GRGRVQLRRIENKINRQVTFSKRRNGLLKKAYELSVLCDAEVALIIFSTRGKLYEF |
| G5471 (17861) | -GRGRVELKRIENKINRQVTFSKRRNGLLKKAYELSVLCDAEVALIIFSGRGKLYEF |
| G5483 (17846) | -GRGRVELKRIENKINRQVTFSKRRNGLLKKAYELSVLCDAEVALIVFSSRGKLYEF |
| G5484 (17849) | -GRGRVEMKRIENKINRQVTFSKRRNGLLKKAYELSVLCDAEVALIIFSSRGKLYEF |
| G142 (2427) | -GRGRVEMKRIENKINRQVTFSKRRNGLLKKAYELSVLCDAEVALIIFSSRGKLYEF |
| G5485 (17920) | -GRGRVELKRIENKINRQVTFSKRRNGLLKKAYELSVLCDAEVALIIFSSRGKLYEF |
| G5486 (17921) | -GRGRVELKRIENKINRQVTFSKRRNGLLKKAYELSVLCDAEVALIIFSSRGKLYEF |
| G5481 (17918) | -GRGRVELKRIENKINRQVTFSKRRNGLLKKAYELSVLCDAEVALIIFSSRGKLYEF |
| G5478 (17915) | -GRGRVELKRIENKINRQVTFSKRRNGLLKKAYELSVLCDAEVALIIFSSRGKLYEF |
| G5477 (17914) | -GRGRVELKRIENKINRQVTFSKRRNGLLKKAYELSVLCDAEVALIIFSSRGKLYEF |
| G5474 (17913) | -GRGRVELKRIENKINRQVTFSKRRNGLLKKAYELSVLCDAEVALIIFSSRGKLYEF |
| G5473 (17912) | -GRGRVELKRIENKINRQVTFSKRRNGLLKKAYELSVLCDAEVALIIFSSRGKLYEF |
| G5472 (17864) | -GRGRVELKRIENKINRQVTFSKRRNGLLKKAYELSVLCDAEVALIIFSSRGKLYEF |
| G5470 (17858) | -GRGRVELKRIENKINRQVTFSKRRNGLLKKAYELSVLCDAEVALIIFSSRGKLYEF |
| G5476 (17855) | -GRGRVELKRIENKINRQVTFSKRRNGLLKKAYELSVLCDAEVALIIFSSRGKLYEF |
| G5475 (17852) | -GRGRVELKRIENKINRQVTFSKRRNGLLKKAYELSVLCDAEVGLIIFSSRGKLYEF |
| G5479 (17916) | -GRGRVELKRIENKINRQVTFSKRRNGLLKKAYELSVLCDAEVGLIIFSSRDKLYEF |
| G5488 (17910) | -GRGRVELKRIENKINRQVTFSKRRNGLLKKAYELSVLCDAEVALIIFSSRGKLYEF |
| G5482 (17919) | -GRGKVELKRIENKINRQVTFSKRRNGLLKKAYELSVLCDAEVALIIFSSRGKLYEF |
| G148 (2431) | MGRGKVEVKRIENKITRQVTFSKRKSGLLKKAYELSVLCDAEVSLIIFSTGGKLYEF |
|  | .*:** :**********.********** . *..**** |

Figure 27

```
G3401  (3493)   GSKNKPKPPIFVTRDSPNALRSHVMEVAGGADVAESIAHFARRRQRGVCVLSGAGTVEDV
G3403 (17879)   GSKNKPKPPIFVTRDSPNALRSHVMEVAGGADVAESIAHFARRRQRGVCVLSGAGTVANV
G3932 (17886)   GSKNKPKPPIFVTRDSPNSLRSHVMEVAGGADVADAIAQFSRRRQRGVCVLSGAGTVANV
G3456  (3522)   GSRNKPKPPIFVTRDSPNALRSHVMEIAVGADVAESVAQFARRRQRGVSILSGSGTVVNV
G1069  (5149)   GSKNKPKAPIFVTRDSPNALRSHVLEISDGSDVADTIAHFSRRRQRGVCVLSGTGSVANV
G2153  (3203)   GSKNKPKPPIFVTRDSPNALKSHVMEIASGTDVIETLATFARRRQRGICILSGNGTVANV
G3462 (17882)   GSKNKPKPPIVIFLSPNALRSHVLEIASGRDVAESIAAFANRRHRGVSVLSGSGIVANV
G3556  (3584)   GSKNKPKPPVVTRESPNAMRSHVLETASGADIVEAIAGFSRRRQRGVSVLSGSGAVTNV
                *.:****. **     :  ::*: *  *  ..*  *:: *  . *:***: ** : ::

G3401  (3493)   ALRQ--------PAAPSA--VVALRGRFEILSLTGTFLPGPAPPGSTGLTVYLAGGQGQVVG
G3403 (17879)   ALRQ--------PSAPGA--VVALHGRFEILSLTGTFLPGPAPPGSTGLTVYLAGGQGQVVG
G3932 (17886)   TLRQ--------PSAPGA--VVALHGRFEILSLTGAFLPGAPPGATGLTVYLAGGQGQVVG
G3456  (3522)   NLRQ--------PTAPGA--VMALHGRFDILSLTGSFLPGSPPGATGLTIYLAGGQGQIVG
G1069  (5149)   TLRQ--------AAAPGG--VVSLQGRFEILSLTGAFLPGSPPGSTGLTVYLAGVQGQVVG
G2153  (3203)   TLRQPSTAAVAAPGGAAVLALQGRFEILSLTGAFLPSPSPSGAFLPSPSGAFLPSPSPSGAFLPSPSGA
G3462 (17882)   TLRQ--------PAAP-AG-VITLHGRFEILSLSGAFLPSPSPSGAFLPAPAPPGATGLAVYLAGGQGQVVG
G3556  (3584)   TLRQ--------PAGTGAA-AVALRGRFEILSMSGAFLPAPAPPGATGLAVYLAGGQGQVVG
                 **            .    . :* **:**::.*:**.      .*:**:: ** :*::*

G3401  (3493)   GSVVGTLTAAGPVMVIASTFANATYERLPLDQ
G3403 (17879)   GSVVGSLIAAGPVMVIASTFANATYERLPLEE
G3932 (17886)   GSVVGSLVAAGPVMVIAATFANATYERLPLEE
G3456  (3522)   GSVVGPLVAAGPVLVMAATFSNATFANATYERLPLED
G1069  (5149)   GSVVGPLLAIGSVMVIAATFSNATYERLPMEE
G2153  (3203)   GSVVGPLMAAGPVMLIAATFSNATYERLPLEE
G3462 (17882)   GNVAGSLVASGPVMVIAATFANATFANATYERLPLED
G3556  (3584)   GSVMGELIASGPVMVIAATFGNATYERLPLD-
                *.: *  :*.*.*: :*:**.**: :*** . 
```

Figure 28

| | | |
|---|---|---|
| G202 | (180061) | KGAWTTEEDKKLISYIHDHGEGGWRDIPQKAGLKRCGKSCRLRWTNYLKPEIKRGEFS |
| G243 | (180063) | KGAWTTEEDKKLISYIHDHGEGGWRDIPEKAGLKRCGKSCRLRWTNYLKPDIKRGEFS |
| G201 | (180051) | KGAWTAEEDKKLISYIHEHGGGWRDIPQKAGLKRCGKSCRLRWANYLKPDIKRGEFS |
| G671 | (180059) | KGAWTPEEDQKLLSYLNRHGEGGWRTLPEKAGLKRCGKSCRLRWANYLRPDIKRGEFT |
| G2340 | (180052) | KGAWTQEEDQKLIAYVQRHGEGGWRTLPDKAGLKRCGKSCRLRWANYLRPDIKRGEFS |
| G656 | (180060) | KGAWTPEEDQKLIAYLHLHGEGGWRTLPEKAGLKRCGKSCRLRWANYLRPDIKRGEFS |
| | | ** *:*: :*.: ***:*:* *.******.***** :*:*:**** |

| | | |
|---|---|---|
| G202 | (180061) | SEEEQIIIMLHASRGNKWSVIARHLPRRTDNEIKNYWNTHLKK |
| G243 | (180063) | YEEEQIIIMLHASRGNKWSVIARHLPKRTDNEVKNYWNTHLKK |
| G201 | (180051) | YEEEQIIIMLHASRGNKWSVIARHLPKRTDNEIKNYWNTHLKK |
| G671 | (180059) | EDEERSIISLHALHGNKWSAIARGLPGRTDNEIKNYWNTHIKK |
| G2340 | (180052) | QDEEDSIINLHAIHGNKWSAIARKIPRRTDNEIKNHWNTHIKK |
| G656 | (180060) | PEEDDTIIKLHALKGNKWAAIATSLAGRTDNEIKNYWNTNLKK |
| | | ** * *: : .: . ***::*.: |

Figure 29

STRESS TOLERANCE IN PLANTS

RELATIONSHIP TO COPENDING APPLICATIONS

This application is a continuation of co-pending U.S. application Ser. No. 14/480,473, filed Sep. 8, 2014, which is a divisional of U.S. application Ser. No. 13/244,288, filed Sep. 24, 2011, which is a continuation in part of U.S. application Ser. No. 12/077,535 (issued as U.S. Pat. No. 8,030,546), which claims the benefit of Application No. 60/961,403, filed Jul. 20, 2007. Application Ser. No. 12/077,535 is a continuation-in-part of application Ser. No. 10/286,264, filed Nov. 1, 2002, which is a divisional of application Ser. No. 09/533,030, filed Mar. 22, 2000, which claims the benefit of Application No. 60/125,814, filed Mar. 23, 1999. Application Ser. No. 12/077,535 is a continuation-in-part of application Ser. No. 10/675,852, filed Sep. 30, 2003. Application Ser. No. 12/077,535 is a continuation-in-part of application Ser. No. 11/479,226, filed Jun. 30, 2006 (issued as U.S. Pat. No. 7,858,848), which is a continuation-in-part of application Ser. No. 09/713,994, filed Nov. 16, 2000, which claims the benefit of Application No. 60/166,228, filed Nov. 17, 1999, which also claims the benefit of Application No. 60/197,899, filed Apr. 17, 2000, which also claims the benefit of Application No. 60/227,439, filed Aug. 22, 2000. Application Ser. No. 12/077,535 is a continuation-in-part of application Ser. No. 10/669,824, filed Sep. 23, 2003, which is a continuation-in-part of, Ser. No. 09/823,676, filed Mar. 30, 2001 (issued as U.S. Pat. No. 6,717,034). Application Ser. No. 12/077,535 is a continuation-in-part of application Ser. No. 11/725,235, filed Mar. 16, 2007 (issued as U.S. Pat. No. 7,601,893), which is a divisional of application Ser. No. 10/225,068, filed Aug. 9, 2002 (issued as U.S. Pat. No. 7,193,129), which claims the benefit of Application No. 60/310,847, filed Aug. 9, 2001, and also claims the benefit of Application No. 60/336,049, filed Nov. 19, 2001, and also claims the benefit of Application No. 60/338,692, filed Dec. 11, 2001; application Ser. No. 10/225,068 is also a continuation-in-part of application Ser. No. 09/837,944, filed Apr. 18, 2001, and is also a continuation-in-part of application Ser. No. 10/171,468, filed Jun. 14, 2002. Application Ser. No. 12/077,535 is a continuation-in-part of application Ser. No. 11/728,567, filed Mar. 26, 2007 (issued as U.S. Pat. No. 7,635,800), which is a divisional of application Ser. No. 10/225,066, filed Aug. 9, 2002 (issued as U.S. Pat. No. 7,238,860), which claims the benefit of Application No. 60/310,847, filed Aug. 9, 2001, and also claims the benefit of Application No. 60/336,049, filed Nov. 19, 2001, and also claims the benefit of Application No. 60/338,692, filed Dec. 11, 2001. Application Ser. No. 10/225,066 is also a continuation-in-part of application Ser. No. 09/837,944, filed Apr. 18, 2001, and is a continuation-in-part of application Ser. No. 10/171,468, filed Jun. 14, 2002. Application Ser. No. 12/077,535 is a continuation-in-part of application Ser. No. 11/375,241, filed Mar. 16, 2006 (issued as U.S. Pat. No. 7,598,429), which claims the benefit of Application No. 60/713,952, filed Aug. 31, 2005. Application Ser. No. 11/375,241 is also a continuation-in-part of application Ser. No. 10/225,067, filed Aug. 9, 2002 (issued as U.S. Pat. No. 7,135,616), which claims the benefit of Application No. 60/310,847, filed Aug. 9, 2001, which also claims the benefit of Application No. 60/336,049, filed Nov. 19, 2001, and also claims the benefit of Application No. 60/338,692, filed Dec. 11, 2001. Application Ser. No. 10/225,067 is also a continuation-in-part of application Ser. No. 09/837,944, filed Apr. 18, 2001, and is also a continuation-in-part of application Ser. No. 10/171,468, filed Jun. 14, 2002. Application Ser. No. 12/077,535 is a continuation-in-part of application Ser. No. 11/069,255, filed Feb. 28, 2005 (issued as U.S. Pat. No. 8,558,059), which is a continuation-in-part of application Ser. No. 10/112,887, filed Mar. 18, 2002. Application Ser. No. 12/077,535 is a continuation-in-part of application Ser. No. 10/374,780, filed Feb. 25, 2003 (issued as U.S. Pat. No. 7,511,190), which is a continuation-in-part of application Ser. No. 09/934,455, filed Aug. 22, 2001, which is a continuation-in-part of application Ser. No. 09/713,994, Nov. 16, 2000, which is also a continuation-in-part of application Ser. No. 09/837,944, filed Apr. 18, 2001, which also claims priority to Application No. 60/227,439, filed Aug. 22, 2000. Application Ser. No. 10/374,780 is also a continuation-in-part of application Ser. No. 10/225,068, filed Aug. 9, 2002 (issued as U.S. Pat. No. 7,193,129), which claims the benefit of Application No. 60/310,847, filed Aug. 9, 2001, and also claims the benefit of Application No. 60/336,049, filed Nov. 19, 2001, and also claims the benefit of Application No. 60/338,692, filed Dec. 11, 2001. Application Ser. No. 10/225,068 is also a continuation-in-part of application Ser. No. 09/837,944, filed Apr. 18, 2001, and is also a continuation-in-part of application Ser. No. 10/171,468, filed Jun. 14, 2002. Application Ser. No. 10/374,780 is also a continuation-in-part of application Ser. No. 10/225,066, filed Aug. 9, 2002 (issued as U.S. Pat. No. 7,238,860), which claims the benefit of Application No. 60/310,847, filed Aug. 9, 2001, which also claims the benefit of Application No. 60/336,049, filed Nov. 19, 2001, which also claims the benefit of Application No. 60/338,692, filed Dec. 11, 2001; application Ser. No. 10/225,066 is also a continuation-in-part of application Ser. No. 09/837,944, filed Apr. 18, 2001, and is also a continuation-in-part of application Ser. No. 10/171,468, filed Jun. 14, 2002. Application Ser. No. 10/374,780 is also a continuation-in-part of application Ser. No. 10/225,067, filed Aug. 9, 2002 (issued as U.S. Pat. No. 7,135,616), which claims the benefit of Application No. 60/310,847, filed Aug. 9, 2001, and also claims the benefit of Application No. 60/336,049, filed Nov. 19, 2001, and also claims the benefit of Application No. 60/338,692, filed Dec. 11, 2001; application Ser. No. 10/225,067 is also a continuation-in-part of application Ser. No. 09/837,944, filed Apr. 18, 2001, and is also a continuation-in-part of application Ser. No. 10/171,468, filed Jun. 14, 2002. Application Ser. No. 12/077,535 is a continuation-in-part of application Ser. No. 10/546,266, filed Aug. 19, 2005 (issued as U.S. Pat. No. 7,659,446), which is a '371 National Stage filing of International Application No. PCT/US2004005654, filed Feb. 25, 2004 (converted), which is a continuation-in-part of application Ser. No. 10/374,780, filed Feb. 25, 2003 (issued as U.S. Pat. No. 7,511,190), and is also a continuation-in-part of application Ser. No. 10/675,852, filed Sep. 30, 2003. Application Ser. No. 12/077,535 is also a continuation-in-part of application Ser. No. 10/412,699, filed Apr. 10, 2003 (issued as U.S. Pat. No. 7,345,217), which is a continuation-in-part of application Ser. No. 10/295,403, filed Nov. 15, 2002, which is a divisional of application Ser. No. 09/394,519, filed Sep. 13, 1999, which claims the benefit of Application No. 60/101,349, filed Sep. 22, 1998, which also claims the benefit of Application No. 60/103,312, filed Oct. 6, 1998, which also claims the benefit of Application No. 60/108,734, filed Nov. 17, 1998, which also claims the benefit of Application No. 60/113,409, filed Dec. 22, 1998. Application Ser. No. 10/412,699 is also a continuation-in-part of application Ser. No. 09/489,376, filed Jan. 21, 2000, which claimed priority to Application No. 60/116,841, filed Jan. 22, 1999. Application Ser. No. 10/412,699 is also a continuation-in-part of application Ser. No. 10/302,267, filed Nov. 22, 2002 (issued as U.S. Pat. No. 7,223,904), which is a divisional of application Ser. No. 09/506,720, filed Feb. 17, 2000, which claims the benefit of Application No. 60/120,880, filed Feb. 18, 1999, which also claims the benefit of Application No. 60/121,037, filed Feb. 22, 1999, which also claims the benefit of Application No. 60/124,278, filed Mar. 11, 1999, which also claims the benefit of Application No. 60/129,450, filed Apr. 15, 1999, which also claims the benefit of Application No. 60/135,134, filed May 20, 1999, which also claims the benefit of Application No. 60/144,153, filed Jul. 15, 1999, which also claims the benefit of Application No. 60/161,143, filed Oct. 22, 1999, which also claims the benefit of Application No. 60/162,656, filed Nov. 1, 1999. Application Ser. No. 10/412,699 is also a continuation-in-part of application Ser. No. 10/278,173, filed Oct. 21, 2002, which is a divisional of application Ser. No. 09/533,392, filed Mar. 22, 2000, which claims the benefit of Application No. 60/125,814, filed Mar. 23, 1999. Application Ser. No. 10/412,699 is also a continuation-in-part of application Ser. No. 09/533,029, filed Mar. 22, 2000 (issued as U.S. Pat. No. 6,664,446), which claims the benefit of Application No. 60/125,814, filed Mar. 23, 1999. Application Ser. No. 10/412,699 is also a continuation-in-part of application Ser. No. 10/278,536, filed Oct. 22, 2002, which is a divisional of application Ser. No. 09/532,591, filed Mar. 22, 2000, which claims priority to Application No. 60/125,814, filed Mar. 23, 1999. Application Ser. No. 10/412,699 is also a continuation-in-part of application Ser. No. 09/713,994, filed Nov. 16, 2000, which claims the benefit of Application No. 60/166,228, filed Nov. 17, 1999, which also claims the benefit of Application No. 60/197,899, filed Apr. 17, 2000, which also claims the benefit of Application No. 60/227,439, filed Aug. 22, 2000. Application Ser. No. 10/412,699 is also a continuation-in-part of application Ser. No. 09/819,142, filed Mar. 27, 2001. Application Ser. No. 10/412,699 is also a continuation-in-part of application Ser. No. 09/934,455, filed Aug. 22, 2001, which is a continuation-in-part of application Ser. No. 09/713,994, filed Nov. 16, 2000, which is also a continuation-in-part of application Ser. No. 09/837,944, filed Apr. 18, 2001, which also claim the benefit of Application No. 60/227,439, filed Aug. 22, 2000. Application Ser. No. 10/412,699 is also a continuation-in-part of application Ser. No. 10/225,068, filed Aug. 9, 2002 (issued as U.S. Pat. No. 7,193,129), which claims the benefit of Application No. 60/310,847, filed Aug. 9, 2001, which also claims the benefit of Application No. 60/336,049, filed Nov. 19, 2001, which also claims the benefit of Application No. 60/338,692, filed Dec. 11, 2001; and, application Ser. No. 10/225,068 is also a continuation-in-part of application Ser. No. 09/837,944, filed Apr. 18, 2001, and is also a continuation-in-part of application Ser. No. 10/171,468, filed Jun. 14, 2002. Application Ser. No. 10/412,699 is also a continuation-in-part of application Ser. No. 10/225,066, filed Aug. 9, 2002 (issued as U.S. Pat. No. 7,238,860), which claims the benefit of Application No. 60/310,847, filed Aug. 9, 2001, which also claims the benefit of Application No. 60/336,049, filed Nov. 19, 2001, which also claims the benefit of Application No. 60/338,692, filed Dec. 11, 2001; and, application Ser. No. 10/225,066 is also a continuation-in-part of application Ser. No. 09/837,944, filed Apr. 18, 2001, and is also a continuation-in-part of application Ser. No. 10/171,468, filed Jun. 14, 2002. Application Ser. No. 10/412,699 is also a continuation-in-part of application Ser. No. 10/225,067, filed Aug. 9, 2002 (issued as U.S. Pat. No. 7,135,616), which claims the benefit of Application No. 60/310,847, filed Aug. 9, 2001, which also claims the benefit of Application No. 60/336,049, filed Nov. 19, 2001, which also claims the benefit of Application No. 60/338,692, filed Dec. 11, 2001; and, application Ser. No. 10/225,067 is also a continuation-in-part of application Ser. No. 09/837,944, filed Apr. 18, 2001, and is also a continuation-in-part of application Ser. No. 10/171,468, filed Jun. 14, 2002. Application Ser. No. 10/412,699 is also a continuation-in-part of application Ser. No. 10/374,780, filed Feb. 25, 2003 (issued as U.S. Pat. No. 7,511,190). Application Ser. No. 12/077,535 is a continuation-in-part of application Ser. No. 10/559,441, filed Dec. 2, 2005, which is a '371 National Stage filing of International Application No. PCT/US2004/017768, filed Jun. 4, 2004 (converted), which is a continuation-in-part of application Ser. No. 10/456,882, filed Jun. 6, 2003. Application Ser. No. 12/077,535 is a continuation-in-part of application Ser. No. 11/642,814, filed Dec. 20, 2006 (issued as U.S. Pat. No. 7,825,296), which is a divisional of application Ser. No. 10/666,642, filed Sep. 18, 2003 (issued as U.S. Pat. No. 7,196,245), which claims the benefit of Application No. 60/411,837, filed Sep. 18, 2002, and also claims the benefit of Application No. 60/434,166, filed Dec. 17, 2002, and also claims the benefit of Application No. 60/465,809, filed Apr. 24, 2003. Application Ser. No. 12/077,535 is a continuation-in-part of application Ser. No. 10/714,887, filed Nov. 13, 2003, which is a continuation-in-part of application Ser. No. 10/456,882, filed Jun. 6, 2003; and application Ser. No. 10/714,887 is also a continuation-in-part of application Ser. No. 10/666,642, filed Sep. 18, 2003 (issued as U.S. Pat. No. 7,196,245), which claims the benefit of Application No. 60/411,837, filed Sep. 18, 2002, which also claims the benefit of Application No. 60/434,166, filed Dec. 17, 2002, which also claims the benefit of Application No. 60/465,809, filed Apr. 24, 2003. Application Ser. No. 12/077,535 is a continuation-in-part of application Ser. No. 11/435,388, filed May 15, 2006 (issued as U.S. Pat. No. 7,663,025), which is a continuation-in-part of International Application No. PCT/US04/37584, filed Nov. 12, 2004 (converted), which is a continuation-in-part of application Ser. No. 10/714,887, filed Nov. 13, 2003, and also claims the benefit of Application No. 60/527,658, filed Dec. 5, 2003, and also claims the benefit of Application No. 60/542,928, filed Feb. 5, 2004. Application Ser. No. 12/077,535 is a continuation-in-part of application Ser. No. 11/632,390, filed Jan. 11, 2007, which is a '371 National Stage filing of International Application No. PCT/US2005/025010, filed Jul. 14, 2005 (converted), which claims the benefit of Application No. 60/588,405, filed Jul. 14, 2004. Application Ser. No. 12/077,535 is a continuation-in-part of application Ser. No. 12/064,961, filed Feb. 26, 2008, which is a continuation-in-part of PCT application PCT/US06/34615, filed Aug. 31, 2006, which claims the benefit of Application No. 60/713,952, filed Aug. 31, 2005. Application Ser. No. 12/077,535 is a continuation-in-part of International Application no. PCT/US2006/34615, filed Aug. 31, 2006, which claims the benefit of Application No. 60/713,952, filed Aug. 31, 2005. Application Ser. No. 12/077,535 is a continuation-in-part of application Ser. No. 10/903,236, filed Jul. 30, 2004, which is a continuation-in-part of application Ser. No. 10/456,882, filed Jun. 6, 2003, and is also a continuation-in-part of application Ser. No. 10/666,642, filed Sep. 18, 2003 (issued as U.S. Pat. No. 7,196,245), which claims the benefit of Application No. 60/411,837, filed Sep. 18, 2002, and also claims the benefit of Application No. 60/465,809, filed Apr. 24, 2003. Application Ser. No. 12/077,535 is a continuation-in-part of application Ser. No. 11/699,973, filed Jan. 29, 2007, which is a continuation-in-part of International Application No. PCT/US2005-027151, filed Jul. 29, 2005 (converted), which is a continuation-in-part of application Ser. No. 10/903,236, filed Jul. 30, 2004. Application Ser. No. 12/077,535 is a continuation-in-part of application Ser. No. 10/870,198, filed Jun. 16, 2004 (issued as U.S. Pat. No. 7,897,843), which claims the benefit of Application No. 60/565,948, filed Apr. 26, 2004, which also claims the benefit of Application No. 60/527,658, filed Dec. 5, 2003, which also claims the benefit of Application No. 60/542,928, filed Feb. 5, 2005; and, application Ser. No. 10/870,198 is also a continuation-in-part of application Ser. No. 10/669,824, filed Sep. 23, 2003, which is a continuation-in-part of application Ser. No. 09/823,676, filed Mar. 30, 2001 (issued as U.S. Pat. No. 6,717,034). Application Ser. No. 12/077,535 is a continuation-in-part of application Ser. No. 10/838,616, filed May 4, 2004 (issued as U.S. Pat. No. 8,283,519), which claims the benefit of Application No. 60/565,948, filed Apr. 26, 2004, and is a continuation-in-part of application Ser. No. 10/685,922, filed Oct. 14, 2003. Application Ser. No. 12/077,535 is a continuation-in-part of International Application No. PCT/US2007/17321, filed Aug. 7, 2006, which claims the benefit of Application No. 60/836,243, filed Aug. 7, 2006. Application Ser. No. 12/077,535 is a continuation-in-part of application Ser. No. 11/705,903, filed Feb. 12, 2007 (issued as U.S. Pat. No. 7,868,229), which is a continuation-in-part of International Application No. PCT/US2006/34615, filed Aug. 31, 2006 (converted), which claims the benefit of Application No. 60/713,952, filed Aug. 31, 2005. Application Ser. No. 12/077,535 is a continuation-in-part of application Ser. No. 11/821,448, filed Jun. 22, 2007 (issued as U.S. Pat. No. 7,692,067), which claims priority to Application No. 60/817,886, filed Jun. 29, 2006. Application Ser. No. 12/077,535 is a continuation-in-part of International Application No. PCT/US2007/09124, filed Apr. 12, 2007, which claims priority to Application No. 60/791,663, filed Apr. 12, 2006. Application Ser. No. 12/077,535 is a continuation-in-part of application Ser. No. 11/986,992, filed Nov. 26, 2007 (issued as U.S. Pat. No. 8,809,630), which is a division of application Ser. No. 10/412,699, filed Apr. 10, 2003 (issued as U.S. Pat. No. 7,345,217). The contents of all applications herein are incorporated by referenced in their entirety.

JOINT RESEARCH AGREEMENT

The claimed invention, in the field of functional genomics and the characterization of plant genes for the improvement of plants, was made by or on behalf of Mendel Biotechnology, Inc. and Monsanto Company as a result of activities undertaken within the scope of a joint research agreement, and in effect on or before the date the claimed invention was made.

FIELD OF THE INVENTION

The present invention relates to plant genomics and plant improvement.

BACKGROUND OF THE INVENTION

Abiotic Stress and Impact on Yield.

Water deficit is a common component of many plant stresses. Water deficit occurs in plant cells when the whole plant transpiration rate exceeds the water uptake. In addition to drought, other stresses, such as salinity and low temperature, produce cellular dehydration (McCue and Hanson, 1990).

Salt (and drought) stress signal transduction consists of ionic and osmotic homeostasis signaling pathways. The ionic aspect of salt stress is signaled via the SOS pathway where a calcium-responsive SOS3-SOS2 protein kinase complex controls the expression and activity of ion transporters such as SOS1. The pathway regulating ion homeostasis in response to salt stress has been reviewed recently by Xiong and Zhu (2002a).

The osmotic component of salt-stress involves complex plant reactions that are possibly overlapping with drought- and/or cold-stress responses. Common aspects of drought-, cold- and salt-stress response have been reviewed by Xiong and Zhu (2002). These include:

Abscisic acid (ABA) biosynthesis is regulated by osmotic stress at multiple steps. Both ABA-dependent and -independent osmotic stress signaling first modify constitutively expressed transcription factors, leading to the expression of early response transcriptional activators, which then activate downstream stress tolerance effector genes.

Based on the commonality of many aspects of cold, drought, and salt stress responses, it can be concluded that genes that increase tolerance to cold or salt stress can also improve drought stress protection. In fact, this has already been demonstrated for transcription factors (in the case of AtCBF/DREB1) and for other genes such as OsCDPK7 (Saijo et al. (2000)), or AVP1 (a vacuolar pyrophosphatase-proton-pump, Gaxiola et al. (2001)).

Heat stress often accompanies conditions of low water availability. Heat itself is seen as an interacting stress and adds to the detrimental effects caused by water deficit conditions. Evaporative demand exhibits near exponential increases with increases in daytime temperatures and can result in high transpiration rates and low plant water potentials (Hall et al. (2000)). High-temperature damage to pollen almost always occurs in conjunction with drought stress, and rarely occurs under well-watered conditions. Thus, separating the effects of heat and drought stress on pollination is difficult. Combined stress can alter plant metabolism in novel ways; therefore, understanding the interaction between different stresses may be important for the development of strategies to enhance stress tolerance by genetic manipulation.

Plant Pathogens and Impact on Yield.

While a number of plant pathogens exist that may significantly impact yield or affect the quality of plant products, specific attention is being given in this application to a small subset of these microorganisms. These include:

*Sclerotinia.*

*Sclerotinia sclerotiorum* is a necrotrophic ascomycete that causes destructive rots of numerous plants (Agrios (1997)). *Sclerotinia* stem rot is a significant pathogen of soybeans in the northern U.S. and Canada.

*Botrytis.*

*Botrytis* causes blight or gray mold, a disease of plants that infects a wide array of herbaceous annual and perennial plants. Environmental conditions favorable to this pathogen can significantly impact ornamental plants, vegetables and fruit. *Botrytis* infections generally occur in spring and summer months following cool, wet weather, and may be particularly damaging when these conditions persist for several days.

*Fusarium.*

*Fusarium* or vascular wilt may affect a variety of plant host species. Seedlings of developing plants may be infected with *Fusarium*, resulting in the grave condition known as "damping-off". *Fusarium* species also cause root, stem, and corn rots of growing plants and pink or yellow molds of fruits during post-harvest storage. The latter affect ornamentals and vegetables, particularly root crops, tubers, and bulbs.

Drought-Disease Interactions.

Plant responses to biotic and abiotic stresses are governed by complex signal transduction networks. There appears to be significant interaction between these networks, both positive and negative. An understanding of the complexity of these interactions will be necessary to avoid unintended consequences when altering plant signal transduction pathways to engineer drought or disease resistance.

Transcription Factors (TFs) and Other Genes Involved in Both Abiotic and Biotic Stress Resistance.

Despite the evidence for negative cross-talk between drought and disease response pathways, a number of genes have been shown to function in both pathways, indicating possible convergence of the signal transduction pathways. There are numerous examples of genes that are inducible by multiple stresses. For instance, a global TxP (transcriptional profile) analysis revealed classes of transcription factor that are mainly induced by abiotic stresses or disease, but also a class of transcription factors induced both by abiotic stress and bacterial infection (Chen et al. (2002a)).

Implications for Crop Improvement.

Plant responses to drought and disease interact at a number of levels. Although dry conditions do not favor most pathogens, plant defenses may be weakened by metabolic stress or hormonal cross-talk, increasing vulnerability to pathogens that can infect under drought conditions. However, there is also evidence for convergence of abiotic and biotic stress response pathways, based on genes that confer tolerance to multiple stresses. Given our incomplete understanding of these signaling interactions, plants with positive alterations in one stress response should be examined carefully for possible alterations in other stress responses.

SUMMARY OF THE INVENTION

The present invention pertains to expression vectors, transgenic plants comprising the expression vectors of the invention, and methods for making and using the transgenic plants of the invention. The expression vectors and transgenic plants each comprise a recombinant polynucleotide of the invention that encodes a transcription factor polypeptide. The recombinant polynucleotide or the transcription factor polypeptide are encompassed by the present invention in that it shares an amino acid or nucleotide percentage identity with any of SEQ ID NO: 1 to 5086 or SEQ ID NO: 5102-5107, or a polypeptide sequence of any of SEQ ID NO: SEQ ID NO 2n-1, where n=1 to 1186, or SEQ ID NO: 2373-3791, or SEQ ID NO: 5107-5111, or SEQ ID NO: 5113-5114, or SEQ ID NO: 5116-5117, or SEQ ID NO: 5119-5120, or SEQ ID NO: 5122-5123, or SEQ ID NO: 5125-5143, or SEQ ID NO: 5145-5149, or SEQ ID NO: 5151-5153, or SEQ ID NO: 5155-5157, or SEQ ID NO: 5159-5160, or SEQ ID NO: 5162-5163, or SEQ ID NO: 17824-17827, or SEQ ID NO: 17829-17831, or SEQ ID NO: 17833-17835, or SEQ ID NO: 17837-17839, or SEQ ID NO: 17841-17843, or SEQ ID NO: 17845-17846, or SEQ ID NO: 17848-17849, or SEQ ID NO: 17851-17852, or SEQ ID NO: 17854-17855, or SEQ ID NO: 17857-17858, or SEQ ID NO: 17860-17861, or SEQ ID NO: 17863-17866, or SEQ ID NO: 17868-17869, or SEQ ID NO: 17871-17872, or SEQ ID NO: 17874-17875, or SEQ ID NO: 17877-17882, or SEQ ID NO: 17884-17898, or SEQ ID NO: 17905, or SEQ ID NO: 17911-17922, or SEQ ID NO: 17928-17937, or SEQ ID NO: 17944-17945, or SEQ ID NO: 17947-17964, or SEQ ID NO: 17993-18049, or SEQ ID NO: 18055-18065, and said percentage identity may be at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100%; or the recombinant nucleic acid sequence the encodes the polypeptide specifically hybridizes to the complement of a DNA sequence set forth in the Sequence Listing, such as SEQ ID NO 2n-1, where n=1 to 1186, or SEQ ID NO: 3792-5086 or 5102-5106, SEQ ID NO: 17828, 17832, 17836, 17840, 17844, 17847, 17850, 17853, 17856, 17859, 17862, 17867, 17870, 17873, 17876, 17883, 17899-17904, 17906-17910, 17923-17927, 17938-17943, 17946, 17965-17992, or 18050-18054, under stringent conditions comprising two wash steps at least as stringent as 6×SSC at 65° C. of 10-30 minutes for each wash step; or 0.2× to 2×SSC and 0.1% SDS at 50° C. to 65° C. for 10-30 minutes per wash step.

The recombinant polypeptides described herein can share an amino acid identity to any of the listed full-length sequence and also share an amino acid sequence identity to one or more conserved domains of the full-length sequence.

When the polypeptide is overexpressed in a plant, the polypeptide is capable of regulating transcription in the plant and confers to the plant at least one regulatory activity. This results in the plant having an altered trait, as compared to a control plant (e.g., a wild-type plant of the same species, or a non-transformed plant, or a plant transformed with an "empty vector" that does not comprise a recombinant nucleic acid sequence encoding a polypeptide of the invention). The altered trait that is conferred to the plant as a result of expressing the polypeptide may be one (or more) of the following, or any trait listed in Table 20: greater resistance to *Erysiphe*; greater resistance to *Sclerotinia*; greater resistance to *Botrytis*; greater resistance to *Fusarium*; greater susceptibility to *Sclerotinia*; greater susceptibility to *Botrytis*; greater tolerance to *Pseudomonas*; greater tolerance to dehydration; greater tolerance to drought; greater tolerance to salt; greater tolerance to water deficit conditions; greater tolerance to hyperosmotic stress; greater tolerance to low nitrogen conditions; greater tolerance to low phosphate conditions; greater tolerance to low potassium conditions; greater tolerance to cold; greater tolerance to heat; greater tolerance to sucrose; greater tolerance to mannitol; greater tolerance to glucose; greater tolerance to polyethylene glycol; greater tolerance to glyphosate; greater tolerance to oxidative stress; greater tolerance to freezing; better recovery from drought; more sensitive to cold; more sensitive to low nitrogen conditions; more sensitive to low phosphate conditions; more sensitive to sucrose; more sensitive to mannitol; more sensitive to glucose; more sensitive to drought; more sensitive to heat; more sensitive to hyperosmotic stress; more sensitive to oxidative stress; more sensitive to ethylene; ethylene insensitive when germinated in the dark on 1-aminocyclopropane 1-carboxylic acid; hypersensitive to 1-aminocyclopropane 1-carboxylic acid; decreased sensitivity to ABA; altered C/N sensing; higher starch level; higher proline level; decreased proline level; darker green color; lighter green color; gray color; greater photosynthetic capacity; reduced photosynthesis; increased chlorophyll level; more chlorophyll a and b; higher total nitrogen concentration level; decreased chlorophyll level; more pigment; greater anthocyanin level; greater leaf anthocyanin level; more anthocyanin in leaf petioles; decreased anthocyanin level; greater carotenoid level; greater ABA level; greater seed oil content; greater seed protein content; greater seed oil content; greater seed protein content; greater total seed oil and protein content; increased seed alpha-tocopherol level; higher seed lutein content; decreased seed lutein content; increased seed xanthophyll 1 level; increase in seed 16:1 fatty acids level; increased seed 18:1 fatty acids level; increased seed 18:2 fatty acids and decrease in seed 18:3 fatty acids level; increased seed 18:1 and 18:2 fatty acids level; increased seed 16:0, 18:0, 20:0, and 18:3 fatty acids, decreased seed 18:2, 20:1, 22:1 fatty acids level; decreased seed 20:1 and 22:1 fatty acids level; decrease in seed 18:1 seed fatty acids level; decrease in 18:2 fatty acids level; altered seed glucosinolate profile; up-regulation of genes involved in secondary metabolism; altered leaf prenyl lipids; reduced chlorophyll a and b levels; increased leaf insoluble sugars level; decreased leaf insoluble sugars level; increased galactose level in leaf cell wall; increased leaf xanthophyll; increased leaf rhamnose level; increased leaf mannose; increased leaf fucose level; increased leaf glucosinolate M39480 level; increased leaf glucosinolate M39481 level; decreased leaf rhamnose level; decreased leaf lutein level; more leaf fatty acids; altered leaf fatty acid composition; reduced leaf 16:3 fatty acids; increased in percentage of 16:0 leaf fatty acids; leaf 16:0 level decreased and leaf 16:3 level increased; greater seedling vigor; faster seedling growth; slower growth; late flowering; late developing; early flowering; early developing; glossy leaves; waxy leaves; more lignin; reduced lignin; reduced internode elongation; short internodes; long internodes; defect in cell elongation; greater internode distance; altered cotyledon shape; elongated cotyledons; cotyledon fusion; thicker stem; altered distribution of stem vascular bundles; reduced branching; curled leaves; serrated leaves; curled leaves; ovoid leaves; flat leaves; heart-shaped leaves; longer leaves; narrower leaves; wrinkled leaves; lobed leaves; light green leaves; larger, flatter leaves at late stage of development; greater number of leaves; altered flowers; abnormal flowers; sporadic defects in flower development; reduced fertility; flowers that do not open; floral organs with bract-like features; bolts that terminate without an inflorescence; aerial rosettes; reduced floral organ abscission; delayed floral organ abscission; reductions in flower organ size; larger floral organs; long flower organs; long sepal and petal; poor anther dehiscence; little pollen production; no pollen production; poor filament elongation; homeotic transformations; bushy inflorescences; altered inflorescences; flowers bunched together; short inflorescence stems; stunted inflorescence growth; numerous secondary inflorescence meristems; altered inflorescence determinacy; homeotic transformation; terminal flower formation; increased carpel size; wider carpels; ectopic carpel tissue; filamentous carpelloid growths on flower pedicels; loss of flower determinacy; floral organ abscission delayed; altered seed color; pale seeds; smaller seeds; rounded seeds; wrinkled seeds; wrinkled sickle-shaped siliques; reduced flower petal number; reduced flower sepal number; reduced flower stamen number; smaller petals and sepals; delayed senescence; premature senescence; premature leaf senescence; premature flower senescence; trilocular silique; more root mass; reduced secondary root growth; greater leaf and hypocotyl necrosis; short pedicels; short inflorescence stems; altered leaf cell expansion; reduced cell differentiation in meristem; increased necrosis; lethal when constitutively overexpressed; embryo lethal; altered light response; long cotyledons; open cotyledons; oval cotyledons; long hypocotyls; long petioles; leaves in a more upright orientation; constitutive photomorphogenesis; more root growth in the dark; greater biomass; larger plants; large darker green rosettes at late stage of development; larger seeds; larger leaves; smaller plants; more root hairs; fewer trichomes; greater trichome size and density; greater trichome density; ectopic trichome formation; ectopic formation of trichomes on abaxial leaf surfaces; greater trichome density on sepals and ectopic trichomes on carpels.

For the methods encompassed by the present invention, an expression vector of the invention may be introduced into a target plant, thus transforming the target plant and producing a transgenic plant having the altered trait as compared to the control plant.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

The Sequence Listing provides exemplary polynucleotide and polypeptide sequences of the invention. The traits associated with the use of the sequences are included in the Examples. The sequence listing was created on Sep. 7, 2011 and is 25,845,198 bytes (24.6 MB) as measured in windows MS-DOS. The entire content of the sequence listing is hereby incorporated by reference.

FIGS. 1-29 show the phylogenetic relationships and sequence comparisons among some of the listed sequences or conserved domains. SEQ ID NOs are shown in parentheses. Identical amino acid residues are indicated by asterisks. Conservative substitutions are indicated by colons. Semiconservative or similar substitutions are indicated by periods.

FIG. 1 shows a conservative estimate of phylogenetic relationships among the orders of flowering plants (modified from Soltis et al. (1997)). Those plants with a single cotyledon (monocots) are a monophyletic clade nested within at least two major lineages of dicots; the eudicots are further divided into rosids and asterids. *Arabidopsis* is a rosid eudicot classified within the order Brassicales; rice is a member of the monocot order Poales. FIG. 1 was adapted from Daly et al. (2001).

For the phylogenetic trees presented in the present Figures, the trees were generally based on a ClustalW alignment of full-length proteins using Mega 2 software (protein sequences are provided in the Sequence Listing). The parameters used include a Gap Opening Penalty:10.00; a Gap Extension Penalty:0.20; Delay divergent sequences: 30%; DNA Transitions Weight:0.50; Protein weight matrix: Gonnet series; DNA weight matrix:IUB; Use negative matrix:OFF. A FastA formatted alignment was then used to generate each phylogenetic tree in MEGA2 using the neighbor joining algorithm and a p-distance model. A test of phylogeny was done via bootstrap with 1000 replications and Random Seed set to default. Cut off values of the bootstrap tree were set to 50%.

For alignments presented in the Figures.

FIG. 2 shows a phylogenetic tree of CCAAT family proteins. There are three main sub-classes within the family: the HAP2 (also known as the NF-YA subclass), HAP3 (NF-YB subclass) and HAP5 (NF-YC subclass) related proteins. Three additional proteins were identified that did not clearly cluster with any of the three main groups and we have designated these as "HAP-like" proteins.

FIGS. 3A-3B are an alignment of various G481 clade member conserved B domains.

FIGS. 5A-5C show an alignment of a major portion of various G1073 clade member second conserved domains.

FIGS. 7A-7B show an alignment of various G28 clade member conserved AP2 domains.

Figure 8:
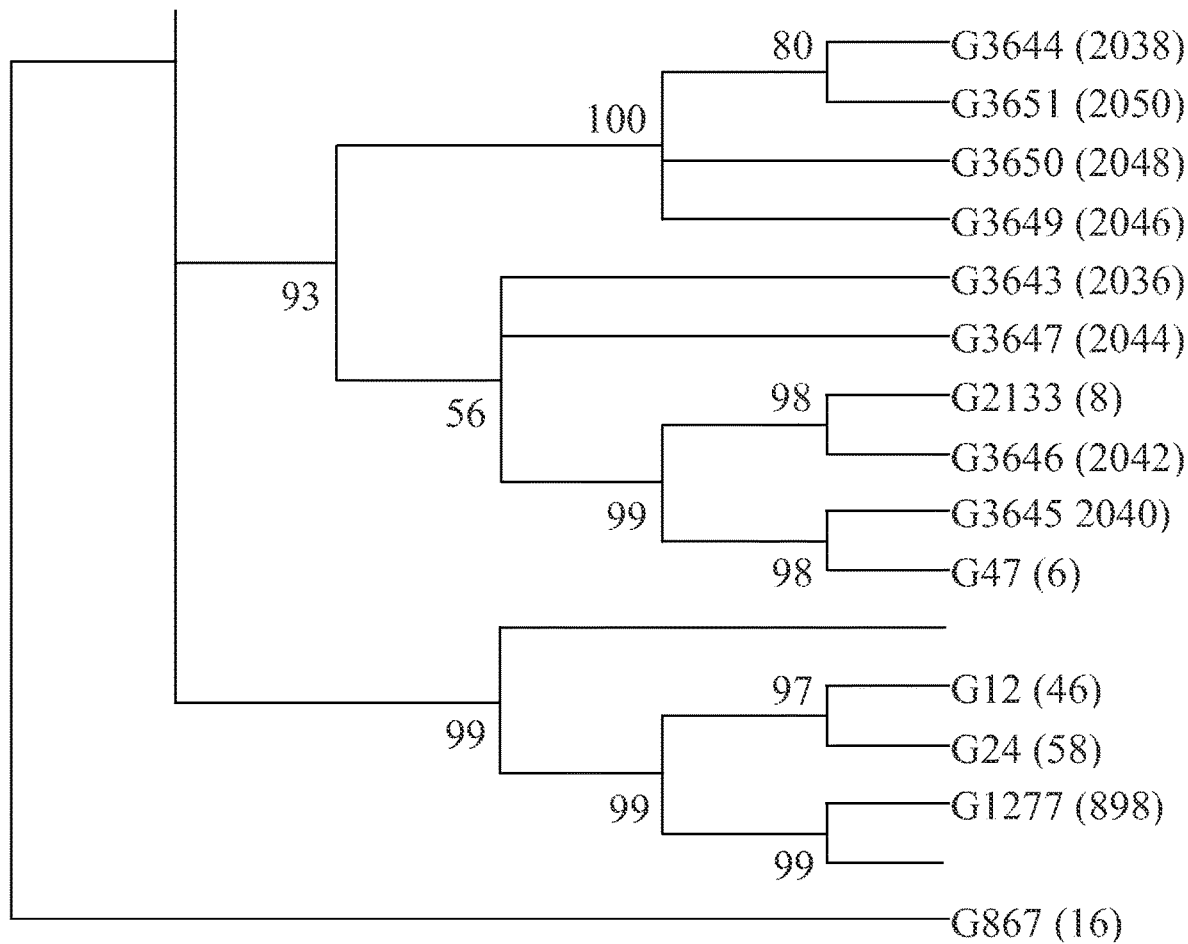

FIG. 8 presents a portion of a phylogenetic tree showing the ancestral relationships of the G47 clade and other related AP2 sequences.

FIG. 9 provides an alignment of various G47 clade member conserved AP2 domains.

Figure 10:
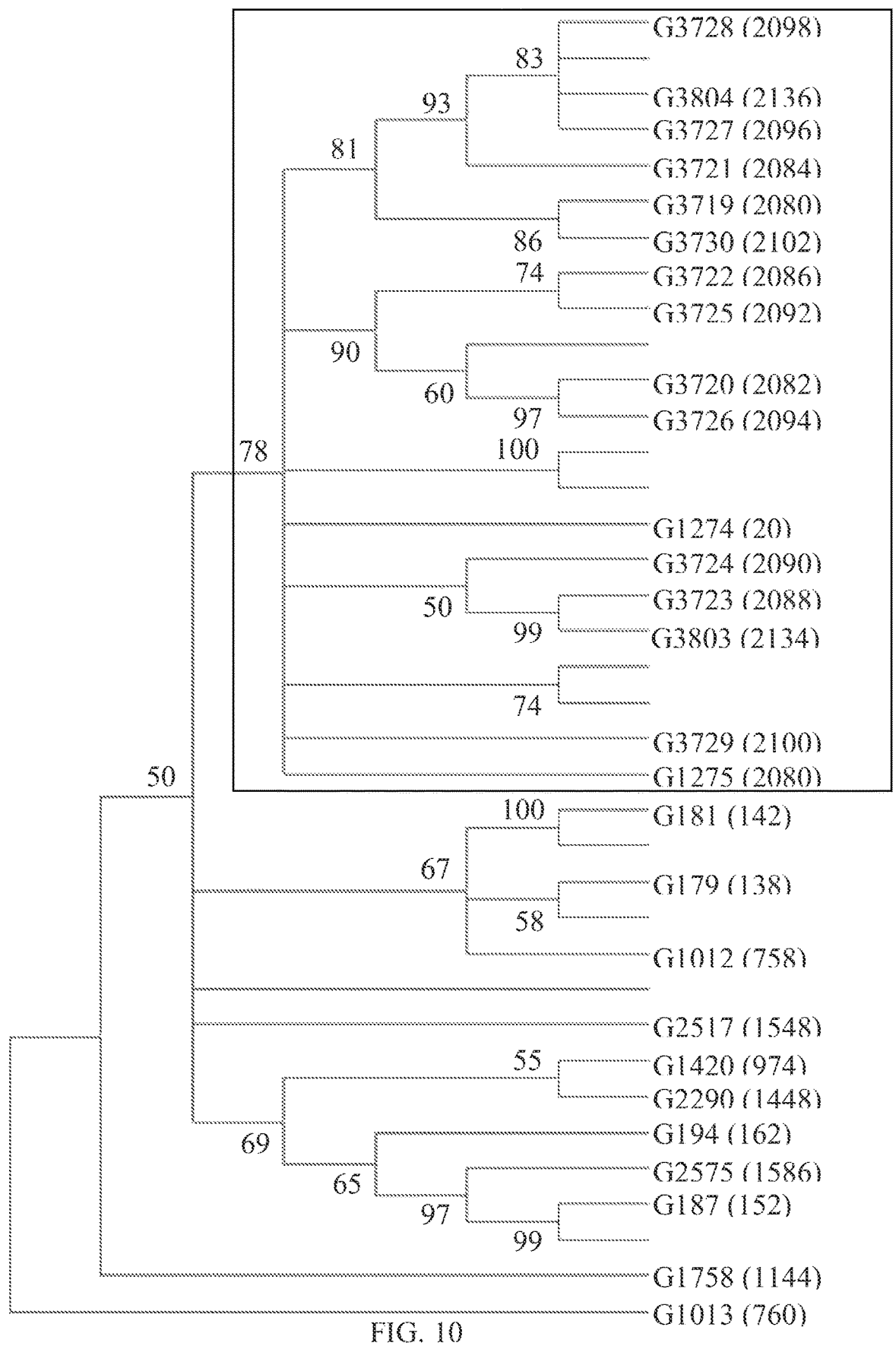

FIG. 10 shows a phylogenetic tree of G1274 clade member sequences. Clade member WRKY sequences are found within the large box.

FIGS. 11A-11B show an alignment of various G1274 clade member conserved WRKY domains.

Figure 12:
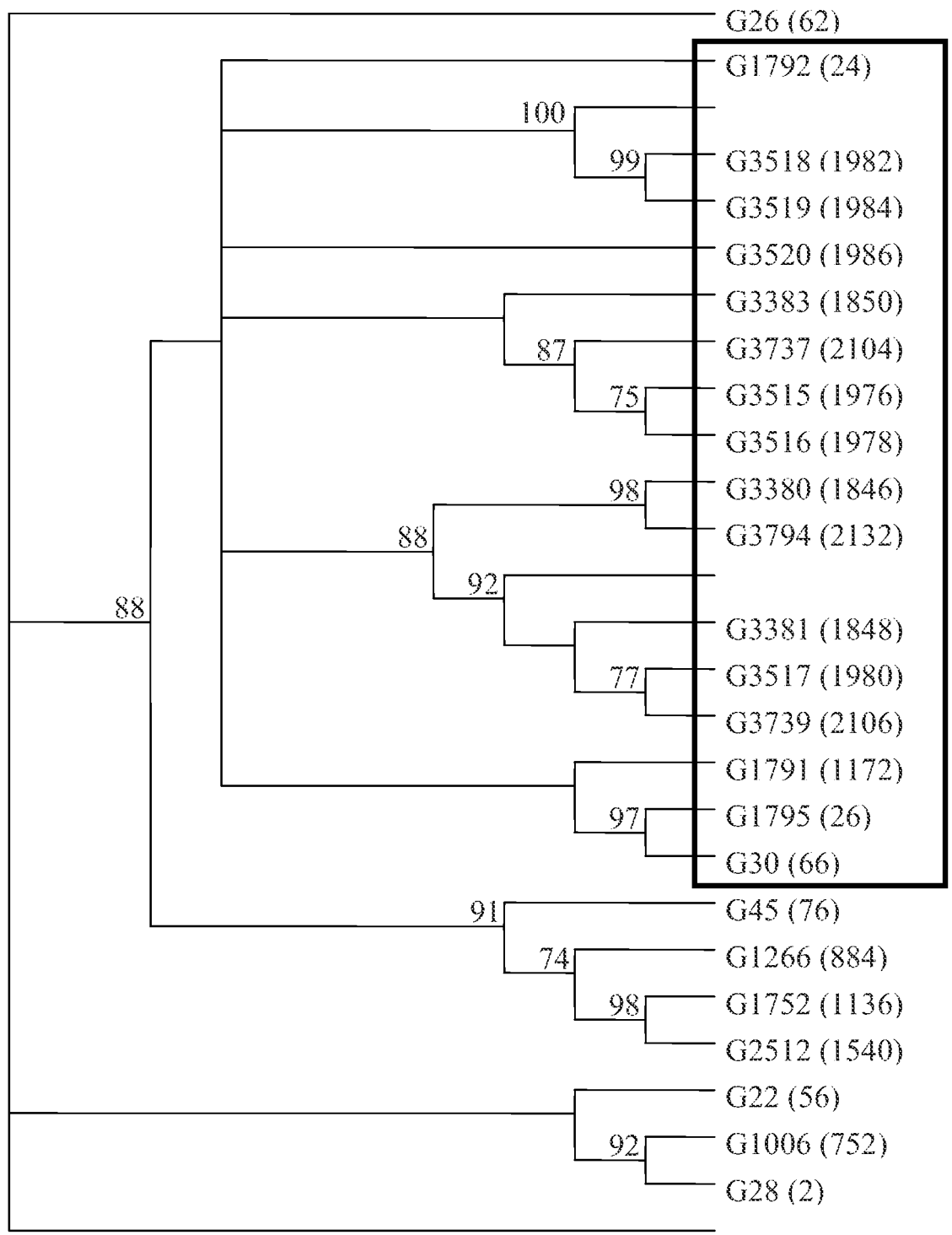

FIG. 12 illustrates phylogenetic relationships in the G1792 clade. Clade member AP2 sequences are found within the large box.

FIGS. 13A-13B show an alignment of various G1792 clade member conserved AP2 domains.

FIG. 14 shows an alignment of various G1792 clade member conserved EDLL domains, said domains being characteristic of these related sequences.

Figure 15:
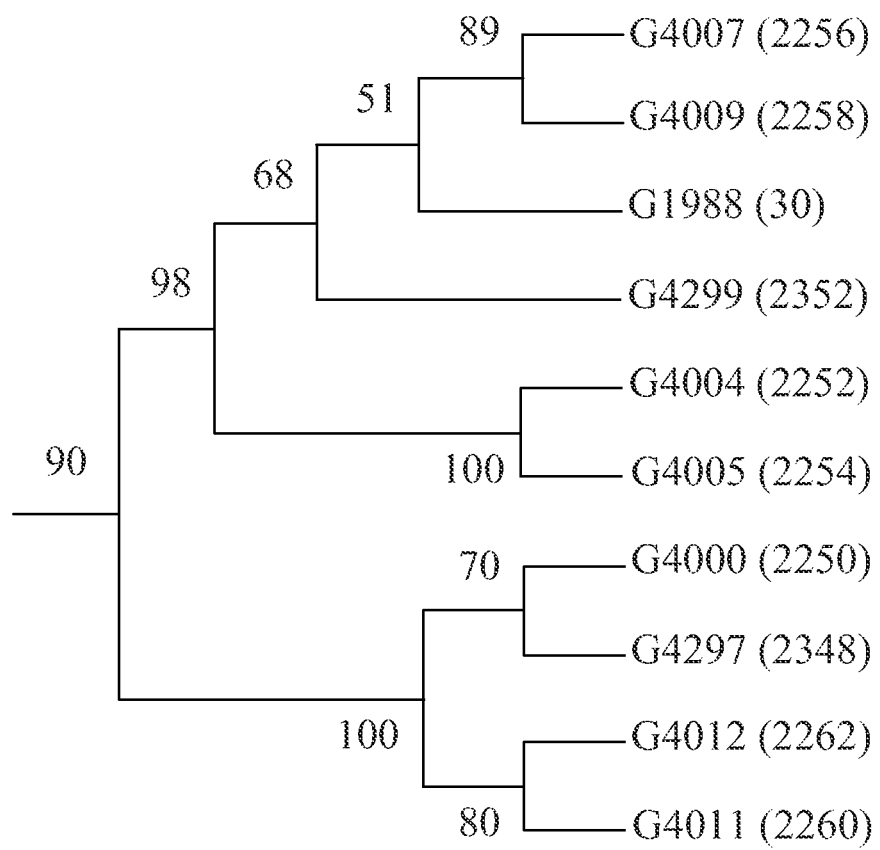

FIG. 15 is a phylogenetic tree of G1988 clade member Z-CO-like (CONSTANS-like) sequences.

FIG. 16 provides an alignment of various G1988 clade member conserved B-box domains.

Figure 17:
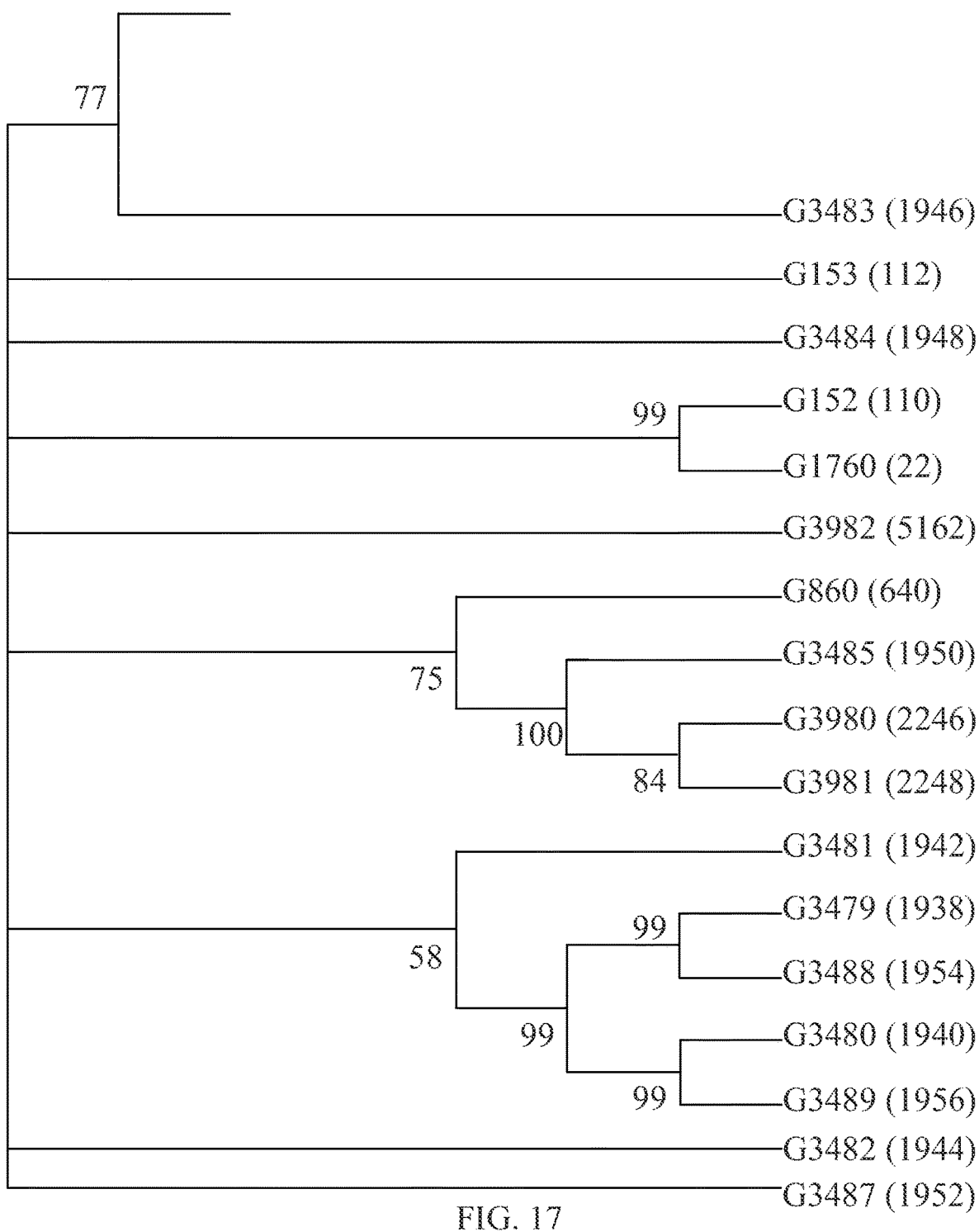

FIG. 17 is a phylogenetic tree of G1760 clade member MADS-box sequences.

FIGS. 18A-18B present an alignment of various G1760 clade member conserved MADS domains.

Figure 19:

FIG. 19 is a phylogenetic tree of the G913 clade member AP2 sequences.

FIG. 20 shows an alignment of various G913 clade member conserved AP2 domains.

FIG. 21 shows an alignment of various G1543 clade member HB domains.

FIG. 22 shows an alignment of various G1543 clade member HALZ domains.

FIG. 23 shows an alignment of various G1266 clade member AP2 domains.

FIG. 24 shows an alignment of the conserved HLH/MYC domains of various G2932 clade members.

FIG. 25 shows an alignment of the conserved MADS domains of various G154 clade members.

FIG. 26 shows an alignment of the conserved CCAAT-binding domains of G1782.

FIG. 27 shows an alignment of the MADS domain of various G142 clade members

FIG. 28 shows an alignment of the second conserved domain of various G2153 clade members.

FIG. 29 shows an alignment of the conserved MYB-(R1) R2R3 domain of G671 clade members

DETAILED DESCRIPTION OF THE INVENTION

The present invention relates to polynucleotides and polypeptides for modifying phenotypes of plants, particularly those associated with greater biomass, increased disease resistance, and/or abiotic stress tolerance. Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Nucleic acid molecule" refers to an oligonucleotide, polynucleotide or any fragment thereof. It may be DNA or RNA of genomic or synthetic origin, double-stranded or single-stranded, and combined with carbohydrate, lipids, protein, or other materials to perform a particular activity such as transformation or form a useful composition such as a peptide nucleic acid (PNA).

"Polynucleotide" is a nucleic acid molecule comprising a plurality of polymerized nucleotides, e.g., at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, e.g., genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976)). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

A "recombinant polynucleotide" is a polynucleotide that is not in its native state, e.g., the polynucleotide comprises a nucleotide sequence not found in nature, or the polynucleotide is in a context other than that in which it is naturally found, e.g., separated from nucleotide sequences with which it typically is in proximity in nature, or adjacent (or contiguous with) nucleotide sequences with which it typically is not in proximity. For example, the sequence at issue can be cloned into a vector, or otherwise recombined with one or more additional nucleic acid.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, e.g., cell lysis, extraction, centrifugation, precipitation, or the like.

A "polypeptide" is an amino acid sequence comprising a plurality of consecutive polymerized amino acid residues e.g., at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a localization domain; (ii) an activation domain; (iii) a repression domain; (iv) an oligomerization domain; (v) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, e.g., more than about 5% enriched, more than about 10% enriched, or more than about 20%, or more than about 50%, or more, enriched, i.e., alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, e.g., by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence similarity found in a comparison of two or more polynucleotide sequences or two or more polypeptide sequences. Closely-related polynucleotides of the invention encoded presently disclosed transcription factors that will have at least about 38% sequence identity including conservative substitutions, or at least about 55% sequence identity, or at least about 56%, or at least about 57%, or at least about 58%, or at least about 59%, or at least about 60%, or at least about 61%, or at least about 62% sequence identity, or at least about 63%, or at least about 64%, or at least about 65%, or at least about 66%, or at least about 67%, or at least about 68%, or at least about 69%, or at least about 70%, or at least about 71%, or at least about 72%, or at least about 73%, or at least about 74%, or at least about 75%, or at least about 76%, or at least about 77%, or at least about 78%, or at least about 79%, or at least about 80%, or at least about 81%, or at least about 82%, or at least about 83%, or at least about 84%, or at least about 85%, or at least about 86%, or at least about 87%, or at least about 88%, or at least about 89%, or at least about 90%, or at least about 91%, or at least about 92%, or at least about 93%, or at least about 94%, or at least about 95%, or at least about 96%, or at least about 97%, or at least about 98%, or at least about 99%, or 100% amino acid residue sequence identity, to a polypeptide of the invention listed in the Sequence Listing or in the present Tables 1-18.

"Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (i.e., nucleotide bases or amino acid residues at corresponding positions) may be visually and readily identified. The fraction or percentage of components in common is related to the homology or identity between the sequences. Alignments such as those of FIGS. 11A-11B may be used to identify conserved domains and relatedness within these domains. An alignment may suitably be determined by means of computer programs known in the art, such as MACVECTOR software (1999) (Accelrys, Inc., San Diego, Calif.).

Two or more sequences may be "optimally aligned" with a similarity scoring method using a defined amino acid substitution matrix such as the BLOSUM62 scoring matrix. The preferred method uses a gap existence penalty and gap extension penalty that arrives at the highest possible score for a given pair of sequences. See, for example, Dayhoff et al. (1978) and Henikoff and Henikoff (1992). The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. Optimal alignment may be accomplished manually or with a computer-based alignment algorithm, such as gapped BLAST 2.0 (Altschul et al, (1997); or at www.ncbi.nlm.nih.gov. See U.S. Patent Application US20070004912.

A "conserved domain" or "conserved region" as used herein refers to a region in heterologous polynucleotide or polypeptide sequences where there is a relatively high degree of sequence identity between the distinct sequences. For example, an "AT-hook" domain", such as is found in a polypeptide member of AT-hook transcription factor family, is an example of a conserved domain. An "AP2" domain", such as is found in a polypeptide member of AP2 transcription factor family, is another example of a conserved domain With respect to polynucleotides encoding presently disclosed transcription factors, a conserved domain is preferably at least nine base pairs (bp) in length. A conserved domain with respect to presently disclosed polypeptides refers to a domain within a transcription factor family that exhibits a higher degree of sequence homology, such as at least about 38% amino acid sequence identity including conservative substitutions, or at least about 42% sequence identity, or at least about 45% sequence identity, or at least about 48% sequence identity, or at least about 50% sequence identity, or at least about 51% sequence identity, or at least about 52% sequence identity, or at least about 53% sequence identity, or at least about 54% sequence identity, or at least about 55% sequence identity, or at least about 56% sequence identity, or at least about 57% sequence identity, or at least about 58% sequence identity, or at least about 59% sequence identity, or at least about 60% sequence identity, or at least about 61% sequence identity, or at least about 62% sequence identity, or at least about 63% sequence identity, or at least about 64% sequence identity, or at least about 65% sequence identity, or at least about 66% sequence identity, or at least about 67% sequence identity, or at least about 68% sequence identity, or at least about 69% sequence identity, or at least about 70% sequence identity, or at least about 71% sequence identity, or at least about 72% sequence identity, or at least about 73% sequence identity, or at least about 74% sequence identity, or at least about 75% sequence identity, or at least about 76% sequence identity, or at least about 77% sequence identity, or at least about 78% sequence identity, or at least about 79% sequence identity, or at least about 80% sequence identity, or at least about 81% sequence identity, or at least about 82% sequence identity, or at least about 83% sequence identity, or at least about 84% sequence identity, or at least about 85% sequence identity, or at least about 86% sequence identity, or at least about 87% sequence identity, or at least about 88% sequence identity, or at least about 89% sequence identity, or at least about 90% sequence identity, or at least about 91% sequence identity, or at least about 92% sequence identity, or at least about 93% sequence identity, or at least about 94% sequence identity, or at least about 95% sequence identity, or at least about 96% sequence identity, or at least about 97% sequence identity, or at least about 98% sequence identity, or at least about 99% sequence identity, or 100% amino acid residue sequence identity, to a conserved domain of a polypeptide of the invention, such as those listed in the present tables or Sequence Listing (e.g., SEQ ID NOs: 2373-3791 or SEQ ID NO: 5107-5111, or SEQ ID NO: 5114, or SEQ ID NO: 5117, or SEQ ID NO: 5120, or SEQ ID NO: 5123, or SEQ ID NO: 5126-5143, or SEQ ID NO: 5146-5149, or SEQ ID NO: 5152-5153, or SEQ ID NO: 5156-5157, or SEQ ID NO: 5160, or SEQ ID NO: 5163, or SEQ ID NO: 17824-17827, SEQ ID NO: 17830, SEQ ID NO: 17831, SEQ ID NO: 17834, SEQ ID NO: 17835, SEQ ID NO: 17838, SEQ ID NO: 17839, SEQ ID NO: 17842, SEQ ID NO: 17843, SEQ ID NO: 17846, SEQ ID NO: 17849, SEQ ID NO: 17852, SEQ ID NO: 17855, SEQ ID NO: 17858, SEQ ID NO: 17861, SEQ ID NO: 17864, SEQ ID NO: 17865, SEQ ID NO: 17866, SEQ ID NO: 17869, SEQ ID NO: 17872, SEQ ID NO: 17875, SEQ ID NO: 17878, SEQ ID NO: 17879, SEQ ID NO: 17882, SEQ ID NO: 17885, SEQ ID NO: 17886, SEQ ID NO: 17911-17922, SEQ ID NO: 17933-17937, SEQ ID NO: 17956-17964, SEQ ID NO: 17993-18020, or SEQ ID NO: 18059-18065). Sequences that possess or encode for conserved domains that meet these criteria of percentage identity, and that have comparable biological activity to the present transcription factor sequences, thus being members of a clade of transcription factor polypeptides, are encompassed by the invention. A fragment or domain can be referred to as outside a conserved domain, outside a consensus sequence, or outside a consensus DNA-binding site that is known to exist or that exists for a particular transcription factor class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al. (2000a, 2000b)). Thus, by using alignment methods well known in the art, the conserved domains of the plant transcription factors, for example, for the AT-hook proteins (Reeves and Beckerbauer (2001); and Reeves (2001)), may be determined.

The conserved domains for many of the transcription factor sequences of the invention are listed in Tables 1-18. Also, the polypeptides of Tables 1-18 have conserved domains specifically indicated by amino acid coordinate start and stop sites. A comparison of the regions of these polypeptides allows one of skill in the art (see, for example, Reeves and Nissen (1995)) to identify domains or conserved domains for any of the polypeptides listed or referred to in this disclosure.

"Complementary" refers to the natural hydrogen bonding by base pairing between purines and pyrimidines. For example, the sequence A-C-G-T (5'->3') forms hydrogen bonds with its complements A-C-G-T (5'->3') or A-C-G-U (5'->3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "highly stringent" or "highly stringent condition" refer to conditions that permit hybridization of DNA strands whose sequences are highly complementary, wherein these same conditions exclude hybridization of significantly mismatched DNAs. Polynucleotide sequences capable of hybridizing under stringent conditions with the polynucleotides of the present invention may be, for example, variants of the disclosed polynucleotide sequences, including allelic or splice variants, or sequences that encode orthologs or paralogs of presently disclosed polypeptides. Nucleic acid hybridization methods are disclosed in detail by Kashima et al. (1985), Sambrook et al. (1989), and by Haymes et al. (1985), which references are incorporated herein by reference.

In general, stringency is determined by the temperature, ionic strength, and concentration of denaturing agents (e.g., formamide) used in a hybridization and washing procedure (for a more detailed description of establishing and determining stringency, see the section "Identifying Polynucleotides or Nucleic Acids by Hybridization", below). The degree to which two nucleic acids hybridize under various conditions of stringency is correlated with the extent of their similarity. Thus, similar nucleic acid sequences from a variety of sources, such as within a plant's genome (as in the case of paralogs) or from another plant (as in the case of orthologs) that may perform similar functions can be isolated on the basis of their ability to hybridize with known transcription factor sequences. Numerous variations are possible in the conditions and means by which nucleic acid hybridization can be performed to isolate transcription factor sequences having similarity to transcription factor sequences known in the art and are not limited to those explicitly disclosed herein. Such an approach may be used to isolate polynucleotide sequences having various degrees of similarity with disclosed transcription factor sequences, such as, for example, encoded transcription factors having 38% or greater identity with the conserved domain of disclosed transcription factors.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (i.e., the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a transcription factor nucleic acid listed in the Sequence Listing, that is, one having a sequence that differs from the one of the polynucleotide sequences in the Sequence Listing, or a complementary sequence, that encodes a functionally equivalent polypeptide (i.e., a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequence. "Allelic variant" and "polypeptide allelic variant" may also be used with respect to polypeptides, and in this case the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in a functionally equivalent transcription factor. Thus, it will be readily appreciated by those of skill in the art, that any of a variety of polynucleotide sequences is capable of encoding the transcription factors and transcription factor homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the transcription factor is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, e.g., replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the transcription factor polynucleotides listed in the Sequence Listing. Exemplary fragments also include fragments that comprise a region that encodes an conserved domain of a transcription factor. Exemplary fragments also include fragments that comprise a conserved domain of a transcription factor. Exemplary fragments include fragments that comprise an conserved domain of a transcription factor, for example, amino acid residues 30-126 of G3866 (SEQ ID NO: 3677).

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode transcription factors and transcription factor derivatives, or fragments thereof, entirely by synthetic chemistry. After production, the synthetic sequence may be inserted into any of the many available expression vectors and cell systems using reagents well known in the art. Moreover, synthetic chemistry may be used to introduce mutations into a sequence encoding transcription factors or any fragment thereof.

"Derivative" refers to the chemical modification of a nucleic acid molecule or amino acid sequence. Chemical modifications can include replacement of hydrogen by an alkyl, acyl, or amino group or glycosylation, pegylation, or any similar process that retains or enhances biological activity or lifespan of the molecule or sequence.

The term "plant" includes whole plants, shoot vegetative organs/structures (for example, leaves, stems and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like) and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, and multicellular algae.

A "control plant" as used in the present invention refers to a plant cell, seed, plant component, plant tissue, plant organ or whole plant used to compare against transgenic or genetically modified plant for the purpose of identifying an enhanced phenotype in the transgenic or genetically modified plant. A control plant may in some cases be a transgenic plant line that comprises an empty vector or marker gene, but does not contain the recombinant polynucleotide of the present invention that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line used to generate a transgenic plant herein.

A "transgenic plant" refers to a plant that contains genetic material not found in a wild-type plant of the same species, variety or cultivar. The genetic material may include a transgene, an insertional mutagenesis event (such as by transposon or T-DNA insertional mutagenesis), an activation tagging sequence, a mutated sequence, a homologous recombination event or a sequence modified by chimeraplasty. Typically, the foreign genetic material has been introduced into the plant by human manipulation, but any method can be used as one of skill in the art recognizes.

A transgenic plant may contain an expression vector or cassette. The expression cassette typically comprises a polypeptide-encoding sequence operably linked (i.e., under regulatory control of) to appropriate inducible or constitutive regulatory sequences that allow for the controlled expression of polypeptide. The expression cassette can be introduced into a plant by transformation or by breeding after transformation of a parent plant. A plant refers to a whole plant as well as to a plant part, such as seed, fruit, leaf, or root, plant tissue, plant cells or any other plant material, e.g., a plant explant, as well as to progeny thereof, and to in vitro systems that mimic biochemical or cellular components or processes in a cell.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a transcription factor expression is altered, e.g., in that it has been knocked out, overexpressed, or ectopically expressed.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, e.g. by measuring tolerance to water deprivation or particular salt or sugar concentrations, or by the observation of the expression level of a gene or genes, e.g., by employing Northern analysis, RT-PCR, microarray gene expression assays, or reporter gene expression systems, or by agricultural observations such as hyperosmotic stress tolerance or yield. Any technique can be used to measure the amount of, comparative level of, or difference in any selected chemical compound or macromolecule in the transgenic plants, however.

"Trait modification" refers to a detectable difference in a characteristic in a plant ectopically expressing a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

The term "transcript profile" refers to the expression levels of a set of genes in a cell in a particular state, particularly by comparison with the expression levels of that same set of genes in a cell of the same type in a reference state. For example, the transcript profile of a particular transcription factor in a suspension cell is the expression levels of a set of genes in a cell knocking out or overexpressing that transcription factor compared with the expression levels of that same set of genes in a suspension cell that has normal levels of that transcription factor. The transcript profile can be presented as a list of those genes whose expression level is significantly different between the two treatments, and the difference ratios. Differences and similarities between expression levels may also be evaluated and calculated using statistical and clustering methods.

With regard to transcription factor gene knockouts as used herein, the term "knockout" refers to a plant or plant cell having a disruption in at least one transcription factor gene in the plant or cell, where the disruption results in a reduced expression or activity of the transcription factor encoded by that gene compared to a control cell. The knockout can be the result of, for example, genomic disruptions, including transposons, tilling, and homologous recombination, antisense constructs, sense constructs, RNA silencing constructs, or RNA interference. A T-DNA insertion within a transcription factor gene is an example of a genotypic alteration that may abolish expression of that transcription factor gene.

"Ectopic expression or altered expression" in reference to a polynucleotide indicates that the pattern of expression in, e.g., a transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible. In reference to a polypeptide, the term "ectopic expression or altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression of that gene in a wild-type plant, cell or tissue, at any developmental or temporal stage. Overexpression can occur when, for example, the genes encoding one or more transcription factors are under the control of a regulatory control element such as a strong or constitutive promoter (e.g., the cauliflower mosaic virus 35S transcription initiation region). Overexpression may also be achieved by placing a gene of interest under the control of an inducible or tissue specific promoter, or may be achieved through integration of transposons or engineered T-DNA molecules into regulatory regions of a target gene. Thus, overexpression may occur throughout a plant, in specific tissues of the plant, or in the presence or absence of particular environmental signals, depending on the promoter or overexpression approach used.

Overexpression may take place in plant cells normally lacking expression of polypeptides functionally equivalent or identical to the present transcription factors. Overexpression may also occur in plant cells where endogenous expression of the present transcription factors or functionally equivalent molecules normally occurs, but such normal expression is at a lower level. Overexpression thus results in a greater than normal production, or "overproduction" of the transcription factor in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors of the present invention possess an conserved domain. The transcription factors of the invention also comprise an amino acid subsequence that forms a transcription activation domain that regulates expression of one or more abiotic stress tolerance genes in a plant when the transcription factor binds to the regulating region.

Transcription Factors Modify Expression of Endogenous Genes

A transcription factor may include, but is not limited to, any polypeptide that can activate or repress transcription of a single gene or a number of genes. As one of ordinary skill in the art recognizes, transcription factors can be identified by the presence of a region or domain of structural similarity or identity to a specific consensus sequence or the presence of a specific consensus DNA-binding site or DNA-binding site motif (see, for example, Riechmann et al. (2000a)). The plant transcription factors of the present invention belong to particular transcription factor families indicated in the Tables found herein (see, for example, Riechmann (2000a, 2000b), Reeves and Beckerbauer (2001); and Reeves (2001)).

Generally, the transcription factors encoded by the present sequences are involved in cell differentiation and proliferation and the regulation of growth. Accordingly, one skilled in the art would recognize that by expressing the present sequences in a plant, one may change the expression of autologous genes or induce the expression of introduced genes. By affecting the expression of similar autologous sequences in a plant that have the biological activity of the present sequences, or by introducing the present sequences into a plant, one may alter a plant's phenotype to one with improved traits related to osmotic stresses. The sequences of the invention may also be used to transform a plant and introduce desirable traits not found in the wild-type cultivar or strain. Plants may then be selected for those that produce the most desirable degree of over- or under-expression of target genes of interest and coincident trait improvement.

The sequences of the present invention may be from any species, particularly plant species, in a naturally occurring form or from any source whether natural, synthetic, semisynthetic or recombinant. The sequences of the invention may also include fragments of the present amino acid sequences. Where "amino acid sequence" is recited to refer to an amino acid sequence of a naturally occurring protein molecule, "amino acid sequence" and like terms are not meant to limit the amino acid sequence to the complete native amino acid sequence associated with the recited protein molecule.

In addition to methods for modifying a plant phenotype by employing one or more polynucleotides and polypeptides of the invention described herein, the polynucleotides and polypeptides of the invention have a variety of additional uses. These uses include their use in the recombinant production (i.e., expression) of proteins; as regulators of plant gene expression, as diagnostic probes for the presence of complementary or partially complementary nucleic acids (including for detection of natural coding nucleic acids); as substrates for further reactions, e.g., mutation reactions, PCR reactions, or the like; as substrates for cloning e.g., including digestion or ligation reactions; and for identifying exogenous or endogenous modulators of the transcription factors. The polynucleotide can be, e.g., genomic DNA or RNA, a transcript (such as an mRNA), a cDNA, a PCR product, a cloned DNA, a synthetic DNA or RNA, or the like. The polynucleotide can comprise a sequence in either sense or antisense orientations.

Expression of genes that encode transcription factors that modify expression of endogenous genes, polynucleotides, and proteins are well known in the art. In addition, transgenic plants comprising isolated polynucleotides encoding transcription factors may also modify expression of endogenous genes, polynucleotides, and proteins. Examples include Peng et al. (1997) and Peng et al. (1999). In addition, many others have demonstrated that an *Arabidopsis* transcription factor expressed in an exogenous plant species elicits the same or very similar phenotypic response. See, for example, Fu et al. (2001); Nandi et al. (2000); Coupland (1995); and Weigel and Nilsson (1995)).

In another example, Mandel et al. (1992), and Suzuki et al. (2001), teach that a transcription factor expressed in another plant species elicits the same or very similar phenotypic response of the endogenous sequence, as often predicted in earlier studies of *Arabidopsis* transcription factors in *Arabidopsis* (see Mandel et al. (1992); Suzuki et al. (2001)). Other examples include Müller et al. (2001); Kim et al. (2001); Kyozuka and Shimamoto (2002); Boss and Thomas (2002); He et al. (2000); and Robson et al. (2001).

In yet another example, Gilmour et al. (1998) teach an *Arabidopsis* AP2 transcription factor, CBF1, which, when overexpressed in transgenic plants, increases plant freezing tolerance. Jaglo et al. (2001) further identified sequences in *Brassica napus* which encode CBF-like genes and that transcripts for these genes accumulated rapidly in response to low temperature. Transcripts encoding CBF-like proteins were also found to accumulate rapidly in response to low temperature in wheat, as well as in tomato. An alignment of the CBF proteins from *Arabidopsis*, *B. napus*, wheat, rye, and tomato revealed the presence of conserved consecutive amino acid residues, PKK/RPAGRxKFxETRHP (SEQ ID NO: 17865) and DSAWR (SEQ ID NO: 17866), which bracket the AP2/EREBP DNA binding domains of the proteins and distinguish them from other members of the AP2/EREBP protein family. (Jaglo et al. (2001))

Transcription factors mediate cellular responses and control traits through altered expression of genes containing cis-acting nucleotide sequences that are targets of the introduced transcription factor. It is well appreciated in the art that the effect of a transcription factor on cellular responses or a cellular trait is determined by the particular genes whose expression is either directly or indirectly (e.g., by a cascade of transcription factor binding events and transcriptional changes) altered by transcription factor binding. In a global analysis of transcription comparing a standard condition with one in which a transcription factor is overexpressed, the resulting transcript profile associated with transcription factor overexpression is related to the trait or cellular process controlled by that transcription factor. For example, the PAP2 gene and other genes in the MYB family have been shown to control anthocyanin biosynthesis through regulation of the expression of genes known to be involved in the anthocyanin biosynthetic pathway (Bruce et al. (2000); and Borevitz et al. (2000)). Further, global transcript profiles have been used successfully as diagnostic tools for specific cellular states (e.g., cancerous vs. non-cancerous; Bhattacharjee et al. (2001); and Xu et al. (2001)). Consequently, it is evident to one skilled in the art that similarity of transcript profile upon overexpression of different transcription factors would indicate similarity of transcription factor function.

Polypeptides and Polynucleotides of the Invention

The present invention provides, among other things, transcription factors (TFs), and transcription factor homolog polypeptides, and isolated or recombinant polynucleotides encoding the polypeptides, or novel sequence variant polypeptides or polynucleotides encoding novel variants of transcription factors derived from the specific sequences provided in the Sequence Listing. Also provided are methods for modifying a plant's biomass by modifying the size or number of leaves or seed of a plant by controlling a number of cellular processes, and for increasing a plant's resistance or tolerance to disease or abiotic stresses, respectively. These methods are based on the ability to alter the expression of critical regulatory molecules that may be conserved between diverse plant species. Related conserved regulatory molecules may be originally discovered in a model system such as *Arabidopsis* and homologous, functional molecules then discovered in other plant species. The latter may then be used to confer increased biomass, disease resistance or abiotic stress tolerance in diverse plant species.

Exemplary polynucleotides encoding the polypeptides of the invention were identified in the *Arabidopsis thaliana* GenBank database using publicly available sequence analysis programs and parameters. Sequences initially identified were then further characterized to identify sequences comprising specified sequence strings corresponding to sequence motifs present in families of known transcription factors. In addition, further exemplary polynucleotides encoding the polypeptides of the invention were identified in the plant GenBank database using publicly available sequence analysis programs and parameters. Sequences initially identified were then further characterized to identify sequences comprising specified sequence strings corresponding to sequence motifs present in families of known transcription factors. Polynucleotide sequences meeting such criteria were confirmed as transcription factors.

Additional polynucleotides of the invention were identified by screening *Arabidopsis thaliana* and/or other plant cDNA libraries with probes corresponding to known transcription factors under low stringency hybridization conditions. Additional sequences, including full length coding sequences, were subsequently recovered by the rapid amplification of cDNA ends (RACE) procedure using a commercially available kit according to the manufacturer's instructions. Where necessary, multiple rounds of RACE are performed to isolate 5' and 3' ends. The full-length cDNA was then recovered by a routine end-to-end polymerase chain reaction (PCR) using primers specific to the isolated 5' and 3' ends. Exemplary sequences are provided in the Sequence Listing.

Many of the sequences in the Sequence Listing, derived from diverse plant species, have been ectopically expressed in overexpressor plants. The changes in the characteristic(s) or trait(s) of the plants were then observed and found to confer increased disease resistance, increase biomass and/or increased abiotic stress tolerance. Therefore, the polynucleotides and polypeptides can be used to improve desirable characteristics of plants.

The polynucleotides of the invention were also ectopically expressed in overexpressor plant cells and the changes in the expression levels of a number of genes, polynucleotides, and/or proteins of the plant cells observed. Therefore, the polynucleotides and polypeptides can be used to change expression levels of a genes, polynucleotides, and/or proteins of plants or plant cells.

The data presented herein represent the results obtained in experiments with transcription factor polynucleotides and polypeptides that may be expressed in plants for the purpose of reducing yield losses that arise from biotic and abiotic stress.

The G482 Clade, Including G481 and Related Sequences

Figure 1:
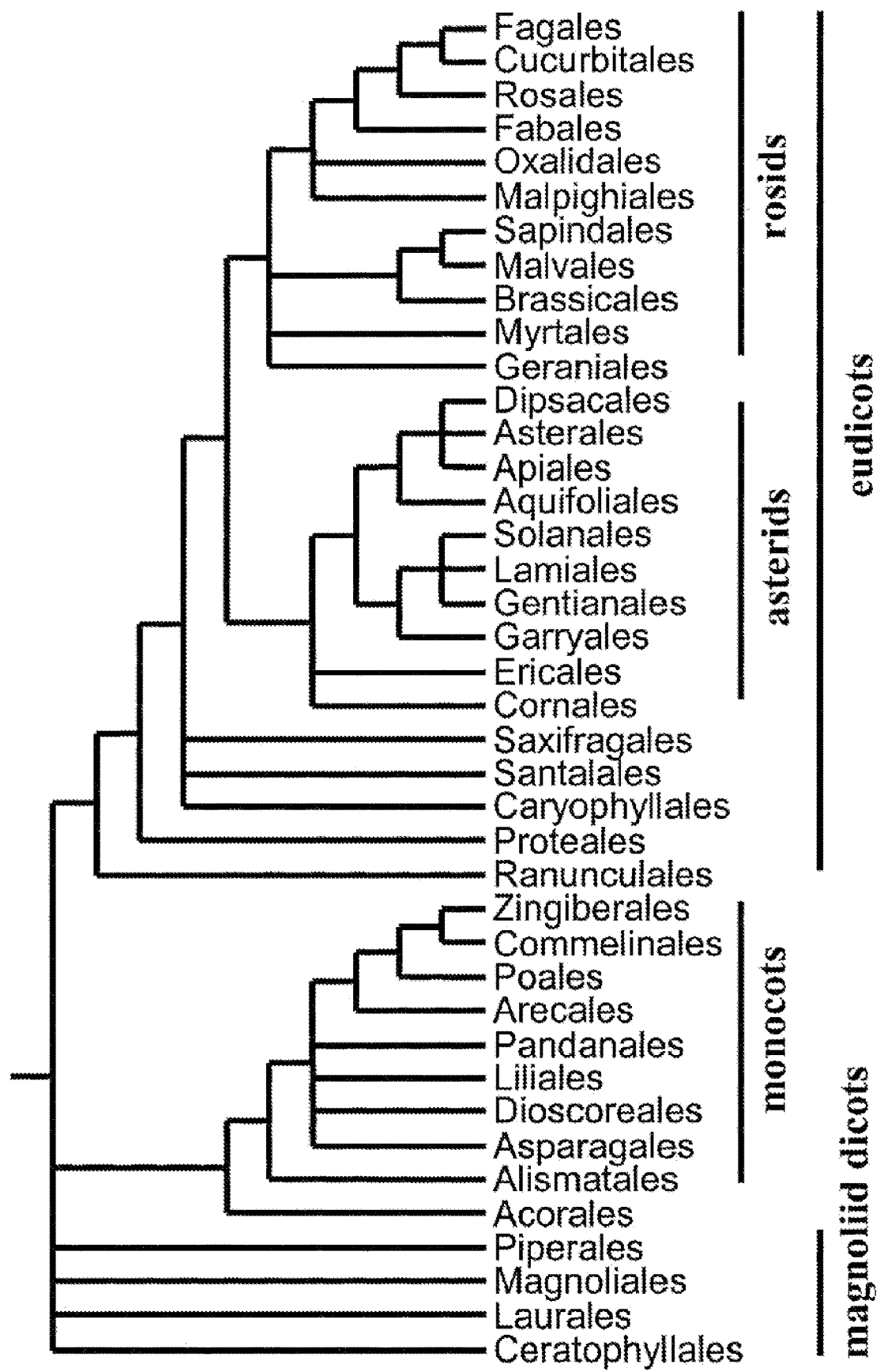
Figure 2:
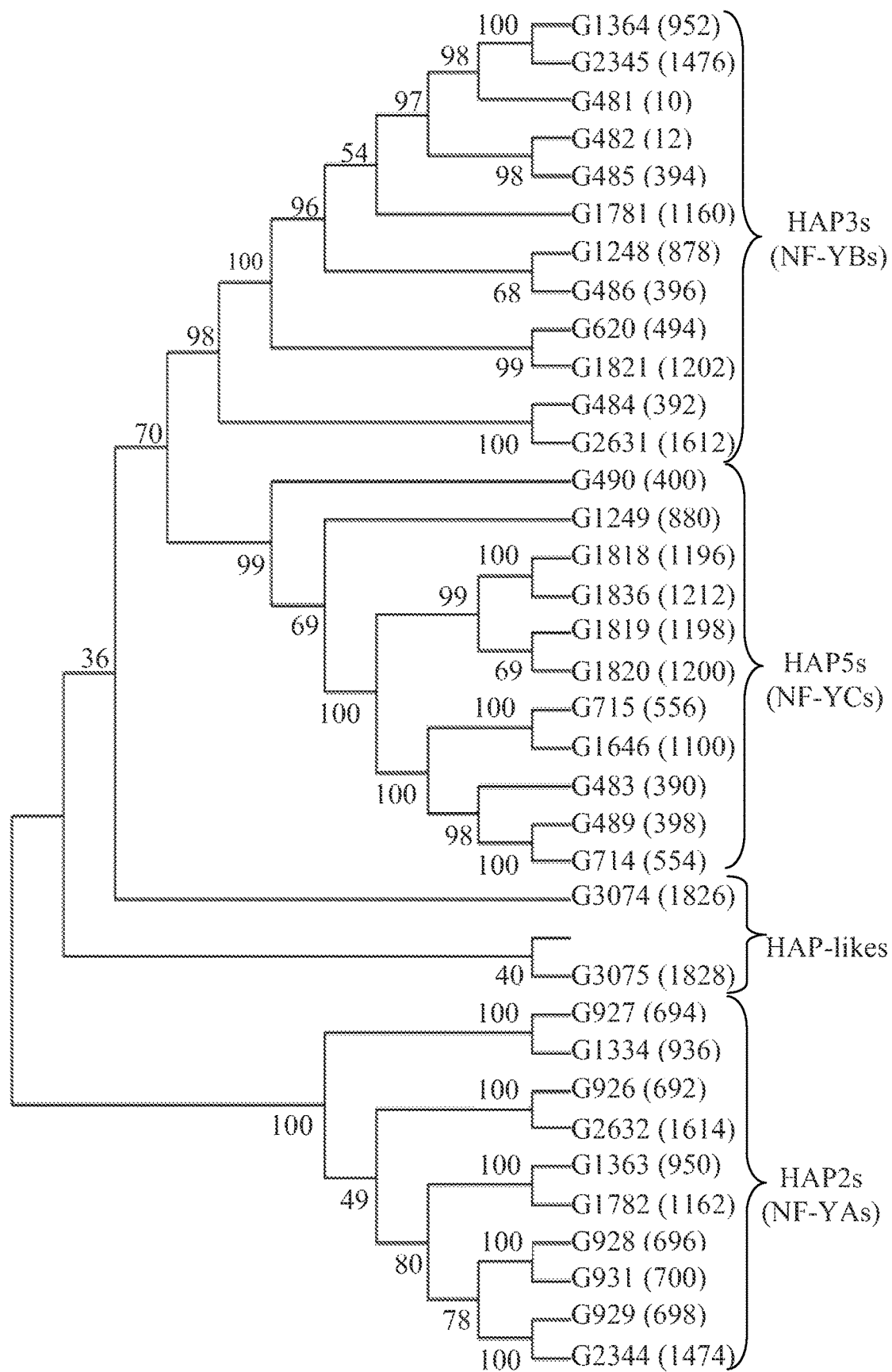
Figure 4:
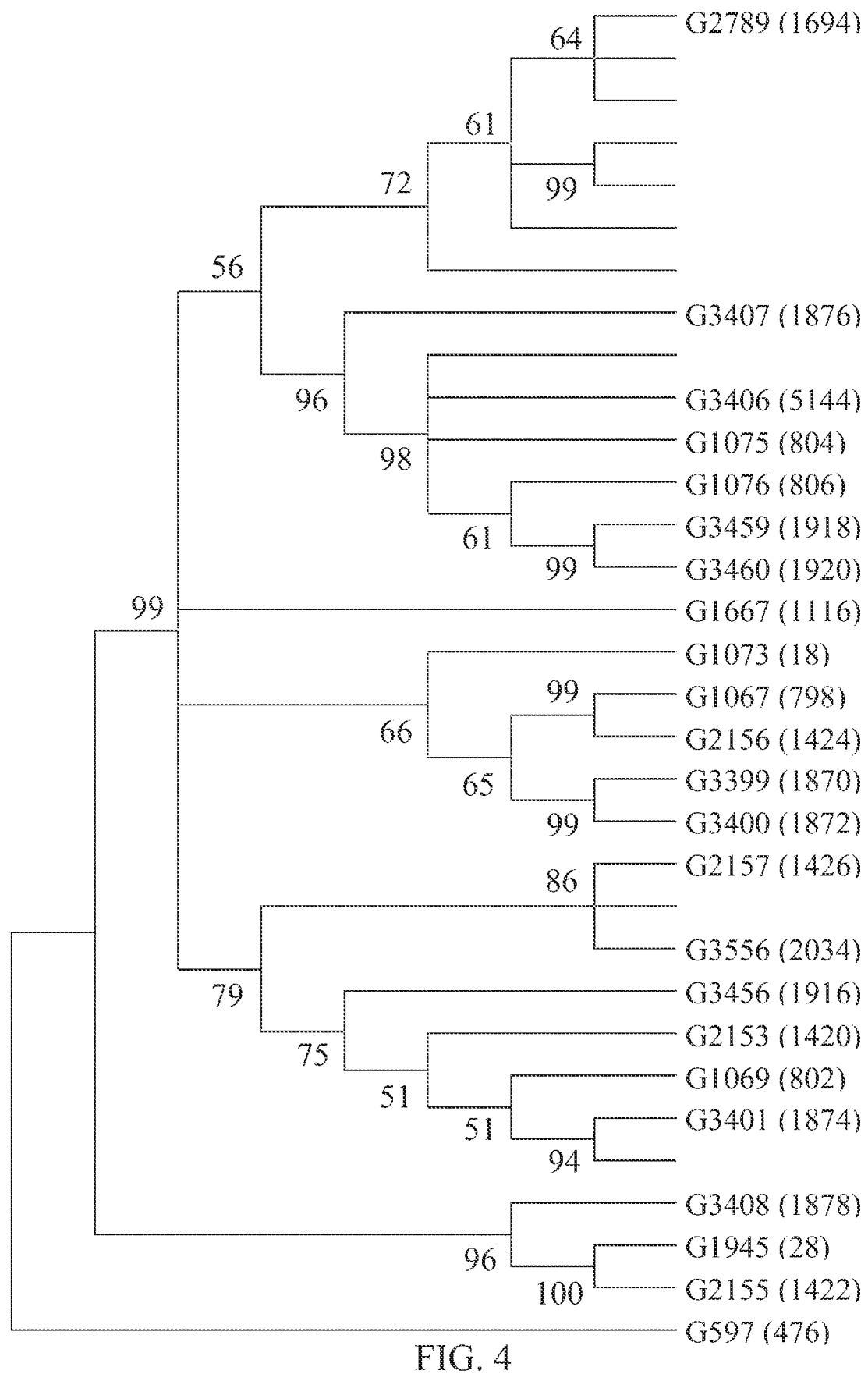
FIG. 4 is a phylogenetic tree of G1073 clade member sequences and include numerous sequences within the clade that have similar functions of conferring, for example, greater biomass and hyperosmotic stress tolerance. The clade is represented by the bracket.
Figure 6:
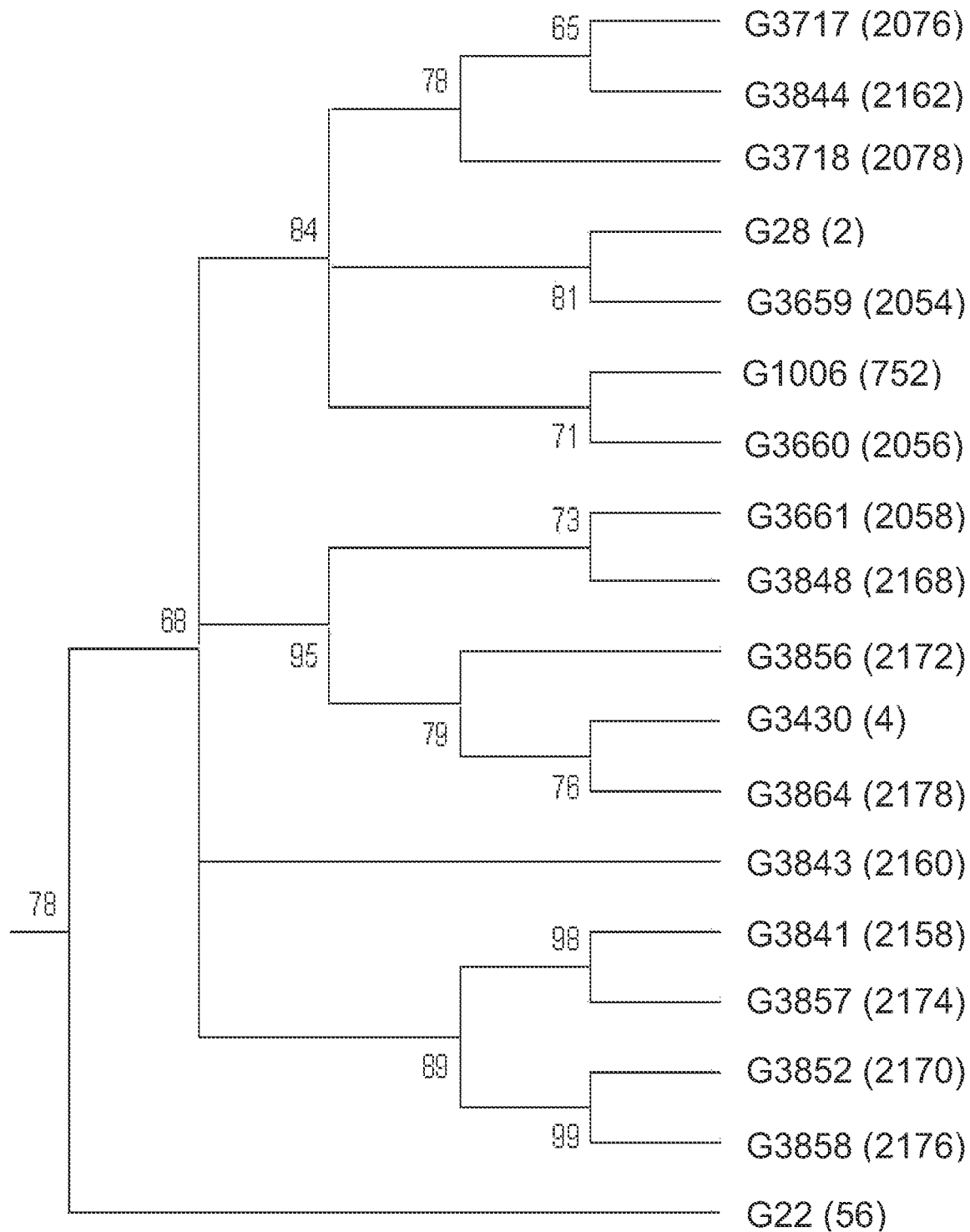
FIG. 6 illustrates a phylogenetic tree of G28 clade member AP2 sequences.

G481 (SEQ ID NOs: 9 and 10; AT2G38880; also known as HAP3A and NF-YB1) from *Arabidopsis* is a member of the HAP3/NF-YB sub-group of the CCAAT binding factor family (CCAAT) of transcription factors (FIG. 2).

Structural Features and Assembly of the NF-Y Subunits.

NF-Y is one of the most heavily studied transcription factor complexes and an extensive literature has accumulated regarding its structure, regulation, and putative roles in various different organisms. Each of the three subunits comprises a region which has been evolutionarily conserved (Li et al. (1992); Mantovani (1999)). In the NF-YA subunits, this conserved region is at the C-terminus, in the NF-YB proteins it is centrally located, and in the NF-YC subunits it is at the N-terminus. The NF-YA and NF-YC subunits also have regions which are rich in glutamine (Q) residues that also show some degree of conservation; these Q-rich regions have an activation domain function. In fact it has been shown that NF-Y contains two transcription activation domains: a glutamine-rich, serine-threonine-rich domain present in the CBF-B (HAP2, NF-YA) subunit and a glutamine-rich domain in the CBF-C(HAP5, CBF-C) subunit (Coustry et al. (1995); Coustry et al. (1996); Coustry et al. (1998); Coustry et al. (2001)).

The NF-YB and NF-YC subunits bear some similarity to histones; the conserved regions of both these subunits contain a histone fold motif (HFM), which is an ancient domain of about 65 amino acids. The HFM has a high degree of structural conservation across all histones and comprises three or four α-helices (four in the case of the NF-Y subunits) which are separated by short loops (L)/strand regions (Arents and Moudrianakis (1995)). In the histones, this HFM domain mediates dimerization and formation of non sequence-specific interactions with DNA (Arents and Moudrianakis (1995)).

Considerable knowledge has now accumulated regarding the biochemistry of NF-Y subunit association and DNA binding. The NF-YB-NF-YC subunits first form a tight dimer, which offers a complex surface for NF-YA association. The resulting trimer can then bind to DNA with high specificity and affinity (Kim and Sheffrey (1990); Bi et al. (1997); Mantovani (1999)). In addition to the NF-Y subunits themselves, a number of other proteins have been implicated in formation of the complex (Mantovani (1999)).

HAP3 (NF-YB) proteins have a modular structure and are comprised of three distinct domains: an amino-terminal A domain, a central B domain and a carboxy-terminal C domain. There is very little sequence similarity between HAP3 proteins within the A and C domains suggesting that those regions could provide a degree of functional specificity to each member of the HAP3 subfamily. The B domain is a highly conserved region that specifies DNA binding and subunit association. Lee et al. (2003) performed an elegant series of domain swap experiments between the LEC1 and a non-LEC1 like HAP3 protein (At4g14540, G485) to demonstrate that the B domain of LEC1 is necessary and sufficient, within the context of the rest of the protein, to confer its activity in embryogenesis. Furthermore, these authors identified a specific defining residue within the B domain (Asp-55) that is required for LEC1 activity and which is sufficient to confer LEC1 function to a non-LEC1 like B domain.

In FIGS. 3A-3B, HAP3 protein B domains from *Arabidopsis*, soybean, rice and corn are aligned with G481.

G1073, the G1073 Clade, and Related Sequences

G1073 (SEQ ID NO: 18, encoded by SEQ ID NO: 17) is a member of the At-hook family of transcription factors. We have now designated this locus as HERCULES 1 (HRC1), in recognition of the increased organ size seen in 35S::G1073 lines.

G1073 contains a single typical AT-hook DNA-binding motif (RRPRGRPAG; SEQ ID NO: 2382) at amino acids 63 to 71. A highly conserved 129 AA domain, with unknown function, can be identified in the single AT-hook domain subgroup. Comprised within this "second conserved domain is the DUF296 domain, which in G1073 occupies amino acids 90-209. According to the National Center for Biotechnology Information (NCBI; www.ncbi.nlm.nih.gov/), "[t]his putative domain is found in proteins that contain AT-hook motifs pfam02178, which strongly suggests a DNA-binding function for the proteins as a whole, however the function of this domain is unknown". Following the second conserved domain, a potential acidic domain spans from position 200 to 219. Additionally, analysis of the protein using PROSITE reveals three potential protein kinase C phosphorylation sites at Ser61, Thr112 and Thr131, and three potential casein kinase II phosphorylation sites at Ser35, Ser99 and Ser276. Additional structural features of G1073 include 1) a short glutamine-rich stretch in the C-terminal region distal to the conserved acidic domain, and 2) possible PEST sequences in the same C-terminal region.

The G1073 clade generally comprises the consensus sequence:

(SEQ ID NO: 5107)
RPRGRPXG, or Arg-Pro-Arg-Gly-Arg-Pro-Xaa-Gly where X or Xaa can be any of a number of amino acid residues; in the examples that have thus far been shown to confer abiotic stress tolerance, Xaa has been shown to represent an alanine, leucine, proline, or serine residue.

Also within the G1073 clade, a second conserved domain exists that generally comprises the consensus sequence: Pro-(Xaa)$_5$-Leu-(Xaa)$_2$-Tyr (SEQ ID NO: 5108), or alternatively Pro-(Xaa)$_5$-Leu-(Xaa)$_2$-Phe (SEQ ID NO: 5109). The tenth position of these latter two sequences is an aromatic residue, specifically tyrosine or phenylalanine, in the G1073 clade sequences that have thus far been examined.

Thus, the AT-hook family transcription factors of the invention each possess an AT-hook domain and a second conserved domain, and include paralogs and orthologs of G1073 found by BLAST analysis, as described below. The AT-hook domains of G1073 and related sequences examined thus far are at least 85% identical to the At-Hook domains of G1073, and the second conserved domains of these related sequences are at least 61% identical to the second conserved domain found in G1073. These transcription factors rely on the binding specificity of their AT-hook domains; many have been shown to have similar or identical functions in plants by increasing the size and biomass of a plant.

Role of at-Hook Proteins.

The At-hook is a short, highly-conserved, DNA binding protein motif that comprises a conserved nine amino acid peptide (Nieto-Sotelo, Ichida and Quail (1994)), the seminal domain of which contains KRPRGRPKK (SEQ ID NO: 5110; Reeves and Nissen, 1990) and is capable of binding to the minor groove of DNA (Reeves and Nissen (1990)). At the center of this AT-hook motif is a short, strongly conserved tripeptide (GRP) comprised of glycine-arginine-proline (Aravind and Landsman (1998)). At-hook motifs were first recognized in the non-histone chromosomal protein HMG-I(Y) but have since been found in other DNA binding proteins from a wide range of organisms. In general, it appears that the AT-hook motif is an auxiliary protein motif cooperating with other DNA-binding activities and facilitating changes in the structure of the chromatin (Aravind and Landsman (1998)). The AT-hook motif can be present in a variable number of copies (1-15) in a given AT-hook protein. For example, the mammalian HMG-I(Y) proteins have three copies of this motif.

Overexpression of G1073 in *Arabidopsis*.

We established that overexpression of G1073 leads to increased vegetative biomass and seed yield compared to control plants. As a result of these phenotypes we assigned the gene name HERCULES1 (HRC1) to G1073. Drought tolerance was observed in 35S::G1073 transgenic lines. We have also observed hyperosmotic stress-tolerance phenotypes, such as tolerance to high salt and high sucrose concentrations, in plate-based assays performed on 35S::G1073 plants.

Due to increased cell size and number, 35S::G1073 *Arabidopsis* lines display enlarged organs. We also conducted some preliminary analyses into the basis of the enhanced biomass of 35S::G1073 *Arabidopsis* lines. We found that the increased mass of 35S::G1073 transgenic plants could be attributed to enlargement of multiple organ types including leaves, stems, roots and floral organs. Petal size in the 35S::G1073 lines was increased by 40-50% compared to wild type controls. Petal epidermal cells in those same lines were approximately 25-30% larger than those of the control plants. Furthermore, we found 15-20% more epidermal cells per petal, compared to wild type. Thus, at least in petals, the increase in size was associated with an increase in cell size as well as in cell number. Additionally, images from the stem cross-sections of 35S::G1073 plants revealed that cortical cells were large and that vascular bundles contained more cells in the phloem and xylem relative to wild type.

Advantages of Root-Specific Expression:

Plants often respond to stresses such as limited water or nutrients by altering their root-shoot ratios, root architecture, or root growth. These changes are mediated through transcriptional responses in both the root and shoot. Since there is evidence that G1073 has a native role in the root, this gene and other genes encoding related proteins from the plant At-hook family may confer drought tolerance by controlling root development or other root responses. Root specific expression of G1073 and other sequences that encode plant At-hook proteins (for example: G1067, G1069, G1073, G1075, G1076, G1667, G1945, G2153, G2155, G2156, G2157, G3399, G3400, G3401, G3406, G3407, G3408, G3456, G3459, G3460, G3556, G597, G605, G1068, G1128, G1399, G1944, G2522 (SEQ ID NOs: 798, 802, 18, 804, 806, 1116, 28, 1420, 1422, 1424, 1426, 1870, 1872, 1874, 5145, 1876, 1878, 1916, 1918, 1920, 2034, 476, 484, 800, 828, 964, 1286, 1552) under the regulatory control of a promoter that drives root specific or root enhanced expression, such as, for example, ARSK1, NAS2, or others [such as the regulator regions from genes discussed recently by Birnbaum et al. (2003) or Brady et al. (2007) as having root specific expression patterns], may be used to produce transformed plants that are water deficit tolerant but lack undesirable developmental effects that may be associated with constitutive overexpression (e.g., for some applications, large plants, or changes in plant organ size or shape may be disadvantageous).

G28, the G28 Clade, and Related Sequences

G28 (SEQ ID NO: 2, encoded by SEQ ID NO: 1) corresponds to AtERF1 (GenBank accession number AB008103) (Fujimoto et al. (2000)). G28 appears as gene At4g17500 in the annotated sequence of *Arabidopsis* chromosome 4 (AL161546.2). G28 has been shown to confer resistance to both necrotrophic and biotrophic pathogens. The G28 polypeptide (SEQ ID NO: 2) is a member of the B-3a subgroup of the ERF subfamily of AP2 transcription factors, defined as having a single AP2 domain and having specific residues in the DNA binding domain that distinguish this large subfamily (65 members) from the DREB subfamily (see below). AtERF1 is apparently orthologous to the AP2 transcription factor Pti4, identified in tomato, which has been shown by Martin and colleagues to function in the Pto disease resistance pathway, and to confer broad-spectrum disease resistance when overexpressed in *Arabidopsis* (Zhou et al. (1997); Gu et al. (2000); Gu et al. (2002)).

AP2 Domain Transcription Factors.

This large transcription factor gene family includes 145 transcription factors (Weigel (1995); Okamuro et al. (1997); Riechmann and Meyerowitz (1998); Riechmann et al. (2000)). Based on the results of our earlier genomics screens it is clear that this family of proteins affect the regulation of a wide range of morphological and physiological processes, including the acquisition of abiotic and biotic stress tolerance. The AP2 family includes the AP2/ERF group which contain a single AP2 domain. This AP2/ERF class can be further categorized into three subgroups:

The DREB ("A") (dehydration responsive element binding) sub-family which comprises 56 genes. Many of the DREBs are involved in regulation of abiotic stress tolerance pathways (Stockinger et al. (1997); Jaglo-Ottosen et al. (1998); Finkelstein et al. (1998); Sakuma et al. (2002)).

The ERF (ethylene response factor) sub-family ("B") which includes 65 genes, several of which are involved in regulation of biotic stress tolerance pathways (Ohme-Takagi and Shinshi (1995); Zhou et al. (1997)). The DREB and ERF sub-groups are distinguished by the amino acids present at position 14 and 19 of the AP2 domain: while DREBs are characterized by Val-14 and Glu-19, ERFs typically have Ala-14 and Asp-19. Recent work indicates that those two amino acids have a key function in determining the target specificity (Sakuma et al. (2002), Hao et al. (2002)).

[3] The RAV class (6 genes) all of which have a B3 DNA binding domain in addition to the AP2 DNA binding domain, and which also regulate abiotic stress tolerance pathways.

The Role of ERF Transcription Factors in Stress Responses: ERF Transcription Factors in Disease Resistance.

The first indication that members of the ERF group might be involved in regulation of plant disease resistance pathways was the identification of Pti4, Pti5 and Pti6 as interactors with the tomato disease resistance protein Pto in yeast 2-hybrid assays (Zhou et al. (1997)). Since that time, many ERF genes have been shown to enhance disease resistance when overexpressed in *Arabidopsis* or other species. These ERF genes include ERF1 (G1266) of *Arabidopsis* (Berrocal-Lobo et al. (2002); Berrocal-Lobo and Molina, (2004)); Pti4 (Gu et al. (2002)) and Pti5 (He et al. (2001)) of tomato; Tsi1 (Park et al. (2001); Shin et al. (2002)), NtERF5 (Fischer and Droge-Laser (2004)), and OPBP1 (Guo et al. (2004)) of tobacco; CaERFLP1 (Lee et al. (2004)) and CaPF1 (Yi et al. (2004)) of hot pepper; and AtERF1 (G28) and TDR1 (G1792) of *Arabidopsis* (our data).

Protein Structure and Properties.

G28 lacks introns and encodes a 266 amino acid protein with a predicted molecular weight of 28.9 kDa. Specific conserved motifs have been identified through alignments with other related ERFs. The AP2 domain of G28 is relatively centrally positioned in the intact protein. G28 has been shown to bind specifically to the AGCCGCC motif (GCC box: Hao et al. (1998); Hao et al. (2002)). Our analysis of the G28 regulon by global transcript profiling is consistent with this, as the 5' regions of genes up-regulated by G28 are enriched for the presence of AGCCGCC motifs. The AP2 domain of AtERF1 (G28) was purified and used by Allen et al. (1998) in solution NMR studies of the AP2 domain and its interaction with DNA. This analysis indicated that certain residues in three beta-strands are involved in DNA recognition, and that an alpha helix provides structural support for the DNA binding domain.

A potential bipartite nuclear localization signal has been reported in the G28 protein. A protein scan also revealed several potential phosphorylation sites, but the conserved motifs used for those predictions are small, have a high probability of occurrence. However, the orthologous Pti4 sequence has been shown to be phosphorylated in multiple locations, which have yet to be mapped in detail. A protein alignment of closely related ERF sequences indicates the presence of conserved domains unique to B-3a ERF proteins. For example, a motif not found in other *Arabidopsis* transcription factors is found directly C-terminal to the AP2 domain in eudicot sequences, but is not found in monocot sequences. Another conserved motif is found 40-50 amino acids N-terminal to the AP2 DNA binding domain. The core of this motif is fairly well conserved in both eudicots and monocots, but extensions of the motif are divergent between eudicots and monocots. The identification of specific motifs unique to small clades of ERF transcription factors suggests that these motifs may be involved in specific interactions with other protein factors involved in transcriptional control, and thereby may determine functional specificity. Known transcriptional activation domains are either acidic, proline rich or glutamine rich (Liu et al. (1999)). The G28 protein contains one acid-enriched region (overlapping with the first eudicot-specific motif). There is also evidence that regions rich in serine, threonine, and proline may function in transcriptional activation (Silver et al. (2003)). There are two ser/pro-enriched regions in the region N-terminal to the AP2 domain None of these domains has yet to be demonstrated directly to have a role in transcriptional activation.

G1792, the G1792 Clade, and Related Sequences

We first identified G1792 (AT3G23230; SEQ ID NO: 23, 24) as a transcription factor in the sequence of BAC clone K14B15 (AB025608, gene K14B15.14). We have assigned the name TRANSCRIPTIONAL REGULATOR OF DEFENSE RESPONSE 1 (TDR1) to this gene, based on its apparent role in disease responses. The G1792 protein contains a single AP2 domain and belongs to the ERF class of AP2 proteins. A review of the different sub-families of proteins within the AP2 family is provided in the information provided for G28, above. The G28 disclosure provided herein includes description of target genes regulated by ERF transcription factors, the role of ERF transcription factors in stress responses: ERF transcription factors in disease resistance, ERF transcription factors in abiotic stress responses, regulation of ERF transcription factors by pathogen and small molecule signaling, etc., which also pertain to G1792.

G1792 Overexpression Increases Survivability in a Soil-Based Drought Assay.

35S::G1792 lines exhibited markedly enhanced drought tolerance in a soil-based drought screen compared to wild-type, both in terms of their appearance at the end of the drought period, and in survival following re-watering.

G1792 Overexpression Increases Tolerance to Growth on Nitrogen-Limiting Conditions.

35S::G1792 transformants showed more tolerance to growth under nitrogen-limiting conditions. In a root growth assay under conditions of limiting N, 35S::G1792 lines were slightly less stunted. In an germination assay that monitors the effect of carbon on nitrogen signaling through anthocyanin production (with high sucrose+/−glutamine; Hsieh et al. (1998)), the 35S::G1792 lines made less anthocyanin on high sucrose (+glutamine), suggesting that the gene could be involved in the plant's ability to monitor carbon and nitrogen status.

G1792 Overexpression Causes Morphological Alterations.

Plants overexpressing G1792 showed several mild morphological alterations: leaves were darker green and shiny, and plants bolted, and subsequently senesced, slightly later than wild-type controls. Among the T1 plants, additional morphological variation (not reproduced later in the T2 plants) was observed: many showed reductions in size as well as aberrations in leaf shape, phyllotaxy, and flower development.

G1792 Overexpression Produces Disease Resistance.

35S::G1792 plants were more resistant to the fungal pathogens *Fusarium oxysporum* and *Botrytis cinerea*: they showed fewer symptoms after inoculation with a low dose of each pathogen. This result was confirmed using individual T2 lines. The effect of G1792 overexpression in increasing resistance to pathogens received further, incidental confirmation. T2 plants of 35S::G1792 lines 5 and 12 were being grown (for other purposes) in a room that suffered a serious powdery mildew infection. For each line, a pot of 6 plants was present in a flat containing 9 other pots of lines from unrelated genes. In either of the two different flats, the only plants that were free from infection were those from the 35S::G1792 line. This observation suggested that G1792 overexpression increased resistance to powdery mildew.

G1792 has three paralogs, G30, G1791 and G1795 (SEQ ID NO: 66, 1172 and 26, respectively), which were not assayed for disease resistance in an earlier genomics program because their overexpression caused severe negative side effects. Some evidence suggested that these genes might play a role in disease resistance: expression of G1795 and G1791 was induced by *Fusarium*, and G1795 by salicylic acid, in RT-PCR experiments, and the lines shared the glossy phenotype observed for G1792. Phylogenetic trees based on whole protein sequences do not always make the relationship of these proteins to G1792 clear; however, the close relationship of these proteins is evident in an alignment and in a phylogenetic analysis based on the conserved AP2 domain and a second conserved motif, the EDLL domain described below.

In this study G1792, G1791, G1795 and G30 were expressed under the control of four different promoters using the two-component system. The promoters chosen were 35S, RBCS3 (mesophyll or photosynthetic-specific), LTP1 (epidermal-specific), and 35S::LexA:GAL4:GR (dexamethasone-inducible). All promoters other than 35S produced substantial amelioration of the negative side effects of transcription factor overexpression.

Five lines for each combination were tested with *Sclerotinia*, *Botrytis*, or *Fusarium*. Interestingly, G1791 and G30 conferred significant resistance to *Sclerotinia* when expressed under RBCS3 or 35S::LexA:GAL4:GR, even though G1792 does not confer *Sclerotinia* resistance. These results support the hypothesis that genes of this clade confer disease resistance when expressed under tissue specific or inducible promoters.

TABLE 1

Disease screening of G1792 and paralogs under different promoters

| | G1792 | | | G1791 | | | G1795 | | | G30 | | |
|---|---|---|---|---|---|---|---|---|---|---|---|---|
| | SEQ ID NO: | | | | | | | | | | | |
| | 24 | | | 1172 | | | 26 | | | 66 | | |
| | B | S | F | B | S | F | B | S | F | B | S | F |
| 35S | ++ | wt | + | nd | nd | nd | nd | nd | nd | nd | nd | nd |
| RBCS3 | + | wt | + | wt | wt | wt | ++ | ++ | wt | + | + | wt |
| LTP1 | wt | wt | nd | + | wt | wt | ++ | + | wt | + | wt | wt |
| 35S, Dexamethasone-induced | ++ | wt | + | ++ | ++ | wt | ++ | ++ | wt | ++ | ++ | wt |

Abbreviations and symbols:
B, *Botrytis*
S, *Sclerotinia*
F, *Fusarium*
Scoring:
wt, wild-type (susceptible) phenotype
+, mild to moderate resistance
++, strong resistance
nd, not determined Domains.

In addition to the AP2 domain (domains of G1792 clade members are shown in Table 7), G1792 contains a putative activation domain. This domain has been designated the "EDLL domain" based on four amino acids that are highly conserved across paralogs and orthologs of G1792 (FIG. 14).

Tertiary Structure.

The solution structure of an ERF type transcription factor domain in complex with the GCC box has been determined (Allen et. al., 1998). It consists of a β-sheet composed of three strands and an α-helix. Flanking sequences of the AP2 domain of this protein were replaced with the flanking sequences of the related CBF1 protein, and the chimeric protein was found to contain the same arrangement of secondary structural elements as the native ERF type protein (Allen et al. (1998)). This implies that the secondary structural motifs may be conserved for similar ERF type transcription factors within the family.

DNA Binding Motifs.

Two amino acid residues in the AP2 domain, Ala-14 and Asp-19, are definitive of the ERF class transcription factors Sakuma et al. (2002). Recent work indicates that these two amino acids have a key function in determining binding specificity (Sakuma et al. (2002), Hao et al. (2002)) and interact directly with DNA. The 3-dimensional structure of the GCC box complex indicates the interaction of the second strand of the β-sheet with the DNA.

G47, the G47 Clade, and Related Sequences

G47 (SEQ ID NO: 5, AT1G22810) encodes a member of the AP2 class of transcription factors (SEQ ID NO: 6) and was included based on the resistance to drought-related abiotic stress exhibited by 35S::G47 *Arabidopsis* lines and by overexpression lines for the closely related paralog, G2133 (SEQ ID NO: 7 and polypeptide SEQ ID NO: 8, AT1G71520). A detailed genetic characterization has not been reported for either of these genes in the public literature.

AP2 Family Transcription Factors.

Based on the results of our earlier genomics screens, it is clear that this family of proteins affect the regulation of a wide range of morphological and physiological processes, including the acquisition of stress tolerance. The AP2 family can be further divided into subfamilies as detailed in the G28 section, above.

G47 and G2133 Protein Structure.

G47 and G2133 and other highly related AP2 proteins (FIG. 8) and are members of the AP2/ERF subfamily Both proteins possess an AP2 domain at the amino terminus and a somewhat acidic region at the C-terminus that might constitute an activation domain. A putative bipartite NLS is located at the start of the AP2 domain in both proteins. Sakuma et al. (Sakuma et al. (2002)) categorized these factors within the A-5 class of the DREB related sub-group based on the presence of a V residue at position 14 within the AP2 domain Importantly, however, position 19 within the AP2 domain is occupied by a V residue in both G2133 and G47, rather than an E residue, as is the case in the majority of DREBs. Additionally, the "RAYD-box" within the AP2 domains of these two proteins is uniquely occupied by the sequence that substitutes a "V" for the "R" and an "H" for the "Y" in the RAYD-box (within SEQ ID NO: 2375, and near the right margin of the top group of subsequences in FIG. 9), a combination not found in any other *Arabidopsis* AP2/ERF protein (Sakuma et al. (2002)). These differences to other AP2 proteins could confer unique DNA binding properties on G2133 and G47.

Morphological Effects of G47 and G2133 Overexpression.

A number of striking morphological effects were observed in 35S::G47 lines. At early stages, the plants were somewhat reduced in size. However, these lines flowered late and eventually developed an apparent increase in rosette size compared to mature wild-type plants. Additionally, the 35S:: G47 plants showed a marked difference in aerial architecture; inflorescences displayed a short stature, had a reduction in apical dominance, and developed thick fleshy stems. When sections from these stems were stained and examined, it was apparent that the vascular bundles were grossly enlarged compared to wild-type. Similar morphological changes were apparent in shoots of 35S::G2133 lines, but most of the 35S::G2133 lines exhibited much more severe dwarfing at early stages compared to 35S::G47 lines. Nevertheless, at later stages, a number of 35S::G2133 lines showed a very similar reduction of apical dominance and a fleshy appearance comparable to that seen in 35S::G47 lines.

Physiological Effects of G47 and G2133 Overexpression.

Both 35S::G2133 lines and 35S::G47 lines exhibited abiotic stress resistance phenotypes in the screens performed during our earlier genomics program. 35S::G47 lines displayed increased tolerance to hyperosmotic stress (PEG) whereas 35S::G2133 lines were more tolerant to the herbicide glyphosate compared to wild type.

The increased tolerance of 35S::G47 lines to PEG, combined with the fleshy appearance and altered vascular structure of the plants, led us to test these lines in a soil drought screen. 35S::G2133 lines were also included in that assay, given the close similarity between the two proteins and the comparable morphological effects obtained. Both 35S::G47 and 35S::G2133 lines showed a strong performance in that screen and exhibited markedly enhanced drought tolerance compared to wild-type, both in terms of their appearance at the end of the drought period, and in survivability following re-watering. In fact, of the approximately 40 transcription factors tested in that screen, 35S::G2133 lines showed the top performance in terms of each of these criteria.

G1274, the G1274 Clade, and Related Sequences

G1274 (SEQ ID NO: 19) from *Arabidopsis* encodes a member of the WRKY family of transcription factors (SEQ ID NO: 20) and was included based primarily on soil-based drought tolerance exhibited by 35S::G1274 *Arabidopsis* lines. G1274 corresponds to AtWRKY51 (At5g64810), a gene for which there is currently no published information.

WRKY Transcription Factors.

In *Arabidopsis* alone, there are more than 70 members of the WRKY superfamily. The defining feature of the family is the ~57 amino acid DNA binding domain that contains a conserved heptapeptide motif. Additionally, all WRKY proteins have a novel zinc-finger motif contained within the DNA binding domain There are three distinct groups within the superfamily, each principally defined by the number of WRKY domains and the structure of the zinc-finger domain (reviewed by Eulgem et al. (2000)). Group I members have two WRKY domains, while Group II members contain only one. Members of the Group II family can be further split into five distinct subgroups (IIa-e) based on conserved structural motifs. Group III members have only one WRKY domain, but contain a zinc finger domain that is distinct from Group II members. The majority of WRKY proteins are Group II members, including G1274 and the related genes being studied here. An additional common feature found among WRKY genes is the existence of a conserved intron found within the region encoding the C-terminal WRKY domain of group I members or the single WRKY domain of group II/III members. In G1274, this intron occurs between the sequence encoding amino acids R130 and N131.

Structural Features of G1274.

The G1274 sequence possesses a potential serine-threonine-rich activation domain and putative nuclear localization signals, the "WRKY" (DNA binding) domain, and zinc finger motif, with the pattern of potential zinc ligands C-X$_{4-5}$-C-X$_{22-23}$-H-X$_1$-H (SEQ ID NO: 5164).

Tables 2-18 list a number of polypeptides of the invention and include the amino acid residue coordinates for the conserved domains, the conserved domain sequences of the respective polypeptides, (sixth column); the identity in percentage terms to the conserved domain of the lead *Arabidopsis* sequence (the first transcription factor listed in each table), and whether the given sequence in each row was shown to confer greater biomass and yield or stress tolerance in plants (+) or has thus far not been shown to confer stress tolerance (−) for each given promoter::gene combination in our experiments. Percentage identities to the sequences listed in Tables 2-18 were determined using BLASTP analysis with defaults of wordlength (W) of 3, an expectation (E) of 10, and the BLOSUM62 scoring matrix Henikoff & Henikoff (1992). When the conserved domain sequences found in Tables 2-18 are optimally aligned using the BLOSUM62 matrix, a gap existence penalty of 11, and a gap extension penalty of 1, similar conserved domains may be identified by virtue of having a minimum specified percentage identity. Said minimum percentage identity may be determined by the percentage identities found within a given clade of transcription factors. Examples of percentage identities to *Arabidopsis* sequences that are clade members are provided in Tables 2-18, although it is anticipated and expected that other percentage identities may be determined by related clade sequences to another *Arabidopsis* sequence, or a sequence from another plant species, where that sequence is a functional clade member.

TABLE 2

Conserved domains of G481 (TF family: CCAAT-binding) and closely related HAP3 sequences

| SEQ ID NO: | Species from which SEQ ID NO: is derived | Gene ID (GID) | Conserved B domain amino acid coordinates | Conserved B domain SEQ ID NO: | Conserved B domain | Percent ID of conserved B domain to G481 conserved B domain |
|---|---|---|---|---|---|---|
| 10 | *Arabidopsis thaliana* | G481 | 20-109 | 2377 | REQDRYLPIANISRIMKKALPPN GKIGKDAKDTVQECVSEFISFIT SEASDKCQKEKRKTVNGDDLL WAMATLGFEDYLEPLKIYLAR YR | 100 |
| 1922 | *Glycine max* | G3470 | 27-116 | 3527 | REQDRYLPIANISRIMKKALPPN GKIAKDAKDTMQECVSEFISFIT SEASEKCQKEKRKTINGDDLL WAMATLGFEDYIEPLKVYLAR YR | 93 |
| 1924 | *Glycine max* | G3471 | 26-115 | 3528 | REQDRYLPIANISRIMKKALPPN GKIAKDAKDTMQECVSEFISFIT SEASEKCQKEKRKTINGDDLL WAMATLGFEDYIEPLKVYLAR YR | 93 |
| 2188 | *Glycine max* | G3875 | 25-114 | 3680 | REQDRYLPIANISRIMKKALPA NGKIAKDAKETVQECVSEFISFI TSEASDKCQREKRKTINGDDLL WAMATLGFEDYIDPLKIYLTRY R | 91 |
| 2190 | *Zea mays* | G3876 | 30-119 | 3681 | REQDRFLPIANISRIMKKAIPAN GKIAKDAKETVQECVSEFISFIT SEASDKCQREKRKTINGDDLL WAMATLGFEDYIEPLKVYLQK YR | 87 |
| 1860 | *Oryza sativa* | G3394 | 38-126 | 3483 | RQDRFLPIANISRIMKKAIPANG KIAKDAKETVQECVSEFISFITS EASDKCQREKRKTINGDDLLW AMATLGFEDYIEPLKVYLQKY R | 87 |
| 1886 | *Zea mays* | G3434 | 18-107 | 3502 | REQDRFLPIANISRIMKKAVPA NGKIAKDAKETLQECVSEFISF VTSEASDKCQKEKRKTINGDD LLWAMATLGFEEYVEPLKIYL QKYK | 85 |
| 952 | *Arabidopsis thaliana* | G1364 | 29-118 | 2941 | REQDRFLPIANISRIMKRGLPAN GKIAKDAKEIVQECVSEFISFVT SEASDKCQREKRKTINGDDLL WAMATLGFEDYMEPLKVYLM RYR | 85 |

TABLE 2-continued

Conserved domains of G481 (TF family: CCAAT-binding) and closely related HAP3 sequences

| SEQ ID NO: | Species from which SEQ ID NO: is derived | Gene ID (GID) | Conserved B domain amino acid coordinates | Conserved B domain SEQ ID NO: | Conserved B domain | Percent ID of conserved B domain to G481 conserved B domain |
|---|---|---|---|---|---|---|
| 1932 | Glycine max | G3475 | 23-112 | 3532 | REQDRFLPIANVSRIMKKALPA NAKISKDAKETVQECVSEFISFI TGEASDKCQREKRKTINGDDL LWAMTTLGFEDYVEPLKGYLQ RFR | 84 |
| 394 | Arabidopsis thaliana | G485 | 20-109 | 2616 | REQDRFLPIANVSRIMKKALPA NAKISKDAKETVQECVSEFISFI TGEASDKCQREKRKTINGDDL LWAMTTLGFEDYVEPLKVYLQ KYR | 84 |
| 1934 | Glycine max | G3476 | 26-115 | 3533 | REQDRFLPIANVSRIMKKALPA NAKISKDAKETVQECVSEFISFI TGEASDKCQREKRKTINGDDL LWAMTTLGFEEYVEPLKIYLQ RFR | 84 |
| 1476 | Arabidopsis thaliana | G2345 | 28-117 | 3234 | REQDRFLPIANISRIMKRGLPLN GKIAKDAKETMQECVSEFISFV TSEASDKCQREKRKTINGDDLL WAMATLGFEDYIDPLKVYLMR YR | 84 |
| 1930 | Glycine max | G3474 | 25-114 | 3531 | REQDRFLPIANVSRIMKKALPA NAKISKEAKETVQECVSEFISFI TGEASDKCQKEKRKTINGDDL LWAMTTLGFEDYVDPLKIYLH KYR | 84 |
| 1936 | Glycine max | G3478 | 23-112 | 3534 | REQDRFLPIANVSRIMKKALPA NAKISKDAKETVQECVSEFISFI TGEASDKCQREKRKTINGDDL LWAMTTLGFEDYVEPLKGYLQ RFR | 84 |
| 12 | Arabidopsis thaliana | G482 | 26-115 | 2378 | REQDRFLPIANVSRIMKKALPA NAKISKDAKETMQECVSEFISF VTGEASDKCQKEKRKTINGDD LLWAMTTLGFEDYVEPLKVYL QRFR | 83 |
| 1888 | Zea mays | G3435 | 22-111 | 3503 | REQDRFLPIANVSRIMKKALPA NAKISKDAKETVQECVSEFISFI TGEASDKCQREKRKTINGDDL LWAMTTLGFEDYVEPLKHYLH KFR | 83 |
| 1926 | Glycine max | G3472 | 25-114 | 3529 | REQDRFLPIANVSRIMKKALPA NAKISKEAKETVQECVSEFISFI TGEASDKCQKEKRKTINGDDL LWAMTTLGFEEYVEPLKVYLH KYR | 83 |
| 1890 | Zea mays | G3436 | 20-109 | 3504 | REQDRFLPIANVSRIMKKALPA NAKISKDAKETVQECVSEFISFI TGEASDKCQREKRKTINGDDL LWAMTTLGFEDYVEPLKLYLH KFR | 83 |
| 1866 | Oryza sativa | G3397 | 23-112 | 3486 | REQDRFLPIANVSRIMKKALPA NAKISKDAKETVQECVSEFISFI TGEASDKCQREKRKTINGDDL LWAMTTLGFEDYVDPLKHYLH KFR | 82 |

TABLE 2-continued

Conserved domains of G481 (TF family: CCAAT-binding) and closely related HAP3 sequences

| SEQ ID NO: | Species from which SEQ ID NO: is derived | Gene ID (GID) | Conserved B domain amino acid coordinates | Conserved B domain SEQ ID NO: | Conserved B domain | Percent ID of conserved B domain to G481 conserved B domain |
|---|---|---|---|---|---|---|
| 1862 | Oryza sativa | G3395 | 19-108 | 3484 | REQDRFLPIANISRIMKKAVPA NGKIAKDAKETLQECVSEFISF VTSEASDKCQKEKRKTINGEDL LFAMGTLGFEEYVDPLKIYLHK YR | 82 |
| 2182 | Zea mays | G3866 | 30-126 | 3677 | REQDRFLPIANISRIMKKAIPAN GKTIPANGKIAKDAKETVQECV SEFISFITSEASDKCQREKRKTIN GDDLLWAMATLGFEDYIEPLK VYLQKYR | 81 |
| 1868 | Oryza sativa | G3398 | 21-110 | 3487 | REQDRFLPIANVSRIMKRALPA NAKISKDAKETVQECVSEFISFI TGEASDKCQREKRKTINGDDL LWAMTTLGFEDYIDPLKLYLH KFR | 81 |
| 1864 | Oryza sativa | G3396 | 21-110 | 3485 | KEQDRFLPIANIGRIMRRAVPE NGKIAKDSKESVQECVSEFISFI TSEASDKCLKEKRKTINGDDLI WSMGTLGFEDYVEPLKLYLRL YR | 77 |
| 1880 | Oryza sativa | G3429 | 40-124 | 3498 | ELPMANLVRLIKKVLPGKAKIG GAAKGLTHDCAVEFVGFVGDE ASEKAKAEHRRTVAPEDYLGS FGDLGFDRYVDPMDAYIHGYR | 42 |
| 2184 | Glycine max | G3873 | 29-118 | 3678 | REQDRFLPIANISRIMKKALPPN GKIAKDAKETVQECVSEFISFV TSEASDKCQREKRKTINGDDLL WAMTTLGFEEYIDPLKVYLAA YR | 86 |
| 2186 | Glycine max | G3874 | 25-114 | 3679 | REQDRYLPIANISRIMKKALPA NGKIAKDAKETVQECVSEFISFI TSEASDKCQREKRKTINGDDLL WAMATLGFEDYMDPLKIYLTR YR | 91 |
|  | Oryza sativa | G3938 | 57-146 |  | KEQDRFLPIANVSRIMKRSLPA NAKISKESKETVQECVSEFISF VTGESDKCQREKRKTINGDDL LWAMTLGFEAYVGPLKSYLN RYR | 76 |
|  | Physcomitrella patens | G3868 | 34-123 |  | REQDRFLPIANVSRIMKKALPS NAKISKDAKETVQECVSEFISFI TGESDKCQREKRKTINGDDLL WAMSLGFEDYVEPLKVYLHK YR | 84 |
|  | Physcomitrella patens | G3870 | 34-123 |  | REQDRFLPIANVSRIMKKALPS NAKISKDAKETVQECVSEFISFI TGEASDKCQREKRKTINGDDL LWAMSLGFEDYVEPLKVYLH KYR | 84 |

TABLE 3

Conserved domains of G928 (TF family: CCAAT-binding) and closely related HAP2 sequences

| SEQ ID NO: | Species from which SEQ ID NO: is derived | Gene ID (GID) | Conserved domain amino acid coordinates | Conserved domain SEQ ID NO: | Conserved domain | Percent ID of conserved domain to G928 conserved domain |
|---|---|---|---|---|---|---|
| 696 | Arabidopsis thaliana | G928 | 179-238 | 2790 | DPVFVNAKQYHAIMRRRQQR AKLEAQNKLIRARKPYLHESR HVHALKRPRGSGGRFLNTK | 100 |
| 700 | Arabidopsis thaliana | G931 | 172-231 | 2792 | fEPVFVNAKQFHAIMRRRQQR AKLEAQNKLIKARKPYLHESR HVHALKRPRGSGGRFLNTK | 95 |
| 2230 | Oryza sativa | G3926 | 164-222 | 3702 | EPIFVNAKQYNAILRRRQTRA KLEAQNKAVKGRKPYLHESR HHHAMKRARGSGGRFLTK | 78 |
| 2224 | Zea mays | G3921 | 148-207 | 3699 | EPIYVNAKQYHAILRRRQTRA KLEAQNKMVKGRKPYLHESR HRHAMKRARGSGGRFLNTK | 80 |
| 2326 | Zea mays | G4264 | 155-214 | 3750 | EPIYVNAKQYHAILRRRQTRA KLEAQNKMVKNRKPYLHESR HRHAMKRARGSGGRFLNTK | 80 |
| 2328 | Zea mays | G4265 | 149-208 | 3751 | EPIYVNAKQYHAILRRRQTRA KLEAQNKMVKGRKPYLHESR HRHAMKRARGSGGRFPHTK | 76 |
| 2334 | Zea mays | G4269 | 103-162 | 3754 | EPIYVNPKQYHGILRRRQLRA KLEAQNKLVRARKPYLHESRH LHAMKRARGSGGRFLNTK | 81 |

TABLE 4

Conserved domains of G1782 (TF family: CCAAT-binding) and closely related HAP2 sequences

| SEQ ID NO: | Species from which SEQ ID NO: is derived | Gene ID (GID) | Conserved domain amino acid coordinates | Conserved domain SEQ ID NO: | Conserved domain | Percent ID of conserved domain to G1782 conserved domain |
|---|---|---|---|---|---|---|
| 1162 | Arabidopsis thaliana | G1782 | 178-237 | 3060 | EPIFVNAKQYHAILRRRKHRA KLEAQNKLIKCRKPYLHESRH LHALKRARGSGGRFLNTK | 100 |
| 950 | Arabidopsis thaliana | G1363 | 171-230 | 2940 | EPIFVNAKQYQAILRRRERRA KLEAQNKLIKVRKPYLHESRH LHALKRVRGSGGRFLNTK | 91 |
| 2222 | Glycine max | G3920 | 149-208 | 3698 | EPVYVNAKQYHGILRRRQSRA KAEIEKKVIKNRKPYLHESRHL HAMRRARGNGGRFLNTK | 76 |
| 2228 | Oryza sativa | G3925 | 138-197 | 3701 | EPIYVNAKQYHAILRRRQLRA KLEAENKLVKNRKPYLHESRH QHAMKRARGTGGRFLNTK | 85 |
| 5116 | Zea mays | G3922 | 171-230 | 5117 | EPIYVNAKQYHAILRRRQTRA KLEAQNKMVKNRKPYLHESR HRHAMKRARGSGGRFLNTK | 86 |
| 2322 | Zea mays | G4262 | 142-201 | 3748 | EPIYVNAKQYHAILRRRQLRA KLEAENKLVKSRKPYLHESRH LHAMKRARGTGGRFLNTK | 86 |

TABLE 4-continued

Conserved domains of G1782 (TF family: CCAAT-binding) and closely related HAP2 sequences

| SEQ ID NO: | Species from which SEQ ID NO: is derived | Gene ID (GID) | Conserved domain amino acid coordinates | Conserved domain SEQ ID NO: | Conserved domain | Percent ID of conserved domain to G1782 conserved domain |
|---|---|---|---|---|---|---|
| 2324 | Zea mays | G4263 | 137-196 | 3749 | EPIYVNAKQYHAILRRRQLRA KLEAENKLVKSRKPYLHESRH LHAMKRARGTGGRFLNTK | 86 |
| 2336 | Zea mays | G4270 | 131-191 | 3755 | EAPIYVNAKQYDAIMRRRCAR AKAERENRLVKGRKPYLHESR HQHALRRPRGSGGRFLNTK | 76 |

TABLE 5

Conserved domains of G28 (TF family: AP2) and closely related AP2 sequences

| SEQ ID NO: | Species from which SEQ ID NO: is derived | Gene ID (GID) | Conserved AP2 domain amino acid coordinates | Conserved AP2 domain SEQ ID NO: | Conserved AP2 domain | Percent ID of conserved AP2 domain to G28 conserved AP2 domain |
|---|---|---|---|---|---|---|
| 2 | Arabidopsis thaliana | G28 | 144-208 | 2373 | KGKHYRGVRQRPWGKFAAEI RDPAKNGARVWLGTFETAED AALAYDRAAFRMRGSRALLN FPLRV | 100 |
| 2054 | Brassica oleracea | G3659 | 130-194 | 3594 | KGKHYRGVRQRPWGKFAAEI RDPAKNGARVWLGTFETAED AALAYDRAAFRMRGSRALLN FPLRV | 100 |
| 752 | Arabidopsis thaliana | G1006 | 113-177 | 2828 | KAKHYRGVRQRPWGKFAAEI RDPAKNGARVWLGTFETAED AALAYDIAAFRMRGSRALLNF PLRV | 98 |
| 2076 | Glycine max | G3717 | 130-194 | 3613 | KGKHYRGVRQRPWGKFAAEI RDPAKNGARVWLGTFETAED AALAYDRAAYRMRGSRALLN FPLRV | 98 |
| 2078 | Glycine max | G3718 | 139-203 | 3614 | KGKHYRGVRQRPWGKFAAEI RDPAKNGARVWLGTFETAED AALAYDRAAYRMRGSRALLN FPLRI | 96 |
| 2056 | Brassica oleracea | G3660 | 119-183 | 3595 | KGKHYRGVRQRPWGKFAAEI RDPAKKGAREWLGTFETAED AALAYDRAAFRMRGSRALLN FPLRV | 96 |
| 2168 | Oryza sativa | G3848 | 149-213 | 3670 | RGKHYRGVRQRPWGKFAAEI RDPAKNGARVWLGTFDTAED AALAYDRAAYRMRGSRALLN FPLRI | 95 |
| 2058 | Zea mays | G3661 | 126-190 | 3596 | RGKHYRGVRQRPWGKFAAEI RDPARNGARVWLGTYDTAED AALAYDRAAYRMRGSRALLN FPLRI | 92 |

TABLE 5-continued

Conserved domains of G28 (TF family: AP2) and closely related AP2 sequences

| SEQ ID NO: | Species from which SEQ ID NO: is derived | Gene ID (GID) | Conserved AP2 domain amino acid coordinates | Conserved AP2 domain SEQ ID NO: | Conserved AP2 domain | Percent ID of conserved AP2 domain to G28 conserved AP2 domain |
|---|---|---|---|---|---|---|
| 2178 | Triticum aestivum | G3864 | 127-191 | 3675 | RGKHFRGVRQRPWGKFAAEI RDPAKNGARVWLGTFDSAED AAVAYDRAAYRMRGSRALLN FPLRI | 90 |
| 2172 | Zea mays | G3856 | 140-204 | 3672 | RGKHYRGVRQRPWGKFAAEI RDPAKNGARVWLGTYDSAED AAVAYDRAAYRMRGSRALLN FPLRI | 90 |
| 4 | Oryza sativa | G3430 | 145-209 | 2374 | RGKHYRGVRQRPWGKFAAEI RDPAKNGARVWLGTFDSAEE AAVAYDRAAYRMRGSRALLN FPLRI | 90 |
| 2158 | Solanum lycopersicum | G3841 | 102-166 | 3665 | KGRHYRGVRQRPWGKFAAEI RDPAKNGARVWLGTYETAEE AAIAYDKAAYRMRGSKAHLN FPHRI | 84 |
| 56 | Arabidopsis thaliana | G22 | 88-152 | 2406 | KGMQYRGVRRRPWGKFAAEI RDPKKNGARVWLGTYETPED AAVAYDRAAFQLRGSKAKLN FPHLI | 81 |

TABLE 6

Conserved domains of G47 (TF family: AP2) and closely related AP2 sequences

| SEQ ID NO: | Species from which SEQ ID NO: is derived | Gene ID (GID) | Conserved AP2 domain amino acid coordinates | Conserved AP2 domain SEQ ID NO: | Conserved AP2 domain | Percent ID of conserved AP2 domain to G47 conserved AP2 domain |
|---|---|---|---|---|---|---|
| 6 | Arabidopsis thaliana | G47 | 10-75 | 2375 | SQSKYKGIRRRKWGKWVSEIR VPGTRDRLWLGSFSTAEGAAV AHDVAFFCLHQPDSLESLNFP HLL | 100 |
| 8 | Arabidopsis thaliana | G2133 | 10-77 | 2376 | DQSKYKGIRRRKWGKWVSEI RVPGTRQRLWLGSFSTAEGAA VAHDVAFYCLHRPSSLDDESF NFPHLL | 89 |
| 2046 | Oryza sativa | G3649 | 15-87 | 3590 | EMMRYRGVRRRWGKWVSE IRVPGTRERLWLGSYATAEAA AVAHDAAVCLLRLGGGRRAA AGGGGGLNFPARA | 79 |
| 2038 | Oryza sativa | G3644 | 52-122 | 3586 | ERCRYRGVRRRRWGKWVSEI RVPGTRERLWLGSYATPEAAA VAHDTAVYFLRGGAGDGGGG GATLNFPERA | 72 |
| 2036 | Glycine max | G3643 | 13-78 | 3585 | TNNKLKGVRRRKWGKWVSEI RVPGTQERLWLGTYATPEAA AVAHDVAVYCLSRPSSLDKLN FPETL | 68 |

TABLE 6-continued

Conserved domains of G47 (TF family: AP2) and closely related AP2 sequences

| SEQ ID NO: | Species from which SEQ ID NO: is derived | Gene ID (GID) | Conserved AP2 domain amino acid coordinates | Conserved AP2 domain SEQ ID NO: | Conserved AP2 domain | Percent ID of conserved AP2 domain to G47 conserved AP2 domain |
|---|---|---|---|---|---|---|
| 2048 | Zea mays | G3650 | 75-139 | 3591 | RRCRYGVRRRAWGKWVSEI RVPGTRERLWLGSYAAPEAA AVAHDAAACLLRGCAGRRLN FPGRA | 65 |

TABLE 7

Conserved domains of G1792 (TF family: AP2) and closely related AP2 sequences

| SEQ ID NO: | Species from which SEQ ID NO: is derived | Gene ID (GID) | Conserved AP2 and EDLL domain amino acid coordinates | Conserved AP2 and EDLL domain SEQ ID NO: | AP2 and EDLL conserved domains | Percent ID of conserved AP2 or EDLL domain to G1792 conserved AP2 or EDLL domain, respectively |
|---|---|---|---|---|---|---|
| 24 | Arabidopsis thaliana | G1792 | AP2: 16-80 | 2386 | AP2: KQARFRGVRRRPWGKFAAEIR DPSRNGARLWLGTFETAEEAA RAYDRAAFNLRGHLAILNFPN EY | 100 |
|  |  |  | EDLL: 117-132 | 5128 | EDLL: VFEFEYLDDKVLEELL | 100 |
| 26 | Arabidopsis thaliana | G1795 | AP2: 11-75 | 2387 | AP2: EHGKYRGVRRRPWGKYAAEI RDSRKHGERVWLGTFDTAEE AARAYDQAAYSMRGQAAILN FPHEY | 69 |
|  |  |  | EDLL: 104-119 | 5129 | EDLL: VFEFEYLDDSVLEELL | 93 |
| 66 | Arabidopsis thaliana | G30 | AP2: 16-80 | 2411 | AP2: EQGKYRGVRRRPWGKYAAEI RDSRKHGERVWLGTFDTAED AARAYDRAAYSMRGKAAILN FPHEY | 70 |
|  |  |  | EDLL: 100-115 | 5130 | EDLL: VFEFEYLDDSVLDELL | 87 |
| 1850 | Oryza sativa | G3383 | AP2: 9-73 | 3475 | AP2: TATKYRGVRRRPWGKFAAEIR DPERGGARVWLGTFDTAEEA ARAYDRAAYAQRGAAAVLNF PAAA | 79 |
|  |  |  | EDLL: 101-116 | 5131 | EDLL: KIEFEYLDDKVLDDLL | 85 |
| 1172 | Arabidopsis thaliana | G1791 | AP2: 10-74 | 3064 | AP2: NEMKYRGVRKRPWGKYAAEI RDSARHGARVWLGTFNTAED AARAYDRAAFGMRGQRAILN FPHEY | 73 |
|  |  |  | EDLL: 108-123 | 5132 | EDLL: VIEFEYLDDSLLEELL | 81 |

TABLE 7-continued

Conserved domains of G1792 (TF family: AP2) and closely related AP2 sequences

| SEQ ID NO: | Species from which SEQ ID NO: is derived | Gene ID (GID) | Conserved AP2 and EDLL domain amino acid coordinates | Conserved AP2 and EDLL domain SEQ ID NO: | AP2 and EDLL conserved domains | Percent ID of conserved AP2 or EDLL domain to G1792 conserved AP2 or EDLL domain, respectively |
|---|---|---|---|---|---|---|
| 1984 | Glycine max | G3519 | AP2: 13-77 | 3558 | AP2: CEVRYRGIRRRPWGKFAAEIR DPTRKGTRIWLGTFDTAEQAA RAYDAAAFHFRGHRAILNFPN EY | 78 |
| | | | EDLL: 128-143 | 5133 | EDLL: TFELEYLDNKLLEELL | 80 |
| 1848 | Oryza sativa | G3381 | AP2: 14-78 | 3474 | AP2: LVAKYRGVRRRPWGKFAAEI RDSSRHGVRVWLGTFDTAEE AARAYDRSAYSMRGANAVLN FPADA | 76 |
| | | | EDLL: 109-124 | 5134 | EDLL: PIEFEYLDDHVLQEML | 78 |
| 2104 | Oryza sativa | G3737 | AP2: 8-72 | 3627 | AP2: AASKYRGVRRRPWGKFAAEI RDPERGGSRVWLGTFDTAEEA ARAYDRAAFAMKGAMAVLN FPGRT | 76 |
| | | | EDLL: 101-116 | 5135 | EDLL: KVELVYLDDKVLDELL | 78 |
| 1976 | Oryza sativa | G3515 | AP2: 11-75 | 3554 | AP2: SSSSYRGVRKRPWGKFAAEIR DPERGGARVWLGTFDTAEEA ARAYDRAAFAMKGATAMLN FPGDH | 75 |
| | | | EDLL: 116-131 | 5136 | EDLL: KVELECLDDKVLEDLL | 78 |
| 1978 | Zea mays | G3516 | AP2: 6-70 | 3555 | AP2: KEGKYRGVRKRPWGKFAAEI RDPERGGSRVWLGTFDTAEEA ARAYDRAAFAMKGATAVLNF PASG | 74 |
| | | | EDLL: 107-122 | 5137 | EDLL: KVELECLDDRVLEELL | 78 |
| 1986 | Glycine max | G3520 | AP2: 14-78 | 3559 | AP2: EEPRYRGVRRRPWGKFAAEIR DPARHGARVWLGTFLTAEEA ARAYDRAAYEMRGALAVLNF PNEY | 80 |
| | | | EDLL: 109-124 | 5138 | EDLL: VIEFECLDDKLLEDLL | 75 |
| 1980 | Zea mays | G3517 | AP2: 13-77 | 3556 | AP2: EPTKYRGVRRRPWGKYAAEIR DSSRHGVRIWLGTFDTAEEAA RAYDRSANSMRGANAVLNFP EDA | 72 |
| | | | EDLL: 103-118 | 5139 | EDLL: VIEFEYLDDEVLQEML | 75 |

TABLE 7-continued

Conserved domains of G1792 (TF family: AP2) and closely related AP2 sequences

| SEQ ID NO: | Species from which SEQ ID NO: is derived | Gene ID (GID) | Conserved AP2 and EDLL domain amino acid coordinates | Conserved AP2 and EDLL domain SEQ ID NO: | AP2 and EDLL conserved domains | Percent ID of conserved AP2 or EDLL domain to G1792 conserved AP2 or EDLL domain, respectively |
|---|---|---|---|---|---|---|
| 1982 | Glycine max | G3518 | AP2: 13-77 | 3557 | AP2: VEVRYRGIRRRPWGKFAAEIR DPTRKGTRIWLGTFDTAEQAA RAYDAAAFHFRGHRAILNFPN EY | 78 |
|  |  |  | EDLL: 135-150 | 5140 | EDLL: TFELEYFDNKLLEELL | 73 |
| 2106 | Zea mays | G3739 | AP2: 13-77 | 3628 | AP2: EPTKYRGVRRRPWGKYAAEIR DSSRHGVRIWLGTFDTAEEAA RAYDRSAYSMRGANAVLNFP EDA | 72 |
|  |  |  | EDLL: 107-122 | 5141 | EDLL: VIELEYLDDEVLQEML | 68 |
| 1846 | Oryza sativa | G3380 | AP2: 18-82 | 3473 | AP2: ETTKYRGVRRRPSGKFAAEIR DSSRQSVRVWLGTFDTAEEAA RAYDRAAYAMRGHLAVLNFP AEA | 77 |
|  |  |  | EDLL: 103-118 | 5142 | EDLL: VIELECLDDQVLQEML | 62 |
| 2132 | Zea mays | G3794 | AP2: 6-70 | 3641 | AP2: EPTKYRGVRRRPSGKFAAEIR DSSRQSVRMWLGTFDTAEEA ARAYDRAAYAMRGQIAVLNF PAEA | 73 |
|  |  |  | EDLL: 102-117 | 5143 | EDLL: VIELECLDDQVLQEML | 62 |

TABLE 8

Conserved domains of G913 (TF family: AP2) and closely related AP2 sequences

| SEQ ID NO: | Species from which SEQ ID NO: is derived | Gene ID (GID) | Conserved AP2 domain amino acid coordinates | Conserved AP2 domain SEQ ID NO: | Conserved AP2 domain | Percent ID of conserved AP2 domain to G913 conserved AP2 domain |
|---|---|---|---|---|---|---|
|  | Arabidopsis thaliana | G913 | 62-128 | 2781 | HSIFRGIRLRNGKWVSEIRE PRKTTRIWLGTYPVPEMA AAAYDVAALALKGPDAVL NFPGLALTYVA | 100 |
|  | Arabidopsis thaliana | G2514 | 16-82 | 3277 | DPVYRGIRCRSGKWVSEIR EPRKTTRIWLGTYPMAEM AAAAYDVAAMALKGREA VLNFPGSVGSYPV | 84 |
|  | Arabidopsis thaliana | G976 | 87-153 | 2806 | NPVYRGIRCRSGKWVSEIR EPKKTTRVWLGTYPTPEM AAAAYDVAALALKGGDT LLNFPDSLGSYPI | 82 |

TABLE 8-continued

Conserved domains of G913 (TF family: AP2) and closely related AP2 sequences

| SEQ ID NO: | Species from which SEQ ID NO: is derived | Gene ID (GID) | Conserved AP2 domain amino acid coordinates | Conserved AP2 domain SEQ ID NO: | Conserved AP2 domain | Percent ID of conserved AP2 domain to G913 conserved AP2 domain |
|---|---|---|---|---|---|---|
| | Arabidopsis thaliana | G1753 | 12-80 | 3046 | HPLYRGVRQRKNSNKWVS EIREPRKPNRIWLGTFSTPE MAAIAYDVAALALKGSQA ELNFPNSVSSLPA | 70 |

TABLE 9

Conserved domains of G1073 (TF family: AT-hook) and closely related AT-hook sequences

| SEQ ID NO: | Species from which SEQ ID NO: is derived | Gene ID (GID) | Conserved AT-hook and 2nd conserved domain amino acid coordinates | AT-hook and 2nd conserved domain SEQ ID NO: | AT-hook and 2nd conserved domains | Percent ID of conserved AT-hook or 2nd domain to G1073 AT-hook or 2nd conserved domains, respectively |
|---|---|---|---|---|---|---|
| 18 | Arabidopsis thaliana | G1073 | AT-hook: 63-71 | 2382 | AT-hook: RRPRGRPAG | 100 |
| | | | 2nd domain: 71-216 | 2383 | 2nd conserved domain: GSKNKPKPPTIITRDSPNVLRS HVLEVTSGSDISEAVSTYATR RGCGVCIISGTGAVTNVTIRQ PAAPAGGGVITLHGRFDILSL TGTALPPPAPPGAGGLTVYLA GGQGQVVGGNVAGSLIASGP VVLMAASFANAVYDRLPIEE | 100 |
| 5145 | Oryza sativa | G3406 | AT-hook: 82-90 | 5146 | AT-hook: RRPRGRPPG | 100 |
| | | | 2nd domain: 90-232 | 5147 | 2nd conserved domain: GSKNKPKPPVIITRESANTLRA HILEVGSGCDVFECVSTYARR RQRGVCVLSGSGVVTNVTLR QPSAPAGAVVSLHGRFEILSL SGSFLPPPAPPGATSLTIFLAG GQGQVVGGNVVGALYAAGP VIVIAASFANVAYERLPL | 70 |
| 1870 | Oryza sativa | G3399 | AT-hook: 99-107 | 3488 | AT-hook: RRPRGRPPG | 100 |
| | | | 2nd domain: 107-253 | 3489 | 2nd conserved domain: GSKNKPKPPIIVTRDSPNALHS HVLEVAGGADVVDCVAEYA RRRGRGVCVLSGGGAVVNV ALRQPGASPPGSMVATLRGR FEILSLTGTVLPPPAPPGASGL TVFLSGGQGQVIGGSVVGPL VAAGPVVLMAASFANAVYE RLPLEG | 71 |
| 798 | Arabidopsis thaliana | G1067 | AT-hook: 86-94 | 2852 | AT-hook: KRPRGRPPG | 85 |
| | | | 2nd domain: | 2853 | 2nd conserved domain: GSKNKAKPPIIVTRDSPNALR | 71 |

TABLE 9-continued

Conserved domains of G1073 (TF family: AT-hook) and closely related AT-hook sequences

| SEQ ID NO: | Species from which SEQ ID NO: is derived | Gene ID (GID) | Conserved AT-hook and 2nd conserved domain amino acid coordinates | AT-hook and 2nd conserved domain SEQ ID NO: | AT-hook and 2nd conserved domains | Percent ID of conserved AT-hook or 2nd domain to G1073 AT-hook or 2nd conserved domains, respectively |
|---|---|---|---|---|---|---|
| | | | 94-247 | | SHVLEVSPGADIVESVSTYAR RRGRGVSVLGGNGTVSNVTL RQPVTPGNGGGVSGGGGVVT LHGRFEILSLTGTVLPPPAPPG AGGLSIFLAGGQGQVVGGSV VAPLIASAPVILMAASFSNAV FERLPIEE | |
| 1918 | Glycine max | G3459 | AT-hook: 77-85 | 3523 | AT-hook: RRPRGRPPG | 100 |
| | | | 2nd domain: 85-228 | 3524 | 2nd conserved domain: GSKNKPKPPVIITRESANTLRA HILEVGSGSDVFDCVTAYAR RRQRGICVLSGSGTVTNVSLR QPAAAGAVVTLHGRFEILSLS GSFLPPPAPPGATSLTIYLAGG QGQVVGGNVIGELTAAGPVI VIAASFTNVAYERLPLEE | 67 |
| 1872 | Oryza sativa | G3400 | AT-hook: 83-91 | 3490 | AT-hook: RRPRGRPLG | 100 |
| | | | 2nd domain: 91-237 | 3491 | 2nd conserved domain: GSKNKPKPPIIVTRDSPNAFHS HVLEVAAGTDIVECVCEFAR RRGRGVSVLSGGGAVANVAL RQPGASPPGSLVATMRGQFEI LSLTGTVLPPPAPPSASGLTVF LSGGQGQVVGGSVAGQLIAA GPVFLMAASFANAVYERLPL DG | 69 |
| 1694 | Arabidopsis thaliana | G2789 | AT-hook: 59-67 | 3364 | AT-hook: RRPRGRPAG | 100 |
| | | | 2nd domain: 67-208 | 3365 | 2nd conserved domain: GSKNKPKAPIIVTRDSANAFR CHVMEITNACDVMESLAVFA RRRQRGVCVLTGNGAVTNVT VRQPGGGVVSLHGRFEILSLS GSFLPPPAPPAASGLKVYLAG GQGQVIGGSVVGPLTASSPVV VMAASFGNASYERLPLEE | 65 |
| 1920 | Glycine max | G3460 | AT-hook: 74-82 | 3525 | AT-hook: RRPRGRPSG | 100 |
| | | | 2nd domain: 82-225 | 3526 | 2nd conserved domain: GSKNKPKPPVIITRESANTLRA HILEVGSGSDVFDCVTAYAR RRQRGICVLSGSGTVTNVSLR QPAAAGAVVRLHGRFEILSLS GSFLPPPAPPGATSLTIYLAGG QGQVVGGNVVGELTAAGPVI VIAASFTNVAYERLPLEE | 67 |
| 1116 | Arabidopsis thaliana | G1667 | AT-hook: 53-61 | 3035 | AT-hook: KRPRGRPAG | 85 |
| | | | 2nd domain: 61-204 | 5148 | 2nd conserved domain: GSKNKPKPPIIVTHDSPNSLRA NAVEISSGCDICETLSDFARR KQRGLCILSANGCVTNVTLR | 65 |

TABLE 9-continued

Conserved domains of G1073 (TF family: AT-hook) and closely related AT-hook sequences

| SEQ ID NO: | Species from which SEQ ID NO: is derived | Gene ID (GID) | Conserved AT-hook and 2nd conserved domain amino acid coordinates | AT-hook and 2nd conserved domain SEQ ID NO: | AT-hook and 2nd conserved domains | Percent ID of conserved AT-hook or 2nd domain to G1073 AT-hook or 2nd conserved domains, respectively |
|---|---|---|---|---|---|---|
| | | | | | QPASSGAIVTLHGRYEILSLLG SILPPPAPLGITGLTIYLAGPQ GQVVGGGVVGGLIASGPVVL MAASFMNAVFDRLPMDD | |
| 1424 | Arabidopsis thaliana | G2156 | AT-hook: 72-80 | 3205 | AT-hook: KRPRGRPPG | 85 |
| | | | 2nd domain: 80-232 | 3206 | 2nd conserved domain: GSKNKPKPPVIVTRDSPNVLR SHVLEVSSGADIVESVTTYAR RRGRGVSILSGNGTVANVSLR QPATTAAHGANGGTGGVVA LHGRFEILSLTGTVLPPPAPPG SGGLSIFLSGVQGQVIGGNVV APLVASGPVILMAASFSNATF ERLPLED | 68 |
| 1916 | Glycine max | G3456 | AT-hook: 44-52 | 3521 | AT-hook: RRPRGRPPG | 100 |
| | | | 2nd domain: 52-195 | 3522 | 2nd conserved domain: GSRNKPKPPIFVTRDSPNALR SHVMEIAVGADIADCVAQFA RRRQRGVSILSGSGTVVNVNL RQPTAPGAVMALHGRFDILSL TGSFLPGPSPPGATGLTIYLAG GQGQIVGGGVVGPLVAAGPV LVMAATFSNATYERLPLED | 64 |
| 1876 | Oryza sativa | G3407 | AT-hook: 63-71 | 3494 | AT-hook: RRPRGRPPG | 100 |
| | | | 2nd domain: 71-220 | 3495 | 2nd conserved domain: GSKNKPKPPVIITRESANALR AHILEVAAGCDVFEALTAYA RRRQRGVCVLSAAGTVANVT LRQPQSAQPGPASPAVATLH GRFEILSLAGSFLPPPAPPGAT SLAAFLAGGQGQVVGGSVAG ALIAAGPVVVVAASFSNVAY ERLPLED | 64 |
| 1874 | Oryza sativa | G3401 | AT-hook: 35-43 | 3492 | AT-hook: RRPRGRPPG | 100 |
| | | | 2nd domain: 43-186 | 3493 | 2nd conserved domain: GSKNKPKPPIFVTRDSPNALR SHVMEVAGGADVAESIAHFA RRRQRGVCVLSGAGTVTDVA LRQPAAPSAVVALRGRFEILS LTGTFLPGPAPPGSTGLTVYL AGGQGQVVGGSVVGTLTAA GPVMVIASTFANATYERLPLD Q | 64 |
| 1420 | Arabidopsis thaliana | G2153 | AT-hook: 80-88 | 3202 | AT-hook: RRPRGRPAG | 100 |
| | | | 2nd domain: 88-239 | 3203 | 2nd conserved domain: GSKNKPKPPIFVTRDSPNALK SHVMEIASGTDVIETLATFAR RRQRGICILSGNGTVANVTLR QPSTAAVAAAPGGAAVLALQ | 63 |

TABLE 9-continued

Conserved domains of G1073 (TF family: AT-hook) and closely related AT-hook sequences

| SEQ ID NO: | Species from which SEQ ID NO: is derived | Gene ID (GID) | Conserved AT-hook and 2nd conserved domain amino acid coordinates | AT-hook and 2nd conserved domain SEQ ID NO: | AT-hook and 2nd conserved domains | Percent ID of conserved AT-hook or 2nd domain to G1073 AT-hook or 2nd conserved domains, respectively |
|---|---|---|---|---|---|---|
| | | | | | GRFEILSLTGSFLPGPAPPGST GLTIYLAGGQGQVVGGSVVG PLMAAGPVMLIAATFSNATY ERLPLEE | |
| 802 | Arabidopsis thaliana | G1069 | AT-hook: 67-75 | 2855 | AT-hook: RRPRGRPPG | 100 |
| | | | 2nd domain: 75-218 | 5149 | 2nd conserved domain: GSKNKPKAPIFVTRDSPNALR SHVLEISDGSDVADTIAHFSR RRQRGVCVLSGTGSVANVTL RQAAAPGGVVSLQGRFEILSL TGAFLPGPSPPGSTGLTVYLA GVQGQVVGGSVVGPLLAIGS VMVIAATFSNATYERLPMEE | 63 |
| 2034 | Oryza sativa | G3556 | AT-hook: 45-53 | 3583 | AT-hook: RRPRGRPPG | 100 |
| | | | 2nd domain: 53-196 | 3584 | 2nd conserved domain: GSKNKPKPPVVVTRESPNAM RSHVLEIASGADIVEAIAGFSR RRQRGVSVLSGSGAVTNVTL RQPAGTGAAAVALRGRFEILS MSGAFLPAPAPPGATGLAVY LAGGQGQVVGGSVMGELIAS GPVMVIAATFGNATYERLPL D | 64 |
| 1426 | Arabidopsis thaliana | G2157 | AT-hook: 88-96 | 3207 | AT-hook: RRPRGRPPG | 100 |
| | | | 2nd domain: 96-240 | 3208 | 2nd conserved domain: GSKNKPKSPVVVTKESPNSLQ SHVLEIATGADVAESLNAFAR RRGRGVSVLSGSGLVTNVTL RQPAASGVVSLRGQFEILSM CGAFLPTSGSPAAAAGLTIYL AGAQGQVVGGGVAGPLIASG PVIVIAATFCNATYERLPIEE | 61 |
| 1878 | Oryza sativa | G3408 | AT-hook: 82-90 | 3496 | AT-hook: KKRRGRPPG | 57 |
| | | | 2nd domain: 90-247 | 3497 | 2nd conserved domain: GSKNKPKPPVVITREAEPAAA MRPHVIEIPGGRDVAEALARF SSRRNLGICVLAGTGAVANV SLRHPSPGVPGSAPAAIVFHG RYEILSLSATFLPPAMSSVAPQ AAVAAAGLSISLAGPHGQIVG GAVAGPLYAATTVVVVAAA FTNPTFHRLPADD | 45 |
| | Oryza sativa | G3403 | AT hook: 58-66 | | AT hook RRPRGRPPG | 88 |
| | | | 2nd domain: 66-209 | | 2nd conserved domain: GSKNKPKPPIFVTRDSPNALR SHVMEVAGGADVADAIAQFS RRRQRGVCVLSGAGTVANV ALRQPSAPGAVVALHGRFEIL SLTGTFLPGPAPPGSTGLTVY | 67 |

TABLE 9-continued

Conserved domains of G1073 (TF family: AT-hook) and closely related AT-hook sequences

| SEQ ID NO: | Species from which SEQ ID NO: is derived | Gene ID (GID) | Conserved AT-hook and 2nd conserved domain amino acid coordinates | AT-hook and 2nd conserved domain SEQ ID NO: | AT-hook and 2nd conserved domains | Percent ID of conserved AT-hook or 2nd domain to G1073 AT-hook or 2nd conserved domains, respectively |
|---|---|---|---|---|---|---|
| | | | | | LAGGQGQVVGGSVVGSLIAA GPVMVIASTFANATYERLPLE E | |
| | Glycine max | G3462 | | 82-90 | AT hook RRPRGRPAG | 100 |
| | | | 17882 | 90-233 | 2nd conserved domain: GSKNKPKPPIVIIFLSPNALRS HVLEIASGRDVAESIAAFANR RHRGVSVLSGSGIVANVTLR QPAAPAGVITLHGRFEILSLSG AFLPSPSPSGATGLTVYLAGG QGQVVGGNVAGSLVASGPV MVIAATFANATYERLPLED | 69 |
| | Glycine max | G3932 | | 41-49 | AT hook RRPRGRPPG | 88 |
| | | | | 49-192 | 2nd conserved domain: GSKNKPKPPIFVTRDSPNSLRS HVMEVAGGADVAESVAQFA RRRQRGVCVLSGSGSVANVT LRQPSAPGAVVALHGRFEILS LTGAFLPGPAPPGATGLTVYL AGGQGQVVGGSVVGSLVAA GPVMVIAATFANATYERLPLE E | 69 |

TABLE 10

Conserved domains of G1274 (TF family: WRKY) and closely related WRKY sequences

| SEQ ID NO: | Species from which SEQ ID NO: is derived | Gene ID (GID) | Conserved WRKY domain amino acid coordinates | Conserved WRKY domain SEQ ID NO: | Conserved WRKY domain | Percent ID of conserved WRKY domain to G1274 conserved WRKY domain |
|---|---|---|---|---|---|---|
| 20 | Arabidopsis thaliana | G1274 | 110-166 | 2384 | DDGFKWRKYGKKSVKNNI NKRNYYKCSSEGCSVKKR VERDGDDAAYVITTYEGVH NH | 100 |
| 2090 | Glycine max | G3724 | 107-163 | 3620 | DDGYKWRKYGKKSVKSSP NLRNYYKCSSGGCSVKKR VERDRDDYSYVITTYEGVH NH | 84 |
| 2098 | Zea mays | G3728 | 108-164 | 3624 | DDGFKWRKYGKKAVKNSP NPRNYYRCSSEGCGVKKRV ERDRDDPRYVITTYDGVHN H | 82 |

TABLE 10-continued

Conserved domains of G1274 (TF family: WRKY) and closely related WRKY sequences

| SEQ ID NO: | Species from which SEQ ID NO: is derived | Gene ID (GID) | Conserved WRKY domain amino acid coordinates | Conserved WRKY domain SEQ ID NO: | Conserved WRKY domain | Percent ID of conserved WRKY domain to G1274 conserved WRKY domain |
|---|---|---|---|---|---|---|
| 2136 | Zea mays | G3804 | 108-164 | 3643 | DDGFKWRKYGKKAVKNSP NPRNYYRCSSEGCGVKKRV ERDRDDPRYVITTYDGVHN H | 82 |
| 2134 | Glycine max | G3803 | 111-167 | 3642 | DDGYKWRKYGKKTVKNN PNPRNYYKCSGEGCNVKK RVERDRDDSNYVLTTYDG VHNH | 80 |
| 2096 | Zea mays | G3727 | 102-158 | 3623 | DDGFKWRKYGKKAVKSSP NPRNYYRCSSEGCGVKKRV ERDRDDPRYVITTYDGVHN H | 80 |
| 2084 | Oryza sativa | G3721 | 96-152 | 3617 | DDGFKWRKYGKKAVKNSP NPRNYYRCSTEGCNVKKR VERDREDHRYVITTYDGVH NH | 78 |
| 2086 | Zea mays | G3722 | 129-185 | 3618 | DDGYKWRKYGKKSVKNSP NPRNYYRCSTEGCNVKKR VERDRDDPRYVVTMYEGV HNH | 78 |
| 2094 | Oryza sativa | G3726 | 135-191 | 3622 | DDGYKWRKYGKKSVKNSP NPRNYYRCSTEGCNVKKR VERDKDDPSYVVTTYEGTH NH | 78 |
| 2082 | Zea mays | G3720 | 135-191 | 3616 | DDGYKWRKYGKKSVKNSP NPRNYYRCSTEGCNVKKR VERDKDDPSYVVTTYEGM HNH | 78 |
| 2088 | Glycine max | G3723 | 112-168 | 3619 | DDGYKWRKYGKKTVKSSP NPRNYYKCSGEGCDVKKR VERDRDDSNYVLTTYDGV HNH | 77 |
| 2080 | Arabidopsis thaliana | G1275 | 113-169 | 2908 | DDGFKWRKYGKKMVKNSP HPRNYYKCSVDGCPVKKR VERDRDDPSFVITTYEGSHN H | 77 |
| 2102 | Oryza sativa | G3730 | 107-163 | 3626 | DDGFKWRKYGKKAVKSSP NPRNYYRCSAAGCGVKKR VERDGDDPRYVVTTYDGV HNH | 77 |
| 2080 | Zea mays | G3719 | 98-154 | 3615 | DDGFKWRKYGKKTVKSSP NPRNYYRCSAEGCGVKKR VERDSDDPRYVVTTYDGV HNH | 77 |
| 2092 | Oryza sativa | G3725 | 158-214 | 3621 | DDGYKWRKYGKKSVKNSP NPRNYYRCSTEGCNVKKR VERDKNDPRYVVTMYEGI HNH | 75 |
| 2100 | Oryza sativa | G3729 | 137-193 | 3625 | DDGYRWRKYGKKMVKNS PNPRNYYRCSSEGCRVKKR VERARDDARFVVTTYDGV HNH | 75 |

TABLE 11

Conserved domains of G1988 (TF family: Z-CONSTANS-like) and closely related Z-CO-like sequences

| SEQ ID NO: | Species from which SEQ ID NO: is derived | Gene ID (GID) | Conserved B-box domain amino acid coordinates | Conserved B-box domain SEQ ID NO: | Conserved B-box domain | Percent ID of conserved B-box domain to G1988 conserved B-box domain |
|---|---|---|---|---|---|---|
| 30 | Arabidopsis thaliana | G1988 | 5-50 | 2389 | CELCGAEADLHCAADSAFLCRS CDAKFHASNFLFARHFRRVICP NC | 100 |
| 2348 | Zea mays | G4297 | 14-55 | 3761 | CELCGGAAAVHCAADSAFLCP RCDAKVHGANFLASRHVRRRL | 70 |
| 2262 | Oryza sativa | G4012 | 15-56 | 3718 | CELCGGVAAVHCAADSAFLCL VCDDKVHGANFLASRHRRRRL | 67 |
| 2350 | Oryza sativa | G4298 | 15-56 | 3762 | CELCGGVAAVHCAADSAFLCL VCDDKVHGANFLASRHPRRRW | 67 |
| 2250 | Zea mays | G4000 | 20-61 | 3712 | CELCGGAAAVHCAADSAFLCL RCDAKVHGANFLASRHVRRRL | 70 |
| 2260 | Oryza sativa | G4011 | 8-49 | 3717 | CALCGAAAAVHCEADAAFLCA ACDAKVHGANFLASRHHRRRV | 65 |
| 2254 | Glycine max | G4005 | 6-51 | 3714 | CELCDQQASLYCPSDSAFLCSD CDAAVHAANFLVARHLRRLLC SKC | 60 |
| 2252 | Glycine max | G4004 | 6-51 | 3713 | CELCHQLASLYCPSDSAFLCFH CDAAVHAANFLVARHLRRLLC SKC | 60 |
| 2256 | Citrus sinensis | G4007 | 5-50 | 3715 | CELCSQEAALHCASDEAFLCFD CDDRVHKANFLVARHVRQTLC SQC | 58 |
| 2352 | Solanum lycopersicum | G4299 | 9-54 | 3763 | CELCNDQAALFCPSDSAFLCFH CDAKVHQANFLVARHLRLTLC SHC | 58 |
| 2258 | Populus trichocarpa | G4009 | 6-51 | 3716 | CELCKGEAGVYCDSDAAYLCF DCDSNVHNANFLVARHIRRVIC SGC | 56 |

TABLE 12

Conserved domains of G1760 (TF family: MADS) and closely related MADS box sequences

| SEQ ID NO: | Species from which SEQ ID NO: is derived | Gene ID (GID) | Conserved MADS DNA binding domain amino acid coordinates | Conserved MADS DNA binding domain SEQ ID NO: | Conserved MADS DNA binding domain | Percent ID of conserved MADS DNA binding domain to G1760 conserved MADS DNA binding domain |
|---|---|---|---|---|---|---|
| 22 | Arabidopsis thaliana | G1760 | 2-57 | 2385 | GRGKIVIQRIDDSTSRQV TFSKRRKGLIKKAKELA ILCDAEVGLIIFSSTGKL YDF | 100 |

TABLE 12-continued

Conserved domains of G1760 (TF family: MADS) and closely related MADS box sequences

| SEQ ID NO: | Species from which SEQ ID NO: is derived | Gene ID (GID) | Conserved MADS DNA binding domain amino acid coordinates | Conserved MADS DNA binding domain SEQ ID NO: | Conserved MADS DNA binding domain | Percent ID of conserved MADS DNA binding domain to G1760 conserved MADS DNA binding domain |
|---|---|---|---|---|---|---|
| 110 | Arabidopsis thaliana | G152 | 2-57 | 2433 | GRGKIVIQKIDDSTSRQV TFSKRRKGLIKKAKELA ILCDAEVCLIIFSNTDKL YDF | 92 |
| 5162 | Antirrhinum majus | G3982 | 2-57 | 5163 | GRGKIVIQRIDKSTSRQV TFSKRRSGLLKKAKELA ILCDAEVGVVIFSSTGKL YEF | 89 |
| 1950 | Glycine max | G3485 | 2-57 | 3541 | GRGKIVIRRIDNSTSRQV TFSKRRNGLLKKAKELA ILCDAEVGVMIFSSTGK LYDF | 89 |
| 2246 | Glycine max | G3980 | 2-57 | 3710 | GRGKIVIRRIDNSTSRQV TFSKRRNGLLKKAKELA ILCDAEVGVMIFSSTGK LYDF | 89 |
| 2248 | Glycine max | G3981 | 2-57 | 3711 | GRGKIVIRRIDNSTSRQV TFSKRRNGLLKKAKELA ILCDAEVGVMIFSSTGK LYDF | 89 |
| 112 | Arabidopsis thaliana | G153 | 2-57 | 2434 | GRGKIVIRRIDNSTSRQV TFSKRRSGLLKKAKELSI LCDAEVGVIIFSSTGKLY DY | 87 |
| 640 | Arabidopsis thaliana | G860 | 2-57 | 2756 | GRGKIAIKRINNSTSRQV TFSKRRNGLLKKAKELA ILCDAEVGVIIFSSTGRL YDF | 85 |
| 1938 | Oryza sativa | G3479 | 2-57 | 3535 | GRGKIVIRRIDNSTSRQV TFSKRRNGIFKKAKELAI LCDAEVGLVIFSSTGRL YEY | 83 |
| 1940 | Oryza sativa | G3480 | 2-57 | 3536 | GRGKIVIRRIDNSTSRQV TFSKRRNGIFKKAKELAI LCDAEVGLMIFSSTGRL YEY | 83 |
| 1942 | Oryza sativa | G3481 | 2-57 | 3537 | GRGKIVIRRIDNSTSRQV TFSKRRNGLLKKAKELS ILCDAEVGLVVFSSTGR LYEF | 83 |
| 1956 | Zea mays | G3489 | 2-57 | 3544 | GRGKIVIRRIDNSTSRQV TFSKRRNGIFKKAKELAI LCDAEVGLVIFSSTGRL YEY | 83 |
| 1948 | Glycine max | G3484 | 2-57 | 3540 | GRGKIAIRRIDNSTSRQV TFSKRRNGLLKKARELS ILCDAEVGLMVFSSTGK LYDY | 82 |
| 1952 | Zea mays | G3487 | 2-57 | 3542 | GRGKIEIKRIDNATSRQV TFSKRRGGLFKKAKELA ILCDAEVGLVVFSSTGR LYHF | 82 |

TABLE 12-continued

Conserved domains of G1760 (TF family: MADS) and closely related MADS box sequences

| SEQ ID NO: | Species from which SEQ ID NO: is derived | Gene ID (GID) | Conserved MADS DNA binding domain amino acid coordinates | Conserved MADS DNA binding domain SEQ ID NO: | Conserved MADS DNA binding domain | Percent ID of conserved MADS DNA binding domain to G1760 conserved MADS DNA binding domain |
|---|---|---|---|---|---|---|
| 1954 | Zea mays | G3488 | 2-57 | 3543 | GRGKIVIRRIDNSTSRQV TFSKRRNGIFKKARELAI LCDAEVGLVIFSSTGRL YEY | 82 |
| 1946 | Oryza sativa | G3483 | 2-57 | 3539 | GRGKIEIKRIDNATSRQV TFSKRRSGLFKKARELSI LCDAEVGLLVFSSTSRL YDF | 78 |

TABLE 13

Conserved domains of G1543 (Family: Homeobox; HD-ZIP proteins) and closely related sequences

| SEQ ID NO: | Species from which SEQ ID NO: is derived | Gene ID (GID) | Conserved HB domain amino acid coordinates | Conserved HB domain SEQ ID NO: | Conserved homeodomain and HALZ domain | Percent ID of conserved HB domain to G1543 homeo and HALZ domains |
|---|---|---|---|---|---|---|
| 1062 | Arabidopsis thaliana | G1543 | 135-195 | 3004 | Homeodomain: APPRKKLRLTREQSRLL EDSFRQNHTLNPKQKEV LAKHLMLRPRQIEVWF QNRRARSKLKQ | 100 |
|  |  |  | 194-237 | 17824 | HALZ: KQTEMECEYLKRWFGS LTEENHRLHREVEELRA IKVGPTTVNSA | 100 |
| 1988 | Glycine max | G3524 | 61-121 | 3560 | Homeodomain: GEPPRKKLRLTKEQSRL LEESFRQNHTLNPKQKE SLAMQLKLRPRQVEVW FQNRRARSKLKQ | 88 |
|  |  |  | 120-162 | 17825 | HALZ: KQTEMECEYLKRWFGS LTEQNRRLQREVEELRA IKVGPPTVIS | 88 |
| 1974 | Oryza sativa | G3510 | 74-134 | 3553 | Homeodomain: PHRPKKLRLSKEQSRLL EESFRLNHTLTPKQKEA LAIKLKLRPRQVEVWFQ NRRARTKLKQ | 75 |
|  |  |  | 133-175 | 17826 | HALZ: KQTEMECEYLKRCFGSL TEENRRLQREVEELRA MRVAPPTVLS | 81 |
| 17829 | Glycine max | G4371 | 61-121 | 17830 | Homeodomain: EPPRKKLRLTKEQSLLL EESFRQNHTLNPKQKES LAMQLKLRPRQVEVWF QNRRARSKLKQ | 86 |

TABLE 13-continued

Conserved domains of G1543 (Family: Homeobox; HD-ZIP proteins) and closely related sequences

| SEQ ID NO: | Species from which SEQ ID NO: is derived | Gene ID (GID) | Conserved HB domain amino acid coordinates | Conserved HB domain SEQ ID NO: | Conserved homeodomain and HALZ domain | Percent ID of conserved HB domain to G1543 homeo and HALZ domains |
|---|---|---|---|---|---|---|
| | | | 120-162 | 17831 | HALZ: KQTEMECEYLKRWFGS LTEQNRRLQREVEELRA IKVGPPTVIS | 88 |
| 1958 | Zea mays | G3490 | 60-120 | 3545 | Homeodomain: PHRAKKLRLSKEQSRLL EESFRLNHTLTPKQKEA LAVKLKLRPRQVEVWF QNRRARTKLKQ | 80 |
| | | | 119-161 | 17827 | HALZ: KQTELECEYLKRCFGSL TEENRRLQREVEELRA MRVAPPTVLS | 79 |
| 17833 | Zea mays | G4369 | 76-136 | 17834 | Homeodomain: PHRAKKLRLSKEQSRLL EESFRLNHTLTPKQKEA LAVKLKLRPRQVEVWF QNRRARTKLKQ | 80 |
| | | | 135-177 | 17835 | HALZ: KQTELECEYLKRCFGSL TEENRRLQREVEELRA MRVAPPTVLS | 79 |
| 17837 | Zea mays | G4370 | 75-135 | 17838 | Homeodomain: PHRPKKLRLSKEQSRLL EESFRLNHTLSPKQKEA LAIKLKLRPRQVEVWFQ NRRARTKLKH | 80 |
| | | | 134-176 | 17839 | HALZ: KHTEMECEYLKRCFGSL TEENRRLQREVEELRA MRMAPPTVLS | 76 |
| 17841 | Arabidopsis thaliana | G2712 | 65-125 | 17842 | Homeodomain: GRRRKKLRLTKEQSHLL EESFIQNHTLTPKQKKD LATFLKLSQRQVEVWF QNRRARSKLKH | 70 |
| | | | 124-163 | 17843 | HALZ: KHTEMECEYLKRWFGS LKEQNRRLQIEVEELRA LKPSSTS | 72 |

TABLE 14

Conserved domains of G142 (Family: MADS) and closely related sequences

| SEQ ID NO: | Species from which SEQ ID NO: is derived | Gene ID (GID) | Conserved MADS domain amino acid coordinates | Conserved MADS domain SEQ ID NO: | Conserved MADS domain | Percent ID of conserved AP2 DNA binding domain to G142 conserved AP2 domain |
|---|---|---|---|---|---|---|
| 98 | Arabidopsis thaliana | G142 | 2-57 | 2427 | GRGRVEMKRIENKINRQ VTFSKRRNGLLKKAYEL SVLCDAEVALIIFSSRGK LYEF | 100 |
| 17845 | Brassica oleracea | G5483 | 2-57 | 17846 | GRGRVEMKRIENKINRQ VTFSKRRNGLLKKAYEL SVLCDAEVALIVFSSRG KLYEF | 98 |
| 17848 | Brassica oleracea | G5484 | 2-57 | 17849 | GRGRVEMKRIENKINRQ VTFSKRRNGLLKKAYEL SVLCDAEVALIVFSSRG KLYEF | 98 |
| 17851 | Oryza sativa | G5475 | 2-57 | 17852 | GRGRVELKRIENKINRQ VTFSKRRNGLLKKAYEL SVLCDAEVALIIFSSRGK LYEF | 98 |
| 17854 | Oryza sativa | G5476 | 2-57 | 17855 | GRGRVELKRIENKINRQ VTFSKRRNGLLKKAYEL SVLCDAEVALIIFSSRGK LYEF | 98 |
| 17857 | Zea mays | G5470 | 2-57 | 17858 | GRGRVELKRIENKINRQ VTFSKRRNGLLKKAYEL SVLCDAEVALIIFSSRGK LYEF | 98 |
| 17863 | Triticum aestivum | G5472 | 2-57 | 17864 | GRGRVELKRIENKINRQ VTFSKRRNGLLKKAYEL SVLCDAEVALIIFSSRGK LYEF | 98 |
| 17860 | Zea mays | G5471 | 2-57 | 17861 | GRGRVELKRIENKINRQ VTFSKRRNGLLKKAYEL SVLCDAEVALIIFSGRGK LYEF | 96 |
| 106 | Arabidopsis thaliana | G148 | 1-57 | 2431 | MGRGKVEVKRIENKITR QVTFSKRKSGLLKKAYE LSVLCDAEVSLIIFSTGG KLYEF | 85 |
| 17897 | Pinus radiata | G5487 | 2-57 | 17911 | GRGRVQLRRIENKINRQ VTFSKRRNGLLKKAYEL SVLCDAEVALIIFSTRGK LYEF | 92 |
| 17887 | Poa annua | G5473 | 2-57 | 17912 | GRGRVELKRIENKINRQ VTFSKRRNGLLKKAYEL SVLCDAEVALIIFSSRGK LYEF | 98 |
| 17888 | Lolium perenne | G5474 | 2-57 | 17913 | GRGRVELKRIENKINRQ VTFSKRRNGLLKKAYEL SVLCDAEVALIIFSSRGK LYEF | 98 |
| 17889 | Vitis vinifera | G5477 | 2-57 | 17914 | GRGRVELKRIENKINRQ VTFSKRRNGLLKKAYEL SVLCDAEVALIIFSSRGK LYEF | 98 |

TABLE 14-continued

Conserved domains of G142 (Family: MADS) and closely related sequences

| SEQ ID NO: | Species from which SEQ ID NO: is derived | Gene ID (GID) | Conserved MADS domain amino acid coordinates | Conserved MADS domain SEQ ID NO: | Conserved MADS domain | Percent ID of conserved AP2 DNA binding domain to G142 conserved AP2 domain |
|---|---|---|---|---|---|---|
| 17890 | Petunia x hybrida | G5478 | 2-57 | 17915 | GRGRVELKRIENKINRQ VTFSKRRNGLLKKAYEL SVLCDAEVALIIFSSRGK LYEF | 98 |
| 17891 | Malus domestica | G5479 | 2-57 | 17916 | GRGRVELKRIENKINRQ VTFSKRRNGLLKKAYEL SVLCDAEVGLIIFSSRGK LYEF | 96 |
| 17892 | Picea abies | G5480 | 2-57 | 17917 | GRGRVQLRRIENKINRQ VTFSKRRNGLLKKAYEL SVLCDAEVALIIFSTRGK LYEF | 92 |
| 17893 | Hordeum vulgare | G5481 | 2-57 | 17918 | GRGRVELKRIENKINRQ VTFSKRRNGLLKKAYEL SVLCDAEVALIIFSSRGK LYEF | 98 |
| 17894 | Dendrocalamus latiflorus | G5482 | 2-57 | 17919 | GRGKVELKRIENKINRQ VTFSKRRNGLLKKAYEL SVLCDAEVALIIFSSRGK LYEF | 96 |
| 17895 | Pinus resinosa | G5485 | 2-57 | 17920 | GRGRVELKRIENKINRQ VTFSKRRNGLLKKAYEL SVLCDAEVALIIFSSRGK LYEF | 98 |
| 17896 | Pinus radiata | G5486 | 2-57 | 17921 | GRGRVELKRIENKINRQ VTFSKRRNGLLKKAYEL SVLCDAEVALIIFSSRGK LYEF | 98 |
| 17898 | Chrysanthemum x morifolium | G5488 | 2-57 | 17910 | GRGRVELKRIENKINRQ VTFSKRRNGLLKKAYEL SVLCDAEVGLIIFSSRDK LYEF | 94 |

TABLE 15

Conserved domains of G1266 (Family: AP2) and closely related sequences

| SEQ ID NO: | Species from which SEQ ID NO: is derived | Gene ID (GID) | Conserved AP2 DNA-binding domain amino acid coordinates | Conserved AP2 DNA-binding domain SEQ ID NO: | Conserved AP2 domain | Percent ID of conserved AP2 DNA binding domain to G1266 conserved AP2 domain |
|---|---|---|---|---|---|---|
| 884 | Arabidopsis thaliana | G1266 | 79-147 | 2902 | EKSYRGVRRRPWGKFA AEIRDSTRNGIRVWLGT FESAEEAALAYDQAAFS MRGSSAILNFSAERVQE SL | 100 |

TABLE 15-continued

Conserved domains of G1266 (Family: AP2) and closely related sequences

| SEQ ID NO: | Species from which SEQ ID NO: is derived | Gene ID (GID) | Conserved AP2 DNA-binding domain amino acid coordinates | Conserved AP2 DNA-binding domain SEQ ID NO: | Conserved AP2 domain | Percent ID of conserved AP2 DNA binding domain to G1266 conserved AP2 domain |
|---|---|---|---|---|---|---|
| 1136 | Arabidopsis thaliana | G1752 | 83-151 | 3045 | ERSYRGVRKRPWGKFA AEIRDSTRNGIRVWLGT FDKAEEAALAYDQAAF ATKGSLATLNFPVEVVR ESL | 81 |
| 1540 | Arabidopsis thaliana | G2512 | 79-147 | 3275 | EKSYRGVRKRPWGKFA AEIRDSTRKGIRVWLGT FDTAEAAALAYDQAAF ALKGSLAVLNFPADVV EESL | 79 |
| 17931 | Zea mays | G5185 | 105-173 | 17933 | PAPYIGVRKRPWGKFA AEIRDSTRKGARVWLG TFDSPEAAAMAYDQAA FSVRGAAAVLNFPVERV QESL | 75 |
| 17929 | Oryza sativa | G5183 | 18-86 | 17934 | QQAFRGVRKRPWGKFA AEIRDSTRNGVRVWLG TFDSAEEAALAYDQAA FAMRGSAAVLNFPMEQ VRRSM | 76 |
| 17930 | Glycine max | G5184 | 71-139 | 17935 | EKSYRGVRRRPWGKFA AEIRDSTRHGMRVWLG TFDSAEAAALAYDQAA FSMRGSAAILNFPAEIVR ESL | 88 |
| 17932 | Glycine max | G5186 | 117-185 | 17936 | KRPFRGVRRRPWGKFA AEIRDSTRNGVRVWIGT FDTAEAAALAYDQAAL STRGSMAVLNF PEEVVRESL | 75 |
| 17928 | Lycopersicon esculentum | G5170 | 94-162 | 17937 | EKHYIGVRKRPWGKYA SEIRDSTRNGIRVWLGT FDTAEEAALAYDQAAL SMRGPWSLLNFPMEHV KKSL | 75 |

TABLE 16

Conserved domains of G2933 (Family: HLH/MYC) and closely related sequences

| SEQ ID NO: | Species from which SEQ ID NO: is derived | Gene ID (GID) | Conserved HLH/MYC domain amino acid coordinates | Conserved HLH/MYC domain SEQ ID NO: | Conserved HLH/MYC domain | Percent ID of conserved HLH/MYC domain to G2933 conserved HLH/MYC domain |
|---|---|---|---|---|---|---|
| 17949 | Arabidopsis thaliana | G2933 | 68-128 | 17956 | PVVVKKLNHNASERDR RKKINTLFSSLRSCLPAS DQSKKLSIPETVSKSLK YIPELQQQVK | 100 |

TABLE 16-continued

Conserved domains of G2933 (Family: HLH/MYC) and closely related sequences

| SEQ ID NO: | Species from which SEQ ID NO: is derived | Gene ID (GID) | Conserved HLH/MYC domain amino acid coordinates | Conserved HLH/MYC domain SEQ ID NO: | Conserved HLH/MYC domain | Percent ID of conserved HLH/MYC domain to G2933 conserved HLH/MYC domain |
|---|---|---|---|---|---|---|
| 17948 | Arabidopsis thaliana | G2932 | 73-133 | 17957 | PVVVKKLNHNASERDR RRKINSLFSSLRSCLPAS GQSKKLSIPATVSRSLK YIPELQEQVK | 90 |
| 17947 | Arabidopsis thaliana | G2928 | 58-118 | 17958 | PVVMKKLNHNASERER RRKINTMFSSLRSCLPPT NQTKKLSVSATVSQAL KYIPELQEQVK | 78 |
| 17954 | Hordeum vulgare | G5193 | 70-126 | 17959 | RKISHNAYERDRRKQLN ELYSDLRSLLPDSDHTK KLSIPITVSRVLKYIPELQ KQV | 69 |
| 17951 | Zea mays | G5190 | 72-128 | 17960 | RKLSHNAYERDRRKQL NDLYSSLRSLLPDADHT KKLSIPTTVSRVLKYIPE LQKQV | 71 |
| 17944 | Vitis vinifera | G5192 | 66-122 | 17961 | PTMVKKLNHNASERDR RRKINSLYSSLRSLLPAA DQAKKLSIPSTVSRVLK YIPELQKQVK | 80 |
| 17950 | Oryza sativa | G5189 | 69-125 | 17962 | RKLSHNAYERDRRKQL NELYSSLRALLPDADHT KKLSIPTTVSRVLKYIPE LQKQVE | 68 |
| 17952 | Glycine max | G5191 | 62-118 | 17963 | KKLSHNASERDRRKKV NHLVSSLRSLLPGPDQT KKMSIPATVSRVLKYIP ELQHQVQ | 73 |
| 17955 | Arabidopsis thaliana | G2936 | 82-142 | 17964 | VVLEKKLNHNASERDR RRKLNALYSSLRALLPL SDQKRKLSIPMTVARVV KYIPEQKQELQ | 65 |

TABLE 17

Conserved domains of G154 (Family: MADS) and closely related sequences

| SEQ ID NO: | Species from which SEQ ID NO: is derived | Gene ID (GID) | Conserved MADS DNA binding domain amino acid coordinates | Conserved MADS DNA binding domain SEQ ID NO: | Conserved MADS domain | Percent ID of conserved MADS DNA binding domain to G154 conserved MADS domain |
|---|---|---|---|---|---|---|
| 114 | Arabidopsis thaliana | G154 | 2-57 | 17993 | VRGKTQMKRIENATSRQVTFSKR RNGLLKKAFELSVLCDAEVSLIIF SPKGKLYEF | 100 |
| 18040 | Medicago truncatula | G5312 | 2-57 | 17994 | VRGKTQMKRIENATSRQVTFSKR RNGLLKKAFELSVLCDAEVALIV FSPRGRLYEF | 92 |

TABLE 17-continued

Conserved domains of G154 (Family: MADS) and closely related sequences

| SEQ ID NO: | Species from which SEQ ID NO: is derived | Gene ID (GID) | Conserved MADS DNA binding domain amino acid coordinates | Conserved MADS DNA binding domain SEQ ID NO: | Conserved MADS domain | Percent ID of conserved MADS DNA binding domain to G154 conserved MADS domain |
|---|---|---|---|---|---|---|
| 18022 | Arabidopsis thaliana | G149 | 2-57 | 17995 | VRGKTEMKRIENATSRQVTFSKR RNGLLKKAFELSVLCDAEVALIIF SPRGKLYEF | 94 |
| 18048 | Arabidopsis thaliana | G627 | 2-57 | 17996 | VRGKTEMKRIENATSRQVTFSKR RNGLLKKAFELSVLCDAEVALVI FSPRSKLYEF | 91 |
| 18021 | Arabidopsis thaliana | G1011 | 2-57 | 17997 | VRGKIEMKKIENATSRQVTFSKR RNGLLKKAYELSVLCDAQLSLIIF SQRGRLYEF | 83 |
| 18023 | Arabidopsis thaliana | G1797 | 2-57 | 17998 | VRGKIEIKKIENVTSRQVTFSKRR SGLFKKAHELSVLCDAQVAAMIF SQKGRLYEF | 75 |
| 18024 | Arabidopsis thaliana | G1798 | 2-57 | 17999 | VRGKIEIKKIENVTSRQVTFSKRR SGLFKKAHELSVLCDAQVAAIVF SQSGRLHEY | 69 |
| 18037 | Populus tremuloides | G5309 | 2-57 | 18000 | VRGKTQMRRIENATSRQVTFSKR RNGLLKKAFELSVLCDAEVALIV FSPRGKLYEF | 92 |
| 18026 | Brassica rapa | G4062 | 2-57 | 18001 | VRGKTQMKRIENATSRQVTFSKR RNGLLKKAFELSVLCDAEVSLIIF SPKAKLYEF | 98 |
| 18035 | Cardamine flexuosa | G5306 | 2-57 | 18002 | VRGKTQMKRIENATSRQVTFSKR RNGLLKKAFELSVLCDAEVSLIIF SPKGKLYEF | 100 |
| 18029 | Zea mays | G4065 | 2-57 | 18003 | VRGKTQMKRIENPTSRQVTFSKR RNGLLKKAFELSVLCDAEVALV VFSPRGKLYEF | 91 |
| 18034 | Gossypium hirsutum | G5305 | 2-57 | 18004 | VRGKTQMKRIENPTSRQVTFSKR RNGLLKKAFELSVLCDVEVALIIF SPRGKPYEF | 91 |
| 18039 | Vitis vinifera | G5311 | 2-57 | 18005 | VRGKTQMRRIENATSRQVTFSKR RNGLFKKAFELSVLCDAEVALIIF SPRGKLYEF | 92 |
| 18041 | Citrus sinensis | G5313 | 2-57 | 18006 | VRGKTQMRRIENATSRQVTFSKR RNGLLKKAFELSVLCDAEVAVIIF SPRGKLSEF | 91 |
| 18044 | Citrus sinensis | G5316 | 2-57 | 18007 | VRGKIQMKKIENDTSRQVTFSKR RNGMLKKAYELSVLCDAEVAVII FSQKGRLYEF | 83 |
| 18042 | Pisum sativum | G5314 | 2-57 | 18065 | VRGKTQMKRIENATSRQVTFSKR RNGLLKKAFELSVLCDAEVALIIF SPRGKLYEF | 96 |
| 18045 | Petunia x hybrida | G5317 | 2-57 | 18008 | VRGKTQMRRIENATSRQVTFSKR RNGLLKKAFELSVLCDAEVSLIIF STRGKLYEF | 94 |
| 18046 | Petunia x hybrida | G5318 | 2-57 | 18009 | VRGKTQMRRIENATSRQVTFSKR RNGLLKKAFELSVLCDAQVGLVI FSPRGKQYEF | 89 |
| 18047 | Petunia x hybrida | G5319 | 2-57 | 18010 | VRGKTQMRRIENATSRQVTFSKR RNGLLKKAFELSVLCDAEVGLVI FSPRGKLYEF | 92 |

TABLE 17-continued

Conserved domains of G154 (Family: MADS) and closely related sequences

| SEQ ID NO: | Species from which SEQ ID NO: is derived | Gene ID (GID) | Conserved MADS DNA binding domain amino acid coordinates | Conserved MADS DNA binding domain SEQ ID NO: | Conserved MADS domain | Percent ID of conserved MADS DNA binding domain to G154 conserved MADS domain |
|---|---|---|---|---|---|---|
| 18030 | Oryza sativa | G4066 | 2-57 | 18011 | VRGKTQMKRIENPTSRQVTFSKR RNGLLKKAFELSVLCDAEVALIV FSPRGKLYEF | 92 |
| 18031 | Oryza sativa | G4067 | 2-57 | 18012 | VRGRTELKRIENPTSRQVTFSKRR NGLLKKAFELSVLCDAEVALIVF SPRGRLYEF | 85 |
| 18027 | Glycine max | G4063 | 2-57 | 18013 | VRGKTQLRRIENATSRQVTFSKR RNGLLKKAFELSVLCDAEVALIIF SPRGKLYEF | 92 |
| 18028 | Glycine max | G4064 | 2-57 | 18014 | VRGKTQMRRIENATSRQVTFSKR RNGLLKKAFELSVLCDAEVALIIF SPRGKLYEF | 94 |
| 18032 | Glycine max | G5303 | 2-57 | 18015 | VRGKTQMKRIENATSRQVTFSKR RNGLLKKAFELSVLCDAEVALIIF SPRGKLYEF | 96 |
| 18033 | Glycine max | G5304 | 2-57 | 18016 | VRGKTQIKRIENATSRQVTFSKRR NGLLKKAFELSVLCDAEVALIIFS SSGKLYEF | 92 |
| 18043 | Ipomoea batatas | G5315 | 2-57 | 18017 | VRGKTQMRRIENATSRQVTFSKR RNGLLKKAFELSVLCDAEVALIIF SPRGKLYEF | 94 |
| 18038 | Nicotiana tabacum | G5310 | 2-57 | 18018 | VRGKTQMRRIENATSRQVTFSKR RNGLLKKAFELSVLCDAEVGLVI FSPRGKLYEF | 92 |
| 18025 | Solanum lycopersicum | G4061 | 2-57 | 18019 | VRGKVEMKRIENSTSRQVTFSKR RNGLTKKAYELSVLCDAEVAFIIF SHKGRLYEF | 83 |
| 18036 | Sinapis alba | G5307 | 2-57 | 18020 | VRGKTQMKRIENATSRQVTFSKR RNGLLKKAFELSVLCDAEVSLIIF SPKGKLYEF | 100 |

TABLE 18

Conserved domain of G671 and closely related sequence

| SEQ ID NO: | Species from which SEQ ID NO: is derived | Gene ID (GID) | Conserved MYB-(R1)R2R3 domain amino acid coordinates | Conserved MYB-(R1)R2R3 domain SEQ ID NO: | Conserved MYB-(R1)R2R3 domain | Percent ID of conserved MYB-(R1)R2R3 domain to G671 conserved MYB-(R1)R2R3 domain |
|---|---|---|---|---|---|---|
| 538 | Arabidopsis thaliana | G671 | 15-115 | 18059 | KGAWTPEEDQKLLSYLNRHGEGG WRTLPEKAGLKRCGKSCRLRWAN YLRPDIKRGEFTEDEERSIISLHALH GNKWSAIARGLPGRTDNEIKNYW NTHIKK | 100 |

TABLE 18-continued

Conserved domain of G671 and closely related sequence

| SEQ ID NO: | Species from which SEQ ID NO: is derived | Gene ID (GID) | Conserved MYB-(R1)R2R3 domain amino acid coordinates | Conserved MYB-(R1)R2R3 domain | Conserved MYB-(R1)R2R3 domain SEQ ID NO: | Percent ID of conserved MYB-(R1)R2R3 domain to G671 conserved MYB-(R1)R2R3 domain |
|---|---|---|---|---|---|---|
| 18058 | Arabidopsis thaliana | G656 | 14-114 | KGAWTPEEDQKLIAYLHLHGEGG WRTLPEKAGLKRCGKSCRLRWAN YLRPDIKRGEFSPEEDDTIIKLHALK GNKWAAIATSLAGRTDNEIKNYW NTNLKK | 18060 | 82 |
| 174 | Arabidopsis thaliana | G202 | 14-114* | KGAWTTEEDKKLISYIHDHGEGG WRDIPQKAGLKRCGKSCRLRWTN YLKPEIKRGEFSSEEEQIIIMLHASR GNKWSVIARHLPRRTDNEIKNYW NTHLKK | 18061 | 76 |
| 172 | Arabidopsis thaliana | G201 | 14-114 | KGAWTAEEDKKLISYIHEHGGGG WRDIPQKAGLKRCGKSCRLRWAN YLKPDIKRGEFSYEEEQIIIMLHASR GNKWSVIARHLPKRTDNEIKNYW NTHLKK | 18051 | 77 |
| 18057 | Arabidopsis thaliana | G243 | 14-114** | KGAWTTEEDKKLISYIHDHGEGG WRDIPEKAGLKRCGKSCRLRWTN YLKPDIKRGEFSYEEEQIIIMLHASR GNKWSVIARHLPKRTDNEVKNYW NTHLKK | 18063 | 77 |
| 18056 | Arabidopsis thaliana | G2340 | 14-114*** | KGAWTQEEDQKLIAYVQRHGEGG WRTLPDKAGLKRCGKSCRLRWAN YLRPDIKRGEFSQDEEDSIINLHAIH GNKWSAIARKIPRRTDNEIKNHWN THIKK | 18052 | 85 |

*The domain is within the larger conserved domain which consists of amino acid residues 13-116.
**The domain is within the larger conserved domain which consists of amino acid residues 12-128.
***The domain is within the larger conserved domain which consists of amino acid residues 14-120.

Orthologs and Paralogs

Homologous sequences as described above can comprise orthologous or paralogous sequences. Several different methods are known by those of skill in the art for identifying and defining these functionally homologous sequences. Three general methods for defining orthologs and paralogs are described; an ortholog or paralog, including equivalogs, may be identified by one or more of the methods described below.

As described by Eisen (1998) *Genome Res.* 8: 163-167, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (i.e., by evolutionary processes) rather than on the sequence similarity itself (Eisen, supra). In fact, many specific examples exist in which gene function has been shown to correlate well with gene phylogeny (Eisen, supra). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994); Higgins et al. (1996)). Groups of similar genes can also be identified with pair-wise BLAST analysis (Feng and Doolittle (1987)). For example, a clade of very similar MADS domain transcription factors from *Arabidopsis* all share a common function in flowering time (Ratcliffe et al. (2001)), and a group of very similar AP2 domain transcription factors from *Arabidopsis* are involved in tolerance of plants to freezing (Gilmour et al. (1998)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001))

Speciation, the production of new species from a parental species, can also give rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al. (1994); Higgins et al. (1996)) potential orthologous sequences can be placed into the phylogenetic tree and their relationship to genes from the species of interest can be determined Orthologous sequences can also be identified by a reciprocal BLAST strategy. Once an orthologous sequence has been identified, the function of the ortholog can be deduced from the identified function of the reference sequence.

Transcription factor gene sequences are conserved across diverse eukaryotic species lines (Goodrich et al. (1993); Lin et al. (1991); Sadowski et al. (1988)). Plants are no exception to this observation; diverse plant species possess transcription factors that have similar sequences and functions.

Orthologous genes from different organisms have highly conserved functions, and very often essentially identical functions (Lee et al. (2002); Remm et al. (2001)). Paralogous genes, which have diverged through gene duplication, may retain similar functions of the encoded proteins. In such cases, paralogs can be used interchangeably with respect to certain embodiments of the instant invention (for example, transgenic expression of a coding sequence). An example of such highly related paralogs is the CBF family, with three well-defined members in *Arabidopsis* and at least one ortholog in *Brassica napus*, all of which control pathways involved in both freezing and drought stress (Gilmour et al. (1998); Jaglo et al. (2001)).

Distinct *Arabidopsis* transcription factors, including G28 (found in U.S. Pat. No. 6,664,446), G482 (found in US Patent Application 20040045049), G867 (found in US Patent Application 20040098764), and G1073 (found in U.S. Pat. No. 6,717,034), have been shown to confer stress tolerance or increased biomass when the sequences are overexpressed. The polypeptides sequences belong to distinct clades of transcription factor polypeptides that include members from diverse species. In each case, a significant number of clade member sequences derived from both eudicots and monocots have been shown to confer greater biomass or tolerance to stress when the sequences were overexpressed (unpublished data). These references may serve to represent the many studies that demonstrate that conserved transcription factor genes from diverse species are likely to function similarly (i.e., regulate similar target sequences and control the same traits), and that transcription factors may be transformed into diverse species to confer or improve traits.

As shown in Tables 1-7, transcription factors that are phylogenetically related to the transcription factors of the invention may have conserved domains that share at least 38% amino acid sequence identity, and have similar functions.

At the nucleotide level, the sequences of the invention will typically share at least about 30% or 40% nucleotide sequence identity, preferably at least about 50%, about 60%, about 70% or about 80% sequence identity, and more preferably about 85%, about 90%, about 95% or about 97% or more sequence identity to one or more of the listed full-length sequences, or to a listed sequence but excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

Percent identity can be determined electronically, e.g., by using the MEGALIGN program (DNASTAR, Inc. Madison, Wis.). The MEGALIGN program can create alignments between two or more sequences according to different methods, for example, the clustal method (see, for example, Higgins and Sharp (1988) The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, e.g., each amino acid gap is weighted as if it were a single amino acid or nucleotide mismatch between the two sequences (see U.S. Pat. No. 6,262,333).

Software for performing BLAST analyses is publicly available, e.g., through the National Center for Biotechnology Information (see internet website at www.ncbi.nlm nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul (1993); Altschul et al. (1990)). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1992). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at www.ncbi.nlm.nih.gov/).

Other techniques for alignment are described by Doolittle (1996). Preferably, an alignment program that permits gaps in the sequence is utilized to align the sequences. The Smith-Waterman is one type of algorithm that permits gaps in sequence alignments (see Shpaer (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

The percentage similarity between two polypeptide sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, e.g., the Jotun Hein method (see, for example, Hein (1990)) Identity between sequences can also be determined by other methods known in the art, e.g., by varying hybridization conditions (see US Patent Application No. 20010010913).

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997)), PFAM, and other databases which contain previously identified and annotated motifs, sequences and gene functions. Methods that search for primary sequence patterns with secondary structure gap penalties (Smith et al. (1992)) as well as algorithms such as Basic Local Alignment Search Tool (BLAST; Altschul (1993); Altschul et al. (1990)), BLOCKS (Henikoff and Henikoff (1991)), Hidden Markov Models (HMM; Eddy (1996); Sonnhammer et al. (1997)), and the like, can be used to manipulate and analyze polynucleotide and polypeptide sequences encoded by polynucleotides. These databases, algorithms and other methods are well known in the art and are described in Ausubel et al. (1997), and in Meyers (1995).

A further method for identifying or confirming that specific homologous sequences control the same function is by comparison of the transcript profile(s) obtained upon overexpression or knockout of two or more related transcription factors. Since transcript profiles are diagnostic for specific cellular states, one skilled in the art will appreciate that genes that have a highly similar transcript profile (e.g., with greater than 50% regulated transcripts in common, or with greater than 70% regulated transcripts in common, or with greater than 90% regulated transcripts in common) will have highly similar functions. Fowler et al. (2002), have shown that three paralogous AP2 family genes (CBF1, CBF2 and CBF3), each of which is induced upon cold treatment, and each of which can condition improved freezing tolerance, have highly similar transcript profiles. Once a transcription factor has been shown to provide a specific function, its transcript profile becomes a diagnostic tool to determine whether paralogs or orthologs have the same function.

Furthermore, methods using manual alignment of sequences similar or homologous to one or more polynucleotide sequences or one or more polypeptides encoded by the polynucleotide sequences may be used to identify regions of similarity and conserved domains. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined Such examples of tertiary structure may comprise predicted alpha helices, beta-sheets, amphipathic helices, leucine zipper motifs, zinc finger motifs, proline-rich regions, cysteine repeat motifs, and the like.

Orthologs and paralogs of presently disclosed transcription factors may be cloned using compositions provided by the present invention according to methods well known in the art. cDNAs can be cloned using mRNA from a plant cell or tissue that expresses one of the present transcription factors. Appropriate mRNA sources may be identified by interrogating Northern blots with probes designed from the present transcription factor sequences, after which a library is prepared from the mRNA obtained from a positive cell or tissue. Transcription factor-encoding cDNA is then isolated using, for example, PCR, using primers designed from a presently disclosed transcription factor gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of orthologs of the *Arabidopsis* polypeptide sequences and their functionally similar orthologs are listed in the Sequence Listing. In addition to the sequences in the Sequence Listing, the invention encompasses isolated nucleotide sequences that are phylogenetically and structurally similar to sequences listed in the Sequence Listing) and can function in a plant by increasing biomass, disease resistance and/or and abiotic stress tolerance when ectopically expressed in a plant. These polypeptide sequences represent transcription factors that show significant sequence similarity the polypeptides of the Sequence Listing particularly in their respective conserved domains, as identified in Tables 1-18.

Since a significant number of these sequences are phylogenetically and sequentially related to each other and have been shown to increase a plant's biomass, disease resistance and/or abiotic stress tolerance, one skilled in the art would predict that other similar, phylogenetically related sequences falling within the present clades of transcription factors would also perform similar functions when ectopically expressed.

Identifying Polynucleotides or Nucleic Acids by Hybridization

Polynucleotides homologous to the sequences illustrated in the Sequence Listing and tables can be identified, e.g., by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (e.g., Sambrook et al. (1989); Berger and Kimmel (1987); and Anderson and Young (1985)).

Encompassed by the invention are polynucleotide sequences that are capable of hybridizing to the claimed polynucleotide sequences, including any of the transcription factor polynucleotides within the Sequence Listing, and fragments thereof under various conditions of stringency (see, for example, Wahl and Berger (1987); and Kimmel (1987)). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al. (1989); Berger (1987), pages 467-469; and Anderson and Young (1985).

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

$T_m(° C.)=81.5+16.6(\log [Na+])+0.41(\% G+C)- 0.62(\% \text{ formamide})-500/L$ (I) DNA-DNA:

$T_m(° C.)=79.8+18.5(\log [Na+])+0.58(\% G+C)+ 0.12(\% G+C)^2-0.5(\% \text{ formamide})-820/L$ (II) DNA-RNA:

$T_m(° C.)=79.8+18.5(\log [Na+])+0.58(\% G+C)+ 0.12(\% G+C)^2-0.35(\% \text{ formamide})-820/L$ (III) RNA-RNA:

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young (1985)). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m-5°$ C. to $T_m-20°$ C., moderate stringency at $T_m-20°$ C. to $T_m-35°$ C. and low stringency at $T_m-35°$ C. to $T_m-50°$ C. for duplex>150 base pairs. Hybridization may be performed at low to moderate stringency (25-50° C. below $T_m$), followed by post-hybridization washes at increasing stringencies. Maximum rates of hybridization in solution are determined empirically to occur at $T_m-25°$ C. for DNA-DNA duplex and $T_m-15°$ C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, e.g., to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, e.g., formamide, whereas high stringency hybridization may be obtained in the presence of at least about 35% formamide, and more preferably at least about 50% formamide Stringent temperature conditions will ordinarily include temperatures of at least about 30° C., more preferably of at least about 37° C., and most preferably of at least about 42° C. with formamide present. Varying additional parameters, such as hybridization time, the concentration of detergent, e.g., sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present transcription factors include, for example:

0.2× to 2×SSC and 0.1% SDS at 50° C., 55° C., 60° C., 65° C., or 50° C. to 65° C.;

6×SSC at 65° C.;

50% formamide, 4×SSC at 42° C.; or 0.5×, 1×, or 1.5×SSC, 0.1% SDS at 50° C., 55° C., 60° C., or 65° C.;

with, for example, two wash steps of 10-30 minutes each. Useful variations on these conditions will be readily apparent to those skilled in the art. A formula for "SSC, 20×" may be found, for example, in Ausubel et al., 1997, in Appendix A1.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, e.g., 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.–68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. 20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a transcription factor known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, e.g., a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the claimed polynucleotide sequences, including any of the transcription factor polynucleotides within the Sequence Listing, and fragments thereof under various conditions of stringency (see, for example, Wahl and Berger (1987), pages 399-407; and Kimmel (1987)). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a transcription factor that is associated with a particular first trait may also be associated with at least one other, unrelated and inherent second trait which was not predicted by the first trait.

Example I. Project Types

A variety of constructs were used to modulate the activity of lead transcription factors, and to test the activity of orthologs and paralogs in transgenic plant material. This platform provided the material for all subsequent analysis.

Transgenic lines from each particular transformation "project" were examined for morphological and physiological phenotypes. An individual project was defined as the analysis of lines for a particular construct or knockout (for example this might be 35S lines for a lead gene, 35S lines for a paralog or ortholog, lines for an RNAi construct, lines for a GAL4 fusion construct, lines in which expression is driven from a particular tissue specific promoter, etc.) In the current lead advancement program, four main areas of analysis were pursued, spanning a variety of different project types (e.g., promoter-gene combinations).

(1) Overexpression/Tissue-Specific/Conditional Expression

The promoters used in our experiments were selected in order to provide for a range of different expression patterns. Details of promoters being used are provided in Example II.

Expression of a given TF from a particular promoter was achieved either by a direct-promoter fusion construct in which that TF was cloned directly behind the promoter of interest or by a two component system. Details of transformation vectors used in these studies are shown in the Vector and Cloning Information (Example III). A list of all constructs used in these analyses (PIDs), including compilations of the sequences of promoter fragments and the expressed transgene sequences within the PIDs, are provided in the Sequence Listing.

The Two-Component Expression System

For the two-component system, two separate constructs were used: Promoter::LexA-GAL4TA and opLexA::TF. The first of these (Promoter::LexA-GAL4TA) comprised a desired promoter cloned in front of a LexA DNA binding domain fused to a GAL4 activation domain. The construct vector backbone (pMEN48, also known as P5375) also carried a kanamycin resistance marker, along with an opLexA::GFP (green fluorescent protein) reporter. Transgenic lines were obtained containing this first component, and a line was selected that shows reproducible expression of the reporter gene in the desired pattern through a number of generations. A homozygous population was established for that line, and the population was supertransformed with the second construct (opLexA::TF) carrying the TF of interest cloned behind a LexA operator site. This second construct vector backbone (pMEN53, also known as P5381) also contained a sulfonamide resistance marker.

Each of the above methods offers a number of pros and cons. A direct fusion approach allows for much simpler genetic analysis if a given promoter-TF line is to be crossed into different genetic backgrounds at a later date. The two-component method, on the other hand, potentially allows for stronger expression to be obtained via an amplification of transcription. Additionally, a range of two-component constructs were available at the start of the Lead Advancement program which had been built using funding from an Advanced Technology Program (ATP) grant.

In general, Arabidopsis TFs from different study groups were expressed from a range of different promoters, often with a two component method. Arabidopsis paralogs were also generally analyzed by the two-component method, but were typically analyzed using the only 35S promoter. However, an alternative promoter was sometimes used for paralogs when there was a specific indication that a different promoter might afford a more useful approach (such as when use of the 35S promoter was known to generate deleterious effects). Putative orthologs from other species were usually analyzed by overexpression from a 35S CaMV promoter via a direct promoter-fusion construct. The vector backbone for most of the direct promoter-fusion overexpression constructs was pMEN65, but pMEN1963 and pMEN20 were sometimes used.

(2) Knock-Out/Knock-Down

Where available, T-DNA insertion lines from either the public or the in-house collections were analyzed.

In cases where a T-DNA insertion line was unavailable, an RNA interference (RNAi) strategy was sometimes used. At the outset of the program, the system was tested with two well-characterized genes [LEAFY (Weigel et al., 1992) and CONSTANS (Putterill et al., 1995)] that gave clear morphological phenotypes when mutated. In each case, RNAi lines were obtained that exhibited characters seen in the null mutants.

(3) Protein Modifications

Deletion Variants

Truncated versions or fragments of the leads were sometimes overexpressed to test hypotheses regarding particular parts of the proteins. Such an approach can result in dominant negative alleles.

Point Mutation and Domain Swap Variants

In order to assess the role of particular conserved residues or domains, mutated versions of lead proteins with substitutions at those residues were overexpressed. In some cases, we also overexpressed chimeric variants of the transcription factor in which one or domains have been exchanged with another transcription factor.

(4) Analytical Tools for Pathway Analysis

Promoter-Reporter Constructs

Promoters were primarily cloned in front of a GUS reporter system. These constructs were used to identify putative upstream transcriptional activators via a transient assay. In most cases approximately 2 kb of the sequence immediately 5' to the ATG of the gene was included in the construct.

In addition to being used in transient assays, the promoter-reporter constructs were transformed into Arabidopsis. The lines were then used to characterize the expression patterns of the lead genes in planta over a variety of tissue types and stress conditions. As well as GUS, a number of fluorescent reporter proteins were used in Promoter-reporter constructs including GFP, YFP (yellow fluorescent protein), CFP (cyan fluorescent protein) and anchored variants of YFP such as YFP-LTI6.

Protein Fusions to Fluorescent Tags

To examine sub-cellular localization of TFs, translational fusions to fluorescent markers such as GFP, CFP, and YFP were used.

Dexamethasone Inducible Lines

Glucocorticoid receptor fusions at the N and C termini of the primary TFs were constructed to allow the identification of their immediate/early targets during array-based studies. We also produced dexamethasone inducible lines via a two-component approach.

TABLE 19

Definitions of particular project types

| Project type | Definition |
| --- | --- |
| Direct promoter-fusion (DPF) | A full-length wild-type version of a gene was directly fused to a promoter that drove its expression in transgenic plants. Such a promoter could be the native promoter or that gene, 35S, or a promoter that drove tissue specific or conditional expression. |
| 2-components-supTfn (TCST) | A full-length wild-type version of a gene was expressed via the 2 component, promoter::LexA-GAL4; opLexA::TF system. In this case, a stable transgenic line was first established containing one of the components and was later supertransformed with the second component. |

TABLE 19-continued

Definitions of particular project types

| Project type | Definition |
|---|---|
| splice_variant_* | A splice variant of a gene was directly fused to a promoter that drove its expression in transgenic plants. Such a promoter was the native promoter or that gene, 35S, or a promoter that drove tissue specific or conditional expression. |
| Direct GR-fusion C-term | A construct contained a TF with a direct C-terminal fusion to a glucocorticoid receptor. |
| Direct GR-fusion N-term | A construct contained a TF with a direct N-terminal fusion to a glucocorticoid receptor. |
| Direct GR-fusion HA C-term | A construct contains a TF with a direct C-terminal fusion to a glucocorticoid receptor in combination with an HA (hemagglutinin) epitope tag in the conformation: TF-GR-HA |
| Direct GR-fusion HA N-term | A construct contained a TF with a direct N-terminal fusion to a glucocorticoid receptor in combination with an HA (hemagglutinin) epitope tag in the conformation: GR-TF-HA |
| GAL4 C-term | A TF with a C-terminal fusion to a GAL4 activation domain was overexpressed. |
| GAL4 N-term | A TF with an N-terminal fusion to a GAL4 activation domain was overexpressed. |
| TF dominant negative deletion | A truncated variant or fragment of a TF was (over)expressed, often with the aim of producing a dominant negative phenotype. Usually the truncated version comprised the DNA binding domain |
| TF dom neg deln 2ndry domain | A truncated variant or fragment of a TF was (over)expressed, often with the aim of producing a dominant negative phenotype. In this case, the truncated version contained a conserved secondary domain (rather than the main DNA binding domain) or a secondary DNA binding domain alone, in the case when a TF had two potential binding domains (e.g. B3 & AP2). |
| deletion_* | A variant of a TF was (over)expressed in which one or more regions had been deleted. |
| site-directed mutation_* | A form of the protein was overexpressed which had had one or more residues changed by site directed mutagenesis. |
| domain swap_* | A form of the protein was overexpressed in which a particular fragment had been substituted with a region from another protein. |
| KO | Describes a line that harbored a mutation in an *Arabidopsis* TF at its endogenous locus. In most cases this was caused by a T-DNA insertion. |
| RNAi (clade) | An RNAi construct designed to knock-down a clade of related genes. |
| RNAi (GS) | An RNAi construct designed to knock-down a specific gene. |
| Promoter-reporter | A construct used to determine the expression pattern of a gene, or in transient assay experiments. This was typically a promoter-GUS or promoter-GFP (or a derivative of GFP) fusion. |
| Protein-GFP-C-fusion | Overexpression of a translational fusion in which the TF had GFP fused to the C-terminus. |
| Protein-YFP-C-fusion | Overexpression of a translational fusion in which the TF had YFP fused to the C-terminus. |
| Protein-CFP-C-fusion | Overexpression of a translational fusion in which the TF had CFP fused to the C-terminus. |
| 2-components-supTfn-TAP-C-term | Overexpression of a translational fusion in which the TF had a TAP tag (Tandem affinity purification epitope, see Rigaut et al., 1999 and Rohila et al., 2004) fused to the C-terminus. This fusion was expressed via the two-component system: promoter::LexA-GAL4; opLexA::TF-TAP. In this case, a stable transgenic line was first established containing the promoter component and was later supertransformed with the TF-TAP component). |
| 2-components-supTfn-HA-C-term | Overexpression of a translational fusion in which the TF had an HA (hemagglutinin) epitope tag fused to the C-terminus. This fusion was expressed via the two-component system: promoter::LexA-GAL4; opLexA::TF-HA. In this case, a stable transgenic line was first established containing the promoter component and was later supertransformed with the TF-HA component). |
| 2-components-supTfn-HA-N-term | Overexpression of a translational fusion in which the TF had an HA (hemagglutinin) epitope tag fused to the N-terminus. This fusion was expressed via the two-component system: promoter::LexA-GAL4; opLexA::HA-TF. In this case, a stable transgenic line was first established containing the promoter component and was later supertransformed with the HA-TF component). |
| Double Overexpression (Double OE) Cross | A transgenic line harboring two different overexpression constructs, created by a genetic crossing approach. |
| Triple Overexpression (Triple OE) Cross | A transgenic line harboring three different overexpression constructs, created by a genetic crossing approach. |

*designates any numeric value

Example II. Promoter Analysis

A major component of the program was to determine the effects of ectopic expression of transcription factors in a variety of different tissue types, and in response to the onset of stress conditions. Primarily this was achieved by using a panel of different promoters via a two-component system.

Component 1: Promoter Driver Lines (Promoter::LexA/GAL4).

In each case, the first component (Promoter::LexA/GAL4) comprised a LexA DNA binding domain fused to a GAL4 activation domain, cloned behind the desired promoter. These constructs were contained within vector backbone pMEN48 (Example III) which also carried a kanamycin resistance marker, along with an opLexA::GFP reporter. The GFP was EGFP, an variant available from Clontech (Mountain View, Calif.) with enhanced signal. EGFP is soluble in the cytoplasm. Transgenic "driver lines" were first obtained containing the Promoter::LexA/GAL4 component.

carrying the TF of interest cloned behind a LexA operator site. In each case this second construct carried a sulfonamide selectable marker and was contained within vector backbone pMEN53 (see Example III).

*Arabidopsis* promoter driver lines are shown in Table 20.

TABLE 20

Expression patterns conferred by promoters used for one (i.e., in some 35S overexpressing lines) and two-component studies.

| Promoter | Expression pattern conferred | Reference |
| --- | --- | --- |
| 35S | Constitutive, high levels of expression in all throughout the plant and fruit | Odell et al. (1985) |
| SUC2 | Vascular/Phloem | Truernit and Sauer (1995) |
| ARSK1 | Root | Hwang and Goodman (1995) |
| CUT1 | Shoot epidermal/guard cell enhanced | Kunst et al. (2000) |
| RBCS3 | Photosynthetic tissue; expression predominately in highly photosynthetic vegetative tissues. Fruit expression predominately in the pericarp | Wanner and Gruissem (1991) |
| RD29A* | Drought/Cold/ABA inducible | Yamaguchi-Shinozaki and Shinozaki (1993) |
| LTP1 | Shoot epidermal/trichome enhanced; in vegetative tissues, expression is predominately in the epidermis. Low levels of expression are also evident in vascular tissue. In the fruit, expression is strongest in the pith-like columella/placental tissue | Thoma et al. (1994) |
| RSI1 | Root meristem and root vascular; expression generally limited to roots. Also expressed in the vascular tissues of the fruit. | Taylor and Scheuring (1994) |
| AP1 | Flower primordia/flower; light expression in leaves increases with maturation. Highest expression in flower primordia and flower organs. In fruits, predominately in pith-like columella/placental tissue | Hempel et al. (1997); Mandel et al. (1992) |
| STM | Expressed in meristematic tissues, including apical meristems, cambium. Low levels of expression also in some differentiating tissues. In fruit, most strongly expressed in vascular tissues and endosperm. | Long and Barton (2000); Long et al. (1996) |
| AS1 | Primordia and young organs; expressed predominately in differentiating tissues. In fruit, most strongly expressed in vascular tissues and in endosperm | Byrne et al. (2000) |
| PG | Phytoene desaturase; high expression throughout the fruit, comparable to 35S. Strongest late in fruit development | Nicholass et al. (1995); Montgomery et al. (1993) |
| PD | Phytoene desaturase; moderate expression in fruit tissues | Corona et al. (1996) |
| CRU | Cruciferin 1; expressed at low levels in fruit vascular tissue and columella. Seed and endosperm expression | Breen and Crouch (1992); Sjodahl et al. (1995) |

Notes:
*Two different RD29A promoter lines, lines 2 and 5, were used. Line 2 has a higher level of background expression than line 5. Expression from the line 2 promoter was expected to produce constitutive moderate basal transcript levels of any gene controlled by it, and to generate an increase in levels following the onset of stress. In contrast, line 5 was expected to produce lower basal levels and a somewhat sharper up-regulation of any gene under its control, following the onset of stress. Although RD29A exhibits up-regulation in response to cold and drought in mature tissues, this promoter produces relatively high levels of expression in embryos and young seedlings.

For each promoter driver, a line was selected which showed reproducible expression of the GFP reporter gene in the desired pattern, through a number of generations. We also tested the plants in our standard plate based physiology assays to verify that the tissue specific pattern was not substantially altered by stress conditions. A homozygous population was then established for that line.

Component 2: TF Construct (opLexA::TF).

Having established a promoter panel, it was possible to overexpress any transcription factor in the precise expression pattern conferred by the driver lines, by super-transforming or crossing in a second construct (opLexA::TF)

Validation of the Promoter-Driver Line Patterns.

To demonstrate that each of the promoter driver lines could generate the desired expression pattern of a second component target at an independent locus arranged in trans, crosses were made to an opLexA::GUS line. Typically, it was confirmed that the progeny exhibited GUS activity in an equivalent region to the GFP seen in the parental promoter driver line. However, GFP can move from cell-to-cell early in development and in meristematic tissues, and hence patterns of GFP in these tissues do not strictly report gene expression.

It was clear that the 35S promoter induces much higher levels of expression compared to the other promoters presently in use.

Example III. Vector and Cloning Information

Vector and Cloning Information: Expression Vectors.

A list of nucleic acid constructs (PIDs) included in this application, indicating the promoter fragment that was used to drive the transgene, along with the cloning vector backbone, is provided in the Sequence listing as SEQ ID NOs 3792-5086 and 5102-5106.

Target sequences were selected to be 100 by long or longer. For constructs designed against a clade rather than a single gene, the target sequences had at least 85% identity to all clade members. Where it is not possible to identify a single 100 by sequence with 85% identity to all clade members, hybrid fragments composed of two shorter sequences were used.

Cloning Methods.

*Arabidopsis* transcription factor clones were created in one of three ways: isolation from a library, amplification from cDNA, or amplification from genomic DNA. The ends of the *Arabidopsis* transcription factor coding sequences were generally confirmed by RACE PCR or by comparison with public cDNA sequences before cloning.

Clones of transcription factor orthologs from rice, maize, and soybean were all made by amplification from cDNA. The ends of the coding sequences were predicted based on homology to *Arabidopsis* or by comparison to public and proprietary cDNA sequences; RACE PCR was not done to confirm the ends of the coding sequences. For cDNA amplification, KOD Hot Start DNA Polymerase (Novagen, Madison, Wis.) was used in combination with 1M betaine and 3% DMSO. This protocol was found to be successful in amplifying cDNA from GC-rich species such as rice and corn, along with some non-GC-rich species such as soybean and tomato, where traditional PCR protocols failed. Primers were designed using at least 30 bases specific to the target sequence, and were designed close to, or overlapping, the start and stop codons of the predicted coding sequence.

Clones were fully sequenced. In the case of rice, high-quality public genomic sequences were available for comparison, and clones with sequence changes that result in changes in amino acid sequence of the encoded protein were rejected. For corn and soy, however, it was often unclear whether sequence differences represent an error or polymorphism in the source sequence or a PCR error in the clone. Therefore, in the cases where the sequence of the clone we obtained differed from the source sequence, a second clone was created from an independent PCR reaction. If the sequences of the two clones agreed, then the clone was accepted as a legitimate sequence variant.

Transformation.

*Agrobacterium* strain ABI was used for all plant transformations. This strain is chloramphenicol, kanamycin and gentamicin resistant.

Example IV. Transformation

Transformation of *Arabidopsis* was performed by an *Agrobacterium*-mediated protocol based on the method of Bechtold and Pelletier (1998). Unless otherwise specified, all experimental work was done using the Columbia ecotype.

Plant Preparation.

*Arabidopsis* seeds were sown on mesh covered pots. The seedlings were thinned so that 6-10 evenly spaced plants remained on each pot 10 days after planting. The primary bolts were cut off a week before transformation to break apical dominance and encourage auxiliary shoots to form. Transformation was typically performed at 4-5 weeks after sowing.

Bacterial Culture Preparation.

*Agrobacterium* stocks were inoculated from single colony plates or from glycerol stocks and grown with the appropriate antibiotics and grown until saturation. On the morning of transformation, the saturated cultures were centrifuged and bacterial pellets were re-suspended in Infiltration Media (0.5×MS, 1×B5 Vitamins, 5% sucrose, 1 mg/ml benzylaminopurine riboside, 200 µl/L Silwet L77) until an A600 reading of 0.8 is reached.

Transformation and Seed Harvest.

The *Agrobacterium* solution was poured into dipping containers. All flower buds and rosette leaves of the plants were immersed in this solution for 30 seconds. The plants were laid on their side and wrapped to keep the humidity high. The plants were kept this way overnight at 4° C. and then the pots were turned upright, unwrapped, and moved to the growth racks.

The plants were maintained on the growth rack under 24-hour light until seeds were ready to be harvested. Seeds were harvested when 80% of the siliques of the transformed plants were ripe (approximately 5 weeks after the initial transformation). This seed was deemed T0 seed, since it was obtained from the T0 generation, and was later plated on selection plates (either kanamycin or sulfonamide, see Example VI). Resistant plants that were identified on such selection plates comprised the T1 generation.

Example V. Morphology

*Arabidopsis* is used as a model plant for the study of plant growth and development. In addition to providing ornamental utility, altered morphological or developmental features may affect stress tolerance and ultimately plant quality or yield. For example, alterations to appendages such as hairs and trichomes, stomata, and the deposition of waxes may enhance a plant's ability to take up nutrients or resist disease or pathogens. Dark color may also contribute to oxidative stress tolerance or enhanced photosynthetic capacity, which in turn could result in yield increases.

Thus, morphological analysis was performed to determine whether changes in transcription factor levels affect plant growth and development. This was primarily carried out on the T1 generation, when at least 10-20 independent lines were examined. However, in cases where a phenotype required confirmation or detailed characterization, plants from subsequent generations were also analyzed.

Primary transformants were typically selected on MS medium with 0.3% sucrose and 50 mg/l kanamycin. T2 and later generation plants were selected in the same manner, except that kanamycin was used at 35 mg/l. In cases where lines carry a sulfonamide marker (as in all lines generated by supertransformation), seeds were selected on MS medium with 0.3% sucrose and 1.5 mg/l sulfonamide KO lines were usually germinated on plates without a selection. Seeds were cold-treated (stratified) on plates for 3 days in the dark (in order to increase germination efficiency) prior to transfer to growth cabinets. Initially, plates were incubated at 22° C. under a light intensity of approximately 100 microEinsteins for 7 days. At this stage, transformants were green, possessed the first two true leaves, and were easily distinguished from bleached kanamycin or sulfonamide-susceptible seedlings. Resistant seedlings were then transferred onto soil (Sunshine potting mix). Following transfer to soil, trays of seedlings were covered with plastic lids for 2-3 days to maintain humidity while they became established. Plants were grown on soil under fluorescent light at an intensity of 70-95 microEinsteins and a temperature of 18-23° C. Light conditions consisted of a 24-hour photoperiod unless otherwise stated. In instances where alterations in flowering time was apparent, flowering was typically re-examined under both 12-hour and 24-hour light to assess whether the phenotype was photoperiod dependent. Under our 24-hour light growth conditions, the typical generation time (seed to seed) was approximately 14 weeks.

Because many aspects of Arabidopsis development are dependent on localized environmental conditions, in all cases plants were evaluated in comparison to controls in the same flat. As noted below, controls for transgenic lines were wild-type plants, plants overexpressing CBF4, or transgenic plants harboring an empty transformation vector selected on kanamycin or sulfonamide. Careful examination was made at the following stages: seedling (1 week), rosette (2-3 weeks), flowering (4-7 weeks), and late seed set (8-12 weeks). Seed was also inspected. Seedling morphology was assessed on selection plates. At all other stages, plants were macroscopically evaluated while growing on soil. All significant differences (including alterations in growth rate, size, leaf and flower morphology, coloration and flowering time) were recorded, but routine measurements were not be taken if no differences were apparent. In certain cases, stem sections were stained to reveal lignin distribution. In these instances, hand-sectioned stems were mounted in phloroglucinol saturated 2M HCl (which stains lignin pink) and viewed immediately under a dissection microscope.

Note that for a given project (gene-promoter combination, GAL4 fusion lines, RNAi lines etc.), ten lines were typically examined in subsequent plate based physiology assays.

Example VI. Physiology Experimental Methods

Plate Assays.

Twelve different plate-based physiological assays (shown below), representing a variety of drought-stress related conditions, were used as a pre-screen to identify top performing lines from each project (i.e. lines from transformation with a particular construct), that may be tested in subsequent soil based assays. Typically, ten lines were subjected to plate assays, from which the best three lines were selected for subsequent soil based assays. However, in projects where significant stress tolerance was not obtained in plate based assays, lines were not submitted for soil assays.

In addition, transgenic lines were subjected to nutrient limitation studies. A nutrient limitation assay was intended to find genes that allow more plant growth upon deprivation of nitrogen. Nitrogen is a major nutrient affecting plant growth and development that ultimately impacts yield and stress tolerance. These assays monitor primarily root but also rosette growth on nitrogen deficient media. In all higher plants, inorganic nitrogen is first assimilated into glutamate, glutamine, aspartate and asparagine, the four amino acids used to transport assimilated nitrogen from sources (e.g. leaves) to sinks (e.g. developing seeds). This process is regulated by light, as well as by C/N metabolic status of the plant. We used a C/N sensing assay to look for alterations in the mechanisms plants use to sense internal levels of carbon and nitrogen metabolites which could activate signal transduction cascades that regulate the transcription of N-assimilatory genes. To determine whether these mechanisms are altered, we exploited the observation that wild-type plants grown on media containing high levels of sucrose (3%) without a nitrogen source accumulate high levels of anthocyanins. This sucrose induced anthocyanin accumulation can be relieved by the addition of either inorganic or organic nitrogen. We used glutamine as a nitrogen source since it also serves as a compound used to transport N in plants.

G1792 and N

The performance of two G1792-overexpressing lines, G1792-311-9 and G1792-312-8, was examined under limited nitrogen growth conditions. Plants were grown in pots filled with fritted clay, sub-irrigated every two hours with a hydroponic growth solution containing 0.1 mM ammonium nitrate as the sole nitrogen source. These conditions represent nitrogen-limited conditions for Arabidopsis growth. Plants were harvested at the rosette stage after 7 weeks of growth under 10 hour light. Chlorophyll content was measured with a SPAD meter, fresh weight was determined, and percent total nitrogen content was determined by dry combustion (Micro-Dumas combustion analysis). As shown in Table 20 provided below, the two G1792 lines were found to have higher chlorophyll content and total nitrogen concentration. One line produced significantly less biomass than controls.

Germination Assays.

NaCl (150 mM), mannitol (300 mM), glucose (5%), sucrose (9.4%), PEG (10%, with Phytogel as gelling agent), ABA (0.3 µM), Heat (32° C.), Cold (8° C.), —N is basal media minus nitrogen plus 3% sucrose and –N/+Gln is basal media minus nitrogen plus 3% sucrose and 1 mM glutamine. In addition to being stresses in their own right, salt, mannitol, heat, PEG and high sugar concentrations (e.g., 9.4% sucrose, 300 mM mannitol, 5% glucose), may contribute to hyperosmotic stress in plants and may also be used to assess tolerance to water deficit.

Growth Assays.

Growth assays consisted of water deficit assays, including severe dehydration assays such as desiccation (plate-based drought assays), or heat (32° C. for 5 days followed by recovery at 22° C.), chilling (8° C.), root development (visual assessment of lateral and primary roots, root hairs and overall growth). For the nitrogen limitation assay, all components of MS medium remained constant except nitrogen was reduced to 20 mg/L of $NH_4NO_3$. Note that 80% MS had 1.32 g/L $NH_4NO_3$ and 1.52 g/L $KNO_3$.

Unless otherwise stated, all experiments were performed with the Arabidopsis thaliana ecotype Columbia (col-0). Assays were usually performed on non-selected segregating T2 populations (in order to avoid the extra stress of selection). Control plants for assays on lines containing direct promoter-fusion constructs were Col-0 plants transformed an empty transformation vector (pMEN65). Controls for 2-component lines (generated by supertransformation) were the background promoter-driver lines (i.e. promoter::LexA-GAL4TA lines), into which the supertransformations were initially performed.

All assays were performed in tissue culture. Growing the plants under controlled temperature and humidity on sterile medium produced uniform plant material that had not been exposed to additional stresses (such as water stress) which could cause variability in the results obtained. All assays were designed to detect plants that were more tolerant or less tolerant to the particular stress condition and were developed with reference to the following publications: Jang et al. (1997), Smeekens (1998), Liu and Zhu (1997), Saleki et al. (1993), Wu et al. (1996), Zhu et al. (1998), Alia et al. (1998), Xin and Browse, (1998), Leon-Kloosterziel et al. (1996). Where possible, assay conditions were originally tested in a blind experiment with controls that had phenotypes related to the condition tested.

Procedures

Prior to plating, seed for all experiments were surface sterilized in the following manner: (1) 5 minute incubation with mixing in 70% ethanol, (2) 20 minute incubation with mixing in 30% bleach, 0.01% triton-X 100, (3) 5× rinses with sterile water, (4) Seeds were re-suspended in 0.1% sterile agarose and stratified at 4° C. for 3-4 days.

All germination assays follow modifications of the same basic protocol. Sterile seeds were sown on the conditional media that had a basal composition of 80% MS+Vitamins. Plates were incubated at 22° C. under 24-hour light (120-130 $\mu E\ m^{-2}\ s^{-1}$) in a growth chamber. Evaluation of germination and seedling vigor was performed 5 days after planting. For assessment of root development, seedlings germinated on 80% MS+Vitamins+1% sucrose were transferred to square plates at 7 days. Evaluation was done 5 days after transfer following growth in a vertical position. Qualitative differences were recorded including lateral and primary root length, root hair number and length, and overall growth.

For chilling (8° C.) and heat sensitivity (32° C.) growth assays, seeds were germinated and grown for 7 days on MS+Vitamins+1% sucrose at 22° C. and then were transferred to chilling or heat stress conditions. Heat stress was applied for 5 days, after which the plants were transferred back to 22° C. for recovery and evaluated after a further 5 days. Plants were subjected to chilling conditions (8° C.) and evaluated at 10 days and 17 days.

For plate-based severe dehydration assays (sometimes referred to as desiccation assays), seedlings were grown for 14 days on MS+Vitamins+1% Sucrose at 22° C. Plates were opened in the sterile hood for 3 hr for hardening and then seedlings were removed from the media and dried for 2 h in the hood. After this time they were transferred back to plates and incubated at 22° C. for recovery. Plants were evaluated after another 5 days.

Data Interpretation

At the time of evaluation, plants were given one of the following scores:

(++) Substantially enhanced performance compared to controls. The phenotype was very consistent and growth was significantly above the normal levels of variability observed for that assay.
(+) Enhanced performance compared to controls. The response was consistent but was only moderately above the normal levels of variability observed for that assay.
(wt) No detectable difference from wild-type controls.
(−) Impaired performance compared to controls. The response was consistent but was only moderately above the normal levels of variability observed for that assay.
(−−) Substantially impaired performance compared to controls. The phenotype was consistent and growth was significantly above the normal levels of variability observed for that assay.
(n/d) Experiment failed, data not obtained, or assay not performed.

Example VII. Soil Drought (Clay Pot)

The soil drought assay (performed in clay pots) was based on that described by Haake et al. (2002).

Experimental Procedure.

Previously, we performed clay-pot assays on segregating T2 populations, sown directly to soil. However, in the current procedure, seedlings were first germinated on selection plates containing either kanamycin or sulfonamide.

Seeds were sterilized by a 2 minute ethanol treatment followed by 20 minutes in 30% bleach/0.01% Tween and five washes in distilled water. Seeds were sown to MS agar in 0.1% agarose and stratified for 3 days at 4° C., before transfer to growth cabinets with a temperature of 22° C. After 7 days of growth on selection plates, seedlings were transplanted to 3.5 inch diameter clay pots containing 80 g of a 50:50 mix of vermiculite:perlite topped with 80 g of ProMix. Typically, each pot contains 14 seedlings, and plants of the transgenic line being tested were in separate pots to the wild-type controls. Pots containing the transgenic line versus control pots were interspersed in the growth room, maintained under 24-hour light conditions (18-23° C., and 90-100 $\mu E\ m^{-2}\ s^{-1}$) and watered for a period of 14 days. Water was then withheld and pots were placed on absorbent paper for a period of 8-10 days to apply a drought treatment. After this period, a visual qualitative "drought score" from 0-6 was assigned to record the extent of visible drought stress symptoms. A score of "6" corresponded to no visible symptoms whereas a score of "0" corresponded to extreme wilting and the leaves having a "crispy" texture. At the end of the drought period, pots were re-watered and scored after 5-6 days; the number of surviving plants in each pot was counted, and the proportion of the total plants in the pot that survived was calculated.

Split-Pot Method.

A variation of the above method was sometimes used, whereby plants for a given transgenic line were compared to wild-type controls in the same pot. For those studies, 7 wild-type seedlings were transplanted into one half of a 3.5 inch pot and 7 seedlings of the line being tested were transplanted into the other half of the pot.

Analysis of Results.

In a given experiment, we typically compared six or more pots of a transgenic line with 6 or more pots of the appropriate control. (In the split pot method, 12 or more pots were used.) The mean drought score and mean proportion of plants surviving (survival rate) were calculated for both the transgenic line and the wild-type pots. In each case a p-value* was calculated, which indicated the significance of the difference between the two mean values. The results for each transgenic line across each planting for a particular project were then presented in a results table.

Calculation of p-Values.

For the assays where control and experimental plants were in separate pots, survival was analyzed with a logistic regression to account for the fact that the random variable was a proportion between 0 and 1. The reported p-value was the significance of the experimental proportion contrasted to the control, based upon regressing the logit-transformed data.

Drought score, being an ordered factor with no real numeric meaning, was analyzed with a non-parametric test between the experimental and control groups. The p-value was calculated with a Mann-Whitney rank-sum test.

For the split-pot assays, matched control and experimental measurements were available for both variables. In lieu of a direct transformed regression technique for these data, the logit-transformed proportions were analyzed by parametric methods. The p-value was derived from a paired-t-test on the transformed data. For the paired score data, the p-value from a Wilcoxon test was reported.

Example VIII. Soil Drought (Single Pot)

These experiments determined the physiological basis for the drought tolerance conferred by each lead and were typically performed under soil grown conditions. Usually, the experiment was performed under photoperiodic conditions of 10-hr or 12-hr light. Where possible, a given project (gene/promoter combination or protein variant) was represented by three independent lines. Plants were usually at late vegetative/early reproductive stage at the time measurements were taken. Typically we assayed three different states: a well-watered state, a mild-drought state and a moderately severe drought state. In each case, we made comparisons to wild-type plants with the same degree of physical stress symptoms (wilting). To achieve this, staggered samplings were often required. Typically, for a given line, ten individual plants were assayed for each state.

The following physiological parameters were routinely measured: relative water content, ABA content, proline content, and photosynthesis rate. In some cases, measurements of chlorophyll levels, starch levels, carotenoid levels, and chlorophyll fluorescence were also made.

Analysis of Results.

In a given experiment, for a particular parameter, we typically compared about 10 samples from a given transgenic line with about 10 samples of the appropriate wild-type control at each drought state. The mean values for each physiological parameter were calculated for both the transgenic line and the wild-type pots. In each case, a P-value (calculated via a simple t-test) was determined, which indicated the significance of the difference between the two mean values. The results for each transgenic line across each planting for a particular project were then presented in a results table.

A typical procedure is described below; this corresponds to method used for the drought time-course experiment which we performed on wild-type plants during our baseline studies at the outset of the drought program.

Procedure.

Seeds were stratified for 3 days at 4° C. in 0.1% agarose and sown on Metromix 200 in 2.25 inch pots (square or round). Plants were maintained in individual pots within flats grown under short days (10:14 L:D). Seedlings were watered as needed to maintain healthy plant growth and development. At 7 to 8 weeks after planting, plants were used in drought experiments.

Plants matched for equivalent growth development (rosette size) were removed from plastic flats and placed on absorbent paper. Pots containing plants used as well-watered controls were placed within a weigh boat and the dish placed on the absorbent paper. The purpose of the weigh boat was to retain any water that might leak from well-watered pots and affect pots containing plants undergoing the drought stress treatment.

On each day of sampling, up to 18 droughted plants and 6 well-watered controls (from each transgenic line) were picked from a randomly generated pool (given that they passed quality control standards). Biochemical analysis for photosynthesis, ABA, and proline was performed on the next three youngest, most fully expanded leaves. Relative water content was analyzed using the remaining rosette tissue.

Example IX. Soil Drought (Biochemical and Physiological Assays)

Background.

The purpose of these measurements was to determine the physiological state of plants in soil drought experiments.

Measurement of Photosynthesis.

Photosynthesis was measured using a LICOR LI-6400. The LI-6400 uses infrared gas analyzers to measure carbon dioxide to generate a photosynthesis measurement. This method is based upon the difference of the $CO_2$ reference (the amount put into the chamber) and the $CO_2$ sample (the amount that leaves the chamber). Since photosynthesis is the process of converting $CO_2$ to carbohydrates, we expected to see a decrease in the amount of $CO_2$ sample. From this difference, a photosynthesis rate can be generated. In some cases, respiration may occur and an increase in $CO_2$ detected. To perform measurements, the LI-6400 was set-up and calibrated as per LI-6400 standard directions. Photosynthesis was measured in the youngest most fully expanded leaf at 300 and 1000 ppm $CO_2$ using a metal halide light source. This light source provided about 700 $\mu E$ $m^{-2}$ $s^{-1}$.

Fluorescence was measured in dark and light adapted leaves using either a LI-6400 (LICOR) with a leaf chamber fluorometer attachment or an OS-1 (Opti-Sciences, Hudson, N.H.) as described in the manufacturer's literature. When the LI-6400 was used, all manipulations were performed under a dark shade cloth. Plants were dark adapted by placing in a box under this shade cloth until used. The OS-30 utilized small clips to create dark adapted leaves.

Measurement of Abscisic Acid and Proline.

The purpose of this experiment was to measure ABA and proline in plant tissue. ABA is a plant hormone believed to be involved in stress responses and proline is an osmoprotectant.

Three of the youngest, most fully expanded mature leaves were harvested, frozen in liquid nitrogen, lyophilized, and a dry weight measurement taken. Plant tissue was then homogenized in methanol to which 500 ng of d6-ABA had been added to act as an internal standard. The homogenate was filtered to removed plant material and the filtrate evaporated to a small volume. To this crude extract, approximately 3 ml of 1% acetic acid was added and the extract was further evaporated to remove any remaining methanol. The volume of the remaining aqueous extract was measured and a small aliquot (usually 200 to 500 µl) removed for proline analysis (Protocol described below). The remaining extract was then partitioned twice against ether, the ether removed by evaporation and the residue methylated using ethereal diazomethane. Following removal of any unreacted diazomethane, the residue was dissolved in 100 to 200 µl ethyl acetate and analyzed by gas chromatography-mass spectrometry. Analysis was performed using an HP 6890 GC coupled to an HP 5973 MSD using a DB-5 ms gas capillary column. Column pressure was 20 psi. Initially, the oven temperature was 150° C. Following injection, the oven was heated at 5° C./min to a final temperature of 250° C. ABA levels were estimated using an isotope dilution equation and normalized to tissue dry weight.

Free proline content was measured according to Bates (Bates et al., 1973). The crude aqueous extract obtained above was brought up to a final volume of 500 µl using distilled water. Subsequently, 500 µl of glacial acetic was added followed by 500 µl of Chinard's Ninhydrin. The samples were then heated at 95 to 100° C. for 1 hour. After this incubation period, samples were cooled and 1.5 ml of toluene were added. The upper toluene phase was removed and absorbance measured at 515 nm. Amounts of proline were estimated using a standard curve generated using L-proline and normalized to tissue dry weight.

[n.b. Chinard's Ninhydrin was prepared by dissolving 2.5 g ninhydrin (triketohydrindene hydrate) in 60 ml glacial acetic acid at 70° C. to which 40 ml of 6 M phosphoric acid was added.]

Measurement of Relative Water Content (RWC).

Relative Water Content (RWC) indicates the amount of water that is stored within the plant tissue at any given time. It was obtained by taking the field weight of the rosette minus the dry weight of the plant material and dividing by the weight of the rosette saturated with water minus the dry weight of the plant material. The resulting RWC value can be compared from plant to plant, regardless of plant size.

$$\text{Relative Water Content} = \frac{\text{Field Weight} - \text{Dry Weight}}{\text{Turgid Weight} - \text{Dry Weight}} \times 100$$

After tissue had been removed for array and ABA/proline analysis, the rosette was cut from the roots using a small pair of scissors. The field weight was obtained by weighing the rosette. The rosette was then immersed in cold water and placed in an ice water bath in the dark. The purpose of this was to allow the plant tissue to take up water while preventing any metabolism which could alter the level of small molecules within the cell. The next day, the rosette was carefully removed, blotted dry with tissue paper, and weighed to obtain the turgid weight. Tissue was then frozen, lyophilized, and weighed to obtain the dry weight.

Starch Determination.

Starch was estimated using a simple iodine based staining procedure. Young, fully expanded leaves were harvested either at the end or beginning of a 12 h light period and placed in tubes containing 80% ethanol or 100% methanol. Leaves were decolorized by incubating tubes in a 70 to 80 C water bath until chlorophyll had been removed from leaf tissue. Leaves were then immersed in water to displace any residual methanol which may be present in the tissue. Starch was then stained by incubating leaves in an iodine stain (2 g KI, 1 g $I_2$ in 100 ml water) for one min and then washing with copious amounts of water. Tissue containing large amounts of starch stained dark blue or black; tissues depleted in starch were colorless.

Chlorophyll/Carotenoid Determination.

For some experiments, chlorophyll was estimated in methanolic extracts using the method of Porra et al. (1989). Carotenoids were estimated in the same extract at 450 nm using an A(1%) of 2500. Chlorophyll was measured with a SPAD-502 (Minolta). Both carotenoid and chlorophyll content and amount could also be determined via HPLC. In this procedure pigments were extracted from leave tissue by homogenizing leaves in acetone:ethyl acetate (3:2). Water was added, the mixture centrifuged, and the upper phase removed for HPLC analysis. Samples were analyzed using a Zorbax C18 (non-endcapped) column (250×4.6) with a gradient of acetonitrile:water (85:15) to acetonitrile:methanol (85:15) in 12.5 minutes. After holding at these conditions for two minutes, solvent conditions were changed to methanol:ethyl acetate (68:32) in two minutes. Carotenoids and chlorophylls were quantified using peak areas and response factors calculated using lutein and beta-carotene as standards.

Quantification of Protein Level.

Protein level quantification was performed for 35S::G481 and related projects. Plants were plated on selective MS media, and transplanted to vertical MS plates after one week of growth. After 17 days of growth (24 h light, 22 C), tissues were harvested from the vertical plates. The shoot tissue from 1 plant was harvested as one biological replicate for each line, and the root tissue from 2 plants were combined as 1 biological replicate. For each line analyzed, two biological replicates each of shoot and root tissue were analyzed. Whole cell protein extracts were prepared in a 96 well format and separated on a 4-20% SDS-PAGE gel, transferred to PVDF membrane for western blotting, and probed with a 1:2000 dilution of anti-G481 antibody in a 1% blocking solution in TBS-T. Protein levels for various samples were estimated by setting a level of one for pMEN65 wild type and three for line G481-6 to describe the amount of G481 protein visible on the blot. The protein level for each of the other lines tested was visually estimated on each blot relative to the pMEN65 and G481-6 standards.

Nuclear and Cytoplasmically-Enriched Fractions.

We developed a platform to prepare nuclear and cytoplasmic protein extracts in a 96-well format using a tungsten carbide beads for cell disruption in a mild detergent and a sucrose cushion to separate cytoplasmic from nuclear fractions. We used histone antibodies to demonstrate that this method effectively separated cytoplasmic from nuclear-enriched fractions. An alternate method (spun only) used the same disruption procedure, but simply pelleted the nuclei to separate them from the cytoplasm without the added purification of a sucrose cushion.

Quantification of mRNA Level.

Three shoot and three root biological replicates were typically harvested for each line, as described above in the protein quantification methods section. RNA was prepared using a 96-well format protocol, and cDNA synthesized from each sample. These preparations were used as templates for RT-PCR experiments. We measured the levels of transcript for a gene of interest (such as G481) relative to 18S RNA transcript for each sample using an ABI 7900 Real-Time RT-PCR machine with SYBR Green technology.

Phenotypic Analysis: Flowering Time.

Plants were grown in soil. Flowering time was determined based on either or both of (i) number to days after planting to the first visible flower bud. (ii) the total number of leaves (rosette or rosette plus cauline) produced by the primary shoot meristem.

Phenotypic Analysis: Heat Stress.

In preliminary experiments described in this report, plants were germinated growth chamber at 30 C with 24 h light for 11 d. Plants were allowed to recover in 22 C with 24 h light for three days, and photographs were taken to record health after the treatment. In a second experiment, seedlings were grown at 22 C for four days on selective media, and the plates transferred to 32 C for one week. They were then allowed to recover at 22 C for three days. Forty plants from two separate plates were harvested for each line, and both fresh weight and chlorophyll content measured.

Phenotypic Analysis: Dark-Induced Senescence.

In preliminary experiments described in this report, plants were grown on soil for 27-30 days in 12 h light at 22 C. They were moved to a dark chamber at 22 C, and visually evaluated for senescence after 10-13 days. In some cases we used Fv/Fm as a measure of chlorophyll (Pourtau et al., 2004) on the youngest most fully-expanded leaf on each plant. The Fv/Fm mean for the 12 plants from each line was normalized to the Fv/Fm mean for the 12 matched controls.

VARIOUS DEFINITIONS USED IN THIS REPORT

RWC=Relative water content (field wt.–dry weight)/(turgid wt.–dry wt.)×100
ABA=Abscisic acid, μg/gdw
Proline=Proline, μmole/gdw A 300=net assimilation rate, μmole $CO_2/m^2/s$ at 300 ppm $CO_2$
A 1000=net assimilation rate, μmole $CO_2/m^2/s$ at 1000 ppm $CO_2$
Chl SPAD=Chlorophyll estimated by a Minolta SPAD-502, ratio of 650 nm to 940 nm
Total Chl=mg/gfw, estimated by HPLC
Carot=mg/gfw, estimated by HPLC
Fo=minimal fluorescence of a dark adapted leaf
Fm=maximal fluorescence of a dark adapted leaf
Fo'=minimal fluorescence of a light adapted leaf
Fm'=maximal fluorescence of a light adapted leaf
Fs=steady state fluorescence of a light adapted leaf
Psi if =water potential (Mpa) of a leaf
Psi p=turgor potential (Mpa) of a leaf
Psi pi=osmotic potential (Mpa) of a leaf
Fv/Fm=(Fm−Fo)/Fm; maximum quantum yield of PSII
Fv'/Fm'=(Fm'−Fo')/Fm'; efficiency of energy harvesting by open PSII reaction centers
PhiPS2=(Fm'−Fs)/Fm', actual quantum yield of PSII
ETR=PhiPS2×light intensity absorbed×0.5; we use 100 μE/$m^2$/s for an average light intensity and 85% as the amount of light absorbed
qP=(Fm'−Fs)/(Fm'−Fo'); photochemical quenching (includes photosynthesis and photorespiration); proportion of open PSII
qN=(Fm−Fm')/(Fm−Fo'); non-photochemical quenching (includes mechanisms like heat dissipation)
NPQ=(Fm−Fm')/Fm'; non-photochemical quenching (includes mechanisms like heat dissipation)

Example X. Disease Physiology, Plate Assays

Overview.

A *Sclerotinia* plate-based assay was used as a pre-screen to identify top performing lines from each project (i.e., lines from transformation with a particular construct) that could be tested in subsequent soil-based assays. Top performing lines were also subjected to *Botrytis cinerea* plate assays as noted. Typically, eight lines were subjected to plate assays, from which the best lines were selected for subsequent soil-based assays. In projects where significant pathogen resistance was not obtained in plate based assays, lines were not submitted for soil assays.

Unless otherwise stated, all experiments were performed with the *Arabidopsis thaliana* ecotype Columbia (Col-0). Similar assays could be devised for other crop plants such as soybean or maize plants. Assays were usually performed on non-selected segregating T2 populations (in order to avoid the extra stress of selection). Control plants for assays on lines containing direct promoter-fusion constructs were wild-type plants or Col-0 plants transformed an empty transformation vector (pMEN65). Controls for 2-component lines (generated by supertransformation) were the background promoter-driver lines (i.e. promoter::LexA-GAL4TA lines), into which the supertransformations were initially performed.

Procedures.

Prior to plating, seed for all experiments were surface sterilized in the following manner: (1) 5 minute incubation with mixing in 70% ethanol; (2) 20 minute incubation with mixing in 30% bleach, 0.01% Triton X-100; (3) five rinses with sterile water. Seeds were resuspended in 0.1% sterile agarose and stratified at 4° C. for 2-4 days.

Sterile seeds were sown on starter plates (15 mm deep) containing the following medium: 50% MS solution, 1% sucrose, 0.05% MES, and 1% Bacto-Agar. 40 to 50 seeds were sown on each plate. Plates were incubated at 22° C. under 24-hour light (95-110 μE $m^{-2}$ $s^{-1}$) in a germination growth chamber. On day 10, seedlings were transferred to assay plates (25 mm deep plates with medium minus sucrose). Each assay plate had nine test seedlings and nine control seedlings on separate halves of the plate. Three or four plates were used per line, per pathogen. On day 14, seedlings were inoculated (specific methods below). After inoculation, plates were put in a growth chamber under a 12-hour light/12-hour dark schedule. Light intensity was lowered to 70-80 μE $m^{-2}$ $s^{-1}$ for the disease assay. Disease symptoms were evaluated starting four days post-inoculation (DPI) up to 10 DPI if necessary. For each plate, the number of dead test plants and control plants were counted. Plants were scored as "dead" if the center of the rosette collapsed (usually brown or water-soaked).

*Sclerotinia* Inoculum Preparation.

A *Sclerotinia* liquid culture was started three days prior to plant inoculation by cutting a small agar plug (¼ sq. inch) from a 14- to 21-day old *Sclerotinia* plate (on Potato Dextrose Agar; PDA) and placing it into 100 ml of half-strength Potato Dextrose Broth (PDB). The culture was allowed to grown in the PDB at room temperature under 24-hour light for three days. On the day of seedling inoculation, the hyphal ball was retrieved from the medium, weighed, and ground in a blender with water (50 ml/gm tissue). After grinding, the mycelial suspension was filtered through two layers of cheesecloth and the resulting suspension was diluted 1:5 in water. Plants were inoculated by spraying to run-off with the mycelial suspension using a Preval aerosol sprayer.

*Botrytis* Inoculum Preparation.

*Botrytis* inoculum was prepared on the day of inoculation. Spores from a 14- to 21-day old plate were resuspended in a solution of 0.05% glucose, 0.03M $KH_2PO_4$ to a final concentration of $10^4$ spores/ml. Seedlings were inoculated with a Preval aerosol sprayer, as with *Sclerotinia* inoculation.

Data Interpretation.

After the plates were evaluated, each line was given one of the following qualitative scores:
(++) Substantially enhanced resistance compared to controls. The phenotype was very consistent across all plates for a given line.
(+) Enhanced resistance compared to controls. The response was consistent but was only moderately above the normal levels of variability observed for that assay.
(wt) No detectable difference from wild-type controls.
(−) Increased susceptibility compared to controls. The response was consistent but was only moderately above the normal levels of variability observed for that assay.
(−−) Substantially impaired performance compared to controls. The phenotype was consistent and growth was significantly above the normal levels of variability observed for that assay.
(n/d) Experiment failed, data not obtained, or assay not performed.

Example XI. Disease Physiology, Soil Assays

Overview.

Lines from transformation with a particular construct were tested in a soil-based assay for resistance to powdery mildew (*Erysiphe cichoracearum*) as noted below. Typically, eight lines per project were subjected to the *Erysiphe* assay.

Unless otherwise stated, all experiments were performed with the *Arabidopsis thaliana* ecotype Columbia (Col-0). Assays were usually performed on non-selected segregating T2 populations (in order to avoid the extra stress of selection). Control plants for assays on lines containing direct promoter-fusion constructs were wild-type plants or Col-0 plants transformed an empty transformation vector (pMEN65). Controls for 2-component lines (generated by supertransformation) were the background promoter-driver lines (i.e. promoter::LexA-GAL4TA lines), into which the supertransformations were initially performed.

In addition, positive hits from the *Sclerotinia* plate assay were subjected to a soil-based *Sclerotinia* assay as noted. This assay was based on hyphal plug inoculation of rosette leaves.

Procedures.

*Erysiphe* inoculum was propagated on a pad4 mutant line in the Col-0 background, which is highly susceptible to *Erysiphe* (Reuber et al., 1998). The inoculum was maintained by using a small paintbrush to dust conidia from a 2-3 week old culture onto new plants (generally three weeks old). For the assay, seedlings were grown on plates for one week under 24-hour light in a germination chamber, then transplanted to soil and grown in a walk-in growth chamber under a 12-hour light/12-hour dark light regimen, 70% humidity. Each line was transplanted to two 13 cm square pots, nine plants per pot. In addition, three control plants were transplanted to each pot for direct comparison with the test line. Approximately 3.5 weeks after transplanting, plants were inoculated using settling towers as described by Reuber et al. (1998). Generally, three to four heavily infested leaves were used per pot for the disease assay. The level of fungal growth was evaluated eight to ten days after inoculation.

Data Interpretation.

After the pots were evaluated, each line was given one of the following overall scores:

(+++) Highly enhanced resistance as compared to controls. The phenotype was very consistent.

(++) Substantially enhanced resistance compared to controls. The phenotype was very consistent in both pots for a given line.

(+) Enhanced resistance compared to controls. The response was consistent but was only moderately above the normal levels of variability observed.

(wt) No detectable difference from wild-type controls.

(−) Increased susceptibility compared to controls. The response was consistent but was only moderately above the normal levels of variability observed.

(−−) Substantially impaired performance compared to controls. The phenotype was consistent and growth was significantly above the normal levels of variability observed.

(n/d) Experiment failed, data not obtained, or assay not performed.

Example XII. Experimental Results

This application provides experimental observations for a number of transcription factors for improved yield and/or increased tolerance to abiotic stresses such as water deficit-related tolerance, low nutrient tolerance, cold tolerance (for example, G481, G867, G1073, G28, G47, G1274, G1792, G1988, and G1760, (SEQ ID NOs: 10, 550, 16, 18, 2, 6, 20, 24, 1794, 1836, 30, 178, 690, 22, and 1336, respectively), two transcription factors for disease resistance (G28, SEQ ID NO: 2, and G1792, SEQ ID NO: 24), and, for each of these transcription factors, a number of phylogenetically and closely related homologs derived from diverse gene sequences. A set of polynucleotides and polypeptides related to each lead transcription factor has been designated as a "study group" and related sequences in these clades have been subsequently analyzed using morphological and phenotypic studies.

Phenotypic Screens: Promoter Combinations.

A panel of promoters was assembled based on domains of expression that had been well characterized in the published literature. These were chosen to represent broad non-constitutive patterns which covered the major organs and tissues of the plant. The following domain-specific promoters were picked, each of which drives expression in a particular tissue or cell-type: ARSK1 (root), RBCS3 (photosynthetic tissue, including leaf tissue), CUT1 (shoot epidermal, guard-cell enhanced), SUC2 (vascular), STM (apical meristem and mature-organ enhanced), AP1 (floral meristem enhanced), AS1 (young organ primordia) and RSI1 (young seedlings, and roots). Also selected was a stress inducible promoter, RD29A, which is able to up-regulate a transgene at drought onset.

The basic strategy was to test each polynucleotide with each promoter to give insight into the following questions: (i) mechanistically, in which part of the plant is activity of the polynucleotide sufficient to produce stress tolerance? (ii) Can we identify expression patterns which produce compelling stress tolerance while eliminating any undesirable effects on growth and development? (iii) Does a particular promoter give an enhanced or equivalent stress tolerance phenotype relative to constitutive expression? Each of the promoters in this panel is considered to be representative of a particular pattern of expression; thus, for example, if a particular promoter such as SUC2, which drives expression in vascular tissue, yields a positive result with a particular transcription factor gene, it would be predicted and expected that a positive result would be obtained with any other promoter that drives the same vascular pattern.

We now have many examples demonstrating the principle that use of a regulated promoter can confer substantial stress tolerance while minimizing deleterious effects. For example, the results from regulating G1792-related genes using regional specific promoters were especially persuasive. When overexpressed constitutively, these genes produced extreme dwarfing. However, when non-constitutive promoters were used to express these sequences ectopically, off-types were substantially ameliorated, and strong disease tolerance was still obtained (for example, with RBCS3::G1792 and RBCS3::G1795 lines).

Additionally, it is feasible to identify promoters which afford high levels of inducible expression. For instance, a major tactic in the disease program is to utilize pathogen inducible promoters; a set of these has now been identified for testing with each of the disease-resistance conferring transcription factors. This approach is expected to be productive as we have shown that inducible expression of G1792 via the dexamethasone system gives effective disease tolerance without off-types. By analogy, it would be useful to take a similar approach for the drought tolerance trait. So far the only drought regulated promoter that we have tested is RD29A, since its utility had been published (Kasuga et al., 1999).

Phenotypic Screens: effects of protein variants for distinct transcription factors. The effects of overexpressing a variety of different types of protein variants including: deletion variants, GAL4 fusions, variants with specific residues mutagenized, and forms in which domains were swapped with other proteins, have been examined Together, these approaches have been informative, and have helped illuminate the role of specific residues (see for example, the site-directed mutagenesis experiments for G1274 or G1792), as well as giving new clues as to the basis of particular phenotypes. For example, overexpression lines for a G481 deletion variant exhibited drought tolerance, suggesting that the G481 drought phenotype might arise from dominant negative type interactions.

Phenotypic Screens: Knockout and Knock-Down Approaches.

Thus far, both T-DNA alleles and RNAi methods have been used to isolate knockouts/knockdown lines for transcription factors of interest. In general, it was determined that the knockout (KO) approach to be more informative and easier to interpret than RNAi based strategies. In particular, RNAi approaches are hampered by the possibility that other related transcription factors might be directly or indirectly knocked-down (even when using a putative gene-specific construct). Thus, a set of RNAi lines showing an interesting phenotype requires a very substantial amount of molecular characterization to prove that the phenotypes are due to reduced activity of the targeted gene. We have found that KO lines have given some useful insights into the relative endogenous roles of particular genes within the CAAT family, and revealed the potential for obtaining stress tolerance traits via knock-down strategies (e.g., G481 knockout/knockdown approaches).

Table 21 summarizes experimental results with plants in which sequences of the invention have either been overexpressed, reduced, or knocked out. These modifications have yielded new and potentially valuable phenotypic traits, relative to control plants, in morphological, physiological or disease assays, as demonstrated in *Arabidopsis*, or alternatively in tomato or other plants where noted. The last column lists the trait that was experimentally observed in plants, relative to control plants, after: either transforming plants with each transcription factor polynucleotide GID (Gene IDentifier, found in the first column) under the listed regulatory control mechanism; or (ii) in the cases where the project is listed as a knockout, expression of the transcription factor was abolished; or (iii) in the cases where the project is listed as "RNAi (GS) or RNAi (clade), the transcription factor was knocked down using RNAi targeting either the gene sequence or the clade of related genes, respectively.

TABLE 21

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G28 | AP2 (145-208) | 2 | G28 | Const. 35S prom. | P174 | 3854 | More tol. to drought* and better recovery from drought treatment* |
| G28 | AP2 (145-208) | 2 | G28 | Const. 35S prom. | P174 | 3854 | Late flowering |
| G28 | AP2 (145-208) | 2 | G28 | Const. 35S prom. | P26537 | 5019 | Late flowering |
| G28 | AP2 (145-208) | 2 | G28 | Const. 35S prom. | P26378 | 4967 | Late flowering |
| G28 | AP2 (145-208) | 2 | G28 | 2 comp. including P6506 (35S prom.) | P7826 | 4605 | Late flowering |
| G28 | AP2 (145-208) | 2 | G28 | Const. 35S prom. | P174 | 3854 | Darker green leaf color |
| G28 | AP2 (145-208) | 2 | G28 | Const. 35S prom. | P26537 | 5019 | Darker green leaf color |
| G28 | AP2 (145-208) | 2 | G28 | Const. 35S prom. | P26378 | 4967 | Darker green leaf color |
| G28 | AP2 (145-208) | 2 | G28 | 2 comp. including P6506 (35S prom.) | P7826 | 4605 | Darker green leaf color |
| G28 | AP2 (145-208) | 2 | G28 | Const. 35S prom. | P174 | 3854 | Altered C/N sensing: greater tol. to low nitrogen conditions in C/N sensing assay |
| G28 | AP2 (145-208) | 2 | G28 | Const. 35S prom. | P174 | 3854 | Greater resistance to *Botrytis* |
| G28 | AP2 (145-208) | 2 | G28 | Const. 35S prom. | P174 | 3854 | Greater resistance to *Sclerotinia* |
| G28 | AP2 (145-208) | 2 | G28 | Const. 35S prom. | P174 | 3854 | Greater resistance to *Erysiphe* |
| G28 | AP2 (145-208) | 2 | G28 | Root-specific ARSK1 prom. | P23541 | 4845 | Early flowering |
| G28 | AP2 (145-208) | 2 | G28 | Epidermal-specific CUT1 prom. | P23441 | 4835 | Greater res. to *Erysiphe* |
| G28 | AP2 (145-208) | 2 | G28 | Epidermal and vascular-specific LTP1 prom. | P23543 | 4846 | Greater res. to *Erysiphe* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G28 | AP2 (145-208) | 2 | G28 | Leaf-specific RBCS3 prom. | P23544 | 4847 | Greater res. to *Erysiphe* |
| G28 | AP2 (145-208) | 2 | G28 | Leaf-specific RBCS3 prom. | P23544 | 4847 | Darker green leaf color |
| G28 | AP2 (145-208) | 2 | G28 | Protein-GFP C terminal fusion, 35S | P26497 | 5015 | Greater res. to *Sclerotinia* |
| G1006 | AP2 (113-177) | 752 | G28 | Const. 35S prom. | P417 | 3931 | Greater res. to *Erysiphe* |
| G1006 | AP2 (113-177) | 752 | G28 | Const. 35S prom. | P417 | 3931 | Greater res. to *Sclerotinia* |
| G1006 | AP2 (113-177) | 752 | G28 | Const. 35S prom. | P417 | 3931 | Darker green leaf color |
| G22 | AP2 (88-152) | 56 | G28 | Const. 35S prom. | P806 | 3977 | Late flowering |
| G22 | AP2 (88-152) | 56 | G28 | Const. 35S prom. | P806 | 3977 | Greater tol. to NaCl (determined with 150 mM NaCl) |
| G22 | AP2 (88-152) | 56 | G28 | 2 comp. including P5326 (AP1 prom.) | P3376 | 4509 | Significantly greater soluble solids (Brix) in tomato plants |
| G22 | AP2 (88-152) | 56 | G28 | 2 comp. including P5318 (STM prom.) | P3376 | 4509 | Significantly greater soluble solids (Brix) in tomato plants |
| G22 | AP2 (88-152) | 56 | G28 | 2 comp. including P5284 (RBCS3 prom.) | P3376 | 4509 | Significantly greater lycopene in tomato plants |
| G3659 | AP2 (130-194) | 2054 | G28 | Const. 35S prom. | P23452 | 4836 | Greater res. to *Erysiphe* |
| G3659 | AP2 (130-194) | 2054 | G28 | Const. 35S prom. | P23452 | 4836 | Late flowering |
| G3659 | AP2 (130-194) | 2054 | G28 | Const. 35S prom. | P23452 | 4836 | Greater res. to *Sclerotinia* |
| G3659 | AP2 (130-194) | 2054 | G28 | Const. 35S prom. | P23452 | 4836 | Glossy leaves |
| G3659 | AP2 (130-194) | 2054 | G28 | Const. 35S prom. | P23452 | 4836 | Darker green leaf color |
| G3660 | AP2 (119-183) | 2056 | G28 | Const. 35S prom. | P23418 | 4831 | Glossy leaves |
| G3660 | AP2 (119-183) | 2056 | G28 | Const. 35S prom. | P23418 | 4831 | Late flowering |
| G3660 | AP2 (119-183) | 2056 | G28 | Const. 35S prom. | P23418 | 4831 | Greater res. to *Sclerotinia* |
| G3660 | AP2 (119-183) | 2056 | G28 | Const. 35S prom. | P23418 | 4831 | Greater res. to *Botrytis* |
| G3660 | AP2 (119-183) | 2056 | G28 | Const. 35S prom. | P23418 | 4831 | Greater res. to *Erysiphe* |
| G3717 | AP2 (130-194) | 2076 | G28 | Const. 35S prom. | P23421 | 4833 | Greater res. to *Erysiphe* |
| G3717 | AP2 (130-194) | 2076 | G28 | Const. 35S prom. | P23421 | 4833 | Greater res. to *Sclerotinia* |
| G3717 | AP2 (130-194) | 2076 | G28 | Const. 35S prom. | P23421 | 4833 | Late flowering |
| G3717 | AP2 (130-194) | 2076 | G28 | Const. 35S prom. | P23421 | 4833 | Glossy leaves |
| G3717 | AP2 (130-194) | 2076 | G28 | Const. 35S prom. | P23421 | 4833 | Darker green leaf color |
| G3717 | AP2 (130-194) | 2076 | G28 | Const. 35S prom. | P23421 | 4833 | Altered C/N sensing: Greater tol. to low nitrogen conditions in C/N sensing assay |
| G3718 | AP2 (139-203) | 2078 | G28 | Const. 35S prom. | P23423 | 4834 | Greater res. to *Erysiphe* |
| G3718 | AP2 (139-203) | 2078 | G28 | Const. 35S prom. | P23423 | 4834 | Greater res. to *Sclerotinia* |
| G3718 | AP2 (139-203) | 2078 | G28 | Const. 35S prom. | P23423 | 4834 | Glossy leaves |
| G3718 | AP2 (139-203) | 2078 | G28 | Const. 35S prom. | P23423 | 4834 | Darker green leaf color |
| G3718 | AP2 (139-203) | 2078 | G28 | Const. 35S prom. | P23423 | 4834 | Late flowering |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3718 | AP2 (139-203) | 2078 | G28 | Const. 35S prom. | P23423 | 4834 | Altered C/N sensing: Greater tol. to low nitrogen conditions in C/N sensing assay |
| G3841 | AP2 (102-166) | 2158 | G28 | Const. 35S prom. | P25573 | 4912 | Greater res. to *Erysiphe* |
| G3841 | AP2 (102-166) | 2158 | G28 | Const. 35S prom. | P26576 | 5021 | Greater res. to *Erysiphe* |
| G3841 | AP2 (102-166) | 2158 | G28 | Const. 35S prom. | P25573 | 4912 | Greater res. to *Sclerotinia* |
| G3841 | AP2 (102-166) | 2158 | G28 | Const. 35S prom. | P26576 | 5021 | Greater res. to *Sclerotinia* |
| G3841 | AP2 (102-166) | 2158 | G28 | Const. 35S prom. | P25573 | 4912 | Late flowering |
| G3841 | AP2 (102-166) | 2158 | G28 | Const. 35S prom. | P26576 | 5021 | Late flowering |
| G3841 | AP2 (102-166) | 2158 | G28 | Const. 35S prom. | P25573 | 4912 | Altered leaf shape |
| G3841 | AP2 (102-166) | 2158 | G28 | Const. 35S prom. | P26576 | 5021 | Altered leaf shape |
| G3841 | AP2 (102-166) | 2158 | G28 | Const. 35S prom. | P25573 | 4912 | Glossy leaves |
| G3841 | AP2 (102-166) | 2158 | G28 | Const. 35S prom. | P26576 | 5021 | Glossy leaves |
| G3841 | AP2 (102-166) | 2158 | G28 | Const. 35S prom. | P25573 | 4912 | Darker green leaf color |
| G3841 | AP2 (102-166) | 2158 | G28 | Const. 35S prom. | P26576 | 5021 | Darker green leaf color |
| G3841 | AP2 (102-166) | 2158 | G28 | Const. 35S prom. | P25573 | 4912 | Altered C/N sensing: Greater tol. to low nitrogen conditions in C/N sensing assay |
| G3841 | AP2 (102-166) | 2158 | G28 | Const. 35S prom. | P26576 | 5021 | Altered C/N sensing: Greater tol. to low nitrogen conditions in C/N sensing assay |
| G3843 | AP2 (130-194) | 2160 | G28 | — | — | | n/d |
| G3852 | AP2 (102-167) | 2170 | G28 | — | — | | n/d |
| G3844 | AP2 (141-205) | 2162 | G28 | — | — | | n/d |
| G3845 | AP2 (101-165) | 2164 | G28 | — | — | | n/d |
| G3846 | AP2 (95-159) | 2166 | G28 | — | — | | n/d |
| G3857 | AP2 (98-162) | 2174 | G28 | — | — | | n/d |
| G3858 | AP2 (108-172) | 2176 | G28 | — | — | | n/d |
| G3430 | AP2 (145-209) | 4 | G28 | Const. 35S prom. | P21267 | 4768 | Greater res. to *Erysiphe* |
| G3430 | AP2 (145-209) | 4 | G28 | Const. 35S prom. | P21267 | 4768 | Greater res. to *Sclerotinia* |
| G3430 | AP2 (145-209) | 4 | G28 | Const. 35S prom. | P21267 | 4768 | Late flowering |
| G3430 | AP2 (145-209) | 4 | G28 | Const. 35S prom. | P21267 | 4768 | Darker green leaf color |
| G3848 | AP2 (149-213) | 2168 | G28 | Const. 35S prom. | P25571 | 4910 | Greater res. to *Erysiphe* |
| G3848 | AP2 (149-213) | 2168 | G28 | Const. 35S prom. | P25571 | 4910 | Greater res. to *Sclerotinia* |
| G3848 | AP2 (149-213) | 2168 | G28 | Const. 35S prom. | P25571 | 4910 | Late flowering |
| G3848 | AP2 (149-213) | 2168 | G28 | Const. 35S prom. | P25571 | 4910 | Glossy leaves |
| G3848 | AP2 (149-213) | 2168 | G28 | Const. 35S prom. | P25571 | 4910 | Darker green leaf color |
| G3856 | AP2 (140-204) | 2172 | G28 | Const. 35S prom. | P25572 | 4911 | Greater res. to *Erysiphe* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3856 | AP2 (140-204) | 2172 | G28 | Const. 35S prom. | P25572 | 4911 | Greater res. to *Sclerotinia* |
| G3856 | AP2 (140-204) | 2172 | G28 | Const. 35S prom. | P25572 | 4911 | Glossy leaves |
| G3856 | AP2 (140-204) | 2172 | G28 | Const. 35S prom. | P25572 | 4911 | Darker green leaf color |
| G3661 | AP2 (126-190) | 2058 | G28 | Const. 35S prom. | P23419 | 4832 | Greater res. to *Erysiphe* |
| G3661 | AP2 (126-190) | 2058 | G28 | Const. 35S prom. | P23419 | 4832 | Late flowering |
| G3661 | AP2 (126-190) | 2058 | G28 | Const. 35S prom. | P23419 | 4832 | Glossy leaves |
| G3864 | AP2 (127-191) | 2178 | G28 | — | — | | n/d |
| G3865 | AP2 (125-189) | 2180 | G28 | — | — | | n/d |
| G47 | AP2 (10-75) | 6 | G47 | Const. 35S prom. | P894 | 3994 | More lignin |
| G47 | AP2 (10-75) | 6 | G47 | 2 comp. including P6506 (35S prom.) | P3853 | 4532 | More lignin |
| G47 | AP2 (10-75) | 6 | G47 | Const. 35S prom. | P894 | 3994 | Altered stem morphology; wider stem diameter, large irregular vascular bundles with a much greater number of xylem vessels; xylem vessels within the bundles appeared narrow and more lignified |
| G47 | AP2 (10-75) | 6 | G47 | 2 comp. including P6506 (35S prom.) | P3853 | 4532 | Altered stem morphology; wider stem diameter, large irregular vascular bundles with a much greater number of xylem vessels; xylem vessels within the bundles appeared narrow and more lignified |
| G47 | AP2 (10-75) | 6 | G47 | Const. 35S prom. | P894 | 3994 | Better root growth under hyperosmotic stress with PEG |
| G47 | AP2 (10-75) | 6 | G47 | 2 comp. including P6506 (35S prom.) | P3853 | 4532 | Better root growth under hyperosmotic stress with PEG |
| G47 | AP2 (10-75) | 6 | G47 | Const. 35S prom. | P894 | 3994 | Late flowering |
| G47 | AP2 (10-75) | 6 | G47 | 2 comp. including P5284 (RBCS3 prom.) | P3853 | 4532 | Late flowering |
| G47 | AP2 (10-75) | 6 | G47 | Const. 35S prom. | P894 | 3994 | Altered architecture and inflorescence development; thick, fleshy inflorescences, reduced apical dominance, reduced internode elongation, stem branching pattern altered - primary shoot 'kinked' at each coflorescence node, reduced fertility, |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G47 | AP2 (10-75) | 6 | G47 | 2 comp. including P6506 (35S prom.) | P3853 | 4532 | small siliques borne on short pedicels held vertically and close against the stem Altered architecture and inflorescence development; thick, fleshy inflorescences, reduced apical dominance, reduced internode elongation, stem branching pattern altered - primary shoot 'kinked' at each coflorescence node, reduced fertility, small siliques borne on short pedicels held vertically and close against the stem |
| G47 | AP2 (10-75) | 6 | G47 | Const. 35S prom. | P894 | 3994 | More tol. to drought* and better recovery from drought treatment* |
| G47 | AP2 (10-75) | 6 | G47 | 2 comp. including P6506 (35S prom.) | P3853 | 4532 | More tol. to drought* and better recovery from drought treatment* |
| G47 | AP2 (10-75) | 6 | G47 | 2 comp. including P5311 (ARSK1 prom.) | P3853 | 4532 | Greater tol. to dehydration |
| G47 | AP2 (10-75) | 6 | G47 | 2 comp. including P5288 (CUT1 prom.) | P3853 | 4532 | Greater tol. to dehydration |
| G47 | AP2 (10-75) | 6 | G47 | 2 comp. including P5288 (CUT1 prom.) | P3853 | 4532 | More tol. to drought* and better recovery from drought treatment* |
| G47 | AP2 (10-75) | 6 | G47 | 2 comp. including P5287 (LTP1 prom.) | P3853 | 4532 | Significantly greater tomato plant volume |
| G47 | AP2 (10-75) | 6 | G47 | 2 comp. including P5284 (RBCS3 prom.) | P3853 | 4532 | Greater tol. to cold (8 C.) |
| G47 | AP2 (10-75) | 6 | G47 | 2 comp. including P5284 (RBCS3 prom.) | P3853 | 4532 | Late flowering |
| G47 | AP2 (10-75) | 6 | G47 | 2 comp. including P9002 (RD29A prom.) | P3853 | 4532 | Decreased sens. to ABA |
| G47 | AP2 (10-75) | 6 | G47 | 2 comp. including P9002 (RD29A prom.) | P3853 | 4532 | Greater tol. to dehydration |
| G47 | AP2 (10-75) | 6 | G47 | 2 comp. including P9002 (RD29A prom.) | P3853 | 4532 | Better recovery from drought treatment* |
| G47 | AP2 (10-75) | 6 | G47 | 2 comp. including P9002 (RD29A prom.) | P3853 | 4532 | Late flowering |
| G47 | AP2 (10-75) | 6 | G47 | 2 comp. including P9002 (RD29A prom.) | P3853 | 4532 | Larger leaf size |
| G47 | AP2 (10-75) | 6 | G47 | 2 comp. including P5318 (STM prom.) | P3853 | 4532 | Larger leaf size |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G47 | AP2 (10-75) | 6 | G47 | 2 comp. including P5318 (STM prom.) | P3853 | 4532 | Greater tol. to cold (8 C.) |
| G47 | AP2 (10-75) | 6 | G47 | 2 comp. including P5318 (STM prom.) | P3853 | 4532 | More tol. to drought* and better recovery from drought treatment* |
| G47 | AP2 (10-75) | 6 | G47 | 2 comp. including P5318 (STM prom.) | P3853 | 4532 | Late flowering |
| G47 | AP2 (10-75) | 6 | G47 | 2 comp. including P5318 (STM prom.) | P3853 | 4532 | Altered sugar sensing; greater tol. to sucrose (determined in 9.4% sucrose) |
| G47 | AP2 (10-75) | 6 | G47 | 2 comp. including P5290 (SUC2 prom.) | P3853 | 4532 | Late flowering |
| G47 | AP2 (10-75) | 6 | G47 | 2 comp. including P5290 (SUC2 prom.) | P3853 | 4532 | Larger leaf size |
| G47 | AP2 (10-75) | 6 | G47 | 2 comp. including P5290 (SUC2 prom.) | P3853 | 4532 | Darker green leaf color |
| G47 | AP2 (10-75) | 6 | G47 | 2 comp. including P5290 (SUC2 prom.) | P3853 | 4532 | Thicker stem |
| G47 | AP2 (10-75) | 6 | G47 | 2 comp. including P5290 (SUC2 prom.) | P3853 | 4532 | Greater tol. to dehydration |
| G47 | AP2 (10-75) | 6 | G47 | GAL4 N-term (Super Active), 35S | P25186 | 4864 | Greater tol. to dehydration |
| G47 | AP2(10-75) | 6 | G47 | GAL4 N-term (Super Active), 35S | P25186 | 4864 | Greater tol. to drought* |
| G47 | AP2 (10-75) | 6 | G47 | GAL4 N-term (Super Active), 35S | P25186 | 4864 | Early flowering |
| G47 | AP2 (10-75) | 6 | G47 | GAL4 N-term (Super Active), 35S | P25186 | 4864 | Greater tol. to 300 mM mannitol |
| G47 | AP2 (10-75) | 6 | G47 | Point mutation, 35S | P25735 | 4921 | Greater tol. to cold (8 C.) |
| G47 | AP2 (10-75) | 6 | G47 | Point mutation, 35S | P25732 | 4920 | Greater tol. to dehydration |
| G47 | AP2 (10-75) | 6 | G47 | Point mutation, 35S | P25732 | 4920 | More tol. to drought* and better recovery from drought treatment* |
| G47 | AP2 (10-75) | 6 | G47 | Domain swap/chimeric variant, 35S | P25182 | 4863 | Greater tol. to cold (8 C.) |
| G47 | AP2 (10-75) | 6 | G47 | Domain swap/chimeric variant, 35S | P25182 | 4863 | Late flowering |
| G47 | AP2 (10-75) | 6 | G47 | Domain swap/chimeric variant, 35S | P25182 | 4863 | Altered leaf shape |
| G47 | AP2 (10-75) | 6 | G47 | Domain swap/chimeric variant, 35S | P25182 | 4863 | Altered leaf orientation; narrow curled leaves held in an upward orientation |
| G2133 | AP2 (10-77) | 8 | G47 | Const. 35S prom. | P1572 | 4192 | Decreased apical dominance and bushy inflorescences |
| G2133 | AP2 (10-77) | 8 | G47 | Const. 35S prom. | P1572 | 4192 | More lignin |
| G2133 | AP2 (10-77) | 8 | G47 | Const. 35S prom. | P1572 | 4192 | Greater tol. to cold (8 C.) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G2133 | AP2 (10-77) | 8 | G47 | Const. 35S prom. | P1572 | 4192 | Greater tol. to dehydration |
| G2133 | AP2 (10-77) | 8 | G47 | Const. 35S prom. | P1572 | 4192 | Thicker stem |
| G2133 | AP2 (10-77) | 8 | G47 | Const. 35S prom. | P1572 | 4192 | More tol. to drought* and better recovery from drought treatment* |
| G2133 | AP2 (10-77) | 8 | G47 | Const. 35S prom. | P1572 | 4192 | Greater tol. to glyphosate |
| G2133 | AP2 (10-77) | 8 | G47 | Const. 35S prom. | P1572 | 4192 | Late flowering |
| G2133 | AP2 (10-77) | 8 | G47 | Const. 35S prom. | P1572 | 4192 | Altered C/N sensing: much greater tol. to low nitrogen conditions in C/N sensing assay |
| G2133 | AP2 (10-77) | 8 | G47 | 2 comp. including P5326 (AP1 prom.) | P4361 | 4552 | Greater tol. to cold (8 C.) |
| G2133 | AP2 (10-77) | 8 | G47 | 2 comp. including P5288 (CUT1 prom.) | P4361 | 4552 | Altered sugar sensing; greater tol. to sucrose (determined in 9.4% sucrose) |
| G2133 | AP2 (10-77) | 8 | G47 | 2 comp. including P5284 (RBCS3 prom.) | P4361 | 4552 | Greater tol. to dehydration |
| G2133 | AP2 (10-77) | 8 | G47 | 2 comp. including P5284 (RBCS3 prom.) | P4361 | 4552 | Greater tol. to cold (8 C.) |
| G2133 | AP2 (10-77) | 8 | G47 | 2 comp. including P9002 (RD29A prom.) | P4361 | 4552 | Better recovery from drought treatment* |
| G2133 | AP2 (10-77) | 8 | G47 | 2 comp. including P9002 (RD29A prom.) | P4361 | 4552 | Greater tol. to dehydration |
| G2133 | AP2 (10-77) | 8 | G47 | 2 comp. including P5318 (STM prom.) | P4361 | 4552 | Greater tol. to cold (8 C.) |
| G2133 | AP2 (10-77) | 8 | G47 | 2 comp. including P5290 (SUC2 prom.) | P4361 | 4552 | Late flowering |
| G2133 | AP2 (10-77) | 8 | G47 | 2 comp. including P5290 (SUC2 prom.) | P4361 | 4552 | Greater biomass |
| G3646 | AP2 (10-77) | 2042 | G47 | — | — |  | n/d |
| G3645 | AP2 (10-75) | 2040 | G47 | — | — |  | n/d |
| G3643 | AP2 (13-78) | 2036 | G47 | Const. 35S prom. | P23465 | 4839 | More tol. to drought* and better recovery from drought treatment* |
| G3643 | AP2 (13-78) | 2036 | G47 | Const. 35S prom. | P23465 | 4839 | Greater tol. to cold (8 C.) |
| G3647 | AP2 (13-78) | 2044 | G47 | — | — |  | n/d |
| G3644 | AP2 (52-122) | 2038 | G47 | Const. 35S prom. | P23455 | 4837 | Thicker stem |
| G3644 | AP2 (52-122) | 2038 | G47 | Const. 35S prom. | P23455 | 4837 | Late flowering |
| G3644 | AP2 (52-122) | 2038 | G47 | Const. 35S prom. | P23455 | 4837 | Greater biomass |
| G3649 | AP2 (15-87) | 2046 | G47 | Const. 35S prom. | P23456 | 4838 | Late flowering |
| G3649 | AP2 (15-87) | 2046 | G47 | Const. 35S prom. | P23456 | 4838 | Thicker stem |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3649 | AP2 (15-87) | 2046 | G47 | Const. 35S prom. | P23456 | 4838 | Decreased apical dominance; short inflorescence internodes |
| G3649 | AP2 (15-87) | 2046 | G47 | Const. 35S prom. | P23456 | 4838 | Greater tol. to cold (8 C.) |
| G3649 | AP2 (15-87) | 2046 | G47 | Const. 35S prom. | P23456 | 4838 | More tol. to drought* and better recovery from drought treatment* |
| G3651 | AP2 (60-130) | 2050 | G47 | — | — | — | n/d |
| G3650 | AP2 (75-139) | 2048 | G47 | — | — | — | n/d |
| G481 | CAAT (20-109) | 10 | G481 | Const. 35S prom. | P46 | 3811 | Late flowering |
| G481 | CAAT (20-109) | 10 | G481 | Const. 35S prom. | P26891 | 5063 | Late flowering |
| G481 | CAAT (20-109) | 10 | G481 | Const. 35S prom. | P26496 | 5014 | Late flowering |
| G481 | CAAT (20-109) | 10 | G481 | 2 comp. including P6506 (35S prom.) | P6812 | 4601 | Late flowering |
| G481 | CAAT (20-109) | 10 | G481 | Const. 35S prom. | P26496 | 5014 | Greater tol. to 300 mM mannitol |
| G481 | CAAT (20-109) | 10 | G481 | Const. 35S prom. | P46 | 3811 | Diurnal fluctuation of malate levels in young leaves |
| G481 | CAAT (20-109) | 10 | G481 | 2 comp. including P6506 (35S prom.) | P6812 | 4601 | Diurnal fluctuation of malate levels in young leaves |
| G481 | CAAT (20-109) | 10 | G481 | Const. 35S prom. | P46 | 3811 | Photosynthesis rate increased |
| G481 | CAAT (20-109) | 10 | G481 | 2 comp. including P6506 (35S prom.) | P6812 | 4601 | Photosynthesis rate increased |
| G481 | CAAT (20-109) | 10 | G481 | Const. 35S prom. | P46 | 3811 | Greater starch levels at specific timepoints and conditions |
| G481 | CAAT (20-109) | 10 | G481 | 2 comp. including P6506 (35S prom.) | P6812 | 4601 | Greater starch levels at specific timepoints and conditions |
| G481 | CAAT (20-109) | 10 | G481 | Const. 35S prom. | P46 | 3811 | Greater proline levels in sink tissues (young leaves and inflorescences) |
| G481 | CAAT (20-109) | 10 | G481 | 2 comp. including P6506 (35S prom.) | P6812 | 4601 | Greater proline levels in sink tissues (young leaves and inflorescences) |
| G481 | CAAT (20-109) | 10 | G481 | Const. 35S prom. | P46 | 3811 | Altered sucrose levels; elevated sucrose levels in specific times and tissues |
| G481 | CAAT (20-109) | 10 | G481 | 2 comp. including P6506 (35S prom.) | P6812 | 4601 | Altered sucrose levels; elevated sucrose levels in specific times and tissues |
| G481 | CAAT (20-109) | 10 | G481 | Const. 35S prom. | P46 | 3811 | Higher chlorophyll level |
| G481 | CAAT (20-109) | 10 | G481 | 2 comp. including P6506 (35S prom.) | P6812 | 4601 | Higher chlorophyll level |
| G481 | CAAT (20-109) | 10 | G481 | Const. 35S prom. | P46 | 3811 | Greater tol. to cold (8 C.) |
| G481 | CAAT (20-109) | 10 | G481 | Const. 35S prom. | P25893 | 4937 | Greater tol. to cold (8 C.) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G481 | CAAT (20-109) | 10 | G481 | 2 comp. including P6506 (35S prom.) | P6812 | 4601 | Greater tol. to cold (8 C.) |
| G481 | CAAT (20-109) | 10 | G481 | Const. 35S prom. | P46 | 3811 | Decreased sens. to ABA |
| G481 | CAAT (20-109) | 10 | G481 | 2 comp. including P6506 (35S prom.) | P6812 | 4601 | Decreased sens. to ABA |
| G481 | CAAT (20-109) | 10 | G481 | Const. 35S prom. | P46 | 3811 | Greater seedling vigor |
| G481 | CAAT (20-109) | 10 | G481 | Const. 35S prom. | P46 | 3811 | Greater water use efficiency |
| G481 | CAAT (20-109) | 10 | G481 | Const. 35S prom. | P46 | 3811 | More tol. to drought* and better recovery from drought treatment* |
| G481 | CAAT (20-109) | 10 | G481 | 2 comp. including P6506 (35S prom.) | P6812 | 4601 | More tol. to drought* and better recovery from drought treatment* |
| G481 | CAAT (20-109) | 10 | G481 | Const. 35S prom. | P46 | 3811 | Greater non-photochemical quenching of chlorophyll fluorescence (NPQ) |
| G481 | CAAT (20-109) | 10 | G481 | 2 comp. including P6506 (35S prom.) | P6812 | 4601 | Greater non-photochemical quenching of chlorophyll fluorescence (NPQ) |
| G481 | CAAT (20-109) | 10 | G481 | Const. 35S prom. | P46 | 3811 | Early flowering |
| G481 | CAAT (20-109) | 10 | G481 | 2 comp. including P6506 (35S prom.) | P6812 | 4601 | Early flowering |
| G481 | CAAT (20-109) | 10 | G481 | Const. 35S prom. | P26496 | 5014 | Altered C/N sensing: greater tol. to low nitrogen conditions in C/N sensing assay |
| G481 | CAAT (20-109) | 10 | G481 | 2 comp. including P5319 (AS1 prom.) | P6812 | 4601 | Greater tol. to cold (8 C.) |
| G481 | CAAT (20-109) | 10 | G481 | 2 comp. including P5319 (AS1 prom.) | P6812 | 4601 | Altered leaf orientation |
| G481 | CAAT (20-109) | 10 | G481 | 2 comp. including P5319 (AS1 prom.) | P6812 | 4601 | Greater seedling vigor |
| G481 | CAAT (20-109) | 10 | G481 | 2 comp. including P5311 (ARSK1 prom.) | P6812 | 4601 | More tol. to drought* and better recovery from drought treatment* |
| G481 | CAAT (20-109) | 10 | G481 | 2 comp. including P5287 (LTP1 prom.) | P6812 | 4601 | Altered sugar sensing; greater tol. to sucrose (determined in 9.4% sucrose) |
| G481 | CAAT (20-109) | 10 | G481 | 2 comp. including P5287 (LTP1 prom.) | P6812 | 4601 | Greater tol. to dehydration |
| G481 | CAAT (20-109) | 10 | G481 | 2 comp. including P5287 (LTP1 prom.) | P6812 | 4601 | Greater tol. to cold (8 C.) |
| G481 | CAAT (20-109) | 10 | G481 | Leaf-specific RBCS3 prom. | P25287 | 4887 | Greater tol. to dehydration |
| G481 | CAAT (20-109) | 10 | G481 | Leaf-specific RBCS3 prom. | P25896 | 4938 | Greater tol. to cold (8 C.) |
| G481 | CAAT (20-109) | 10 | G481 | 2 comp. including P9002 (RD29A prom.) | P6812 | 4601 | Better recovery from drought treatment* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G481 | CAAT (20-109) | 10 | G481 | 2 comp. including P5310 (RS1 prom.) | P6812 | 4601 | Late flowering |
| G481 | CAAT (20-109) | 10 | G481 | Vascular-specific SUC2 prom. | P21522 | 4824 | Late flowering |
| G481 | CAAT (20-109) | 10 | G481 | 2 comp. including P5290 (SUC2 prom.) | P6812 | 4601 | Late flowering |
| G481 | CAAT (20-109) | 10 | G481 | Vascular-specific SUC2 prom. | P21522 | 4824 | Greater tol. to cold (8 C.) |
| G481 | CAAT (20-109) | 10 | G481 | 2 comp. including P5290 (SUC2 prom.) | P6812 | 4601 | Greater tol. to cold (8 C.) |
| G481 | CAAT (20-109) | 10 | G481 | Vascular-specific SUC2 prom. | P21522 | 4824 | Greater tol. to dehydration |
| G481 | CAAT (20-109) | 10 | G481 | 2 comp. including P5290 (SUC2 prom.) | P6812 | 4601 | Greater tol. to dehydration |
| G481 | CAAT (20-109) | 10 | G481 | Vascular-specific SUC2 prom. | P21522 | 4824 | More tol. to drought* and better recovery from drought treatment* |
| G481 | CAAT (20-109) | 10 | G481 | Vascular-specific SUC2 prom. | P21522 | 4824 | Darker green leaf color |
| G481 | CAAT (20-109) | 10 | G481 | Protein-GFP C terminal fusion, 35S | P25281 | 4886 | Greater tol. to hyperosmotic stress; more tol. to 9.4% sucrose or 150 mM NaCl |
| G481 | CAAT (20-109) | 10 | G481 | Protein-CFP C terminal fusion, 35S | P26040 | 4941 | Greater tol. to dehydration |
| G481 | CAAT (20-109) | 10 | G481 | GAL4 C-term (Super Active), 35S | P21146 | 4746 | Early flowering |
| G481 | CAAT (20-109) | 10 | G481 | GAL4 C-term (Super Active), 35S | P21146 | 4746 | Greater seedling vigor |
| G481 | CAAT (20-109) | 10 | G481 | GAL4 C-term (Super Active), 35S | P21146 | 4746 | Greater tol. to heat (32 C.) |
| G481 | CAAT (20-109) | 10 | G481 | GAL4 C-term (Super Active), 35S | P21146 | 4746 | Greater tol. to NaCl (determined with 150 mM NaCl) |
| G481 | CAAT (20-109) | 10 | G481 | 2 comp. hemagglutinin (HA) epitope C-terminal tag, 35S (w/P5486) | P21281 | 4775 | Early flowering |
| G481 | CAAT (20-109) | 10 | G481 | Hemagglutinin (HA) epitope N-terminal tag, 35S | P21287 | 4776 | Early flowering |
| G481 | CAAT (20-109) | 10 | G481 | 2 comp. hemagglutinin (HA) epitope C-terminal tag, 35S (w/P5486) | P26263 | 4964 | Greater seedling vigor |
| G481 | CAAT (20-109) | 10 | G481 | Point mutation, 35S | P25889 | 4934 | Greater seedling vigor, without marked changes in flowering time. |
| G481 | CAAT (20-109) | 10 | G481 | Deletion variant, 35S | P21274 | 4772 | More tol. to drought* and better recovery from drought treatment* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G481 | CAAT (20-109) | 10 | G481 | Deletion variant, 35S | P21274 | 4772 | Greater tol. to NaCl (determined with 150 mM NaCl) |
| G481 | CAAT (20-109) | 10 | G481 | Deletion variant, 35S | P21274 | 4772 | Late flowering |
| G481 | CAAT (20-109) | 10 | G481 | Deletion variant, 35S | P21274 | 4772 | Early flowering |
| G481 | CAAT (20-109) | 10 | G481 | Deletion variant, 35S | P21274 | 4772 | Altered leaf shape |
| G481 | CAAT (20-109) | 10 | G481 | Deletion variant, 35S | P21274 | 4772 | Darker green leaf color |
| G481 | CAAT (20-109) | 10 | G481 | Deletion variant, 35S | P21274 | 4772 | Greater ABA level |
| G481 | CAAT (20-109) | 10 | G481 | Deletion variant, 35S | P21274 | 4772 | Greater carotenoid level |
| G481 | CAAT (20-109) | 10 | G481 | Deletion variant, 35S | P21274 | 4772 | Higher chlorophyll level |
| G481 | CAAT (20-109) | 10 | G481 | Deletion variant, 35S | P21274 | 4772 | Higher proline level |
| G481 | CAAT (20-109) | 10 | G481 | Domain swap/chimeric variant, 35S | P25891 | 4935 | Early flowering |
| G481 | CAAT (20-109) | 10 | G481 | RNAi (clade) targeted to conserved domain, 35S | P21159 | 4747 | Late flowering |
| G481 | CAAT (20-109) | 10 | G481 | RNAi (clade) targeted to conserved domain, 35S | P21300 | 4779 | Late flowering |
| G481 | CAAT (20-109) | 10 | G481 | RNAi (clade) targeted to conserved domain, 35S | P21305 | 4783 | Late flowering |
| G481 | CAAT (20-109) | 10 | G481 | RNAi (clade) targeted to conserved domain, 35S | P21159 | 4747 | Greater tol. to heat (32 C.) |
| G481 | CAAT (20-109) | 10 | G481 | RNAi (clade) targeted to conserved domain, 35S | P21300 | 4779 | Greater tol. to heat (32 C.) |
| G481 | CAAT (20-109) | 10 | G481 | RNAi (clade) targeted to conserved domain, 35S | P21305 | 4783 | Greater tol. to heat (32 C.) |
| G481 | CAAT (20-109) | 10 | G481 | RNAi (clade) targeted to conserved domain, 35S | P21159 | 4747 | Altered leaf shape |
| G481 | CAAT (20-109) | 10 | G481 | RNAi (clade) targeted to conserved domain, 35S | P21300 | 4779 | Altered leaf shape |
| G481 | CAAT (20-109) | 10 | G481 | RNAi (clade) targeted to conserved domain, 35S | P21305 | 4783 | Altered leaf shape |
| G481 | CAAT (20-109) | 10 | G481 | RNAi (clade) targeted to conserved domain, 35S | P21159 | 4747 | Darker green leaf color |
| G481 | CAAT (20-109) | 10 | G481 | RNAi (clade) targeted to conserved domain, 35S | P21300 | 4779 | Darker green leaf color |
| G481 | CAAT (20-109) | 10 | G481 | RNAi (clade) targeted to conserved domain, 35S | P21305 | 4783 | Darker green leaf color |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G481 | CAAT (20-109) | 10 | G481 | RNAi (clade) targeted to conserved domain, 35S | P21305 | 4783 | Greater tol. to hyperosmotic stress; more tol. to 9.4% sucrose, 300 mM mannitol or 150 mM NaCl |
| G481 | CAAT (20-109) | 10 | G481 | RNAi (clade) targeted to conserved domain, 35S | P21159 | 4747 | Greater seedling vigor |
| G481 | CAAT (20-109) | 10 | G481 | RNAi (clade) targeted to conserved domain, 35S | P21300 | 4779 | Greater seedling vigor |
| G481 | CAAT (20-109) | 10 | G481 | RNAi (clade) targeted to conserved domain, 35S | P21305 | 4783 | Greater seedling vigor |
| G481 | CAAT (20-109) | 10 | G481 | RNAi Gene-Specific (GS), 35S | P21294 | 4777 | Greater tol. to cold (8 C.) |
| G481 | CAAT (20-109) | 10 | G481 | RNAi Gene-Specific (GS), 35S | P21294 | 4777 | More tol. to drought* and better recovery from drought treatment* |
| G481 | CAAT (20-109) | 10 | G481 | Knockout | not applicable | | Early flowering |
| G481 | CAAT (20-109) | 10 | G481 | Knockout | not applicable | | Decreased tol. to NaCl (determined with 150 mM NaCl) |
| G482 | CAAT (26-115) | 12 | G481 | 2 comp. including P6506 (35S prom.) | P5072 | 4594 | More tol. to drought* and better recovery from drought treatment* |
| G482 | CAAT (26-115) | 12 | G481 | Const. 35S prom. | P47 | 3812 | Early flowering |
| G482 | CAAT (26-115) | 12 | G481 | 2 comp. including P6506 (35S prom.) | P5072 | 4594 | Early flowering |
| G482 | CAAT (26-115) | 12 | G481 | Const. 35S prom. | P47 | 3812 | Greater tol. to 300 mM mannitol |
| G482 | CAAT (26-115) | 12 | G481 | 2 comp. including P6506 (35S prom.) | P5072 | 4594 | Greater tol. to 300 mM mannitol |
| G482 | CAAT (26-115) | 12 | G481 | Const. 35S prom. | P47 | 3812 | Greater tol. to heat (32 C.) |
| G482 | CAAT (26-115) | 12 | G481 | 2 comp. including P6506 (35S prom.) | P5072 | 4594 | Greater tol. to heat (32 C.) |
| G482 | CAAT (26-115) | 12 | G481 | 2 comp. including P5290 (SUC2 prom.) | P5072 | 4594 | Early flowering |
| G482 | CAAT (26-115) | 12 | G481 | Protein-CFP C-terminal fusion, 35S | P26041 | 4942 | Early flowering |
| G482 | CAAT (26-115) | 12 | G481 | Knockout | not applicable | | More tol. to drought* and better recovery from drought treatment* |
| G482 | CAAT (26-115) | 12 | G481 | Knockout | not applicable | | Late flowering |
| G485 | CAAT (20-109) | 394 | G481 | 2 comp. including P6506 (35S prom.) | P4190 | 4541 | Greater tol. to cold (8 C.) |
| G485 | CAAT (20-109) | 394 | G481 | 2 comp. including P6506 (35S prom.) | P4190 | 4541 | Greater tol. to hyperosmotic stress; more tol. to 9.4% sucrose or 150 mM NaCl |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G485 | CAAT (20-109) | 394 | G481 | Const. 35S prom. | P1441 | 4145 | More tol. to drought* and better recovery from drought treatment* |
| G485 | CAAT (20-109) | 394 | G481 | 2 comp. including P6506 (35S prom.) | P4190 | 4541 | More tol. to drought* and better recovery from drought treatment* |
| G485 | CAAT (20-109) | 394 | G481 | 2 comp. including P6506 (35S prom.) | P4190 | 4541 | Less sens. to ABA |
| G485 | CAAT (20-109) | 394 | G481 | 2 comp. including P6506 (35S prom.) | P4190 | 4541 | Greater tol. to NaCl (determined with 150 mM NaCl) |
| G485 | CAAT (20-109) | 394 | G481 | 2 comp. including P6506 (35S prom.) | P4190 | 4541 | Altered sugar sensing; greater tol. to sucrose (determined in 9.4% sucrose) |
| G485 | CAAT (20-109) | 394 | G481 | 2 comp. including P6506 (35S prom.) | P4190 | 4541 | Early flowering |
| G485 | CAAT (20-109) | 394 | G481 | 2 comp. including P5319 (AS1 prom.) | P4190 | 4541 | Greater tol. to cold (8 C.) |
| G485 | CAAT (20-109) | 394 | G481 | 2 comp. including P5319 (AS1 prom.) | P4190 | 4541 | Greater tol. to dehydration |
| G485 | CAAT (20-109) | 394 | G481 | 2 comp. including P5319 (AS1 prom.) | P4190 | 4541 | Greater seedling vigor |
| G485 | CAAT (20-109) | 394 | G481 | Protein-GFP C terminal fusion, 35S | P26044 | 4944 | Greater tol. to cold (8 C.) |
| G485 | CAAT (20-109) | 394 | G481 | Protein-GFP C terminal fusion, 35S | P26044 | 4944 | Greater tol. to dehydration |
| G485 | CAAT (20-109) | 394 | G481 | Domain swap/chimeric variant, 35S | P25892 | 4936 | Late flowering |
| G485 | CAAT (20-109) | 394 | G481 | Domain swap/chimeric variant, 35S | P25892 | 4936 | Darker green leaf color |
| G485 | CAAT (20-109) | 394 | G481 | Knockout | not applicable | | More tol. to drought* and better recovery from drought treatment* |
| G485 | CAAT (20-109) | 394 | G481 | Knockout | not applicable | | Less sens. to ABA |
| G485 | CAAT (20-109) | 394 | G481 | Knockout | not applicable | | Greater tol. to NaCl (determined with 150 mM NaCl) |
| G485 | CAAT (20-109) | 394 | G481 | Knockout | not applicable | | Late flowering |
| G1364 | CAAT (29-118) | 952 | G481 | 2 comp. including P6506 (35S prom.) | P4357 | 4550 | Better recovery from drought treatment* |
| G1364 | CAAT (29-118) | 952 | G481 | 2 comp. including P6506 (35S prom.) | P4357 | 4550 | Late flowering |
| G1364 | CAAT (29-118) | 952 | G481 | 2 comp. including P5284 (RBCS3 prom.) | P4357 | 4550 | Greater tol. to 300 mM mannitol |
| G1364 | CAAT (29-118) | 952 | G481 | 2 comp. including P5284 (RBCS3 prom.) | P4357 | 4550 | Greater tol. to cold (8 C.) |
| G1364 | CAAT (29-118) | 952 | G481 | 2 comp. including P9002 (RD29A prom.) | P4357 | 4550 | Greater tol. to cold (8 C.) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1364 | CAAT (29-118) | 952 | G481 | 2 comp. including P9002 (RD29A prom.) | P4357 | 4550 | Greater tol. to NaCl (determined with 150 mM NaCl) |
| G1364 | CAAT (29-118) | 952 | G481 | Protein-CFP C-terminal fusion, 35S | P26108 | 4953 | More tol. to drought* and better recovery from drought treatment* |
| G1364 | CAAT (29-118) | 952 | G481 | Protein-CFP C-terminal fusion, 35S | P26108 | 4953 | Late flowering |
| G1364 | CAAT (29-118) | 952 | G481 | Protein-CFP C-terminal fusion, 35S | P26108 | 4953 | Darker green leaf color |
| G2345 | CAAT (28-117) | 1476 | G481 | 2 comp. including P6506 (35S prom.) | P8079 | 4607 | More tol. to drought* and better recovery from drought treatment* |
| G2345 | CAAT (28-117) | 1476 | G481 | 2 comp. including P6506 (35S prom.) | P8079 | 4607 | Greater tol. to cold (8 C.) |
| G3470 | CAAT (27-116) | 1922 | G481 | GAL4 C-term (Super Active), 35S | P26500 | 5018 | Early flowering |
| G3470 | CAAT (27-116) | 1922 | G481 | Const. 35S prom. | P21341 | 4792 | Greater tol. to cold (8 C.) |
| G3470 | CAAT (27-116) | 1922 | G481 | Const. 35S prom. | P21341 | 4792 | More tol. to drought* and better recovery from drought treatment* |
| G3470 | CAAT (27-116) | 1922 | G481 | Const. 35S prom. | P21341 | 4792 | Late flowering |
| G3470 | CAAT (27-116) | 1922 | G481 | Const. 35S prom. | P21341 | 4792 | Greater tol. to dehydration |
| G3470 | CAAT (27-116) | 1922 | G481 | Const. 35S prom. | P21471 | 4818 | Less sens. to ABA |
| G3470 | CAAT (27-116) | 1922 | G481 | Const. 35S prom. | P21341 | 4792 | Darker green leaf color |
| G3470 | CAAT (27-116) | 1922 | G481 | Const. 35S prom. | P21471 | 4818 | Darker green leaf color |
| G3470 | CAAT (27-116) | 1922 | G481 | Const. 35S prom. | P21471 | 4818 | Greater tol. to hyperosmotic stress; more tol to 9.4% sucrose, 300 mM mannitol or 150 mM NaCl |
| G3470 | CAAT (27-116) | 1922 | G481 | Const. 35S prom. | P21471 | 4818 | Greater seedling vigor |
| G3470 | CAAT (27-116) | 1922 | G481 | Const. 35S prom. | P21471 | 4818 | Greater seedling vigor |
| G3470 | CAAT (27-116) | 1922 | G481 | Const. 35S prom. | P21471 | 4818 | Greater tol. to NaCl (determined with 150 mM NaCl) |
| G3470 | CAAT (27-116) | 1922 | G481 | Const. 35S prom. | P21471 | 4818 | Greater tol. to NaCl (determined with 150 mM NaCl) |
| G3471 | CAAT (26-115) | 1924 | G481 | Const. 35S prom. | P21342 | 4793 | More tol. to drought* and better recovery from drought treatment* |
| G3471 | CAAT (26-115) | 1924 | G481 | Const. 35S prom. | P21342 | 4793 | Darker green leaf color |
| G3471 | CAAT (26-115) | 1924 | G481 | Const. 35S prom. | P21342 | 4793 | Late flowering |
| G3472 | CAAT (25-114) | 1926 | G481 | Const. 35S prom. | P21348 | 4797 | More root hair |
| G3472 | CAAT (25-114) | 1926 | G481 | Const. 35S prom. | P21348 | 4797 | Greater tol. to NaCl (determined with 150 mM NaCl) |
| G3474 | CAAT (25-114) | 1930 | G481 | Const. 35S prom. | P21344 | 4794 | Early flowering |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3474 | CAAT (25-114) | 1930 | G481 | Const. 35S prom. | P21469 | 4817 | Early flowering |
| G3475 | CAAT (23-112) | 1932 | G481 | Const. 35S prom. | P21347 | 4796 | Early flowering |
| G3475 | CAAT (23-112) | 1932 | G481 | Const. 35S prom. | P21347 | 4796 | Greater tol. to cold (8 C.) |
| G3476 | CAAT (26-115) | 1934 | G481 | Const. 35S prom. | P21345 | 4795 | Greater tol. to cold (8 C.) |
| G3476 | CAAT (26-115) | 1934 | G481 | Const. 35S prom. | P21345 | 4795 | More tol. to drought* and better recovery from drought treatment* |
| G3476 | CAAT (26-115) | 1934 | G481 | Const. 35S prom. | P21345 | 4795 | Greater tol. to dehydration |
| G3476 | CAAT (26-115) | 1934 | G481 | Const. 35S prom. | P21345 | 4795 | Early flowering |
| G3478 | CAAT (23-112) | 1936 | G481 | Const. 35S prom. | P21350 | 4798 | Early flowering |
| G3873 | CAAT (29-118) | 2184 | G481 | Const. 35S prom. | P25777 | 4932 | Late flowering |
| G3874 | CAAT (25-114) | 2186 | G481 | Const. 35S prom. | P25778 | 4933 | Early flowering |
| G3874 | CAAT (25-114) | 2186 | G481 | Const. 35S prom. | P25778 | 4933 | Greater seedling vigor |
| G3875 | CAAT (25-114) | 2188 | G481 | Const. 35S prom. | P26609 | 5042 | Altered flowering time; some lines flowered early, others late |
| G3875 | CAAT (25-114) | 2188 | G481 | Const. 35S prom. | P26609 | 5042 | Greater tol. to cold (8 C.) |
| G3875 | CAAT (25-114) | 2188 | G481 | Const. 35S prom. | P26609 | 5042 | Darker green leaf color |
| G3473 | CAAT (23-113) | 1928 | G481 | — | — | | n/d |
| G3394 | CAAT (38-126) | 1860 | G481 | Const. 35S prom. | P23384 | 4830 | Late flowering |
| G3394 | CAAT (38-126) | 1860 | G481 | Const. 35S prom. | P23481 | 4840 | Late flowering |
| G3394 | CAAT (38-126) | 1860 | G481 | Const. 35S prom. | P21248 | 4756 | Early flowering |
| G3395 | CAAT (19-108) | 1862 | G481 | Const. 35S prom. | P21253 | 4759 | Altered flowering time; some lines flowered early, others late |
| G3395 | CAAT (19-108) | 1862 | G481 | Const. 35S prom. | P21253 | 4759 | More tol. to drought* and better recovery from drought treatment* |
| G3396 | CAAT (21-110) | 1864 | G481 | Const. 35S prom. | P23304 | 4826 | Greater tol. to cold (8 C.) |
| G3396 | CAAT (21-110) | 1864 | G481 | Const. 35S prom. | P23304 | 4826 | Late flowering |
| G3396 | CAAT (21-110) | 1864 | G481 | Const. 35S prom. | P23304 | 4826 | Less sens. to ABA |
| G3396 | CAAT (21-110) | 1864 | G481 | Const. 35S prom. | P23304 | 4826 | Larger leaf size |
| G3396 | CAAT (21-110) | 1864 | G481 | Const. 35S prom. | P23304 | 4826 | Altered leaf shape |
| G3396 | CAAT (21-110) | 1864 | G481 | Const. 35S prom. | P23304 | 4826 | Darker green leaf color |
| G3396 | CAAT (21-110) | 1864 | G481 | Const. 35S prom. | P23304 | 4826 | More tol. to drought* and better recovery from drought treatment* |
| G3396 | CAAT (21-110) | 1864 | G481 | GAL4 C-term (Super Active), 35S | P26499 | 5017 | Early flowering |
| G3397 | CAAT (23-112) | 1866 | G481 | Const. 35S prom. | P21265 | 4766 | Early flowering |
| G3397 | CAAT (23-112) | 1866 | G481 | Const. 35S prom. | P21265 | 4766 | Greater tol. to cold (8 C.) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3397 | CAAT (23-112) | 1866 | G481 | Const. 35S prom. | P21265 | 4766 | Greater seedling vigor |
| G3398 | CAAT (21-110) | 1868 | G481 | Const. 35S prom. | P21252 | 4758 | Early flowering |
| G3398 | CAAT (21-110) | 1868 | G481 | Const. 35S prom. | P21252 | 4758 | More tol. to drought* and better recovery from drought treatment* |
| G3429 | CAAT (40-124) | 1880 | G481 | Const. 35S prom. | P21251 | 4757 | Late flowering |
| G3429 | CAAT (40-124) | 1880 | G481 | Const. 35S prom. | P21251 | 4757 | Greater tol. to NaCl (determined with 150 mM NaCl) |
| G3434 | CAAT (18-107) | 1886 | G481 | Const. 35S prom. | P21466 | 4815 | Greater tol. to dehydration |
| G3434 | CAAT (18-107) | 1886 | G481 | Const. 35S prom. | P21466 | 4815 | Early flowering |
| G3434 | CAAT (18-107) | 1886 | G481 | Const. 35S prom. | P21466 | 4815 | Greater tol. to NaCl (determined with 150 mM NaCl) |
| G3434 | CAAT (18-107) | 1886 | G481 | Const. 35S prom. | P21466 | 4815 | More tol. to drought* and better recovery from drought treatment* |
| G3434 | CAAT (18-107) | 1886 | G481 | Const. 35S prom. | P21466 | 4815 | Greater tol. to hyperosmotic stress; more tol. to 9.4% sucrose, 300 mM mannitol or 150 mM NaCl |
| G3434 | CAAT (18-107) | 1886 | G481 | Point mutation, 35S | P26921 | 5064 | Greater biomass |
| G3434 | CAAT (18-107) | 1886 | G481 | Point mutation, 35S | P26921 | 5064 | Late flowering |
| G3434 | CAAT (18-107) | 1886 | G481 | Point mutation, 35S | P26922 | 5065 | Early flowering |
| G3435 | CAAT (22-111) | 1888 | G481 | Const. 35S prom. | P21314 | 4784 | More tol. to drought* and better recovery from drought treatment* |
| G3435 | CAAT (22-111) | 1888 | G481 | Const. 35S prom. | P21314 | 4784 | Early flowering |
| G3436 | CAAT (20-109) | 1890 | G481 | Const. 35S prom. | P21381 | 4805 | Early flowering |
| G3436 | CAAT (20-109) | 1890 | G481 | Const. 35S prom. | P21315 | 4785 | Early flowering |
| G3436 | CAAT (20-109) | 1890 | G481 | Const. 35S prom. | P21381 | 4805 | Greater tol. to heat (32 C.) |
| G3436 | CAAT (20-109) | 1890 | G481 | Const. 35S prom. | P21315 | 4785 | Greater tol. to heat (32 C.) |
| G3866 | CAAT (30-126) | 2182 | G481 | Const. 35S prom. | P26548 | 5020 | Late flowering |
| G3866 | CAAT (30-126) | 2182 | G481 | Const. 35S prom. | P26548 | 5020 | Darker green leaf color |
| G3866 | CAAT (30-126) | 2182 | G481 | Const. 35S prom. | P26548 | 5020 | Greater seedling vigor |
| G3866 | CAAT (30-126) | 2182 | G481 | GAL4 C-term (Super Active), 35S | P26587 | 5025 | Early flowering |
| G3866 | CAAT (30-126) | 2182 | G481 | GAL4 C-term (Super Active), 35S | P26587 | 5025 | Greater tol. to dehydration |
| G3866 | CAAT (30-126) | 2182 | G481 | Point mutation, 35S | P26888 | 5060 | Altered flowering time; some lines flowered early, others flowered late |
| G3866 | CAAT (30-126) | 2182 | G481 | Point mutation, 35S | P26889 | 5061 | Altered flowering time; some lines flowered early, others flowered late |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3866 | CAAT (30-126) | 2182 | G481 | Point mutation, 35S | P26890 | 5062 | Altered flowering time; some lines flowered early, others flowered late |
| G3866 | CAAT (30-126) | 2182 | G481 | Point mutation, 35S | P26888 | 5060 | Darker green leaf color |
| G3866 | CAAT (30-126) | 2182 | G481 | Point mutation, 35S | P26889 | 5061 | Darker green leaf color |
| G3866 | CAAT (30-126) | 2182 | G481 | Point mutation, 35S | P26890 | 5062 | Darker green leaf color |
| G3866 | CAAT (30-126) | 2182 | G481 | Point mutation, 35S | P27228 | 5081 | Darker green leaf color |
| G3866 | CAAT (30-126) | 2182 | G481 | Point mutation, 35S | P27229 | 5082 | Darker green leaf color |
| G3876 | CAAT (30-119) | 2190 | G481 | Const. 35S prom. | P25657 | 4913 | Greater tol. to cold (8 C.) |
| G3876 | CAAT (30-119) | 2190 | G481 | Const. 35S prom. | P25657 | 4913 | Greater tol. to dehydration |
| G3876 | CAAT (30-119) | 2190 | G481 | Const. 35S prom. | P25657 | 4913 | More tol. to drought* and better recovery from drought treatment* |
| G3437 | CAAT (54-143) | 1892 | G481 | — | — | — | n/d |
| G4272 | CAAT (22-118) | 2338 | G481 | — | — | — | n/d |
| G4276 | CAAT (19-108) | 2344 | G481 | — | — | — | n/d |
| G928 | CAAT (179-238) | 696 | G928 | Const. 35S prom. | P143 | 3842 | Greater tol. to cold (8 C.) |
| G928 | CAAT (179-238) | 696 | G928 | Const. 35S prom. | P143 | 3842 | Better recovery from drought treatment* |
| G928 | CAAT (179-238) | 696 | G928 | Const. 35S prom. | P143 | 3842 | Altered sugar sensing; greater tol. to sucrose (determined in 9.4% sucrose) |
| G928 | CAAT (179-238) | 696 | G928 | Protein-YFP C terminal fusion, 35S | P26223 | 4960 | Late flowering |
| G928 | CAAT (179-238) | 696 | G928 | Protein-YFP C terminal fusion, 35S | P26223 | 4960 | Darker green leaf color |
| G928 | CAAT (179-238) | 696 | G928 | Protein-YFP C terminal fusion, 35S | P26223 | 4960 | Greater seedling vigor |
| G931 | CAAT (172-231) | 700 | G928 | Protein-YFP C-terminal fusion, 35S | P26230 | 4961 | Darker green leaf color |
| G931 | CAAT (172-231) | 700 | G928 | Const. 35S prom. | P1608 | 4204 | Greater biomass |
| G3926 | CAAT (164-222) | 2230 | G928 | Const. 35S prom. | P26600 | 5035 | Darker green leaf color |
| G3926 | CAAT (164-222) | 2230 | G928 | Const. 35S prom. | P26600 | 5035 | Greater tol. to cold (8 C.) |
| G3926 | CAAT (164-222) | 2230 | G928 | Const. 35S prom. | P26600 | 5035 | Long petiole |
| G3926 | CAAT (164-222) | 2230 | G928 | Const. 35S prom. | P26600 | 5035 | Altered leaf orientation |
| G3926 | CAAT (164-222) | 2230 | G928 | Const. 35S prom. | P26600 | 5035 | Greater seedling vigor |
| G3921 | CAAT (148-207) | 2224 | G928 | — | — | — | n/d |
| G4264 | CAAT (155-214) | 2326 | G928 | Const. 35S prom. | P26593 | 5029 | Greater tol. to cold (8 C.) |
| G4264 | CAAT (155-214) | 2326 | G928 | Const. 35S prom. | P26593 | 5029 | Greater tol. to dehydration |
| G4264 | CAAT (155-214) | 2326 | G928 | Const. 35S prom. | P26593 | 5029 | Greater seedling vigor |
| G4264 | CAAT (155-214) | 2326 | G928 | Const. 35S prom. | P26593 | 5029 | Late flowering |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G4264 | CAAT (155-214) | 2326 | G928 | Const. 35S prom | P26593 | 5029 | Greater biomass |
| G4264 | CAAT (155-214) | 2326 | G928 | Const. 35S prom. | P26593 | 5029 | Greater biomass |
| G4265 | CAAT (149-208) | 2328 | G928 | — | — | — | n/d |
| G4269 | CAAT (103-162) | 2334 | G928 | — | — | — | n/d |
| G1782 | CAAT (178-237) | 1162 | G1782 | Const. 35S prom. | P966 | 4010 | Greater biomass |
| G1782 | CAAT (178-237) | 1162 | G1782 | Const. 35S prom. | P966 | 4010 | Darker green leaf color |
| G1363 | CAAT (171-230) | 950 | G1782 | Const. 35S prom. | P724 | 3956 | Early flowering |
| G1363 | CAAT (171-230) | 950 | G1782 | Const. 35S prom. | P724 | 3956 | Darker green leaf color |
| G1363 | CAAT (171-230) | 950 | G1782 | Const. 35S fprom. | P724 | 3956 | Greater resistance to *Fusarium* |
| G1363 | CAAT (171-230) | 950 | G1782 | Protein-YFP C-terminal fusion, 35S | P26121 | 4954 | Late flowering |
| G1363 | CAAT (171-230) | 950 | G1782 | Protein-YFP C-terminal fusion, 35S | P26121 | 4954 | Larger leaf size |
| G1363 | CAAT (171-230) | 950 | G1782 | Protein-YFP C-terminal fusion, 35S | P26121 | 4954 | Darker green leaf color |
| G3920 | CAAT (149-208) | 2222 | G1782 | Const. 35S prom. | P26608 | 5041 | More tol. to drought* and better recovery from drought treatment* |
| G3920 | CAAT (149-208) | 2222 | G1782 | Const. 35S prom. | P26608 | 5041 | Greater seedling vigor |
| G3925 | CAAT (138-197) | 2228 | G1782 | Const. 35S prom. | P26597 | 5032 | Darker green leaf color |
| G3925 | CAAT (138-197) | 2228 | G1782 | Const. 35S prom. | P26597 | 5032 | Late flowering |
| G4262 | CAAT (142-201) | 2322 | G1782 | — | — | — | n/d |
| G4263 | CAAT (137-196) | 2324 | G1782 | — | — | — | n/d |
| G4270 | CAAT (131-191) | 2336 | G1782 | — | — | — | n/d |
| G482 & G485 | CAAT (26-115) & CAAT (20-109) | 12 & 394 | G481-related sequences, double knockouts | Double Knockout | not applicable | — | Late flowering |
| G664 | MYB-(R1)R2R3 (14-116) | 528 | G664 | Const. 35S prom. | P98 | 3827 | Better germination and growth in cold (8 C.) |
| G664 | MYB-(R1)R2R3 (14-116) | 528 | G664 | Const. 35S prom. | P98 | 3827 | Altered light response; greater shade tol.; lack of shade avoidance phenotype |
| G197 | MYB-(R1)R2R3 (14-116) | 166 | G664 | Const. 35S prom. | P814 | 3980 | No positive physiological results (only 3 lines generated) |
| G255 | MYB-(R1)R2R3 (14-116) | 228 | G664 | Const. 35S prom. | P787 | 3968 | No positive physiological results (only 3 lines generated) |
| G255 | MYB-(R1)R2R3 (14-116) | 228 | G664 | Const. 35S prom. | P1277 | 4094 | Early flowering |
| G3529 | MYB-(R1)R2R3 (14-116) | 1994 | G664 | — | — | — | n/d |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3527 | MYB-(R1)R2R3 (13-117) | 1990 | G664 | — | — | — | n/d |
| G3528 | MYB-(R1)R2R3 (13-117) | 1992 | G664 | — | — | — | n/d |
| G3503 | MYB-(R1)R2R3 (14-116) | 1960 | G664 | — | — | — | n/d |
| G3504 | MYB-(R1)R2R3 (14-116) | 1962 | G664 | — | — | — | n/d |
| G3505 | MYB-(R1)R2R3 (14-116) | 1964 | G664 | — | — | — | n/d |
| G3506 | MYB-(R1)R2R3 (14-116) | 1966 | G664 | — | — | — | n/d |
| G3507 | MYB-(R1)R2R3 (14-116) | 1968 | G664 | — | — | — | n/d |
| G3508 | MYB-(R1)R2R3 (14-116) | 1970 | G664 | — | — | — | n/d |
| G3509 | MYB-(R1)R2R3 (14-116) | 1972 | G664 | — | — | — | n/d |
| G3531 | MYB-(R1)R2R3 (14-116) | 1996 | G664 | — | — | — | n/d |
| G3532 | MYB-(R1)R2R3 (14-116) | 1998 | G664 | — | — | — | n/d |
| G3533 | MYB-(R1)R2R3 (14-116) | 2000 | G664 | — | — | — | n/d |
| G3534 | MYB-(R1)R2R3 (14-116) | 2002 | G664 | — | — | — | n/d |
| G4637 | MYB-(R1)R2R3 (14-116) | 2366 | G664 | — | — | — | n/d |
| G4638 | MYB-(R1)R2R3 (14-116) | 2368 | G664 | — | — | — | n/d |
| G4639 | MYB-(R1)R2R3 (14-116) | 2370 | G664 | — | — | — | n/d |
| G4640 | MYB-(R1)R2R3 (76-178) | 2372 | G664 | — | — | — | n/d |
| G913 | AP2 (62-128) | 682 | G913 | Const. 35S prom. | P929 | 4001 | Darker green leaf color |
| G913 | AP2 (62-128) | 682 | G913 | 2 comp. including P6506 (35S prom.) | P3598 | 4516 | Darker green leaf color |
| G913 | AP2 (62-128) | 682 | G913 | Const. 35S prom. | P929 | 4001 | More tolerant to freezing |
| G913 | AP2 (62-128) | 682 | G913 | Const. 35S prom. | P929 | 4001 | Late flowering |
| G913 | AP2 (62-128) | 682 | G913 | 2 comp. including P9002 (RD29A prom.) | P3598 | 4516 | Greater tol. to dehydration |
| G913 | AP2 (62-128) | 682 | G913 | 2 comp. including P9002 (RD29A prom.) | P3598 | 4516 | Greater tol. to cold (8 C.) |
| G913 | AP2 (62-128) | 682 | G913 | 2 comp. including P9002 (RD29A prom.) | P3598 | 4516 | More tol. to drought* and better recovery from drought treatment* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G913 | AP2 (62-128) | 682 | G913 | 2 comp. including P9002 (RD29A prom.) | P3598 | 4516 | Decreased proline |
| G913 | AP2 (62-128) | 682 | G913 | 2 comp. including P9002 (RD29A prom.) | P3598 | 4516 | Photosynthesis rate reduced |
| G913 | AP2 (62-128) | 682 | G913 | 2 comp. including P9002 (RD29A prom.) | P3598 | 4516 | Late flowering |
| G913 | AP2 (62-128) | 682 | G913 | 2 comp. including P9002 (RD29A prom.) | P3598 | 4516 | Less sens. to ABA |
| G913 | AP2 (62-128) | 682 | G913 | 2 comp. including P9002 (RD29A prom.) | P3598 | 4516 | Darker green leaf color |
| G913 | AP2 (62-128) | 682 | G913 | 2 comp. including P9002 (RD29A prom.) | P3598 | 4516 | Greater tol. to NaCl (determined with 150 mM NaCl) |
| G913 | AP2 (62-128) | 682 | G913 | 2 comp. including P5290 (SUC2 prom.) | P3598 | 4516 | Late flowering |
| G913 | AP2 (62-128) | 682 | G913 | 2 comp. including P5290 (SUC2 prom.) | P3598 | 4516 | Darker green leaf color |
| G976 | AP2 (87-153) | 732 | G913 | Const. 35S prom. | P409 | 3930 | Darker green leaf color |
| G976 | AP2 (87-153) | 732 | G913 | Const. 35S prom. | P409 | 3930 | Waxy leaves |
| G976 | AP2 (87-153) | 732 | G913 | Const. 35S prom. | P409 | 3930 | Late flowering |
| G2514 | AP2 (16-82) | 1544 | G913 | Const. 35S prom | P2404.1 | 5102 | Darker green leaf color |
| G2514 | AP2 (16-82) |  | G913 | Const. 35S prom | — | — | Late flowering |
| G1753 | AP2 (12-80) | 1138 | G913 | Const. 35S prom. | P3326 | 4499 | Altered inflorescence architecture; inflorescences had short internodes, which led to a more compact bushier architecture |
| G1753 | AP2 (12-80) | 1138 | G913 | Const. 35S prom. | P3326 | 4499 | Altered sugar sensing and/or inc. tol. to hyperosmotic stress; greater tol. to sucrose (determined in 9.4% sucrose) |
| G1753 | AP2 (12-80) | 1138 | G913 | Const. 35S prom. | P3326 | 4499 | Inc. tol. to hyperosmotic stress (determined in 9.4% sucrose) |
| G1753 | AP2 (12-80) | 1138 | G913 | Const. 35S prom. | P3326 | 4499 | Darker green leaf color |
| G1073 | AT-hook (63-71, 71-216) | 18 | G1073 | Const. 35S prom. | P448 | 3936 | Altered branching, short internodes |
| G1073 | AT-hook (63-71, 71-216) | 18 | G1073 | Const. 35S prom. | P448 | 3936 | Greater to substantially greater plant size |
| G1073 | AT-hook (63-71, 71-216) | 18 | G1073 | Const. 35S prom. | P448 | 3936 | Greater seed yield |
| G1073 | AT-hook (63-71, 71-216) | 18 | G1073 | Const. 35S prom. | P448 | 3936 | More root hair |
| G1073 | AT-hook (63-71, 71-216) | 18 | G1073 | Const. 35S prom. | P448 | 3936 | Greater root mass |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1073 | AT-hook (63-71, 71-216) | 18 | G1073 | 2 comp. including P6506 (35S prom.) | P3369 | 4504 | Greater tol. to hyperosmotic stress; more tol. to 9.4% sucrose, 300 mM mannitol or 150 mM NaCl |
| G1073 | AT-hook (63-71, 71-216) | 18 | G1073 | Const. 35S prom. | P25703 | 4919 | Greater tol. to dehydration |
| G1073 | AT-hook (63-71, 71-216) | 18 | G1073 | Const. 35S prom. | P448 | 3936 | More tol. to drought* and better recovery from drought treatment* |
| G1073 | AT-hook (63-71, 71-216) | 18 | G1073 | Const. 35S prom. | P25703 | 4919 | More tol. to drought* and better recovery from drought treatment* |
| G1073 | AT-hook (63-71, 71-216) | 18 | G1073 | 2 comp. including P6506 (35S prom.) | P3369 | 4504 | More tol. to drought* and better recovery from drought treatment* |
| G1073 | AT-hook (63-71, 71-216) | 18 | G1073 | Const. 35S prom. | P448 | 3936 | Large flower |
| G1073 | AT-hook (63-71, 71-216) | 18 | G1073 | Const. 35S prom. | P25703 | 4919 | Large flower |
| G1073 | AT-hook (63-71, 71-216) | 18 | G1073 | 2 comp. including P6506 (35S prom.) | P3369 | 4504 | Large flower |
| G1073 | AT-hook (63-71, 71-216) | 18 | G1073 | 2 comp. including P5326 (AP1 prom.) | P3369 | 4504 | Greater tol. to cold (8 C.) |
| G1073 | AT-hook (63-71, 71-216) | 18 | G1073 | 2 comp. including P5311 (ARSK1 prom.) | P3369 | 4504 | Greater tol. to NaCl (determined with 150 mM NaCl) |
| G1073 | AT-hook (63-71, 71-216) | 18 | G1073 | 2 comp. including P5311 (ARSK1 prom.) | P3369 | 4504 | More tol. to drought* and better recovery from drought treatment* |
| G1073 | AT-hook (63-71, 71-216) | 18 | G1073 | 2 comp. including P5311 (ARSK1 prom.) | P3369 | 4504 | Greater tol. to NaCl (determined with 150 mM NaCl) |
| G1073 | AT-hook (63-71, 71-216) | 18 | G1073 | 2 comp. including P5319 (AS1 prom.) | P3369 | 4504 | Greater tol. to cold (8 C.) |
| G1073 | AT-hook (63-71, 71-216) | 18 | G1073 | 2 comp. including P5319 (AS1 prom.) | P3369 | 4504 | Greater seedling vigor |
| G1073 | AT-hook (63-71, 71-216) | 18 | G1073 | 2 comp. including P5288 (CUT1 prom.) | P3369 | 4504 | More tol. to hyperosmotic stress; greater tol. to 9.4% sucrose, 300 mM mannitol or 150 mM NaCl |
| G1073 | AT-hook (63-71, 71-216) | 18 | G1073 | 2 comp. including P5288 (CUT1 prom.) | P3369 | 4504 | More tol. to hyperosmotic stress; greater tol. to 9.4% sucrose, 300 mM mannitol or 150 mM NaCl |
| G1073 | AT-hook (63-71, 71-216) | 18 | G1073 | 2 comp. including P5284 (RBCS3 prom.) | P3369 | 4504 | Greater tol. to heat (32 C.) |
| G1073 | AT-hook (63-71, 71-216) | 18 | G1073 | 2 comp. including P5284 (RBCS3 prom.) | P3369 | 4504 | Late flowering |
| G1073 | AT-hook (63-71, 71-216) | 18 | G1073 | 2 comp. including P5284 (RBCS3 prom.) | P3369 | 4504 | Greater biomass |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1073 | AT-hook (63-71, 71-216) | 18 | G1073 | 2 comp. including P5284 (RBCS3 prom.) | P3369 | 4504 | Greater tol. to NaCl (determined with 150 mM NaCl) |
| G1073 | AT-hook (63-71, 71-216) | 18 | G1073 | 2 comp. including P5318 (STM prom.) | P3369 | 4504 | Greater tol. to dehydration |
| G1073 | AT-hook (63-71, 71-216) | 18 | G1073 | 2 comp. including P5318 (STM prom.) | P3369 | 4504 | More tol. to drought* and better recovery from drought treatment* |
| G1073 | AT-hook (63-71, 71-216) | 18 | G1073 | Vascular-specific SUC2 prom. | P21521 | 4823 | More tol. to drought* and better recovery from drought treatment* |
| G1073 | AT-hook (63-69, 71-216) | 18 | G1073 | Vascular-specific SUC2 prom. | P21521 | 4823 | Greater biomass |
| G1073 | AT-hook (63-69, 71-216) | 18 | G1073 | 2 comp. including P5290 (SUC2 prom.) | P3369 | 4504 | Greater biomass |
| G1073 | AT-hook (63-71, 71-216) | 18 | G1073 | Vascular-specific SUC2 prom. | P21521 | 4823 | Greater tol. to cold (8 C.) |
| G1073 | AT-hook (63-71, 71-216) | 18 | G1073 | 2 comp. including P5290 (SUC2 prom.) | P3369 | 4504 | Greater tol. to cold (8 C.) |
| G1073 | AT-hook (63-71, 71-216) | 18 | G1073 | Vascular-specific SUC2 prom. | P21521 | 4823 | Late flowering |
| G1073 | AT-hook (63-71, 71-216) | 18 | G1073 | 2 comp. including P5290 (SUC2 prom.) | P3369 | 4504 | Late flowering |
| G1073 | AT-hook (63-71, 71-216) | 18 | G1073 | GAL4 N-term (Super Active), 35S | P21199 | 4751 | Late flowering |
| G1073 | AT-hook (63-71, 71-216) | 18 | G1073 | GAL4 N-term (Super Active), 35S | P21199 | 4751 | Less sens. to ABA |
| G1073 | AT-hook (63-71, 71-216) | 18 | G1073 | GAL4 N-term (Super Active), 35S | P21199 | 4751 | Altered leaf shape |
| G1073 | AT-hook (63-71, 71-216) | 18 | G1073 | GAL4 N-term (Super Active), 35S | P21199 | 4751 | Darker green leaf color |
| G1073 | AT-hook (63-71, 71-216) | 18 | G1073 | GAL4 C-term (Super Active), 35S | P21145 | 4745 | Greater tol. to dehydration |
| G1073 | AT-hook (63-71, 71-216) | 18 | G1073 | GAL4 C-term (Super Active), 35S | P21145 | 4745 | More tol. to drought* and better recovery from drought treatment* |
| G1073 | AT-hook (63-71, 71-216) | 18 | G1073 | Protein-GFP C terminal fusion, 35S | P25263 | 4884 | More tol. to drought* and better recovery from drought treatment* |
| G1073 | AT-hook (63-71, 71-216) | 18 | G1073 | RNAi (clade) targeted to conserved domain, 35S | P21301 | 4780 | Greater tol. to dehydration |
| G1073 | AT-hook (63-71, 71-216) | 18 | G1073 | RNAi (clade) targeted to conserved domain, 35S | P21160 | 4748 | Greater tol. to dehydration |
| G1073 | AT-hook (63-71, 71-216) | 18 | G1073 | RNAi Gene-Specific (GS), 35S | P21117 | 4743 | Greater tol. to dehydration |
| G1073 | AT-hook (63-71, 71-216) | 18 | G1073 | RNAi Gene-Specific (GS), 35S | P21117 | 4743 | Greater tol. to NaCl (determined with 150 mM NaCl) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1073 | AT-hook (63-71, 71-216) | 18 | G1073 | Deletion variant, 35S | P21271 | 4770 | Greater biomass |
| G1073 | AT-hook (63-71, 71-216) | 18 | G1073 | Deletion variant, 35S | P21272 | 4771 | Altered leaf shape |
| G1073 | AT-hook (63-71, 71-216) | 18 | G1073 | Knockout | not applicable | | Greater tol. to drought* |
| G1073 | AT-hook (63-71, 71-216) | 18 | G1073 | Knockout | not applicable | | Greater root mass |
| G1069 | AT-hook (67-75, 75-218) | 802 | G1073 | Const. 35S prom. | P1178 | 4058 | Larger leaf size |
| G1069 | AT-hook (67-75, 75-218) | 802 | G1073 | Const. 35S prom. | P1178 | 4058 | Altered leaf shape |
| G1069 | AT-hook (67-75, 75-218) | 802 | G1073 | Const. 35S prom. | P1178 | 4058 | Less sens. to ABA |
| G1069 | AT-hook (67-75, 75-218) | 802 | G1073 | Const. 35S prom. | P1178 | 4058 | Altered sugar sensing; greater tol. to sucrose (determined in 9.4% sucrose) |
| G1069 | AT-hook (67-75, 75-218) | 802 | G1073 | Const. 35S prom. | P1178 | 4058 | Altered C/N sensing: greater tol. to low nitrogen conditions in C/N sensing assay |
| G1069 | AT-hook (67-75, 75-218) | 802 | G1073 | Const. 35S prom. | P1178 | 4058 | Altered leaf glucosinolate composition; inc. M39497 |
| G1069 | AT-hook (67-75, 75-218) | 802 | G1073 | Const. 35S prom. | P1178 | 4058 | Altered light response; greater shade tol.; lack of shade avoidance phenotype |
| G1069 | AT-hook (67-75, 75-218) | 802 | G1073 | Const. 35S prom. | P1178 | 4058 | More tol. to drought* |
| G1067 | AT-hook (86-94, 94-247) | 798 | G1073 | 2 comp. including P6506 (35S prom.) | P7832 | 4606 | Greater tol. to cold (8 C.) |
| G1067 | AT-hook (86-94, 94-247) | 798 | G1073 | 2 comp. including P6506 (35S prom.) | P7832 | 4606 | More tol. to drought* and better recovery from drought treatment* |
| G1067 | AT-hook (86-94, 94-247) | 798 | G1073 | 2 comp. including P6506 (35S prom.) | P7832 | 4606 | Altered leaf shape; twisted and up-curled rosette leaves |
| G1067 | AT-hook (86-94, 94-247) | 798 | G1073 | 2 comp. including P6506 (35S prom.) | P7832 | 4606 | Smaller plants |
| G1067 | AT-hook (86-94, 94-247) | 798 | G1073 | 2 comp. including P6506 (35S prom.) | P7832 | 4606 | Reduced fertility |
| G1067 | AT-hook (86-94, 94-247) | 798 | G1073 | 2 comp. including P6506 (35S prom.) | P7832 | 4606 | Less sens. to ABA |
| G1067 | AT-hook (86-94, 94-247) | 798 | G1073 | 2 comp. including P5311 (ARSK1 prom.) | P7832 | 4606 | Greater tol. to dehydration |
| G1067 | AT-hook (86-94, 94-247) | 798 | G1073 | 2 comp. including P5311 (ARSK1 prom.) | P7832 | 4606 | Greater tol. to NaCl (determined with 150 mM NaCl) |
| G1067 | AT-hook (86-94, 94-247) | 798 | G1073 | 2 comp. including P5311 (ARSK1 prom.) | P7832 | 4606 | Greater tol. to NaCl (determined with 150 mM NaCl) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1067 | AT-hook (86-94, 94-247) | 798 | G1073 | 2 comp. including P5284 (RBCS3 prom.) | P7832 | 4606 | Larger leaf size |
| G1067 | AT-hook (86-94, 94-247) | 798 | G1073 | 2 comp. including P5284 (RBCS3 prom.) | P7832 | 4606 | More tol. to drought* and better recovery from drought treatment* |
| G1067 | AT-hook (86-94, 94-247) | 798 | G1073 | 2 comp. including P5284 (RBCS3 prom.) | P7832 | 4606 | Late flowering |
| G1067 | AT-hook (86-94, 94-247) | 798 | G1073 | 2 comp. including P5284 (RBCS3 prom.) | P7832 | 4606 | Altered leaf shape |
| G1067 | AT-hook (86-94, 94-247) | 798 | G1073 | 2 comp. including P5284 (RBCS3 prom.) | P7832 | 4606 | Greater tol. to NaCl (determined with 150 mM NaCl) |
| G1067 | AT-hook (86-94, 94-247) | 798 | G1073 | 2 comp. including P9002 (RD29A prom.) | P7832 | 4606 | Greater tol. to dehydration |
| G1067 | AT-hook (86-94, 94-247) | 798 | G1073 | 2 comp. including P9002 (RD29A prom.) | P7832 | 4606 | More tol. to drought* and better recovery from drought treatment* |
| G1067 | AT-hook (86-94, 94-247) | 798 | G1073 | 2 comp. including P9002 (RD29A prom.) | P7832 | 4606 | Larger leaf size |
| G1067 | AT-hook (86-94, 94-247) | 798 | G1073 | 2 comp. including P9002 (RD29A prom.) | P7832 | 4606 | More root hair |
| G1067 | AT-hook (86-94, 94-247) | 798 | G1073 | 2 comp. including P9002 (RD29A prom.) | P7832 | 4606 | Late flowering |
| G1067 | AT-hook (86-94, 94-247) | 798 | G1073 | 2 comp. including P9002 (RD29A prom.) | P7832 | 4606 | Altered leaf shape |
| G1067 | AT-hook (86-94, 94-247) | 798 | G1073 | 2 comp. including P9002 (RD29A prom.) | P7832 | 4606 | Greater tol. to 300 mM mannitol or to NaCl (determined with 150 mM NaCl) |
| G1067 | AT-hook (86-94, 94-247) | 798 | G1073 | 2 comp. including P9002 (RD29A prom.) | P7832 | 4606 | Greater tol. to NaCl (determined with 150 mM NaCl) |
| G1667 | AT-hook (53-61, 61-204) | 1116 | G1073 | Const. 35S prom. | P1079 | 4046 | Inc. seed protein, decreased seed oil, inc. leaf ?-carotene levels |
| G1075 | AT-hook (78-86, 86-229) | 804 | G1073 | Const. 35S prom. | P450 | 3937 | Reduced or absent flower petals, sepals or stamens |
| G1075 | AT-hook (78-86, 86-229) | 804 | G1073 | Const. 35S prom. | P450 | 3937 | Reduced fertility |
| G2153 | AT-hook (80-88, 88-239) | 1420 | G1073 | Const. 35S prom. | P1740 | 4245 | Less sens. to ABA |
| G2153 | AT-hook (80-88, 88-239) | 1420 | G1073 | 2 comp. including P6506 (35S prom.) | P4524 | 4568 | Less sens. to ABA |
| G2153 | AT-hook (80-88, 88-239) | 1420 | G1073 | Const. 35S prom. | P1740 | 4245 | Greater tol. to cold (8 C.) |
| G2153 | AT-hook (80-88, 88-239) | 1420 | G1073 | 2 comp. including P6506 (35S prom.) | P4524 | 4568 | Greater tol. to cold (8 C.) |
| G2153 | AT-hook (80-88, 88-239) | 1420 | G1073 | Const. 35S prom. | P1740 | 4245 | Large flower |
| G2153 | AT-hook (80-88, 88-239) | 1420 | G1073 | 2 comp. including P6506 (35S prom.) | P4524 | 4568 | Large flower |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G2153 | AT-hook (80-88, 88-239) | 1420 | G1073 | Const. 35S prom. | P1740 | 4245 | Late flowering |
| G2153 | AT-hook (80-88, 88-239) | 1420 | G1073 | 2 comp. including P6506 (35S prom.) | P4524 | 4568 | Late flowering |
| G2153 | AT-hook (80-88, 88-239) | 1420 | G1073 | Const. 35S prom. | P1740 | 4245 | Greater biomass |
| G2153 | AT-hook (80-88, 88-239) | 1420 | G1073 | 2 comp. including P6506 (35S prom.) | P4524 | 4568 | Greater biomass |
| G2153 | AT-hook (80-88, 88-239) | 1420 | G1073 | Const. 35S prom. | P1740 | 4245 | More tol. to drought* and better recovery from drought treatment* |
| G2153 | AT-hook (80-88, 88-239) | 1420 | G1073 | Const. 35S prom. | P1740 | 4245 | More tol to hyperosmotic stress; better germination in 9.4% sucrose or 150 mM NaCl |
| G2153 | AT-hook (80-88, 88-239) | 1420 | G1073 | 2 comp. including P6506 (35S prom.) | P4524 | 4568 | More tol to hyperosmotic stress; better germination in 9.4% sucrose or 150 mM NaCl |
| G3462 | AT hook | | G2153 | Const. 35S prom. | | | Late flowering |
| G2156 | AT-hook (72-80, 80-232) | 1424 | G1073 | 2 comp. including P6506 (35S prom.) | P4418 | 4565 | Less sens. to ABA |
| G2156 | AT-hook (72-80, 80-232) | 1424 | G1073 | Const. 35S prom. | P1721 | 4238 | Large flower |
| G2156 | AT-hook (72-80, 80-232) | 1424 | G1073 | 2 comp. including P6506 (35S prom.) | P4418 | 4565 | Large flower |
| G2156 | AT-hook (72-80, 80-232) | 1424 | G1073 | Const. 35S prom. | P1721 | 4238 | Larger leaf size |
| G2156 | AT-hook (72-80, 80-232) | 1424 | G1073 | Const. 35S prom. | P1721 | 4238 | Greater biomass |
| G2156 | AT-hook (72-80, 80-232) | 1424 | G1073 | Const. 35S prom. | P1721 | 4238 | Late flowering |
| G2156 | AT-hook (72-80, 80-232) | 1424 | G1073 | 2 comp. including P6506 (35S prom.) | P4418 | 4565 | Late flowering |
| G2156 | AT-hook (72-80, 80-232) | 1424 | G1073 | Const. 35S prom. | P1721 | 4238 | Greater tol. to cold (8 C.) |
| G2156 | AT-hook (72-80, 80-232) | 1424 | G1073 | 2 comp. including P6506 (35S prom.) | P4418 | 4565 | Greater tol. to cold (8 C.) |
| G2156 | AT-hook (72-80, 80-232) | 1424 | G1073 | Const. 35S prom. | P1721 | 4238 | Greater tol. to hyperosmotic stress; more tol. to 9.4% sucrose or 150 mM NaCl |
| G2156 | AT-hook (72-80, 80-232) | 1424 | G1073 | 2 comp. including P6506 (35S prom.) | P4418 | 4565 | Greater tol. to hyperosmotic stress; more tol. to 9.4% sucrose or 150 mM NaCl |
| G2156 | AT-hook (72-80, 80-232) | 1424 | G1073 | Const. 35S prom. | P1721 | 4238 | More tol. to drought* and better recovery from drought treatment* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G2156 | AT-hook (72-80, 80-232) | 1424 | G1073 | 2 comp. including P5311 (ARSK1 prom.) | P4418 | 4565 | Late flowering |
| G2156 | AT-hook (72-80, 80-232) | 1424 | G1073 | 2 comp. including P5311 (ARSK1 prom.) | P4418 | 4565 | Greater tol. to dehydration |
| G2156 | AT-hook (72-80, 80-232) | 1424 | G1073 | 2 comp. including P5284 (RBCS3 prom.) | P4418 | 4565 | Larger leaf size |
| G2156 | AT-hook (72-80, 80-232) | 1424 | G1073 | 2 comp. including P5284 (RBCS3 prom.) | P4418 | 4565 | Greater biomass |
| G2156 | AT-hook (72-80, 80-232) | 1424 | G1073 | 2 comp. including P5284 (RBCS3 prom.) | P4418 | 4565 | Late flowering |
| G2156 | AT-hook (72-80, 80-232) | 1424 | G1073 | 2 comp. including P5284 (RBCS3 prom.) | P4418 | 4565 | Less sens. to ABA |
| G2156 | AT-hook (72-80, 80-232) | 1424 | G1073 | 2 comp. including P5284 (RBCS3 prom.) | P4418 | 4565 | Altered leaf shape |
| G2156 | AT-hook (72-80, 80-232) | 1424 | G1073 | 2 comp. including P9002 (RD29A prom.) | P4418 | 4565 | Late flowering |
| G2156 | AT-hook (72-80, 80-232) | 1424 | G1073 | 2 comp. including P9002 (RD29A prom.) | P4418 | 4565 | Less sens. to ABA |
| G2156 | AT-hook (72-80, 80-232) | 1424 | G1073 | 2 comp. including P9002 (RD29A prom.) | P4418 | 4565 | Greater biomass |
| G2157 | AT-hook (88-96, 96-240) | 1426 | G1073 | Const. 35S prom. | P1722 | 4239 | Altered leaf shape |
| G2157 | AT-hook (88-96, 96-240) | 1426 | G1073 | Const. 35S prom. | P1722 | 4239 | Greater tol. to dehydration |
| G2157 | AT-hook (88-96, 96-240) | 1426 | G1073 | Const. 35S prom. | P1722 | 4239 | Larger leaf size |
| G2157 | AT-hook (88-96, 96-240) | 1426 | G1073 | 2 comp. including P5326 (AP1 prom.) | P4419 | 4566 | Significantly greater tomato plant volume |
| G2157 | AT-hook (88-96, 96-240) | 1426 | G1073 | 2 comp. including P5287 (LTP1 prom.) | P4419 | 4566 | Significantly greater tomato plant volume |
| G2157 | AT-hook (88-96, 96-240) | 1426 | G1073 | 2 comp. including P5318 (STM prom.) | P4419 | 4566 | Significantly greater plant volume in tomato plants |
| G3456 | AT-hook (44-52, 52-195) | 1916 | G1073 | Const. 35S prom. | P21328 | 4789 | More tol. to drought* and better recovery from drought treatment* |
| G3456 | AT-hook (44-52, 52-195) | 1916 | G1073 | Const. 35S prom. | P21328 | 4789 | Greater tol. to cold (8 C.) |
| G3456 | AT-hook (44-52, 52-195) | 1916 | G1073 | Const. 35S prom. | P21328 | 4789 | Greater tol. to NaCl (determined with 150 mM NaCl) |
| G3456 | AT-hook (44-52, 52-195) | 1916 | G1073 | Const. 35S prom. | P21328 | 4789 | Larger leaf size |
| G3456 | AT-hook (44-52, 52-195) | 1916 | G1073 | Const. 35S prom. | P21467 | 4816 | Larger leaf size |
| G3456 | AT-hook (44-52, 52-195) | 1916 | G1073 | Const. 35S prom. | P21328 | 4789 | Greater biomass |
| G3456 | AT-hook (44-52, 52-195) | 1916 | G1073 | Const. 35S prom. | P21467 | 4816 | Greater biomass |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3456 | AT-hook (44-52, 52-195) | 1916 | G1073 | Const. 35S prom. | P21328 | 4789 | Darker green leaf color |
| G3456 | AT-hook (44-52, 52-195) | 1916 | G1073 | Const. 35S prom. | P21467 | 4816 | Darker green leaf color |
| G3456 | AT-hook (44-52, 52-195) | 1916 | G1073 | Const. 35S prom. | P21328 | 4789 | Delayed senescence |
| G3456 | AT-hook (44-52, 52-195) | 1916 | G1073 | Const. 35S prom. | P21467 | 4816 | Delayed senescence |
| G3456 | AT-hook (44-52, 52-195) | 1916 | G1073 | Const. 35S prom. | P21328 | 4789 | Decreased apical dominance; slightly short inflorescence internodes leading to a somewhat bushy architecture |
| G3456 | AT-hook (44-52, 52-195) | 1916 | G1073 | Const. 35S prom. | P21467 | 4816 | Decreased apical dominance; slightly short inflorescence internodes leading to a somewhat bushy architecture |
| G3456 | AT-hook (44-52, 52-195) | 1916 | G1073 | Const. 35S prom. | P21328 | 4789 | Late flowering |
| G3456 | AT-hook (44-52, 52-195) | 1916 | G1073 | Const. 35S prom. | P21467 | 4816 | Late flowering |
| G3456 | AT-hook (44-52, 52-195) | 1916 | G1073 | Const. 35S prom. | P21328 | 4789 | Altered leaf shape; curled leaves |
| G3456 | AT-hook (44-52, 52-195) | 1916 | G1073 | Const. 35S prom. | P21467 | 4816 | Altered leaf shape; curled leaves |
| G3459 | AT-hook (77-85, 85-228) | 1918 | G1073 | Const. 35S prom. | P21331 | 4790 | Greater tol. to cold (8 C.) |
| G3459 | AT-hook (77-85, 85-228) | 1918 | G1073 | Const. 35S prom. | P21331 | 4790 | Multiple alterations |
| G3459 | AT-hook (77-85, 85-228) | 1918 | G1073 | Const. 35S prom. | P21331 | 4790 | Late flowering |
| G3459 | AT-hook (77-85, 85-228) | 1918 | G1073 | Const. 35S prom. | P21331 | 4790 | Greater tol. to heat (32 C.) |
| G3459 | AT-hook (77-85, 85-228) | 1918 | G1073 | Const. 35S prom. | P21331 | 4790 | Larger leaf size |
| G3459 | AT-hook (77-85, 85-228) | 1918 | G1073 | Const. 35S prom. | P21331 | 4790 | Greater tol. to NaCl (determined with 150 mM NaCl) |
| G3460 | AT-hook (74-82, 82-225) | 1920 | G1073 | Const. 35S prom. | P21332 | 4791 | Greater biomass |
| G3460 | AT-hook (74-82, 82-225) | 1920 | G1073 | Const. 35S prom. | P21332 | 4791 | More tol. to drought* and better recovery from drought treatment* |
| G3460 | AT-hook (74-82, 82-225) | 1920 | G1073 | Const. 35S prom. | P21332 | 4791 | Greater tol. to heat (32 C.) |
| G3460 | AT-hook (74-82, 82-225) | 1920 | G1073 | Const. 35S prom. | P21332 | 4791 | Darker green leaf color |
| G3460 | AT-hook (74-82, 82-225) | 1920 | G1073 | Const. 35S prom. | P21332 | 4791 | Late flowering |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3407 | AT-hook (63-71, 71-220) | 1876 | G1073 | Const. 35S prom. | P21243 | 4753 | Greater seedling vigor |
| G3400 | AT-hook (83-91, 91-237) | 1872 | G1073 | Const. 35S prom. | P21244 | 4754 | Greater biomass |
| G3400 | AT-hook (83-91, 91-237) | 1872 | G1073 | Const. 35S prom. | P21244 | 4754 | Large flower |
| G3400 | AT-hook (83-91, 91-237) | 1872 | G1073 | Const. 35S prom. | P21244 | 4754 | Late flowering |
| G3400 | AT-hook (83-91, 91-237) | 1872 | G1073 | Const. 35S prom. | P21244 | 4754 | Larger leaf size |
| G3400 | AT-hook (83-91, 91-237) | 1872 | G1073 | Const. 35S prom. | P21244 | 4754 | Altered leaf shape |
| G3400 | AT-hook (83-91, 91-237) | 1872 | G1073 | Const. 35S prom. | P21244 | 4754 | Greater tol. to cold (8 C.) |
| G3400 | AT-hook (83-91, 91-237) | 1872 | G1073 | Const. 35S prom. | P21244 | 4754 | More tol. to drought* and better recovery from drought treatment* |
| G3401 | AT-hook (35-43, 43-186) | 1874 | G1073 | Const. 35S prom. | P21264 | 4765 | More tol. to drought* and better recovery from drought treatment* |
| G3401 | AT-hook (35-43, 43-186) | 1874 | G1073 | Const. 35S prom. | P21264 | 4765 | Late flowering |
| G3401 | AT-hook (35-43, 43-186) | 1874 | G1073 | Const. 35S prom. | P21264 | 4765 | Larger leaf size |
| G3401 | AT-hook (35-43, 43-186) | 1874 | G1073 | Const. 35S prom. | P21264 | 4765 | Altered sugar sensing; greater tol. to sucrose (determined in 9.4% sucrose) |
| G3399 | AT-hook (99-107, 107-253) | 1870 | G1073 | Const. 35S prom. | P21465 | 4814 | More tol. to drought* and better recovery from drought treatment* |
| G3399 | AT-hook (99-107, 107-253) | 1870 | G1073 | Const. 35S prom. | P21465 | 4814 | Large flower |
| G3399 | AT-hook (99-107, 107-253) | 1870 | G1073 | Const. 35S prom. | P21465 | 4814 | Greater tol. to dehydration |
| G3399 | AT-hook (99-107, 107-253) | 1870 | G1073 | Const. 35S prom. | P21269 | 4769 | Greater biomass |
| G3399 | AT-hook (99-107, 107-253) | 1870 | G1073 | Const. 35S prom. | P21465 | 4814 | Greater biomass |
| G3399 | AT-hook (99-107, 107-253) | 1870 | G1073 | Const. 35S prom. | P21269 | 4769 | Late flowering |
| G3399 | AT-hook (99-107, 107-253) | 1870 | G1073 | Const. 35S prom. | P21465 | 4814 | Late flowering |
| G3399 | AT-hook (99-107, 107-253) | 1870 | G1073 | Const. 35S prom. | P21269 | 4769 | Larger leaf size |
| G3399 | AT-hook (99-107, 107-253) | 1870 | G1073 | Const. 35S prom. | P21465 | 4814 | Larger leaf size |
| G3399 | AT-hook (99-105, 107-253) | 1870 | G1073 | Const. 35S prom. | P21269 | 4769 | More root hair |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3399 | AT-hook (99-107, 107-253) | 1870 | G1073 | Const. 35S prom. | P21465 | 4814 | More root hair |
| G3399 | AT-hook (99-107, 107-253) | 1870 | G1073 | Const. 35S prom. | P21269 | 4769 | More root mass |
| G3399 | AT-hook (99-107, 107-253) | 1870 | G1073 | Const. 35S prom. | P21465 | 4814 | More root mass |
| G3556 | AT-hook (45-53, 53-196) | 2034 | G1073 | Const. 35S prom. | P21493 | 4819 | Greater tol. to dehydration |
| G3556 | AT-hook (45-53, 53-196) | 2034 | G1073 | Const. 35S prom. | P21493 | 4819 | Greater tol. to NaCl (determined with 150 mM NaCl) |
| G1266 | AP2 (79-147) | 884 | G1266 | Const. 35S prom. | P483 | 3944 | Greater res. to *Botrytis* |
| G1266 | AP2 (79-147) | 884 | G1266 | Const. 35S prom. | P483 | 3944 | Greater res. to *Erysiphe* |
| G1266 | AP2 (79-147) | 884 | G1266 | Const. 35S prom. | P483 | 3944 | Greater res. to *Sclerotinia* |
| G1266 | AP2 (79-147) | 884 | G1266 | Const. 35S prom. | P483 | 3944 | Less sens. to ABA |
| G1266 | AP2 (79-147) | 884 | G1266 | Const. 35S prom. | P483 | 3944 | Late flowering |
| G1266 | AP2 (79-147) | 884 | G1266 | Const. 35S prom. | P483 | 3944 | Darker green leaf color |
| G1266 | AP2 (79-147) | 884 | G1266 | Const. 35S prom. | P483 | 3944 | Reduced sens. to ABA |
| G1266 | AP2 (79-147) | 884 | G1266 | Const. 35S prom. | P483 | 3944 | Altered C/N sensing: greater tol. to low nitrogen conditions in C/N sensing assay |
| G1266 | AP2 (79-147) | 884 | G1266 | Const. 35S prom. | P483 | 3944 | Altered leaf insoluble sugars, including rhamnose, arabinose, xylose, and mannose, and galactose |
| G1266 | AP2 (79-147) | 884 | | Const. 35S prom. | P483 | 3944 | Greater resistance to *Erysiphe* |
| G1266 | AP2 (79-147) | 884 | | Const. 35S prom. | P483 | 3944 | Reduced sens. to ABA |
| G1274 | WRKY (110-166) | 20 | G1274 | 2 comp. including P6506 (35S prom.) | P8239 | 4609 | Less sens. to ABA |
| G1274 | WRKY (110-166) | 20 | G1274 | Const. 35S prom. | P15038 | 4665 | Greater res. to *Erysiphe* |
| G1274 | WRKY (110-166) | 20 | G1274 | Const. 35S prom. | P15038 | 4665 | Trilocular silique |
| G1274 | WRKY (110-166) | 20 | G1274 | Const. 35S prom. | P15038 | 4665 | Greater seed number |
| G1274 | WRKY (110-166) | 20 | G1274 | Const. 35S prom. | P15038 | 4665 | Altered sugar sensing; greater tol. to sucrose (determined in 9.4% sucrose) |
| G1274 | WRKY (110-166) | 20 | G1274 | Const. 35S prom. | P15038 | 4665 | Greater tol. to cold (8 C.) |
| G1274 | WRKY (110-166) | 20 | G1274 | 2 comp. including P6506 (35S prom.) | P8239 | 4609 | Greater tol. to cold (8 C.) |
| G1274 | WRKY (110-166) | 20 | G1274 | 2 comp. including P6506 (35S prom.) | P8239 | 4609 | Large leaves, greater biomass |
| G1274 | WRKY (110-166) | 20 | G1274 | Const. 35S prom. | P15038 | 4665 | More tol. to drought* and better recovery from drought treatment* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1274 | WRKY (110-166) | 20 | G1274 | 2 comp. including P6506 (35S prom.) | P8239 | 4609 | More tol. to drought* and better recovery from drought treatment* |
| G1274 | WRKY (110-166) | 20 | G1274 | 2 comp. including P5311 (ARSK1 prom.) | P8239 | 4609 | Greater tol. to dehydration |
| G1274 | WRKY (110-166) | 20 | G1274 | 2 comp. including P5319 (AS1 prom.) | P8239 | 4609 | More root hair |
| G1274 | WRKY (110-166) | 20 | G1274 | 2 comp. including P5319 (AS1 prom.) | P8239 | 4609 | More root mass |
| G1274 | WRKY (110-166) | 20 | G1274 | 2 comp. including P5288 (CUT1 prom.) | P8239 | 4609 | Altered C/N sensing: greater tol. to low nitrogen conditions in C/N sensing assay |
| G1274 | WRKY (110-166) | 20 | G1274 | 2 comp. including P5284 (RBCS3 prom.) | P8239 | 4609 | Less sens. to ABA |
| G1274 | WRKY (110-166) | 20 | G1274 | 2 comp. including P5284 (RBCS3 prom.) | P8239 | 4609 | Altered C/N sensing: greater tol. to low nitrogen conditions in C/N sensing assay |
| G1274 | WRKY (110-166) | 20 | G1274 | 2 comp. including P5284 (RBCS3 prom.) | P8239 | 4609 | Greater tol. to 300 mM mannitol |
| G1274 | WRKY (110-166) | 20 | G1274 | 2 comp. including P9002 (RD29A prom.) | P8239 | 4609 | Better recovery from drought treatment* |
| G1274 | WRKY (110-166) | 20 | G1274 | 2 comp. including P5318 (STM prom.) | P8239 | 4609 | Greater tol. to cold (8 C.) |
| G1274 | WRKY (110-166) | 20 | G1274 | 2 comp. including P5318 (STM prom.) | P8239 | 4609 | Greater tol. to dehydration |
| G1274 | WRKY (110-166) | 20 | G1274 | 2 comp. including P5318 (STM prom.) | P8239 | 4609 | Better recovery from drought treatment* |
| G1274 | WRKY (110-166) | 20 | G1274 | 2 comp. including P5290 (SUC2 prom.) | P8239 | 4609 | Greater tol. to dehydration |
| G1274 | WRKY (110-166) | 20 | G1274 | 2 comp. including P5290 (SUC2 prom.) | P8239 | 4609 | Altered C/N sensing: greater tol. to low nitrogen conditions in C/N sensing assay |
| G1274 | WRKY (110-166) | 20 | G1274 | GAL4 N-term (Super Active), 35S | P25659 | 4915 | Greater tol. to dehydration |
| G1274 | WRKY (110-166) | 20 | G1274 | GAL4 C-term (Super Active), 35S | P25658 | 4914 | Decreased apical dominance; short bushy inflorescences |
| G1274 | WRKY (110-166) | 20 | G1274 | GAL4 C-term (Super Active), 35S | P25658 | 4914 | Larger leaf size |
| G1274 | WRKY (110-166) | 20 | G1274 | GAL4 C-term (Super Active), 35S | P25658 | 4914 | Greater tol. to dehydration |
| G1274 | WRKY (110-166) | 20 | G1274 | Point mutation, 35S | P25744 | 4929 | Less sens. to ABA |
| G1274 | WRKY (110-166) | 20 | G1274 | Point mutation, 35S | P25744 | 4929 | Greater tol. to dehydration |
| G1274 | WRKY (110-166) | 20 | G1274 | Point mutation, 35S | P25746 | 4931 | Greater tol. to low nitrogen conditions |
| G1274 | WRKY (110-166) | 20 | G1274 | Point mutation, 35S | P25742 | 4927 | Altered sugar sensing; greater tol. to sucrose (determined in 9.4% sucrose) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1274 | WRKY (110-166) | 20 | G1274 | Point mutation, 35S | P25746 | 4931 | Altered sugar sensing; greater tol. to sucrose (determined in 9.4% sucrose) |
| G1274 | WRKY (110-166) | 20 | G1274 | Point mutation, 35S | P25742 | 4927 | Altered C/N sensing: greater tol. to low nitrogen conditions in C/N sensing assay |
| G1274 | WRKY (110-166) | 20 | G1274 | Point mutation, 35S | P25743 | 4928 | Altered C/N sensing: greater tol. to low nitrogen conditions in C/N sensing assay |
| G1274 | WRKY (110-166) | 20 | G1274 | Point mutation, 35S | P25745 | 4930 | Altered C/N sensing: greater tol. to low nitrogen conditions in C/N sensing assay |
| G1274 | WRKY (110-166) | 20 | G1274 | Point mutation, 35S | P25742 | 4927 | Greater tol. to cold (8 C.) |
| G1274 | WRKY (110-166) | 20 | G1274 | Point mutation, 35S | P25743 | 4928 | Greater tol. to cold (8 C.) |
| G1274 | WRKY (110-166) | 20 | G1274 | Point mutation, 35S | P25745 | 4930 | Greater tol. to cold (8 C.) |
| G1274 | WRKY (110-166) | 20 | G1274 | Point mutation, 35S | P25746 | 4931 | Greater tol. to cold (8 C.) |
| G1274 | WRKY (110-166) | 20 | G1274 | Point mutation, 35S | P25742 | 4927 | More tol. to drought* and show better recovery from drought treatment* |
| G1274 | WRKY (110-166) | 20 | G1274 | Point mutation, 35S | P25743 | 4928 | More tol. to drought* and show better recovery from drought treatment* |
| G1274 | WRKY (110-166) | 20 | G1274 | Point mutation, 35S | P25745 | 4930 | More tol. to drought* and show better recovery from drought treatment* |
| G1274 | WRKY (110-166) | 20 | G1274 | Point mutation, 35S | P25746 | 4931 | More tol. to drought* and show better recovery from drought treatment* |
| G1274 | WRKY (110-166) | 20 | G1274 | Point mutation, 35S | P25742 | 4927 | Larger leaf size |
| G1274 | WRKY (110-166) | 20 | G1274 | Point mutation, 35S | P25743 | 4928 | Larger leaf size |
| G1274 | WRKY (110-166) | 20 | G1274 | Point mutation, 35S | P25745 | 4930 | Larger leaf size |
| G1274 | WRKY (110-166) | 20 | G1274 | Point mutation, 35S | P25746 | 4931 | Larger leaf size |
| G1274 | WRKY (110-166) | 20 | G1274 | Point mutation, 35S | P25744 | 4929 | Larger leaf size |
| G1274 | WRKY (110-166) | 20 | G1274 | Point mutation, 35S | P25742 | 4927 | Inflorescence: decreased apical dominance |
| G1274 | WRKY (110-166) | 20 | G1274 | Point mutation, 35S | P25743 | 4928 | Inflorescence: decreased apical dominance |
| G1274 | WRKY (110-166) | 20 | G1274 | Point mutation, 35S | P25745 | 4930 | Inflorescence: decreased apical dominance |
| G1274 | WRKY (110-166) | 20 | G1274 | Point mutation, 35S | P25746 | 4931 | Inflorescence: decreased apical dominance |
| G1274 | WRKY (110-166) | 20 | G1274 | Point mutation, 35S | P25744 | 4929 | Inflorescence: decreased apical dominance |
| G1274 | WRKY (110-166) | 20 | G1274 | Domain swap/chimeric variant, 35S | P25435 | 4901 | Greater tol. to cold (8 C.) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1274 | WRKY (110-166) | 20 | G1274 | Domain swap/chimeric variant, 35S | P25435 | 4901 | Altered C/N sensing: greater tol. to low nitrogen conditions in C/N sensing assay |
| G1274 | WRKY (110-166) | 20 | G1274 | Domain swap/chimeric variant, 35S | P25435 | 4901 | Greater tol. to dehydration |
| G1274 | WRKY (110-166) | 20 | G1274 | Domain swap/chimeric variant, 35S | P25435 | 4901 | Larger leaf size |
| G1274 | WRKY (110-166) | 20 | G1274 | Domain swap/chimeric variant, 35S | P25435 | 4901 | Altered sugar sensing; greater tol. to sucrose (determined in 9.4% sucrose) |
| G1274 | WRKY (110-166) | 20 | G1274 | Knockout | not applicable | | Altered C/N sensing: greater tol. to low nitrogen conditions in C/N sensing assay |
| G1275 | WRKY (113-169) | 894 | G1274 | Const. 35S prom. | P486 | 3946 | Greater tol. to cold (8 C.) |
| G1275 | WRKY (113-169) | 894 | G1274 | Const. 35S prom. | P486 | 3946 | Greater tol. to heat (32 C.) |
| G1275 | WRKY (113-169) | 894 | G1274 | Const. 35S prom. | P486 | 3946 | Reduced apical dominance |
| G1275 | WRKY (113-169) | 894 | G1274 | Const. 35S prom. | P486 | 3946 | Smaller plants |
| G1275 | WRKY (113-169) | 894 | G1274 | 2 comp. including P5319 (AS1 prom.) | P3412 | 4511 | More root mass |
| G1275 | WRKY (113-169) | 894 | G1274 | 2 comp. including P5319 (AS1 prom.) | P3412 | 4511 | Larger leaf size |
| G1275 | WRKY (113-169) | 894 | G1274 | 2 comp. including P5288 (CUT1 prom.) | P3412 | 4511 | Greater tol. to cold (8 C.) |
| G1275 | WRKY (113-169) | 894 | G1274 | 2 comp. including P5288 (CUT1 prom.) | P3412 | 4511 | Better recovery from drought treatment* |
| G1275 | WRKY (113-169) | 894 | G1274 | 2 comp. including P5288 (CUT1 prom.) | P3412 | 4511 | Altered C/N sensing: greater tol. to low nitrogen conditions in C/N sensing assay |
| G1275 | WRKY (113-169) | 894 | G1274 | 2 comp. including P5288 (CUT1 prom.) | P3412 | 4511 | Altered sugar sensing; greater tol. to sucrose (determined in 9.4% sucrose) |
| G1275 | WRKY (113-169) | 894 | G1274 | 2 comp. including P9002 (RD29A prom.) | P3412 | 4511 | More tol. to drought* and better recovery from drought treatment* |
| G1275 | WRKY (113-169) | 894 | G1274 | 2 comp. including P9002 (RD29A prom.) | P3412 | 4511 | Less sens. to ABA |
| G1275 | WRKY (113-169) | 894 | G1274 | 2 comp. including P5318 (STM prom.) | P3412 | 4511 | Greater tol. to low nitrogen conditions |
| G1275 | WRKY (113-169) | 894 | G1274 | 2 comp. including P5290 (SUC2 prom.) | P3412 | 4511 | Altered C/N sensing: greater tol. to low nitrogen conditions in C/N sensing assay |
| G1275 | WRKY (113-169) | 894 | G1274 | 2 comp. including P5290 (SUC2 prom.) | P3412 | 4511 | Late flowering |
| G1275 | WRKY (113-169) | 894 | G1274 | 2 comp. including P5290 (SUC2 prom.) | P3412 | 4511 | Darker green leaf color |
| G1275 | WRKY (113-169) | 894 | G1274 | 2 comp. including P5290 (SUC2 prom.) | P3412 | 4511 | Decreased root mass |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G194 | WRKY (174-230) | 162 | G1274 | Const. 35S prom. | P197 | 3863 | Greater tol. to dehydration |
| G194 | WRKY (174-230) | 162 | G1274 | Const. 35S prom. | P197 | 3863 | Small plant |
| G1758 | WRKY (109-165) | 1144 | G1274 | Const. 35S prom. | P1224 | 4071 | Greater tol. to cold (8 C.) |
| G2517 | WRKY (117-177) | 1548 | G1274 | Const. 35S prom. | P1833 | 4268 | Greater tol. to dehydration |
| G2517 | WRKY (117-177) | 1548 | G1274 | Const. 35S prom. | P1833 | 4268 | Early flowering |
| G2517 | WRKY (117-177) | 1548 | G1274 | Const. 35S prom. | P1833 | 4268 | More tol. to glyphosate |
| G179 | WRKY (65-121) | 138 | G1274 | Domain swap/chimeric variant, 35S | P25439 | 4904 | Less sens. to ABA |
| G179 | WRKY (65-121) | 138 | G1274 | Domain swap/chimeric variant, 35S | P25439 | 4904 | Altered sugar sensing; greater tol. to sucrose (determined in 9.4% sucrose) |
| G3723 | WRKY (112-168) | 2088 | G1274 | Const. 35S prom. | P25208 | 4868 | Inflorescence: decreased apical dominance |
| G3723 | WRKY (112-168) | 2088 | G1274 | Const. 35S prom. | P25208 | 4868 | Larger leaf size |
| G3723 | WRKY (112-168) | 2088 | G1274 | Const. 35S prom. | P25208 | 4868 | Altered leaf shape |
| G3723 | WRKY (112-168) | 2088 | G1274 | Const. 35S prom. | P25208 | 4868 | Greater seedling vigor |
| G3724 | WRKY (107-163) | 2090 | G1274 | Const. 35S prom. | P25384 | 4895 | Greater tol. to cold (8 C.) |
| G3724 | WRKY (107-163) | 2090 | G1274 | Const. 35S prom. | P25384 | 4895 | Less sens. to ABA |
| G3724 | WRKY (107-163) | 2090 | G1274 | Const. 35S prom. | P25384 | 4895 | Larger leaf size |
| G3724 | WRKY (107-163) | 2090 | G1274 | Const. 35S prom. | P25384 | 4895 | More root mass |
| G3724 | WRKY (107-163) | 2090 | G1274 | Const. 35S prom. | P25384 | 4895 | Greater biomass |
| G3724 | WRKY (107-163) | 2090 | G1274 | Const. 35S prom. | P25384 | 4895 | Greater tol. to NaCl (determined with 150 mM NaCl) |
| G3724 | WRKY (107-163) | 2090 | G1274 | Const. 35S prom. | P25384 | 4895 | More tol. to drought* and better recovery from drought treatment* |
| G3724 | WRKY (107-163) | 2090 | G1274 | Const. 35S prom. | P25384 | 4895 | Late flowering |
| G3724 | WRKY (107-163) | 2090 | G1274 | Const. 35S prom. | P25384 | 4895 | Altered leaf shape |
| G3724 | WRKY (107-163) | 2090 | G1274 | Const. 35S prom. | P25384 | 4895 | Greater tol. to hyperosmotic stress; more tol. to 9.4% sucrose or to 150 mM NaCl |
| G3803 | WRKY (111-167) | 2134 | G1274 | Const. 35S prom. | P25218 | 4874 | Inflorescence: decreased apical dominance |
| G3803 | WRKY (111-167) | 2134 | G1274 | Const. 35S prom. | P25218 | 4874 | Decreased tol. to cold (8 C.) |
| G3803 | WRKY (111-167) | 2134 | G1274 | Const. 35S prom. | P25218 | 4874 | Late flowering |
| G3803 | WRKY (111-167) | 2134 | G1274 | Const. 35S prom. | P25218 | 4874 | Early flowering |
| G3803 | WRKY (111-167) | 2134 | G1274 | Const. 35S prom. | P25218 | 4874 | Altered leaf shape |
| G3803 | WRKY (111-167) | 2134 | G1274 | Const. 35S prom. | P25218 | 4874 | Altered silique development |
| G3721 | WRKY (96-152) | 2084 | G1274 | Const. 35S prom. | P25368 | 4893 | Greater tol. to cold (8 C.) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3721 | WRKY (96-152) | 2084 | G1274 | Const. 35S prom. | P25368 | 4893 | More tol. to drought* and better recovery from drought treatment* |
| G3721 | WRKY (96-152) | 2084 | G1274 | Const. 35S prom. | P25368 | 4893 | Less sens. to ABA |
| G3721 | WRKY (96-152) | 2084 | G1274 | Const. 35S prom. | P25368 | 4893 | Greater tol. to NaCl (determined with 150 mM NaCl) |
| G3721 | WRKY (96-152) | 2084 | G1274 | Const. 35S prom. | P25368 | 4893 | Inflorescence: decreased apical dominance |
| G3721 | WRKY (96-152) | 2084 | G1274 | Const. 35S prom. | P25368 | 4893 | Greater tol. to 300 mM mannitol or to NaCl (determined with 150 mM NaCl) |
| G3725 | WRKY (158-214) | 2092 | G1274 | Const. 35S prom. | P25210 | 4869 | More root mass |
| G3726 | WRKY (135-191) | 2094 | G1274 | Const. 35S prom. | P25211 | 4870 | Inflorescence: decreased apical dominance |
| G3726 | WRKY (135-191) | 2094 | G1274 | Const. 35S prom. | P25211 | 4870 | Greater tol. to cold (8 C.) |
| G3726 | WRKY (135-191) | 2094 | G1274 | Const. 35S prom. | P25211 | 4870 | More tol. to drought* and better recovery from drought treatment* |
| G3726 | WRKY (135-191) | 2094 | G1274 | Const. 35S prom. | P25211 | 4870 | Early flowering |
| G3729 | WRKY (137-193) | 2100 | G1274 | Const. 35S prom. | P25214 | 4872 | Altered C/N sensing: greater tol. to low nitrogen conditions in C/N sensing assay |
| G3729 | WRKY (137-193) | 2100 | G1274 | Const. 35S prom. | P25214 | 4872 | Greater tol. to cold (8 C.) |
| G3729 | WRKY (137-193) | 2100 | G1274 | Const. 35S prom. | P25214 | 4872 | Larger leaf size |
| G3729 | WRKY (137-193) | 2100 | G1274 | Const. 35S prom. | P25214 | 4872 | Trilocular silique |
| G3729 | WRKY (137-193) | 2100 | G1274 | Const. 35S prom. | P25214 | 4872 | Greater seed number |
| G3729 | WRKY (137-193) | 2100 | G1274 | Const. 35S prom. | P25214 | 4872 | Greater biomass |
| G3730 | WRKY (107-163) | 2102 | G1274 | Const. 35S prom. | P25215 | 4873 | Inflorescence: decreased apical dominance |
| G3730 | WRKY (107-163) | 2102 | G1274 | Const. 35S prom. | P25215 | 4873 | Late flowering |
| G3730 | WRKY (107-163) | 2102 | G1274 | Const. 35S prom. | P25215 | 4873 | Altered leaf shape |
| G3730 | WRKY (107-163) | 2102 | G1274 | Const. 35S prom. | P25215 | 4873 | Leaf orientation |
| G3730 | WRKY (107-163) | 2102 | G1274 | Const. 35S prom. | P25215 | 4873 | Trilocular silique |
| G3730 | WRKY (107-163) | 2102 | G1274 | Const. 35S prom. | P25215 | 4873 | Greater seed number |
| G3719 | WRKY (98-154) | 2080 | G1274 | Const. 35S prom. | P25204 | 4865 | Inflorescence: decreased apical dominance |
| G3720 | WRKY (135-191) | 2082 | G1274 | Const. 35S prom. | P25205 | 4866 | Inflorescence: decreased apical dominance |
| G3720 | WRKY (135-191) | 2082 | G1274 | Const. 35S prom. | P25205 | 4866 | Greater tol. to low nitrogen conditions |
| G3722 | WRKY (129-185) | 2086 | G1274 | Const. 35S prom. | P25207 | 4867 | Inflorescence: decreased apical dominance |
| G3722 | WRKY (129-185) | 2086 | G1274 | Const. 35S prom. | P25207 | 4867 | Altered C/N sensing: greater tol. to low nitrogen conditions in C/N sensing assay |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3727 | WRKY (102-158) | 2096 | G1274 | Const. 35S prom. | P25385 | 4896 | Inflorescence: decreased apical dominance |
| G3727 | WRKY (102-158) | 2096 | G1274 | Const. 35S prom. | P25385 | 4896 | Early flowering |
| G3727 | WRKY (102-158) | 2096 | G1274 | Const. 35S prom. | P25385 | 4896 | Greater tol. to low nitrogen conditions |
| G3727 | WRKY (102-158) | 2096 | G1274 | Const. 35S prom. | P25385 | 4896 | Trilocular silique |
| G3727 | WRKY (102-158) | 2096 | G1274 | Const. 35S prom. | P25385 | 4896 | Greater seed number |
| G3728 | WRKY (108-164) | 2098 | G1274 | Const. 35S prom. | P25213 | 4871 | Inflorescence: decreased apical dominance |
| G3728 | WRKY (108-164) | 2098 | G1274 | Const. 35S prom. | P25213 | 4871 | Altered silique development |
| G3804 | WRKY (108-164) | 2136 | G1274 | Const. 35S prom. | P25219 | 4875 | More tol. to drought* and better recovery from drought treatment* |
| G3804 | WRKY (108-164) | 2136 | G1274 | Const. 35S prom. | P25219 | 4875 | Greater tol. to cold (8 C.) |
| G3804 | WRKY (108-164) | 2136 | G1274 | Const. 35S prom. | P25219 | 4875 | Greater tol. to cold (8 C.) |
| G3804 | WRKY (108-164) | 2136 | G1274 | Const. 35S prom. | P25219 | 4875 | Early flowering |
| G3804 | WRKY (108-164) | 2136 | G1274 | Const. 35S prom. | P25219 | 4875 | Altered leaf shape |
| G3804 | WRKY (108-164) | 2136 | G1274 | Const. 35S prom. | P25219 | 4875 | Trilocular silique |
| G1543 | HB (135-195) | 1062 | G1543 | Const. 35S prom. | P1051 | 4038 | Altered architecture, compact plant |
| G1543 | HB (135-195) | 1062 | G1543 | Const. 35S prom. | P1051 | 4038 | Darker green color |
| G1543 | HB (135-195) | 1062 | G1543 | Const. 35S prom. | P1051 | 4038 | Decreased seed oil content |
| G1543 | HB (135-195) | 1062 | G1543 | Const. 35S prom. | P1051 | 4038 | Altered leaf prenyl lipids; more chlorophyll a and b |
| G1543 | HB (135-195) | 1062 | G1543 | 2 comp. including P5287 (LTP1 prom.) | P3424 | 4512 | Significantly greater tomato plant volume |
| G1543 | HB (135-195) | 1062 | G1543 | 2 comp. including P5297 (PG prom.) | P3424 | 4512 | Significantly greater tomato plant volume |
| G3524 | HB (60-121) | 1988 | G1543 | — | — | | n/d |
| G3510 | HB (74-134) | 1974 | G1543 | — | — | | n/d |
| G3490 | HB (60-120) | 1958 | G1543 | — | — | | n/d |
| G4369 | HB (76-136) | 17833 | G1543 | — | — | | n/d |
| G4370 | HB (80-140) | 17837 | G1543 | — | — | | n/d |
| G4371 | HB (62-121) | 17829 | G1543 | — | — | | n/d |
| G1760 | MADS (2-57) | 22 | G1760 | 2 comp. including P6506 (35S prom.) | P3371 | 4505 | Greater tol. to cold (8 C.) |
| G1760 | MADS (2-57) | 22 | G1760 | Const. 35S prom. | P1461 | 4152 | Altered C/N sensing: greater tol. to low nitrogen conditions in C/N sensing assay |
| G1760 | MADS (2-57) | 22 | G1760 | 2 comp. including P6506 (35S prom.) | P3371 | 4505 | Altered C/N sensing: greater tol. to low nitrogen conditions in C/N sensing assay |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1760 | MADS (2-57) | 22 | G1760 | 2 comp. including P6506 (35S prom.) | P3371 | 4505 | Altered sugar sensing; greater tol. to sucrose (determined in 9.4% sucrose) |
| G1760 | MADS (2-57) | 22 | G1760 | Const. 35S prom | — | — | Early flowering, etiolated seedling |
| G1760 | MADS (2-57) | 22 | G1760 | STM | — | — | Increased fruit weight |
| G152 | MADS (2-57) | 110 | G1760 | Const. 35S prom. | P896 | 3996 | Only 3 lines produced, no positive physiological results at this time |
| G153 | MADS (2-57) | 112 | G1760 | Const. 35S prom. | P15260 | 4691 | Altered C/N sensing: greater tol. to low nitrogen conditions in C/N sensing assay |
| G153 | MADS (2-57) | 112 | G1760 | Const. 35S prom. | P15260 | 4691 | Greater tol. to low nitrogen conditions |
| G153 | MADS (2-57) | 112 | G1760 | Const. 35S prom. | P15260 | 4691 | Early flowering |
| G860 | MADS (2-57) | 640 | G1760 | Const. 35S prom. | P1269 | 4091 | Only 3 lines produced, no positive physiological results at this time |
| G860 | MADS (2-57) | 640 | G1760 | Const. 35S prom | — | — | Increased trichome density, Brighter leaf color |
| G3484 | MADS (2-57) | 1948 | G1760 | Const. 35S prom. | P26744 | 5049 | Reduced or delayed floral organ abscission |
| G3484 | MADS (2-57) | 1948 | G1760 | Const. 35S prom. | P26744 | 5049 | Early flowering |
| G3485 | MADS (2-57) | 1950 | G1760 | — | — | — | n/d |
| G3980 | MADS (2-57) | 2246 | G1760 | Const. 35S prom. | P26799 | 5052 | Early flowering |
| G3981 | MADS (2-57) | 2248 | G1760 | — | — | — | n/d |
| G3479 | MADS (2-57) | 1938 | G1760 | Const. 35S prom. | P26738 | 5048 | Early flowering |
| G3480 | MADS (2-57) | 1940 | G1760 | — | — | — | n/d |
| G3481 | MADS (2-57) | 1942 | G1760 | — | — | — | n/d |
| G3482 | MADS (2-57) | 1944 | G1760 | — | — | — | n/d |
| G3483 | MADS (2-57) | 1946 | G1760 | — | — | — | n/d |
| G3487 | MADS (2-57) | 1952 | G1760 | — | — | — | n/d |
| G3488 | MADS (2-57) | 1954 | G1760 | — | — | — | n/d |
| G3489 | MADS (2-57) | 1956 | G1760 | — | — | — | n/d |
| G1792 | AP2 (16-80) | 24 | G1792 | Const. 35S prom. | P6071 | 4598 | Greater tol. to cold (8 C.) |
| G1792 | AP2 (16-80) | 24 | G1792 | 2 comp. including P6506 (35S prom.) | P6071 | 4598 | Altered C/N sensing: greater tol. to low nitrogen conditions in C/N sensing assay |
| G1792 | AP2 (16-80) | 24 | G1792 | Const. 35S prom. | P1695 | 4227 | Altered C/N sensing: greater tol. to low nitrogen conditions in C/N sensing assay |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1792 | AP2 (16-80) | 24 | G1792 | Const. 35S prom. | P1695 | 4227 | More tol. to nitrogen-limited medium |
| G1792 | AP2 (16-80) | 24 | G1792 | 2 comp. including P6506 (35S prom.) | P6071 | 4598 | More root hair |
| G1792 | AP2 (16-80) | 24 | G1792 | Const. 35S prom. | P1695 | 4227 | More root hair |
| G1792 | AP2 (16-80) | 24 | G1792 | 2 comp. including P6506 (35S prom.) | P6071 | 4598 | More root mass |
| G1792 | AP2 (16-80) | 24 | G1792 | Const. 35S prom. | P1695 | 4227 | More root mass |
| G1792 | AP2 (16-80) | 24 | G1792 | Const. 35S prom. | P1695 | 4227 | Two lines of plants had higher chlorophyll content and higher total nitrogen concentration |
| G1792 | AP2 (16-80) | 24 | G1792 | 2 comp. including P6506 (35S prom.) | P6071 | 4598 | Altered leaf shape |
| G1792 | AP2 (16-80) | 24 | G1792 | Const. 35S prom. | P1695 | 4227 | Altered leaf shape |
| G1792 | AP2 (16-80) | 24 | G1792 | Const. 35S prom. | P26498 | 5016 | Altered leaf shape |
| G1792 | AP2 (16-80) | 24 | G1792 | 2 comp. including P6506 (35S prom.) | P6071 | 4598 | Darker green leaf color, shiny leaves |
| G1792 | AP2 (16-80) | 24 | G1792 | Const. 35S prom. | P1695 | 4227 | Darker green leaf color, shiny leaves |
| G1792 | AP2 (16-80) | 24 | G1792 | Const. 35S prom. | P26498 | 5016 | Darker green leaf color, shiny leaves |
| G1792 | AP2 (16-80) | 24 | G1792 | Const. 35S prom. | P1695 | 4227 | Greater resistance to *Erysiphe* |
| G1792 | AP2 (16-80) | 24 | G1792 | Const. 35S prom. | P1695 | 4227 | Greater resistance to *Botrytis* |
| G1792 | AP2 (16-80) | 24 | G1792 | Const. 35S prom. | P1695 | 4227 | Greater resistance to *Fusarium* |
| G1792 | AP2 (16-80) | 24 | G1792 | 2 comp. including P6506 (35S prom.) | P6071 | 4598 | More tol. to dehydration |
| G1792 | AP2 (16-80) | 24 | G1792 | Const. 35S prom. | P1695 | 4227 | More tol. to dehydration |
| G1792 | AP2 (16-80) | 24 | G1792 | Const. 35S prom. | P26498 | 5016 | More tol. to dehydration |
| G1792 | AP2 (16-80) | 24 | G1792 | Const. 35S prom. | P1695 | 4227 | Inc. seed oil content |
| G1792 | AP2 (16-80) | 24 | G1792 | 2 comp. including P6506 (35S prom.) | P6071 | 4598 | More tol. to drought* and better recovery from drought treatment* |
| G1792 | AP2 (16-80) | 24 | G1792 | Const. 35S prom. | P1695 | 4227 | More tol. to drought* and better recovery from drought treatment* |
| G1792 | AP2 (16-80) | 24 | G1792 | Const. 35S prom. | P26498 | 5016 | More tol. to drought* and better recovery from drought treatment* |
| G1792 | AP2 (16-80) | 24 | G1792 | 2 comp. including P5326 (AP1 prom.) | P6071 | 4598 | Altered sugar sensing; greater tol. to sucrose (determined in 9.4% sucrose) |
| G1792 | AP2 (16-80) | 24 | G1792 | 2 comp. including P5326 (AP1 prom.) | P6071 | 4598 | Greater tol. to dehydration |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1792 | AP2 (16-80) | 24 | G1792 | 2 comp. including P5319 (AS1 prom.) | P6071 | 4598 | Altered C/N sensing: greater tol. to low nitrogen conditions in C/N sensing assay |
| G1792 | AP2 (16-80) | 24 | G1792 | 2 comp. including P5288 (CUT1 prom.) | P6071 | 4598 | Altered C/N sensing: greater tol. to low nitrogen conditions in C/N sensing assay |
| G1792 | AP2 (16-80) | 24 | G1792 | 2 comp. including P5288 (CUT1 prom.) | P6071 | 4598 | Greater tol. to cold (8 C.) |
| G1792 | AP2 (16-80) | 24 | G1792 | 2 comp. including P5288 (CUT1 prom.) | P6071 | 4598 | Better recovery from drought treatment* |
| G1792 | AP2 (16-80) | 24 | G1792 | 2 comp. including P5288 (CUT1 prom.) | P6071 | 4598 | Late flowering |
| G1792 | AP2 (16-80) | 24 | G1792 | 2 comp. including P5287 (LTP1 prom.) | P6071 | 4598 | Greater tol. to low nitrogen conditions |
| G1792 | AP2 (16-80) | 24 | G1792 | 2 comp. including P5284 (RBCS3 prom.) | P6071 | 4598 | More res. to *Botrytis* |
| G1792 | AP2 (16-80) | 24 | G1792 | 2 comp. including P5284 (RBCS3 prom.) | P6071 | 4598 | Darker green leaf color |
| G1792 | AP2 (16-80) | 24 | G1792 | 2 comp. including P5284 (RBCS3 prom.) | P6071 | 4598 | Greater tol. to NaCl (determined with 150 mM NaCl) |
| G1792 | AP2 (16-80) | 24 | G1792 | 2 comp. including P9002 (RD29A prom.) | P6071 | 4598 | More tol. to drought* and better recovery from drought treatment* |
| G1792 | AP2 (16-80) | 24 | G1792 | 2 comp. including P9002 (RD29A prom.) | P6071 | 4598 | Less sens. to ABA |
| G1792 | AP2 (16-80) | 24 | G1792 | 2 comp. including P9002 (RD29A prom.) | P6071 | 4598 | Greater tol. to low nitrogen conditions |
| G1792 | AP2 (16-80) | 24 | G1792 | 2 comp. including P9002 (RD29A prom.) | P6071 | 4598 | Greater tol. to NaCl (determined with 150 mM NaCl) |
| G1792 | AP2 (16-80) | 24 | G1792 | 2 comp. including P5310 (RS1 prom.) | P6071 | 4598 | Altered C/N sensing: greater tol. to low nitrogen conditions in C/N sensing assay |
| G1792 | AP2 (16-80) | 24 | G1792 | 2 comp. including P5318 (STM prom.) | P6071 | 4598 | Greater tol. to cold (8 C.) |
| G1792 | AP2 (16-80) | 24 | G1792 | 2 comp. including P5318 (STM prom.) | P6071 | 4598 | Greater tol. to 300 mM mannitol |
| G1792 | AP2 (16-80) | 24 | G1792 | 2 comp. including P5290 (SUC2 prom.) | P6071 | 4598 | Greater tol. to dehydration |
| G1792 | AP2 (16-80) | 24 | G1792 | 2 comp. including P5290 (SUC2 prom.) | P6071 | 4598 | Altered C/N sensing: greater tol. to low nitrogen conditions in C/N sensing assay |
| G1792 | AP2 (16-80) | 24 | G1792 | 2 comp. including P5290 (SUC2 prom.) | P6071 | 4598 | Greater tol. to cold (8 C.) |
| G1792 | AP2 (16-80) | 24 | G1792 | Deletion variant, 35S | P25437 | 4902 | Gray leaf color |
| G1792 | AP2 (16-80) | 24 | G1792 | Domain swap/chimeric variant, 35S | P25448 | 4909 | More tol. to drought* and better recovery from drought treatment* |
| G1792 | AP2 (16-80) | 24 | G1792 | Domain swap/chimeric variant, 35S | P25446 | 4907 | Greater res. to *Erysiphe* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1792 | AP2 (16-80) | 24 | G1792 | Domain swap/chimeric variant, 35S | P25447 | 4908 | Greater res. to *Erysiphe* |
| G1792 | AP2 (16-80) | 24 | G1792 | Domain swap/chimeric variant, 35S | P25448 | 4909 | Greater res. to *Erysiphe* |
| G1792 | AP2 (16-80) | 24 | G1792 | Domain swap/chimeric variant, 35S | P25445 | 4906 | Greater res. to *Erysiphe* |
| G1792 | AP2 (16-80) | 24 | G1792 | Domain swap/chimeric variant, 35S | P25448 | 4909 | Altered C/N sensing: greater tol. to low nitrogen conditions in C/N sensing assay |
| G1792 | AP2 (16-80) | 24 | G1792 | Domain swap/chimeric variant, 35S | P25446 | 4907 | Greater res. to *Sclerotinia* |
| G1792 | AP2 (16-80) | 24 | G1792 | Domain swap/chimeric variant, 35S | P25448 | 4909 | Greater res. to *Sclerotinia* |
| G1792 | AP2 (16-80) | 24 | G1792 | Domain swap/chimeric variant, 35S | P25445 | 4906 | Greater res. to *Sclerotinia* |
| G1792 | AP2 (16-80) | 24 | G1792 | Domain swap/chimeric variant, 35S | P25438 | 4903 | Late flowering |
| G1792 | AP2 (16-80) | 24 | G1792 | Domain swap/chimeric variant, 35S | P25446 | 4907 | Late flowering |
| G1792 | AP2 (16-80) | 24 | G1792 | Domain swap/chimeric variant, 35S | P25447 | 4908 | Late flowering |
| G1792 | AP2 (16-80) | 24 | G1792 | Domain swap/chimeric variant, 35S | P25448 | 4909 | Late flowering |
| G1792 | AP2 (16-80) | 24 | G1792 | Domain swap/chimeric variant, 35S | P25445 | 4906 | Late flowering |
| G1792 | AP2 (16-80) | 24 | G1792 | Domain swap/chimeric variant, 35S | P25438 | 4903 | Altered leaf shape |
| G1792 | AP2 (16-80) | 24 | G1792 | Domain swap/chimeric variant, 35S | P25446 | 4907 | Altered leaf shape |
| G1792 | AP2 (16-80) | 24 | G1792 | Domain swap/chimeric variant, 35S | P25447 | 4908 | Altered leaf shape |
| G1792 | AP2 (16-80) | 24 | G1792 | Domain swap/chimeric variant, 35S | P25448 | 4909 | Altered leaf shape |
| G1792 | AP2 (16-80) | 24 | G1792 | Domain swap/chimeric variant, 35S | P25445 | 4906 | Altered leaf shape |
| G1792 | AP2 (16-80) | 24 | G1792 | Domain swap/chimeric variant, 35S | P25438 | 4903 | Glossy leaves |
| G1792 | AP2 (16-80) | 24 | G1792 | Domain swap/chimeric variant, 35S | P25446 | 4907 | Glossy leaves |
| G1792 | AP2 (16-80) | 24 | G1792 | Domain swap/chimeric variant, 35S | P25447 | 4908 | Glossy leaves |
| G1792 | AP2 (16-80) | 24 | G1792 | Domain swap/chimeric variant, 35S | P25448 | 4909 | Glossy leaves |
| G1792 | AP2 (16-80) | 24 | G1792 | Domain swap/chimeric variant, 35S | P25445 | 4906 | Glossy leaves |
| G1792 | AP2 (16-80) | 24 | G1792 | Domain swap/chimeric variant, 35S | P25438 | 4903 | Darker green leaf color |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1792 | AP2 (16-80) | 24 | G1792 | Domain swap/chimeric variant, 35S | P25446 | 4907 | Darker green leaf color |
| G1792 | AP2 (16-80) | 24 | G1792 | Domain swap/chimeric variant, 35S | P25447 | 4908 | Darker green leaf color |
| G1792 | AP2 (16-80) | 24 | G1792 | Domain swap/chimeric variant, 35S | P25448 | 4909 | Darker green leaf color |
| G1792 | AP2 (16-80) | 24 | G1792 | Domain swap/chimeric variant, 35S | P25445 | 4906 | Darker green leaf color |
| G1792 | AP2 (16-80) | 24 | G1792 | Glucocorticoid receptor (GR) fusion (dexamethasone-inducible), 35S prom. (w/P5486) | P6071 | 4598 | More res. to *Botrytis* |
| G1792 | AP2 (16-80) | 24 | G1792 | Glucocorticoid receptor (GR) fusion (dexamethasone-inducible), 35S prom. (w/P5486) | P6071 | 4598 | More res. to *Fusarium* |
| G1792 | AP2 (16-80) | 24 | G1792 | 2 comp. hemagglutinin (HA) epitope C-terminal tag, 35S (w/P5486) | P25118 | 4853 | More res. to *Botrytis* |
| G1792 | AP2 (16-80) | 24 | G1792 | 2 comp. hemagglutinin (HA) epitope C-terminal tag, 35S (w/P5486) | P25118 | 4853 | More tol. to drought* and better recovery from drought treatment* |
| G1792 | AP2 (16-80) | 24 | G1792 | 2 comp. hemagglutinin (HA) epitope C-terminal tag, 35S (w/P5486) | P25118 | 4853 | Greater res. to *Erysiphe* |
| G1792 | AP2 (16-80) | 24 | G1792 | 2 comp. hemagglutinin (HA) epitope C-terminal tag, 35S (w/P5486) | P25118 | 4853 | Altered C/N sensing: greater tol. to low nitrogen conditions in C/N sensing assay |
| G1792 | AP2 (16-80) | 24 | G1792 | 2 comp. hemagglutinin (HA) epitope C-terminal tag, 35S (w/P5486) | P25118 | 4853 | Greater tol. to cold (8 C.) |
| G1792 | AP2 (16-80) | 24 | G1792 | 2 comp. hemagglutinin (HA) epitope C-terminal tag, 35S (w/P5486) | P25118 | 4853 | Late flowering |
| G1792 | AP2 (16-80) | 24 | G1792 | 2 comp. hemagglutinin (HA) epitope C-terminal tag, 35S (w/P5486) | P25118 | 4853 | Glossy leaves |
| G1792 | AP2 (16-80) | 24 | G1792 | 2 comp. hemagglutinin (HA) epitope C-terminal tag, 35S (w/P5486) | P25118 | 4853 | Darker green leaf color |
| G1792 | AP2 (16-80) | 24 | G1792 | 2 comp. hemagglutinin (HA) epitope C-terminal tag, 35S (w/P5486) | P25118 | 4853 | Greater res. to *Sclerotinia* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1792 | AP2 (16-80) | 24 | G1792 | 2 comp. hemagglutinin (HA) epitope C-terminal tag, 35S (w/P5486) | P25118 | 4853 | Altered sugar sensing; greater tol. to sucrose (determined in 9.4% sucrose) |
| G1792 | AP2 (16-80) | 24 | G1792 | 2 comp. hemagglutinin (HA) epitope C-terminal tag, 35S (w/P5486) | P26259 | 4963 | Altered sugar sensing; greater tol. to sucrose (determined in 9.4% sucrose) |
| G1792 | AP2 (16-80) | 24 | G1792 | 2 comp. hemagglutinin (HA) epitope C-terminal tag, 35S (w/P5486) | P26259 | 4963 | More tol. to drought* and better recovery from drought treatment* |
| G1792 | AP2 (16-80) | 24 | G1792 | 2-components-supertransformation-TAP-C-terminus (w/P5486) | P25119 | 4854 | More tol. to drought* and better recovery from drought treatment* |
| G1792 | AP2 (16-80) | 24 | G1792 | Protein-GFP C terminal fusion, 35S | P25271 | 4885 | More tol. to drought* and better recovery from drought treatment* |
| G1792 | AP2 (16-80) | 24 | G1792 | Protein-GFP C terminal fusion, 35S | P25271 | 4885 | Greater res. to *Erysiphe* |
| G1792 | AP2 (16-80) | 24 | G1792 | Protein-GFP C terminal fusion, 35S | P25271 | 4885 | Altered C/N sensing: greater tol. to low nitrogen conditions in C/N sensing assay |
| G1792 | AP2 (16-80) | 24 | G1792 | Protein-GFP C terminal fusion, 35S | P25271 | 4885 | Greater tol. to dehydration |
| G1792 | AP2 (16-80) | 24 | G1792 | Protein-GFP C terminal fusion, 35S | P25271 | 4885 | Greater res. to *Sclerotinia* |
| G1792 | AP2 (16-80) | 24 | G1792 | Protein-GFP C terminal fusion, 35S | P25271 | 4885 | Greater tol. to cold (8 C.) |
| G1792 | AP2 (16-80) | 24 | G1792 | Protein-GFP C terminal fusion, 35S | P25271 | 4885 | Late flowering |
| G1792 | AP2 (16-80) | 24 | G1792 | Protein-GFP C terminal fusion, 35S | P25271 | 4885 | Altered leaf shape |
| G1792 | AP2 (16-80) | 24 | G1792 | Protein-GFP C terminal fusion, 35S | P25271 | 4885 | Glossy leaves |
| G1792 | AP2 (16-80) | 24 | G1792 | Protein-GFP C terminal fusion, 35S | P25271 | 4885 | Darker green leaf color |
| G1792 | AP2 (16-80) | 24 | G1792 | Protein-GFP C terminal fusion, 35S | P25271 | 4885 | Greater tol. to low nitrogen conditions |
| G1792 | AP2 (16-80) | 24 | G1792 | Point mutation, 35S | P25738 | 4923 | Greater res. to *Erysiphe* |
| G1792 | AP2 (16-80) | 24 | G1792 | Point mutation, 35S | P25739 | 4924 | Greater res. to *Erysiphe* |
| G1792 | AP2 (16-80) | 24 | G1792 | Point mutation, 35S | P25739 | 4924 | Gray leaf color |
| G1792 | AP2 (16-80) | 24 | G1792 | Point mutation, 35S | P25740 | 4925 | Gray leaf color |
| G1792 | AP2 (16-80) | 24 | G1792 | Point mutation, 35S | P25741 | 4926 | Gray leaf color |
| G1792 | AP2 (16-80) | 24 | G1792 | Point mutation, 35S | P25739 | 4924 | Altered C/N sensing: greater tol. to low nitrogen conditions in C/N sensing assay |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1792 | AP2 (16-80) | 24 | G1792 | Point mutation, 35S | P25740 | 4925 | Altered C/N sensing: greater tol. to low nitrogen conditions in C/N sensing assay |
| G1792 | AP2 (16-80) | 24 | G1792 | Point mutation, 35S | P25739 | 4924 | Greater tol. to low nitrogen conditions |
| G1792 | AP2 (16-80) | 24 | G1792 | Point mutation, 35S | P25740 | 4925 | Altered sugar sensing; greater tol. to sucrose (determined in 9.4% sucrose) |
| G1792 | AP2 (16-80) | 24 | G1792 | Point mutation, 35S | P25739 | 4924 | Greater res. to *Botrytis* and *Erysiphe* |
| G1792 | AP2 (16-80) | 24 | G1792 | Point mutation, 35S | P25739 | 4924 | More tol. to drought* and better recovery from drought treatment* |
| G1792 | AP2 (16-80) | 24 | G1792 | Point mutation, 35S | P25741 | 4926 | More tol. to drought* and better recovery from drought treatment* |
| G1792 | AP2 (16-80) | 24 | G1792 | Direct disease-inducible prom. fusion | P27085 | 5076 | Greater res. to *Erysiphe* |
| G1792 | AP2 (16-80) | 24 | G1792 | Direct disease-inducible prom. fusion | P27086 | 5077 | Greater res. to *Erysiphe* |
| G1792 | AP2 (16-80) | 24 | G1792 | Direct disease-inducible prom. fusion | P27087 | 5078 | Greater res. to *Erysiphe* |
| G1792 | AP2 (16-80) | 24 | G1792 | Direct disease-inducible prom. fusion | P27035 | 5067 | Greater res. to *Erysiphe* |
| G1792 | AP2 (16-80) | 24 | G1792 | Direct disease-inducible prom. fusion | P27201 | 5080 | Greater res. to *Erysiphe* |
| G1792 | AP2 (16-80) | 24 | G1792 | Direct disease-inducible prom. fusion | P27036 | 5068 | Greater res. to *Botrytis* and *Erysiphe* |
| G1792 | AP2 (16-80) | 24 | G1792 | Direct disease-inducible prom. fusion | P27030 | 5066 | Greater res. to *Botrytis* and *Erysiphe* |
| G1792 | AP2 (16-80) | 24 | G1792 | Direct disease-inducible prom. fusion | P27199 | 5079 | Greater res. to *Botrytis* and *Erysiphe* |
| G1791 | AP2 (10-74) | 1172 | G1792 | 2 comp. including P5319 (AS1 prom.) | P4406 | 4562 | More res. to *Botrytis* |
| G1791 | AP2 (10-74) | 1172 | G1792 | 2 comp. including P5319 (AS1 prom.) | P4406 | 4562 | Altered C/N sensing: greater tol. to low nitrogen conditions in C/N sensing assay |
| G1791 | AP2 (10-74) | 1172 | G1792 | 2 comp. including P5319 (AS1 prom.) | P4406 | 4562 | Greater tol. to cold (8 C.) |
| G1791 | AP2 (10-74) | 1172 | G1792 | 2 comp. including P5319 (AS1 prom.) | P4406 | 4562 | Late flowering |
| G1791 | AP2 (10-74) | 1172 | G1792 | 2 comp. including P5288 (CUT1 prom.) | P4406 | 4562 | Greater tol. to dehydration |
| G1791 | AP2 (10-74) | 1172 | G1792 | 2 comp. including P5288 (CUT1 prom.) | P4406 | 4562 | Greater res. to *Sclerotinia* |
| G1791 | AP2 (10-74) | 1172 | G1792 | 2 comp. including P5287 (LTP1 prom.) | P4406 | 4562 | More res. to *Botrytis* |
| G1791 | AP2 (10-74) | 1172 | G1792 | 2 comp. including P5284 (RBCS3 prom.) | P4406 | 4562 | Less sens. to ABA |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1791 | AP2 (10-74) | 1172 | G1792 | 2 comp. including P5284 (RBCS3 prom.) | P4406 | 4562 | Greater tol. to cold (8 C.) |
| G1791 | AP2 (10-74) | 1172 | G1792 | 2 comp. including P5284 (RBCS3 prom.) | P4406 | 4562 | More tol. to drought* and better recovery from drought treatment* |
| G1791 | AP2 (10-74) | 1172 | G1792 | 2 comp. including P5284 (RBCS3 prom.) | P4406 | 4562 | Late flowering |
| G1791 | AP2 (10-74) | 1172 | G1792 | 2 comp. including P9002 (RD29A prom.) | P4406 | 4562 | Late flowering |
| G1791 | AP2 (10-74) | 1172 | G1792 | 2 comp. including P9002 (RD29A prom.) | P4406 | 4562 | Greater tol. to low nitrogen conditions |
| G1791 | AP2 (10-74) | 1172 | G1792 | 2 comp. including P5290 (SUC2 prom.) | P4406 | 4562 | Late flowering |
| G1791 | AP2 (10-74) | 1172 | G1792 | 2 comp. including P5290 (SUC2 prom.) | P4406 | 4562 | Glossy leaves |
| G1791 | AP2 (10-74) | 1172 | G1792 | 2 comp. including P5290 (SUC2 prom.) | P4406 | 4562 | Altered C/N sensing: greater tol. to low nitrogen conditions in C/N sensing assay |
| G1791 | AP2 (10-74) | 1172 | G1792 | 2 comp. including P5297 (PG prom.) | P4406 | 4562 | Significantly greater soluble solids (Brix) in tomato plants |
| G1791 | AP2 (10-74) | 1172 | G1792 | Glucocorticoid receptor (GR) fusion (dexamethasone-inducible), 35S prom. (w/P5486) | P4406 | 4562 | More res. to *Botrytis* |
| G1791 | AP2 (10-74) | 1172 | G1792 | Glucocorticoid receptor (GR) fusion (dexamethasone-inducible), 35S prom. (w/P5486) | P4406 | 4562 | Greater res. to *Sclerotinia* |
| G1791 | AP2 (10-74) | 1172 | G1792 | Knockout | not applicable | | Altered C/N sensing: greater tol. to low nitrogen conditions in C/N sensing assay |
| G1791 | AP2 (10-74) | 1172 | G1792 | Knockout | not applicable | | Altered sugar sensing; greater tol. to sucrose (determined in 9.4% sucrose) |
| G1795 | AP2 (11-75) | 26 | G1792 | 2 comp. including P5288 (CUT1 prom.) | P6424 | 4600 | Greater res. to *Erysiphe* |
| G1795 | AP2 (11-75) | 26 | G1792 | 2 comp. including P5288 (CUT1 prom.) | P6424 | 4600 | Late flowering |
| G1795 | AP2 (11-75) | 26 | G1792 | 2 comp. including P5288 (CUT1 prom.) | P6424 | 4600 | Glossy leaves |
| G1795 | AP2 (11-75) | 26 | G1792 | 2 comp. including P5288 (CUT1 prom.) | P6424 | 4600 | Darker green leaf color |
| G1795 | AP2 (11-75) | 26 | G1792 | 2 comp. including P5288 (CUT1 prom.) | P6424 | 4600 | Greater res. to *Sclerotinia* |
| G1795 | AP2 (11-75) | 26 | G1792 | 2 comp. including P5288 (CUT1 prom.) | P6424 | 4600 | Greater tol. to dehydration |
| G1795 | AP2 (11-75) | 26 | G1792 | 2 comp. including P5287 (LTP1 prom.) | P6424 | 4600 | More res. to *Botrytis* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1795 | AP2 (11-75) | 26 | G1792 | 2 comp. including P5287 (LTP1 prom.) | P6424 | 4600 | Greater res. to *Erysiphe* |
| G1795 | AP2 (11-75) | 26 | G1792 | 2 comp. including P5287 (LTP1 prom.) | P6424 | 4600 | Greater res. to *Sclerotinia* |
| G1795 | AP2 (11-75) | 26 | G1792 | 2 comp. including P5287 (LTP1 prom.) | P6424 | 4600 | Late flowering |
| G1795 | AP2 (11-75) | 26 | G1792 | 2 comp. including P5287 (LTP1 prom.) | P6424 | 4600 | Glossy leaves |
| G1795 | AP2 (11-75) | 26 | G1792 | 2 comp. including P5287 (LTP1 prom.) | P6424 | 4600 | Darker green leaf color |
| G1795 | AP2 (11-75) | 26 | G1792 | 2 comp. including P5287 (LTP1 prom.) | P6424 | 4600 | Early flowering |
| G1795 | AP2 (11-75) | 26 | G1792 | 2 comp. including P5284 (RBCS3 prom.) | P6424 | 4600 | More res. to *Botrytis* |
| G1795 | AP2 (11-75) | 26 | G1792 | 2 comp. including P5284 (RBCS3 prom.) | P6424 | 4600 | Greater res. to *Erysiphe* |
| G1795 | AP2 (11-75) | 26 | G1792 | 2 comp. including P5284 (RBCS3 prom.) | P6424 | 4600 | Greater res. to *Sclerotinia* |
| G1795 | AP2 (11-75) | 26 | G1792 | 2 comp. including P5284 (RBCS3 prom.) | P6424 | 4600 | Late flowering |
| G1795 | AP2 (11-75) | 26 | G1792 | 2 comp. including P5284 (RBCS3 prom.) | P6424 | 4600 | Glossy leaves |
| G1795 | AP2 (11-75) | 26 | G1792 | 2 comp. including P5284 (RBCS3 prom.) | P6424 | 4600 | Darker green leaf color |
| G1795 | AP2 (11-75) | 26 | G1792 | 2 comp. including P5290 (SUC2 prom.) | P6424 | 4600 | Greater res. to *Sclerotinia* |
| G1795 | AP2 (11-75) | 26 | G1792 | 2 comp. including P5290 (SUC2 prom.) | P6424 | 4600 | Less sens. to ABA |
| G1795 | AP2 (11-75) | 26 | G1792 | 2 comp. including P5290 (SUC2 prom.) | P6424 | 4600 | Greater tol. to 300 mM mannitol |
| G1795 | AP2 (11-75) | 26 | G1792 | 2 comp. including P5290 (SUC2 prom.) | P6424 | 4600 | Greater tol. to dehydration |
| G1795 | AP2 (11-75) | 26 | G1792 | 2 comp. including P5290 (SUC2 prom.) | P6424 | 4600 | Better recovery from drought treatment* |
| G1795 | AP2 (11-75) | 26 | G1792 | 2 comp. including P5290 (SUC2 prom.) | P6424 | 4600 | Late flowering |
| G1795 | AP2 (11-75) | 26 | G1792 | 2 comp. including P5290 (SUC2 prom.) | P6424 | 4600 | Altered leaf shape |
| G1795 | AP2 (11-75) | 26 | G1792 | 2 comp. including P5290 (SUC2 prom.) | P6424 | 4600 | Glossy leaves |
| G1795 | AP2 (11-75) | 26 | G1792 | 2 comp. including P5290 (SUC2 prom.) | P6424 | 4600 | Darker green leaf color |
| G1795 | AP2 (11-75) | 26 | G1792 | 2 comp. including P5290 (SUC2 prom.) | P6424 | 4600 | Greater tol. to low nitrogen conditions |
| G1795 | AP2 (11-75) | 26 | G1792 | Direct disease-inducible prom. fusion | P26467 | 5003 | Altered C/N sensing: inc. tol. to low nitrogen conditions in C/N sensing assay |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1795 | AP2 (11-75) | 26 | G1792 | Direct disease-inducible prom. fusion | P26402 | 4973 | Greater res. to *Sclerotinia* and *Erysiphe* |
| G1795 | AP2 (11-75) | 26 | G1792 | Direct disease-inducible prom. fusion | P26396 | 4971 | Greater res. to *Erysiphe* |
| G1795 | AP2 (11-75) | 26 | G1792 | Direct disease-inducible prom. fusion | P26398 | 4972 | Greater res. to *Sclerotinia* and *Erysiphe* |
| G1795 | AP2 (11-75) | 26 | G1792 | Direct disease-inducible prom. fusion | P26404 | 4974 | Greater res. to *Sclerotinia* and *Erysiphe* |
| G1795 | AP2 (11-75) | 26 | G1792 | Direct disease-inducible prom. fusion | P26409 | 4978 | Greater res. to *Sclerotinia* |
| G1795 | AP2 (11-75) | 26 | G1792 | Direct disease-inducible prom. fusion | P26411 | 4980 | Greater res. to *Sclerotinia* and *Erysiphe* |
| G1795 | AP2 (11-75) | 26 | G1792 | Direct disease-inducible prom. fusion | P26407 | 4976 | Greater res. to *Sclerotinia* and *Erysiphe* |
| G1795 | AP2 (11-75) | 26 | G1792 | Direct disease-inducible prom. fusion | P26412 | 4981 | Greater res. to *Sclerotinia* and *Erysiphe* |
| G1795 | AP2 (11-75) | 26 | G1792 | Direct disease-inducible prom. fusion | P26410 | 4979 | Greater res. to *Sclerotinia* and *Erysiphe* |
| G1795 | AP2 (11-75) | 26 | G1792 | Direct disease-inducible prom. fusion | P26406 | 4975 | Greater res. to *Sclerotinia* and *Erysiphe* |
| G1795 | AP2 (11-75) | 26 | G1792 | Direct disease-inducible prom. fusion | P26408 | 4977 | Greater res. to *Sclerotinia* and *Erysiphe* |
| G1795 | AP2 (11-75) | 26 | G1792 | Direct disease-inducible prom. fusion | P26447 | 4986 | Greater res. to *Sclerotinia* and *Erysiphe* |
| G1795 | AP2 (11-75) | 26 | G1792 | Direct disease-inducible prom. fusion | P26448 | 4987 | Greater res. to *Sclerotinia* and *Erysiphe* |
| G1795 | AP2 (11-75) | 26 | G1792 | Direct disease-inducible prom. fusion | P26460 | 4997 | Greater res. to *Sclerotinia* and *Erysiphe* |
| G1795 | AP2 (11-75) | 26 | G1792 | Direct disease-inducible prom. fusion | P26472 | 5008 | Greater res. to *Sclerotinia* and *Erysiphe* |
| G1795 | AP2 (11-75) | 26 | G1792 | Direct disease-inducible prom. fusion | P26462 | 4999 | Greater res. to *Erysiphe* |
| G1795 | AP2 (11-75) | 26 | G1792 | Direct disease-inducible prom. fusion | P26463 | 5000 | Greater res. to *Sclerotinia* and *Erysiphe* |
| G1795 | AP2 (11-75) | 26 | G1792 | Direct disease-inducible prom. fusion | P26465 | 5001 | Greater res. to *Sclerotinia* and *Erysiphe* |
| G1795 | AP2 (11-75) | 26 | G1792 | Direct disease-inducible prom. fusion | P26466 | 5002 | Greater res. to *Sclerotinia* and *Erysiphe* |
| G1795 | AP2 (11-75) | 26 | G1792 | Direct disease-inducible prom. fusion | P26467 | 5003 | Greater res. to *Sclerotinia* and *Erysiphe* |
| G1795 | AP2 (11-75) | 26 | G1792 | Direct disease-inducible prom. fusion | P26468 | 5004 | Greater res. to *Sclerotinia* and *Erysiphe* |
| G1795 | AP2 (11-75) | 26 | G1792 | Direct disease-inducible prom. fusion | P26469 | 5005 | Greater res. to *Sclerotinia* and *Erysiphe* |
| G1795 | AP2 (11-75) | 26 | G1792 | Direct disease-inducible prom. fusion | P26470 | 5006 | Greater res. to *Sclerotinia* and *Erysiphe* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1795 | AP2 (11-75) | 26 | G1792 | Direct disease-inducible prom. fusion | P26471 | 5007 | Greater res. to *Sclerotinia* and *Erysiphe* |
| G1795 | AP2 (11-75) | 26 | G1792 | Direct disease-inducible prom. fusion | P26582 | 5024 | Greater res. to *Sclerotinia* and *Erysiphe* |
| G1795 | AP2 (11-75) | 26 | G1792 | Direct disease-inducible prom. fusion | P26579 | 5022 | Greater res. to *Sclerotinia* and *Erysiphe* |
| G1795 | AP2 (11-75) | 26 | G1792 | Direct disease-inducible prom. fusion | P26477 | 5011 | Greater res. to *Sclerotinia* and *Erysiphe* |
| G1795 | AP2 (11-75) | 26 | G1792 | Direct disease-inducible prom. fusion | P26479 | 5012 | Greater res. to *Sclerotinia* and *Erysiphe* |
| G1795 | AP2 (11-75) | 26 | G1792 | Direct disease-inducible prom. fusion | P26481 | 5013 | Greater res. to *Sclerotinia* and *Erysiphe* |
| G1795 | AP2 (11-75) | 26 | G1792 | Direct disease-inducible prom. fusion | P26442 | 4982 | Greater res. to *Sclerotinia* and *Erysiphe* |
| G1795 | AP2 (11-75) | 26 | G1792 | Direct disease-inducible prom. fusion | P26443 | 4983 | Greater res. to *Sclerotinia* and *Erysiphe* |
| G1795 | AP2 (11-75) | 26 | G1792 | Direct disease-inducible prom. fusion | P26445 | 4984 | Greater res. to *Sclerotinia* and *Erysiphe* |
| G1795 | AP2 (11-75) | 26 | G1792 | Direct disease-inducible prom. fusion | P26580 | 5023 | Greater res. to *Sclerotinia* and *Erysiphe* |
| G1795 | AP2 (11-75) | 26 | G1792 | Direct disease-inducible prom. fusion | P26446 | 4985 | Greater res. to *Sclerotinia* and *Erysiphe* |
| G1795 | AP2 (11-75) | 26 | G1792 | Direct disease-inducible prom. fusion | P26449 | 4988 | Greater res. to *Sclerotinia* and *Erysiphe* |
| G1795 | AP2 (11-75) | 26 | G1792 | Direct disease-inducible prom. fusion | P26450 | 4989 | Greater res. to *Sclerotinia* and *Erysiphe* |
| G1795 | AP2 (11-75) | 26 | G1792 | Direct disease-inducible prom. fusion | P26452 | 4990 | Greater res. to *Sclerotinia* and *Erysiphe* |
| G1795 | AP2 (11-75) | 26 | G1792 | Direct disease-inducible prom. fusion | P26453 | 4991 | Greater res. to *Sclerotinia* and *Erysiphe* |
| G1795 | AP2 (11-75) | 26 | G1792 | Direct disease-inducible prom. fusion | P26454 | 4992 | Greater res. to *Sclerotinia* and *Erysiphe* |
| G1795 | AP2 (11-75) | 26 | G1792 | Direct disease-inducible prom. fusion | P26474 | 5009 | Greater res. to *Sclerotinia* |
| G1795 | AP2 (11-75) | 26 | G1792 | Direct disease-inducible prom. fusion | P26456 | 4993 | Greater res. to *Sclerotinia* and *Erysiphe* |
| G1795 | AP2 (11-75) | 26 | G1792 | Direct disease-inducible prom. fusion | P26457 | 4994 | Greater res. to *Sclerotinia* and *Erysiphe* |
| G1795 | AP2 (11-75) | 26 | G1792 | Direct disease-inducible prom. fusion | P26458 | 4995 | Greater res. to *Sclerotinia* and *Erysiphe* |
| G1795 | AP2 (11-75) | 26 | G1792 | Direct disease-inducible prom. fusion | P26708 | 5047 | Greater res. to *Sclerotinia* and *Erysiphe* |
| G1795 | AP2 (11-75) | 26 | G1792 | Direct disease-inducible prom. fusion | P26459 | 4996 | Greater res. to *Sclerotinia* and *Erysiphe* |
| G1795 | AP2 (11-75) | 26 | G1792 | Direct disease-inducible prom. fusion | P26461 | 4998 | Greater res. to *Sclerotinia* and *Erysiphe* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1795 | AP2 (11-75) | 26 | G1792 | Direct disease-inducible prom. fusion | P26707 | 5046 | Greater res. to *Sclerotinia* and *Erysiphe* |
| G1795 | AP2 (11-75) | 26 | G1792 | Direct disease-inducible prom. fusion | P26476 | 5010 | Greater res. to *Sclerotinia* and *Erysiphe* |
| G1795 | AP2 (11-75) | 26 | G1792 | Glucocorticoid receptor (GR) fusion (dexamethasone-inducible), 35S prom. (w/P5486) | P6424 | 4600 | More res. to *Botrytis* |
| G1795 | AP2 (11-75) | 26 | G1792 | Glucocorticoid receptor (GR) fusion (dexamethasone-inducible), 35S prom. (w/P5486) | P6424 | 4600 | Greater res. to *Sclerotinia* |
| G30 | AP2 (16-80) | 66 | G1792 | Const. 35S prom. | P893 | 3993 | Glossy darker green leaves |
| G30 | AP2 (16-80) | 66 | G1792 | Const. 35S prom. | P893 | 3993 | Altered light response; greater shade tol.; lack of shade avoidance phenotype; long cotyledon petioles and hypocotyls |
| G30 | AP2 (16-80) | 66 | G1792 | 2 comp. including P5318 (STM prom.) | P3852 | 4531 | Late flowering |
| G30 | AP2 (16-80) | 66 | G1792 | 2 comp. including P5318 (STM prom.) | P3852 | 4531 | Glossy leaves |
| G30 | AP2 (16-80) | 66 | G1792 | 2 comp. including P5318 (STM prom.) | P3852 | 4531 | Darker green leaf color |
| G30 | AP2 (16-80) | 66 | G1792 | 2 comp. including P5319 (AS1 prom.) | P3852 | 4531 | Greater res. to *Erysiphe* |
| G30 | AP2 (16-80) | 66 | G1792 | 2 comp. including P5319 (AS1 prom.) | P3852 | 4531 | Leaf orientation |
| G30 | AP2 (16-80) | 66 | G1792 | 2 comp. including P5319 (AS1 prom.) | P3852 | 4531 | Greater res. to *Sclerotinia* |
| G30 | AP2 (16-80) | 66 | G1792 | 2 comp. including P5319 (AS1 prom.) | P3852 | 4531 | Late flowering |
| G30 | AP2 (16-80) | 66 | G1792 | 2 comp. including P5319 (AS1 prom.) | P3852 | 4531 | Darker green leaf color |
| G30 | AP2 (16-80) | 66 | G1792 | 2 comp. including P5288 (CUT1 prom.) | P3852 | 4531 | Greater tol. to cold (8 C.) |
| G30 | AP2 (16-80) | 66 | G1792 | 2 comp. including P5288 (CUT1 prom.) | P3852 | 4531 | Late flowering |
| G30 | AP2 (16-80) | 66 | G1792 | 2 comp. including P5288 (CUT1 prom.) | P3852 | 4531 | Darker green leaf color |
| G30 | AP2 (16-80) | 66 | G1792 | 2 comp. including P5288 (CUT1 prom.) | P3852 | 4531 | Leaf orientation |
| G30 | AP2 (16-80) | 66 | G1792 | 2 comp. including P5287 (LTP1 prom.) | P3852 | 4531 | Greater tol. to cold (8 C.) |
| G30 | AP2 (16-80) | 66 | G1792 | 2 comp. including P5287 (LTP1 prom.) | P3852 | 4531 | Late flowering |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G30 | AP2 (16-80) | 66 | G1792 | 2 comp. including P5287 (LTP1 prom.) | P3852 | 4531 | Darker green leaf color |
| G30 | AP2 (16-80) | 66 | G1792 | 2 comp. including P5287 (LTP1 prom.) | P3852 | 4531 | Greater tol. to low nitrogen conditions |
| G30 | AP2 (16-80) | 66 | G1792 | 2 comp. including P5284 (RBCS3 prom.) | P3852 | 4531 | More res. to *Botrytis* |
| G30 | AP2 (16-80) | 66 | G1792 | 2 comp. including P5284 (RBCS3 prom.) | P3852 | 4531 | Greater res. to *Sclerotinia* |
| G30 | AP2 (16-80) | 66 | G1792 | 2 comp. including P5284 (RBCS3 prom.) | P3852 | 4531 | Late flowering |
| G30 | AP2 (16-80) | 66 | G1792 | 2 comp. including P5284 (RBCS3 prom.) | P3852 | 4531 | Darker green leaf color |
| G30 | AP2 (16-80) | 66 | G1792 | 2 comp. including P9002 (RD29A prom.) | P3852 | 4531 | Greater tol. to NaCl (determined with 150 mM NaCl) |
| G30 | AP2 (16-80) | 66 | G1792 | 2 comp. including P9002 (RD29A prom.) | P3852 | 4531 | Late flowering |
| G30 | AP2 (16-80) | 66 | G1792 | 2 comp. including P9002 (RD29A prom.) | P3852 | 4531 | Less sens. to ABA |
| G30 | AP2 (16-80) | 66 | G1792 | 2 comp. including P9002 (RD29A prom.) | P3852 | 4531 | Glossy leaves |
| G30 | AP2 (16-80) | 66 | G1792 | 2 comp. including P9002 (RD29A prom.) | P3852 | 4531 | Darker green leaf color |
| G30 | AP2 (16-80) | 66 | G1792 | 2 comp. including P5310 (RSI prom.) | P3852 | 4531 | Greater tol. to cold (8 C.) |
| G30 | AP2 (16-80) | 66 | G1792 | 2 comp. including P5310 (RS1 prom.) | P3852 | 4531 | Darker green leaf color |
| G30 | AP2 (16-80) | 66 | G1792 | 2 comp. including P5290 (SUC2 prom.) | P3852 | 4531 | Greater tol. to cold (8 C.) |
| G30 | AP2 (16-80) | 66 | G1792 | 2 comp. including P5290 (SUC2 prom.) | P3852 | 4531 | Altered C/N sensing: greater tol. to low nitrogen conditions in C/N sensing assay |
| G30 | AP2 (16-80) | 66 | G1792 | 2 comp. including P5290 (SUC2 prom.) | P3852 | 4531 | Glossy leaves |
| G30 | AP2 (16-80) | 66 | G1792 | 2 comp. including P5290 (SUC2 prom.) | P3852 | 4531 | Greater tol. to 300 mM mannitol |
| G30 | AP2 (16-80) | 66 | G1792 | 2 comp. including P5290 (SUC2 prom.) | P3852 | 4531 | Greater tol. to dehydration |
| G30 | AP2 (16-80) | 66 | G1792 | 2 comp. including P5290 (SUC2 prom.) | P3852 | 4531 | Late flowering |
| G30 | AP2 (16-80) | 66 | G1792 | 2 comp. including P5290 (SUC2 prom.) | P3852 | 4531 | Darker green leaf color |
| G30 | AP2 (16-80) | 66 | G1792 | 2 comp. including P5290 (SUC2 prom.) | P3852 | 4531 | Greater tol. to low nitrogen conditions |
| G30 | AP2 (16-80) | 66 | G1792 | Knockout | not applicable | | C/N sensing: greater sens. |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G30 | AP2 (16-80) | 66 | G1792 | Glucocorticoid receptor (GR) fusion (dexamethasone-inducible), 35S prom. (w/P5486) | P3852 | 4531 | More res. to *Botrytis* |
| G30 | AP2 (16-80) | 66 | G1792 | Glucocorticoid receptor (GR) fusion (dexamethasone-inducible), 35S prom. | P25086 | 4849 | Greater res. to *Sclerotinia* |
| G30 | AP2 (16-80) | 66 | G1792 | Glucocorticoid receptor (GR) fusion (dexamethasone-inducible), 35S prom. (w/P5486) | P3852 | 4531 | Greater res. to *Sclerotinia* |
| G3518 | AP2 (13-77) | 1982 | G1792 | Const. 35S prom. | P21404 | 4809 | Greater tol. to cold (8 C.) |
| G3518 | AP2 (13-77) | 1982 | G1792 | Const. 35S prom. | P21404 | 4809 | More tol. to drought* and better recovery from drought treatment* |
| G3518 | AP2 (13-77) | 1982 | G1792 | Const. 35S prom. | P21404 | 4809 | Greater res. to *Erysiphe* |
| G3518 | AP2 (13-77) | 1982 | G1792 | Const. 35S prom. | P21404 | 4809 | Altered C/N sensing: greater tol. to low nitrogen conditions in C/N sensing assay |
| G3518 | AP2 (13-77) | 1982 | G1792 | Const. 35S prom. | P21404 | 4809 | Greater tol. to NaCl (determined with 150 mM NaCl) |
| G3518 | AP2 (13-77) | 1982 | G1792 | Const. 35S prom. | P21404 | 4809 | Greater sens, to heat (32 C.) |
| G3518 | AP2 (13-77) | 1982 | G1792 | Const. 35S prom. | P21404 | 4809 | Altered leaf shape |
| G3518 | AP2 (13-77) | 1982 | G1792 | Const. 35S prom. | P21404 | 4809 | Glossy leaves |
| G3518 | AP2 (13-77) | 1982 | G1792 | Const. 35S prom. | P21404 | 4809 | Darker green leaf color |
| G3519 | AP2 (13-77) | 1984 | G1792 | Const. 35S prom. | P21405 | 4810 | Greater res. to *Erysiphe* |
| G3519 | AP2 (13-77) | 1984 | G1792 | Const. 35S prom. | P21405 | 4810 | Late flowering |
| G3519 | AP2 (13-77) | 1984 | G1792 | Const. 35S prom. | P21405 | 4810 | Altered leaf shape |
| G3519 | AP2 (13-77) | 1984 | G1792 | Const. 35S prom. | P21405 | 4810 | Glossy leaves |
| G3519 | AP2 (13-77) | 1984 | G1792 | Const. 35S prom. | P21405 | 4810 | Darker green leaf color |
| G3520 | AP2 (14-78) | 1986 | G1792 | Const. 35S prom. | P21406 | 4811 | Greater res. to *Erysiphe* |
| G3520 | AP2 (14-78) | 1986 | G1792 | Const. 35S prom. | P21406 | 4811 | Altered C/N sensing: greater tol. to low nitrogen conditions in C/N sensing assay |
| G3520 | AP2 (14-78) | 1986 | G1792 | Const. 35S prom. | P21406 | 4811 | Greater res. to *Sclerotinia* |
| G3520 | AP2 (14-78) | 1986 | G1792 | Const. 35S prom. | P21406 | 4811 | Late flowering |
| G3520 | AP2 (14-78) | 1986 | G1792 | Const. 35S prom. | P21406 | 4811 | Altered leaf shape |
| G3520 | AP2 (14-78) | 1986 | G1792 | Const. 35S prom. | P21406 | 4811 | Glossy leaves |
| G3520 | AP2 (14-78) | 1986 | G1792 | Const. 35S prom. | P21406 | 4811 | Darker green leaf color |
| G3380 | AP2 (18-82) | 1846 | G1792 | Const. 35S prom. | P21460 | 4812 | More tol. to drought* and better recovery from drought treatment* |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3380 | AP2 (18-82) | 1846 | G1792 | Const. 35S prom. | P21460 | 4812 | Greater res. to *Erysiphe* |
| G3380 | AP2 (18-82) | 1846 | G1792 | Const. 35S prom. | P21460 | 4812 | Less sens. to ABA |
| G3380 | AP2 (18-82) | 1846 | G1792 | Const. 35S prom. | P21460 | 4812 | Greater tol. to 300 mM mannitol |
| G3380 | AP2 (18-82) | 1846 | G1792 | Const. 35S prom. | P21460 | 4812 | Greater tol. to cold (8 C.) |
| G3380 | AP2 (18-82) | 1846 | G1792 | Const. 35S prom. | P21460 | 4812 | Late flowering |
| G3381 | AP2 (14-78) | 1848 | G1792 | Const. 35S prom. | P21461 | 4813 | Greater tol. to cold (8 C.) |
| G3381 | AP2 (14-78) | 1848 | G1792 | Const. 35S prom. | P21461 | 4813 | Greater res. to *Erysiphe* |
| G3381 | AP2 (14-78) | 1848 | G1792 | Const. 35S prom. | P21461 | 4813 | Greater res. to *Sclerotinia* |
| G3381 | AP2 (14-78) | 1848 | G1792 | Const. 35S prom. | P21461 | 4813 | More tol. to drought* and better recovery from drought treatment* |
| G3381 | AP2 (14-78) | 1848 | G1792 | Const. 35S prom. | P21461 | 4813 | Late flowering |
| G3381 | AP2 (14-78) | 1848 | G1792 | Const. 35S prom. | P21461 | 4813 | Darker green leaf color |
| G3381 | AP2 (14-78) | 1848 | G1792 | Const. 35S prom. | P21461 | 4813 | Greater tol. to hyperosmotic stress; more tol. to 300 mM mannitol or to NaCl (determined with 150 mM NaCl) |
| G3383 | AP2 (9-73) | 1850 | G1792 | Const. 35S prom. | P23523 | 4844 | Greater tol. to cold (8 C.) |
| G3383 | AP2 (9-73) | 1850 | G1792 | Const. 35S prom. | P23523 | 4844 | Greater tol. to dehydration |
| G3383 | AP2 (9-73) | 1850 | G1792 | Const. 35S prom. | P23523 | 4844 | Greater tol. to 300 mM mannitol |
| G3515 | AP2 (11-75) | 1976 | G1792 | Const. 35S prom. | P21401 | 4806 | More tol. to drought* and better recovery from drought treatment* |
| G3515 | AP2 (11-75) | 1976 | G1792 | Const. 35S prom. | P21401 | 4806 | More root hair |
| G3515 | AP2 (11-75) | 1976 | G1792 | Const. 35S prom. | P21401 | 4806 | More root mass |
| G3737 | AP2 (8-72) | 2104 | G1792 | Const. 35S prom. | P25089 | 4850 | Greater tol. to cold (8 C.) |
| G3737 | AP2 (8-72) | 2104 | G1792 | Const. 35S prom. | P25089 | 4850 | More tol. to drought* and better recovery from drought treatment* |
| G3737 | AP2 (8-72) | 2104 | G1792 | Const. 35S prom. | P25089 | 4850 | Less sens. to ABA |
| G3737 | AP2 (8-72) | 2104 | G1792 | Const. 35S prom. | P25089 | 4850 | Greater tol. to dehydration |
| G3737 | AP2 (8-72) | 2104 | G1792 | Const. 35S prom. | P25089 | 4850 | Greater tol. to NaCl (determined with 150 mM NaCl) |
| G3737 | AP2 (8-72) | 2104 | G1792 | Const. 35S prom. | P25089 | 4850 | Inflorescence: decreased apical dominance |
| G3737 | AP2 (8-72) | 2104 | G1792 | Const. 35S prom. | P25089 | 4850 | Greater res. to *Erysiphe* |
| G3737 | AP2 (8-72) | 2104 | G1792 | Const. 35S prom. | P25089 | 4850 | Late flowering |
| G3737 | AP2 (8-72) | 2104 | G1792 | Const. 35S prom. | P25089 | 4850 | Altered leaf shape |
| G3737 | AP2 (8-72) | 2104 | G1792 | Const. 35S prom. | P25089 | 4850 | Darker green leaf color |
| G3737 | AP2 (8-72) | 2104 | G1792 | Const. 35S prom. | P25089 | 4850 | Glossy leaves |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G3516 | AP2 (6-70) | 1978 | G1792 | Const. 35S prom. | P21402 | 4807 | Greater tol. to cold (8 C.) |
| G3516 | AP2 (6-70) | 1978 | G1792 | Const. 35S prom. | P21402 | 4807 | Altered C/N sensing: greater tol. to low nitrogen conditions in C/N sensing assay |
| G3517 | AP2 (13-77) | 1980 | G1792 | Const. 35S prom. | P21403 | 4808 | Greater res. to *Erysiphe* |
| G3517 | AP2 (13-77) | 1980 | G1792 | Const. 35S prom. | P21403 | 4808 | More res. to *Botrytis* |
| G3517 | AP2 (13-77) | 1980 | G1792 | Const. 35S prom. | P21403 | 4808 | Greater tol. to cold (8 C.) |
| G3517 | AP2 (13-77) | 1980 | G1792 | Const. 35S prom. | P21403 | 4808 | Greater tol. to heat (32 C.) |
| G3739 | AP2 (13-77) | 2106 | G1792 | Const. 35S prom. | P25090 | 4851 | Greater res. to *Erysiphe* |
| G3739 | AP2 (13-77) | 2106 | G1792 | Const. 35S prom. | P25090 | 4851 | Greater tol. to 300 mM mannitol |
| G3739 | AP2 (13-77) | 2106 | G1792 | Const. 35S prom. | P25090 | 4851 | Greater tol. to cold (8 C.) |
| G3739 | AP2 (13-77) | 2106 | G1792 | Const. 35S prom. | P25090 | 4851 | Greater tol. to dehydration |
| G3739 | AP2 (13-77) | 2106 | G1792 | Const. 35S prom. | P25090 | 4851 | Less sens. to ABA |
| G3739 | AP2 (13-77) | 2106 | G1792 | Const. 35S prom. | P25090 | 4851 | Altered inflorescence: decreased apical dominance |
| G3739 | AP2 (13-77) | 2106 | G1792 | Const. 35S prom. | P25090 | 4851 | Late flowering |
| G3739 | AP2 (13-77) | 2106 | G1792 | Const. 35S prom. | P25090 | 4851 | Altered leaf shape |
| G3739 | AP2 (13-77) | 2106 | G1792 | Const. 35S prom. | P25090 | 4851 | Glossy leaves |
| G3739 | AP2 (13-77) | 2106 | G1792 | Const. 35S prom. | P25090 | 4851 | Darker green leaf color |
| G3794 | AP2 (6-70) | 2132 | G1792 | Const. 35S prom. | P25092 | 4852 | Greater tol. to cold (8 C.) |
| G3794 | AP2 (6-70) | 2132 | G1792 | Const. 35S prom. | P25092 | 4852 | Greater tol. to dehydration |
| G3794 | AP2 (6-70) | 2132 | G1792 | Const. 35S prom. | P25092 | 4852 | Altered leaf shape |
| G1988 | Z—CO-like (5-50) | 30 | G1988 | Const. 35S prom. | P2499 | 4407 | Altered sugar sensing; greater tol. to sucrose (determined in 9.4% sucrose) |
| G1988 | Z—CO-like (5-50) | 30 | G1988 | Const. 35S prom. | P2499 | 4407 | Greater tol. to dehydration |
| G1988 | Z—CO-like (5-50) | 30 | G1988 | Const. 35S prom. | P2499 | 4407 | Better recovery from drought treatment* |
| G1988 | Z—CO-like (5-50) | 30 | G1988 | Const. 35S prom. | P2499 | 4407 | Late developing |
| G1988 | Z—CO-like (5-50) | 30 | G1988 | Const. 35S prom. | P2499 | 4407 | More root mass |
| G1988 | Z—CO-like (5-50) | 30 | G1988 | Const. 35S prom. | P2499 | 4407 | Altered light response; greater shade tol.; lack of shade avoidance phenotype; altered leaf orientation; upright leaves, longer hypocotyls, elongated petioles |
| G1988 | Z—CO-like (5-50) | 30 | G1988 | Const. 35S prom. | P2499 | 4407 | Altered C/N sensing: greater tol. to low nitrogen conditions in C/N sensing assay |
| G1988 | Z—CO-like (5-50) | 30 | G1988 | Const. 35S prom. | P2499 | 4407 | Greater tol. to cold (8 C.) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1988 | Z—CO-like (5-50) | 30 | G1988 | Const. 35S prom. | P2499 | 4407 | Improved yield |
| G4004 | Z—CO-like (6-51) | 2252 | G1988 | Const. 35S prom. | P26748 | 5050 | Greater tol. to cold (8 C.) |
| G4004 | Z—CO-like (6-51) | 2252 | G1988 | Const. 35S prom. | P26748 | 5050 | Long petiole |
| G4004 | Z—CO-like (6-51) | 2252 | G1988 | Const. 35S prom. | P26748 | 5050 | Altered light response; greater shade tol.; lack of shade avoidance phenotype; altered leaf orientation; upright leaves, longer hypocotyls, elongated and upright petioles |
| G4004 | Z—CO-like (6-51) | 2252 | G1988 | Const. 35S prom. | P26748 | 5050 | Altered C/N sensing: greater tol. to low nitrogen conditions in C/N sensing assay |
| G4004 | Z—CO-like (6-51) | 2252 | G1988 | Const. 35S prom. | P26748 | 5050 | Long hypocotyls |
| G4004 | Z—CO-like (6-51) | 2252 | G1988 | Const. 35S prom. | P26748 | 5050 | Late developing |
| G4005 | Z—CO-like (6-51) | 2254 | G1988 | Const. 35S prom. | P26749 | 5051 | Long petiole |
| G4005 | Z—CO-like (6-51) | 2254 | G1988 | Const. 35S prom. | P26749 | 5051 | Altered light response; greater shade tol.; lack of shade avoidance phenotype; altered leaf orientation; upright leaves, light green, elongated and upright petioles |
| G4005 | Z—CO-like (6-51) | 2254 | G1988 | Const. 35S prom. | P26749 | 5051 | Late developing |
| G4005 | Z—CO-like (6-51) | 2254 | G1988 | Const. 35S prom. | P26749 | 5051 | Altered C/N sensing: greater tol. to low nitrogen conditions in C/N sensing assay |
| G4005 | Z—CO-like (6-51) | 2254 | G1988 | Const. 35S prom. | P26749 | 5051 | Some lines have decreased tol. to cold (8 C.), but more lines are more tol to cold (8 C.) |
| G4005 | Z—CO-like (6-51) | 2254 | G1988 | Const. 35S prom. | P26749 | 5051 | Altered sugar sensing; some lines have decreased tol. to 9.4% sucrose, but more lines are more tol to 9.4% sucrose |
| G4007 | Z—CO-like (5-50) | 2256 | G1988 | — | — | — | n/d |
| G4011 | Z—CO-like (8-49) | 2260 | G1988 | Const. 35S prom | P27405 | 5084 | Altered sugar sensing; greater tol. to sucrose (determined in 9.4% sucrose) |
| G4011 | Z—CO-like (8-49) | 2260 | G1988 | Const. 35S prom | P27405 | 5084 | More tol. to cold (8 C.) |
| G4011 | Z—CO-like (8-49) | 2260 | G1988 | Const. 35S prom | P27405 | 5084 | Altered C/N sensing: greater tol. to low nitrogen conditions in C/N sensing assay |
| G4012 | Z—CO-like (15-56) | 2262 | G1988 | Const. 35S prom | P27406 | 5085 | Altered light response; greater shade tol.; lack of shade avoidance phenotype; altered leaf orientation; |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| | | | | | | | upright leaves, longer hypocotyls, elongated and upright petioles |
| G4012 | Z—CO-like (15-56) | 2262 | G1988 | Const. 35S prom | P27406 | 5085 | Late flowering |
| G4012 | Z—CO-like (15-56) | 2262 | G1988 | Const. 35S prom | P27406 | 5085 | Altered sugar sensing; greater tol. to sucrose (determined in 9.4% sucrose) |
| G4012 | Z—CO-like (15-56) | 2262 | G1988 | Const. 35S prom | P27406 | 5085 | More tol. to cold (8 C.) |
| G4012 | Z—CO-like (15-56) | 2262 | G1988 | Const. 35S prom | P27406 | 5085 | Altered C/N sensing: greater tol. to low nitrogen conditions in C/N sensing assay |
| G4298 | Z—CO-like (15-56) | 2350 | G1988 | — | — | | n/d |
| G4009 | Z—CO-like (6-51) | 2258 | G1988 | — | — | | n/d |
| G4299 | Z—CO-like (9-54) | 2352 | G1988 | Const. 35S prom. | P27428 | 5086 | Long petiole |
| G4299 | Z—CO-like (9-54) | 2352 | G1988 | Const. 35S prom. | P27428 | 5086 | Long hypocotyls |
| G4299 | Z—CO-like (9-54) | 2352 | G1988 | Const. 35S prom. | P27428 | 5086 | Altered light response; greater shade tol.; lack of shade avoidance phenotype; altered leaf orientation; upright pale leaves, longer hypocotyls |
| G4299 | Z—CO-like (9-54) | 2352 | G1988 | Const. 35S prom. | P27428 | 5086 | Late developing |
| G4299 | Z—CO-like (9-54) | 2352 | G1988 | Const. 35S prom. | P27428 | 5086 | Altered sugar sensing; greater tol. to sucrose (determined in 9.4% sucrose) |
| G4299 | Z—CO-like (9-54) | 2352 | G1988 | Const. 35S prom. | P27428 | 5086 | More tol. to cold (8 C.) |
| G4299 | Z—CO-like (9-54) | 2352 | G1988 | Const. 35S prom. | P27428 | 5086 | Altered C/N sensing: greater tol. to low nitrogen conditions in C/N sensing assay |
| G4000 | Z—CO-like (20-61) | 2250 | G1988 | Const. 35S prom. | P27404 | 5083 | Altered light response; greater shade tol.; lack of shade avoidance phenotype; altered leaf orientation; narrow upright leaves, longer hypocotyls |
| G4000 | Z—CO-like (20-61) | 2250 | G1988 | Const. 35S prom. | P27404 | 5083 | Late developing |
| G903 | Z-C2H2 (68-92) | 670 | | Const. 35S prom. | P138 | 3840 | Altered leaf morphology; narrow twisted leaves |
| G4000 | Z—CO-like (20-61) | 2250 | G1988 | Const. 35S prom. | P27404 | 5083 | Some lines more sens. to cold (8 C.) |
| G4000 | Z—CO-like (20-61) | 2250 | G1988 | Const. 35S prom. | P27404 | 5083 | Altered sugar sensing; greater tol. to sucrose (determined in 9.4% sucrose) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G4000 | Z—CO-like (20-61) | 2250 | G1988 | Const. 35S prom. | P27404 | 5083 | Altered C/N sensing: greater tol. to low nitrogen conditions in C/N sensing assay |
| G4297 | Z—CO-like (14-55) | 2348 | G1988 | — | — | — | n/d |
| G142 | MADS (2-57) | 98 | G142 | Const. 35S prom. | P2109 | 4352 | Early flowering |
| G148 | MADS (1-57) | 106 | G142 | Const. 35S prom. | P13734 | 4636 | Early flowering |
| G154 | MADS (2-57) | 114 | G154 | Const. 35S prom. | P1223 | 4070 | Altered C/N sensing: greater tol. to low nitrogen conditions in C/N sensing assay |
| G154 | MADS (2-57) | 114 | G154 | Const. 35S prom. | — | — | Early flowering |
| G154 | MADS (2-57) | 114 | G154 | SUC2 | — | — | Early flowering |
| G1011 | MADS (2-57) | | G154 | Const. 35S prom. | — | — | Reduced petal abscission, early flowering, decreased biomass |
| G627 | MADS (2-57) | | G154 | Const. 35S prom. | — | — | Early flowering |
| G1797 | MADS (2-57) | | G154 | Const. 35S prom. | — | — | Reduced petal abscission |
| G1797 | MADS (2-57) | | G154 | RBCS3 | — | — | Increased Brix, increased lycopene |
| G1798 | MADS (2-57) | | G154 | Const. 35S prom. | — | — | Multiple inflorescence defects; increasd trichome density, darker leaf color, early flowering |
| G201 | MYB-(R1)R2R3 (14-114) | 172 | | Const. 35S prom. | P3 | 3793 | Higher seed protein content |
| G201 | MYB-(R1)R2R3 (14-114) | 172 | | Const. 35S prom. | P3 | 3793 | Decreased seed oil content |
| G202 | MYB-(R1)R2R3 (13-116) | 174 | | Const. 35S prom. | P4 | 3794 | Decreased seed oil content |
| G671 | MYB-(R1)R2R3 (15-115) | 538 | | Const. 35S prom. | P995 | 4025 | Altered inflorescence stem structure; bolts terminated in flowers or aborted flowers, secondary bolts replaced by leaf-like structures, bolts of small plants oddly shaped, changing direction slightly at each node |
| G671 | MYB-(R1)R2R3 (15-115) | 538 | | Const. 35S prom. | P995 | 4025 | Reduced petal abscission |
| G671 | MYB-(R1)R2R3 (15-115) | 538 | | Const. 35S prom. | P995 | 4025 | Altered leaf shape; true leaves curled under, petioles were upright, some plants had curled cotyledons |
| G671 | MYB-(R1)R2R3 (15-115) | 538 | | Const. 35S prom. | P995 | 4025 | Small plant |
| G671 | MYB-(R1)R2R3 (15-115) | 538 | | Const. 35S prom. | P995 | 4025 | Reduced fertility |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G201 | MYB-(R1)R2R3 (14-114) | 172 | | Const. 35S prom. | | | Increased Seed protein content; Decreased Seed oil content; |
| G243 | MYB-(R1)R2R3 | 18057 | | AP1 prom. | | | Increased Brix |
| G189 | WRKY (240-297) | 156 | | Const. 35S prom. | P970 | 4013 | Greater leaf size |
| G189 | WRKY (240-297) | 156 | | Const. 35S prom. | P970 | 4013 | Altered C/N sensing: greater tol. to low nitrogen conditions in C/N sensing assay |
| G287 | MISC (293-354) | 256 | | Const. 35S prom. | P13371 | 4614 | Inc. biomass; inc. rosette biomass at later stages of development |
| G748 | Z-Dof (112-140) | 580 | | Const. 35S prom. | P346 | 3902 | Altered seed prenyl lipids; more lutein content |
| G748 | Z-Dof (112-140) | 580 | | Const. 35S prom. | P346 | 3902 | Altered stem morphology; more vascular bundles in stem |
| G748 | Z-Dof (112-140) | 580 | | Const. 35S prom. | P346 | 3902 | Late flowering |
| G878 | WRKY (250-305, 415-475) | 656 | | Const. 35S prom. | P1345 | 4111 | Delayed senescence |
| G878 | WRKY (250-305, 415-475) | 656 | | Const. 35S prom. | P1345 | 4111 | Late flowering |
| G878 | WRKY (250-305, 415-475) | 656 | | Const. 35S prom. | P1345 | 4111 | Darker green |
| G878 | WRKY (250-305, 415-475) | 656 | | Const. 35S prom. | P1345 | 4111 | Shorter stems |
| G1730 | RING/C3H2C3 (103-144) | 1128 | | Const. 35S prom. | P15024 | 4660 | Inc. tol. to hyperosmotic stress; seedlings more tol. to 300 mM mannitol |
| G1730 | RING/C3H2C3 (103-144) | 1128 | | Const. 35S prom. | P15024 | 4660 | Altered sugar sensing; seedlings larger, greener and had higher germination efficiency in 5% glucose |
| G1730 | RING/C3H2C3 (103-144) | 1128 | | Const. 35S prom. | P15024 | 4660 | More tol. to drought* |
| G2142 | HLH/MYC (42-100) | 1406 | | Const. 35S prom. | P2444 | 4393 | More tolerant to phosphate deprivation in a root growth assay |
| G2142 | HLH/MYC (42-100) | 1406 | | Const. 35S prom. | P2444 | 4393 | Early flowering |
| G2379 | TH (19-110, 173-232) | 1492 | | Const. 35S prom. | P1951 | 4289 | Altered sugar sensing; greater tol. to sucrose (determined in 9.4% sucrose) |
| G2552 | HLH/MYC (124-181) | 1568 | | Const. 35S prom. | P2068 | 4338 | Increase leaf glucosinolate M39480 |
| G2724 | MYB-(R1)R2R3 (7-113) | 1660 | | Const. 35S prom. | P2014 | 4311 | Darker green leaves |
| G2933 | HLH/MYC (68-128) | 1754 | | Const. 35S prom. | P2392 | 4371 | Larger seeds |
| G2933 | HLH/MYC (68-128) | 1754 | | Const. 35S prom. | P2392 | 4371 | More tol. to cold (8 C.) |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G2936 | HLH/MYC (82-142) | | | RSI1 prom. | — | | Increased Lycopene |
| G2936 | HLH/MYC (82-142) | | | STM prom. | — | | Increased fruit weight |
| G2936 | HLH/MYC (82-142) | | | RBCS3 prom. | — | | Increased fruit weight |
| G1073 and G1274 | AT-hook (63-71, 71-216) and WRKY (110-166) | 18 and 20 | G1073 and G1274 | Double transcription factor overexpression; const. 35S prom. | P448, P15038 | 3936 and 4665 | Greater biomass, additive effect relative to either parent overexpressor line |
| G1073 and G3086 | AT-hook (63-71, 71-216) and HLH/MYC (307-365) | 18 and 1836 | G1073 and G3086 | Double transcription factor overexpression; const. 35S prom. | P448 and P15046 | 3936 and 4668 | Early flowering; G3086 OE overcomes delayed flowering associated with G1073 OE |
| G481 and G3086 | CAAT (20-109) and HLH/MYC (307-365) | 10 and 1836 | G481 and G3086 | Double transcription factor overexpression; const. 35S prom. | P46 and P15046 | 3811 and 4668 | Early flowering; G3086 OE overcomes delayed flowering associated with G481 OE |
| G481 and G1274 | CAAT (20-109) and WRKY (110-166) | 10 and 20 | G481 and G1274 | Double transcription factor overexpression; const. 35S prom. | P46 and P15038 | 3811 and 4665 | Greater seedling vigor; novel phenotype not typically seen in either single parental overexpressor line |
| G481 and, G1073 | CAAT (20-109) and AT-hook (63-71, 71-216) | 10 and 18 | G481 and, G1073 | Double transcription factor overexpression; const. 35S prom. | P46 and P448 | 3811 and 3936 | Late flowering was enhanced compared to either parental line |
| G481 and G1073 | CAAT (20-109) and AT-hook (63-71, 71-216) | 10 and 18 | G481 and G1073 | Double transcription factor overexpression; const. 35S prom. | P46 and P448 | 3811 and 3936 | Darker green leaves, additive phenotype compared to either parental overexpressor line |
| G481 and G867 | CAAT (20-109) and AP2 (59-124, 184-276) | 10 and 16 | G481 and G867 | Double transcription factor overexpression; const. 35S prom. | P46 and P26372 | 3811 and 4966 | Darker green leaves, additive phenotype compared to either parental overexpressor line |
| G28 and G1266 | AP2 (145-208) and AP2 (79-147) | 2 and 884 | G28 and G1266 | Double transcription factor overexpression; const. 35S prom. | P174 and P26385 | 3854 and 4969 | More res. to *Botrytis*; additive phenotype relative to either parental overexpressor line |
| G28 and G1266 | AP2 (145-208) and AP2 (79-147) | 2 and 884 | G28 and G1266 | Double transcription factor overexpression; const. 35S prom. | P174 and P26385 | 3854 and 4969 | Greater res. to *Fusarium*; new phenotype not previously observed in either parental overexpressor line |
| G28 and G1266 | AP2 (145-208) and AP2 (79-147) | 2 and 884 | G28 and G1266 | Double transcription factor overexpression; const. 35S prom. | P174 and P26385 | 3854 and 4969 | Greater res. to *Sclerotinia*; additive phenotype relative to either parental overexpressor line |
| G28 and G1919 | AP2 (145-208) and RING/C3HC4 (214-287) | 2 and 1268 | G28 and G1919 | Double transcription factor overexpression; const. 35S prom. | P174 and P26383 | 3854 and 4968 | Greater res. to *Fusarium*; new phenotype not previously observed in either parental overexpressor line |

TABLE 21-continued

Phenotypic traits conferred by transcription factors in morphological, physiological or disease assays

| GID | TF family (amino acid coordinates of characteristic conserved domain) | SEQ ID NO: of GID | Phylogenetic relationship; closely related to: | Expression system | Construct containing TF | SEQ ID NO: of Construct | Experimental observation (trait compared to controls) |
|---|---|---|---|---|---|---|---|
| G1073 and G1274 | AT-hook (63-71, 71-216) and WRKY (110-166) | 18 and 20 | G1073 and G1274 | Double transcription factor overexpression; const. 35S prom. | P448 and P15038 | 3936 and 4665 | Reduced apical dominance characteristic of G1274 OE lines, indicating that G1274 OE can overcome increased branching effects of G1073 OE |
| G47, G481 and, G1073 | AP2 (10-75), CAAT (20-109) and AT-hook (63-71, 71-216) | 6, 10, and 18 | G47, G481 and, G1073 | Double and triple transcription factor overexpression; const. 35S prom. | P26388, P46, and P448 | 4970, 3811, and 3936 | Water deficit (determined in a drought assay*) tol. was more marked than was typically obtained with any of the parental overexpressor lines |
| G481, G1073 and G3086 | CAAT (20-109), AT-hook (63-71, 71-216) and HLH/MYC (307-365) | 10, 18, and 1836 | G481, G1073 and G3086 | Triple transcription factor overexpression; const. 35S prom. | P46, P448, and P15046 | 3811, 3936, and 4668 | Greater tol. to water deficit (determined in a drought assay*); flowered at the same time as wild-type in contrast to late flowering in double G1073-G481 OEs; thus, G3086 OE mitigates delayed flowering or maturation associated with G481 and G1073 OE |

Abbreviations for Table 20

At: *Arabidopsis thaliana*; Bo: *Brassica oleracea*; Cs: Br: *Brassica rapa*; *Citrus sinensis*; Dc: *Daucus carota*; Gm: *Glycine max*; Os: *Oryza sativa*; Ga: *Gossypium arboreum*; Gh: *Gossypium hirsutum*; Gr: *Gossypium raimondii*; Mt: *Medicago truncatula*; Nb: *Nicotiana benthamiana*; Nt: *Nicotiana tabacum*; Pt: *Populus trichocarpa*; Sc: *Saccharomyces cerevisiae*; Sl: *Solanum lycopersicum*; So: *Saccharum officinarum*; St: *Solanum tuberosum*; Ta: *Triticum aestivum*; Vv: *Vitis vinifera*; Ze: *Zinnia elegans*; Zm: *Zea mays* ABA=abscisic acid; ACC=1-aminocyclopropane 1-carboxylic acid; OE=overexpress(ed), overexpression or overexpressor(s); inc.=increase(d); tol.=tolerance; res.=resistance; sens.=sensitive; const.=constitutive; prom.=promoter; 35S=cauliflower mosaic virus 35S promoter; PEG=polyethylene glycol

* drought tolerance determined in soil-based assays as opposed to plate-based drought or dehydration assays Note: * the sequence was introduced into in tomato. In this Example, unless otherwise indicted, morphological and physiological traits are disclosed in comparison to wild-type control plants. That is, a transformed plant that is described as large and/or drought tolerant is large and more tolerant to drought with respect to a wild-type control plant. When a plant is said to have a better performance than controls, it generally showed less stress symptoms than control plants. The better performing lines may, for example, produce less anthocyanin, or be larger, greener, or more vigorous in response to a particular stress, as noted below. Better performance generally implies greater tolerance to a particular biotic or abiotic stress, less sensitivity to ABA, or better recovery from a stress (as in the case of a drought treatment) than controls.

Example XIII. Transformation of Eudicots for Greater Biomass, Disease Resistance or Abiotic Stress Tolerance Crop species including tomato and soybean plants that overexpress any of a considerable number of the transcription factor polypeptides of the invention have been shown experimentally to produce plants with increased drought tolerance and/or biomass in field trials. For example, tomato plants overexpressing the G2153 polypeptide have been found to be larger than wild-type control tomato plants. For example, soy plants overexpressing a number of G481, G682, G867 and G1073, their orthologs or putative orthologs, and other sequences listed above have been shown to be more water deficit-tolerant than control plants. These observations indicate that these genes, when overexpressed, will result in larger yields than non-transformed plants in both stressed and non-stressed conditions.

Thus, transcription factor polynucleotide sequences listed in the Sequence Listing recombined into, for example, one of the expression vectors of the invention, or another suitable expression vector, may be transformed into a plant for the purpose of modifying plant traits for the purpose of improving yield and/or quality. The expression vector may contain a constitutive, tissue-specific or inducible promoter operably linked to the transcription factor polynucleotide. The cloning vector may be introduced into a variety of plants by means well known in the art such as, for example, direct DNA transfer or *Agrobacterium tumefaciens*-mediated transformation. It is now routine to produce transgenic plants using most eudicot plants (see Weissbach and Weissbach, (1989); Gelvin et al. (1990); Herrera-Estrella et al. (1983); Bevan (1984); and Klee (1985)). Methods for analysis of traits are routine in the art and examples are disclosed above.

Numerous protocols for the transformation of tomato and soy plants have been previously described, and are well known in the art. Gruber et al. (1993), and Glick and Thompson (1993) describe several expression vectors and culture methods that may be used for cell or tissue transformation and subsequent regeneration. For soybean transformation, methods are described by Miki et al. (1993); and U.S. Pat. No. 5,563,055, (Townsend and Thomas), issued Oct. 8, 1996.

There are a substantial number of alternatives to *Agrobacterium*-mediated transformation protocols, other methods for the purpose of transferring exogenous genes into soybeans or tomatoes. One such method is microprojectile-mediated transformation, in which DNA on the surface of microprojectile particles is driven into plant tissues with a biolistic device (see, for example, Sanford et al. (1987); Christou et al. (1992); Sanford (1993); Klein et al. (1987); U.S. Pat. No. 5,015,580 (Christou et al), issued May 14, 1991; and U.S. Pat. No. 5,322,783 (Tomes et al.), issued Jun. 21, 1994).

Alternatively, sonication methods (see, for example, Zhang et al. (1991)); direct uptake of DNA into protoplasts using $CaCl_2$ precipitation, polyvinyl alcohol or poly-L-ornithine (Hain et al. (1985); Draper et al. (1982)); liposome or spheroplast fusion (see, for example, Deshayes et al. (1985); Christou et al. (1987)); and electroporation of protoplasts and whole cells and tissues (see, for example, Donn et al. (1990); D'Halluin et al. (1992); and Spencer et al. (1994)) have been used to introduce foreign DNA and expression vectors into plants.

After a plant or plant cell is transformed (and the latter regenerated into a plant), the transformed plant may be crossed with itself or a plant from the same line, a non-transformed or wild-type plant, or another transformed plant from a different transgenic line of plants. Crossing provides the advantages of producing new and often stable transgenic varieties. Genes and the traits they confer that have been introduced into a tomato or soybean line may be moved into distinct line of plants using traditional backcrossing techniques well known in the art. Transformation of tomato plants may be conducted using the protocols of Koornneef et al (1986), and in U.S. Pat. No. 6,613,962, the latter method described in brief here. Eight day old cotyledon explants are precultured for 24 hours in Petri dishes containing a feeder layer of *Petunia hybrida* suspension cells plated on MS medium with 2% (w/v) sucrose and 0.8% agar supplemented with 10 µM □-naphthalene acetic acid and 4.4 µM 6-benzylaminopurine. The explants are then infected with a diluted overnight culture of *Agrobacterium tumefaciens* containing an expression vector comprising a polynucleotide of the invention for 5-10 minutes, blotted dry on sterile filter paper and cocultured for 48 hours on the original feeder layer plates. Culture conditions are as described above. Overnight cultures of *Agrobacterium tumefaciens* are diluted in liquid MS medium with 2% (w/v/) sucrose, pH 5.7) to an $OD_{600}$ of 0.8.

Following cocultivation, the cotyledon explants are transferred to Petri dishes with selective medium comprising MS medium with 4.56 µM zeatin, 67.3 µM vancomycin, 418.9 µM cefotaxime and 171.6 µM kanamycin sulfate, and cultured under the culture conditions described above. The explants are subcultured every three weeks onto fresh medium. Emerging shoots are dissected from the underlying callus and transferred to glass jars with selective medium without zeatin to form roots. The formation of roots in a kanamycin sulfate-containing medium is a positive indication of a successful transformation.

Transformation of soybean plants may be conducted using the methods found in, for example, U.S. Pat. No. 5,563,055 (Townsend et al., issued Oct. 8, 1996), described in brief here. In this method soybean seed is surface sterilized by exposure to chlorine gas evolved in a glass bell jar. Seeds are germinated by plating on ¹/₁₀ strength agar solidified medium without plant growth regulators and culturing at 28° C. with a 16 hour day length. After three or four days, seed may be prepared for cocultivation. The seedcoat is removed and the elongating radicle removed 3-4 mm below the cotyledons.

Overnight cultures of *Agrobacterium tumefaciens* harboring the expression vector comprising a polynucleotide of the invention are grown to log phase, pooled, and concentrated by centrifugation. Inoculations are conducted in batches such that each plate of seed is treated with a newly resuspended pellet of *Agrobacterium*. The pellets are resuspended in 20 ml inoculation medium. The inoculum is poured into a Petri dish containing prepared seed and the cotyledonary nodes are macerated with a surgical blade. After 30 minutes the explants are transferred to plates of the same medium that has been solidified. Explants are embedded with the adaxial side up and level with the surface of the medium and cultured at 22° C. for three days under white fluorescent light. These plants may then be regenerated according to methods well established in the art, such as by moving the explants after three days to a liquid counter-selection medium (see U.S. Pat. No. 5,563,055).

The explants may then be picked, embedded and cultured in solidified selection medium. After one month on selective media transformed tissue becomes visible as green sectors of regenerating tissue against a background of bleached, less healthy tissue. Explants with green sectors are transferred to an elongation medium. Culture is continued on this medium with transfers to fresh plates every two weeks. When shoots are 0.5 cm in length they may be excised at the base and placed in a rooting medium.

Example XIV: Transformation of Monocots for Greater Biomass, Disease Resistance or Abiotic Stress Tolerance Cereal plants such as, but not limited to, corn, wheat, rice, sorghum, barley, switchgrass or *Miscanthus* may be transformed with the present polynucleotide sequences, including monocot or eudicot-derived sequences such as those presented in the present Tables, cloned into a vector such as pGA643 and containing a kanamycin-resistance marker, and expressed constitutively under, for example, the CaMV 35S or COR15 promoters, or with tissue-specific or inducible promoters. The expression vectors may be one found in the Sequence Listing, or any other suitable expression vector may be similarly used. For example, pMEN020 may be modified to replace the NptII coding region with the BAR gene of *Streptomyces hygroscopicus* that confers resistance to phosphinothricin. The KpnI and BglII sites of the Bar gene are removed by site-directed mutagenesis with silent codon changes.

The cloning vector may be introduced into a variety of cereal plants by means well known in the art including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10^9$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from SPrime-3Prime Inc. (Boulder, Colo.).

It is also routine to use other methods to produce transgenic plants of most cereal crops (Vasil (1994)) such as corn, wheat, rice, sorghum (Cassas et al. (1993)), and barley (Wan and Lemeaux (1994)). DNA transfer methods such as the microprojectile method can be used for corn (Fromm et al. (1990); Gordon-Kamm et al. (1990); Ishida (1990)), wheat (Vasil et al. (1992); Vasil et al. (1993); Weeks et al. (1993)), and rice (Christou (1991); Hiei et al. (1994); Aldemita and Hodges (1996); and Hiei et al. (1997)). For most cereal plants, embryogenic cells derived from immature scutellum tissues are the preferred cellular targets for transformation (Hiei et al. (1997); Vasil (1994)). For transforming corn embryogenic cells derived from immature scutellar tissue using microprojectile bombardment, the A 188XB73 genotype is the preferred genotype (Fromm et al. (1990); Gordon-Kamm et al. (1990)). After microprojectile bombardment the tissues are selected on phosphinothricin to identify the transgenic embryogenic cells (Gordon-Kamm et al. (1990)). Transgenic plants are regenerated by standard corn regeneration techniques (Fromm et al. (1990); Gordon-Kamm et al. (1990)).

Example XV: Transcription Factor Expression and Analysis of Disease Resistance or Abiotic Stress Tolerance Northern blot analysis, RT-PCR or microarray analysis of the regenerated, transformed plants may be used to show expression of a transcription factor polypeptide or the invention and related genes that are capable of inducing disease resistance, abiotic stress tolerance, and/or larger size.

To verify the ability to confer stress resistance, mature plants overexpressing a transcription factor of the invention, or alternatively, seedling progeny of these plants, may be challenged by a stress such as a disease pathogen, drought, heat, cold, high salt, or desiccation. Alternatively, these plants may challenged in a hyperosmotic stress condition that may also measure altered sugar sensing, such as a high sugar condition. By comparing control plants (for example, wild type) and transgenic plants similarly treated, the transgenic plants may be shown to have greater tolerance to the particular stress.

After a eudicot plant, monocot plant or plant cell has been transformed (and the latter regenerated into a plant) and shown to have greater size or tolerance to abiotic stress, or produce greater yield relative to a control plant under the stress conditions, the transformed monocot plant may be crossed with itself or a plant from the same line, a non-transformed or wild-type monocot plant, or another transformed monocot plant from a different transgenic line of plants.

These experiments would demonstrate that transcription factor polypeptides of the invention can be identified and shown to confer larger size, greater yield, greater disease resistance and/or abiotic stress tolerance in eudicots or monocots, including tolerance or resistance to multiple stresses.

Example XVI: Sequences that Confer Significant Improvements to Non-*Arabidopsis* Species The function of specific transcription factors of the invention, including closely-related orthologs, have been analyzed and may be further characterized and incorporated into crop plants. The ectopic overexpression of these sequences may be regulated using constitutive, inducible, or tissue specific regulatory elements. Genes that have been examined and have been shown to modify plant traits (including increasing biomass, disease resistance and/or abiotic stress tolerance) encode transcription factor polypeptides found in the Sequence Listing. In addition to these sequences, it is expected that newly discovered polynucleotide and polypeptide sequences closely related to polynucleotide and polypeptide sequences found in the Sequence Listing can also confer alteration of traits in a similar manner to the sequences found in the Sequence Listing, when transformed into a any of a considerable variety of plants of different species, and including eudicots and monocots. The polynucleotide and polypeptide sequences derived from monocots (e.g., the rice sequences) may be used to transform both monocot and eudicot plants, and those derived from eudicots (e.g., the *Arabidopsis* and soy genes) may be used to transform either group, although it is expected that some of these sequences will function best if the gene is transformed into a plant from the same group as that from which the sequence is derived.

As an example of a first step to determine drought-related tolerance, seeds of these transgenic plants are subjected to germination assays to measure sucrose sensing. Sterile monocot seeds, including, but not limited to, corn, rice, wheat, rye and sorghum, as well as eudicots including, but not limited to soybean and alfalfa, are sown on 80% MS medium plus vitamins with 9.4% sucrose; control media lack sucrose. All assay plates are then incubated at 22° C. under 24-hour light, 120-130 µEin/m$^2$/s, in a growth chamber. Evaluation of germination and seedling vigor is then conducted three days after planting. Plants overexpressing sequences of the invention may be found to be more tolerant to high sucrose by having better germination, longer radicles, and more cotyledon expansion. These methods have been used to show that overexpressors of numerous sequences of the invention are involved in sucrose-specific sugar sensing. It is expected that structurally similar orthologs of these sequences, including those found in the Sequence Listing, are also involved in sugar sensing, an indication of altered osmotic stress tolerance.

Plants overexpressing the transcription factor sequences of the invention may also be subjected to soil-based drought assays to identify those lines that are more tolerant to water deprivation than wild-type control plants. A number of the lines of plants overexpressing transcription factor polypeptides of the invention, including newly discovered closely-related species, will be significantly larger and greener, with less wilting or desiccation, than wild-type control plants, particularly after a period of water deprivation is followed by rewatering and a subsequent incubation period. The sequence of the transcription factor may be overexpressed under the regulatory control of constitutive, tissue specific or inducible promoters, or may comprise a GAL4 transactivation domain fused to either the N- or the C terminus of the polypeptide. The results presented in Examples above indicate that these transcription factors may confer disease resistance or abiotic stress tolerance when they are overexpressed under the regulatory control of non-constitutive promoters or a transactivation domain fused to the clade member, without having a significant adverse impact on plant morphology and/or development. The lines that display useful traits may be selected for further study or commercial development.

Monocotyledonous plants, including rice, corn, wheat, rye, sorghum, barley and others, may be transformed with a plasmid containing a transcription factor polynucleotide. The transcription factor gene sequence may include eudicot or monocot-derived sequences such as those presented herein. These transcription factor genes may be cloned into an expression vector containing a kanamycin-resistance marker, and then expressed constitutively or in a tissue-specific or inducible manner.

The cloning vector may be introduced into monocots by, for example, means described in the previous Example, including direct DNA transfer or *Agrobacterium tumefaciens*-mediated transformation. The latter approach may be accomplished by a variety of means, including, for example, that of U.S. Pat. No. 5,591,616, in which monocotyledon callus is transformed by contacting dedifferentiating tissue with the *Agrobacterium* containing the cloning vector.

The sample tissues are immersed in a suspension of $3 \times 10^{-9}$ cells of *Agrobacterium* containing the cloning vector for 3-10 minutes. The callus material is cultured on solid medium at 25° C. in the dark for several days. The calli grown on this medium are transferred to Regeneration medium. Transfers are continued every 2-3 weeks (2 or 3 times) until shoots develop. Shoots are then transferred to Shoot-Elongation medium every 2-3 weeks. Healthy looking shoots are transferred to rooting medium and after roots have developed, the plants are placed into moist potting soil.

The transformed plants are then analyzed for the presence of the NPTII gene/kanamycin resistance by ELISA, using the ELISA NPTII kit from SPrime-3Prime Inc. (Boulder, Colo.).

Northern blot analysis, RT-PCR or microarray analysis of the regenerated, transformed plants may be used to show expression of a transcription factor polypeptide of the invention that is capable of conferring abiotic stress tolerance, disease resistance, or increased size or yield, in the transformed plants.

To verify the ability to confer abiotic stress tolerance, mature plants or seedling progeny of these plants expressing a monocot-derived equivalog gene may be challenged using methods described in the above Examples. By comparing wild type plants and the transgenic plants, the latter are shown be more tolerant to abiotic stress, more resistant to disease, and/or have greater biomass, as compared to wild type control plants similarly treated.

It is expected that the same methods may be applied to identify other useful and valuable sequences of the present transcription factor clades, and the sequences may be derived from a diverse range of species.

REFERENCES CITED

Abe et al. (1997) *Plant Cell* 9: 1859-1868
Abe et al. (2003) *Plant Cell* 15: 63-78
Affolter et al. (1990) *Curr. Opin. Cell. Biol.* 2: 485-495
Agrios, G. N. (1997) *Plant Pathology.* 4$^{th}$ edition. (Academic Press, San Diego, New York)
Aldemita and Hodges (1996) *Planta* 199: 612-617
Alia et al. (1998) *Plant J.* 16: 155-161
Allen (1998) *EMBO J.* 17: 5484-5496.
Altschul (1990) *J Mol. Biol.* 215: 403-410
Altschul (1993) *J. Mol. Evol.* 36: 290-300
Altschul et al. (1997) *Nucleic Acids Res.* 25: 3389-3402
Anderson and Young (1985) "Quantitative Filter Hybridisation", In: Hames and Higgins, ed., *Nucleic Acid Hybridisation, A Practical Approach*. Oxford, IRL Press, 73-111
Anderson et al. (2004) Plant Cell 16: 3460-3479.
Aravind and Landsman (1998) *Nucleic Acids Res.* 26: 4413-4421
Arents and Moudrianakis (1995) *Proc. Natl. Acad. Sci. USA* 92: 11170-11174
Atchley and Fitch (1997) *Proc. Natl. Acad. Sci. USA* 94: 5172-5176
Atchley et al. (1999) *J. Mol. Evol.* 48: 501-516
Ausubel et al. (1997) *Short Protocols in Molecular Biology*, John Wiley & Sons, New York, N.Y., unit 7.7
Bailey et al. (2003) *Plant Cell* 15: 2497-2502
Bairoch et al. (1997) *Nucleic Acids Res.* 25: 217-221
Bänzinger et al. (2000) Breeding for drought and nitrogen stress tolerance in maize. From theory to practice. (Mexico: CIMMYT (The International Maize and Wheat Improvement Center))
Barthelemy et al. (1996) *Biochem. Biophys. Res. Commun.* 224: 870-876
Bates et al. (1973) *Plant Soil* 39: 205-207
Baudino and Cleveland (2001) *Mol. Cell. Biol.* 21: 691-702
Bechtold and Pelletier (1998) *Methods Mol. Biol.* 82: 259-266
Berger and Kimmel (1987) "Guide to Molecular Cloning Techniques", in Methods in Enzymology, vol. 152, Academic Press, Inc., San Diego, Calif.
Berger et al. (1998) *Curr. Biol.* 8: 421-430
Berrocal-Lobo et al. (2002) *Plant J.* 29: 23-32
Berrocal-Lobo and Molina (2004) *Mol. Plant Microbe Interact.* 17: 763-770
Bevan (1984) *Nucleic Acids Res.* 12: 8711-8721
Bezhani et al. (2001) *J. Biol. Chem.* 276: 23785-23789
Bhattacharjee et al. (2001) *Proc. Natl. Acad. Sci. USA* 98: 13790-13795
Bi et al. (1997) *J. Biol. Chem.* 272: 26562-26572
Birnbaum et al. (2003) *Science* 302: 1956-1960
Boter (2004) *Genes Dev.* 18: 1577-1591
Borevitz et al. (2000) *Plant Cell* 12: 2383-2393
Boss and Thomas (2002) *Nature* 416: 847-850
Boyer (1995) *Annu. Rev. Phytopathol.* 33: 251-274.
Brady et al. (2007) *Science* 318: 801-806
Breen and Crouch (1992) *Plant Mol. Biol.* 19:1049-1055
Brown et al. (2003) *Plant Physiol.* 132: 1020-1032
Brownlie et al. (1997) *Structure* 5: 509-520
Bruce et al. (2000) *Plant Cell* 12: 65-79
Bucher and Trifonov (1988) *J. Biomol. Struct. Dyn.* 5: 1231-1236
Bucher (1990) *J. Mol. Biol.* 212: 563-578

Buck and Atchley (2003) *J. Mol. Evol.* 56: 742-750
Burglin (1997) *Nucleic Acids Res.* 25: 4173-4180
Burglin (1998) *Dev. Genes Evol.* 208: 113-116
Byrne (2000) *Nature* 408: 967-971
Caretti et al. (2003) *J. Biol. Chem.* 278: 30435-30440
Cane and Kay (1995) *Plant Cell* 7: 2039-2051
Carroll (2000) *Cell* 101: 577-580
Carson et al. (1997) *Plant J.* 12: 1231-1240
Cassas et al. (1993) *Proc. Natl. Acad. Sci. USA* 90: 11212-11216
Chae et al. (2004) *Oncogene* 23: 4084-4088
Chakravarthy et al. (2003) *Plant Cell* 15: 3033-3050
Chang and Liu (1994) *J. Biol. Chem.* 269: 17893-17898
Chase et al. (1993) *Ann. Missouri Bot. Gard.* 80: 528-580
Chen et al. (2002a) *Plant Cell* 14: 559-574.
Chen and Chen (2002) *Plant Physiol.* 129: 706-716
Cheong et al. (2002) *Plant Physiol.* 129: 661-677
Cheong et al. (2003) *Plant Physiol.* 132: 1961-1972
Chini et al. (2004) *Plant J.* 38: 810-822.
Chinnusamy et al. (2003) *Genes Dev.* 17: 1043-1054
Chinthapalli et al. (2002) in *Reviews in Plant Biochemistry and Biotechnology*, Goyal, A. et al (eds.) pp. 143-159
Christou et al. (1987) *Proc. Natl. Acad. Sci. USA* 84: 3962-3966
Christou (1991) *Bio/Technol.* 9:957-962
Christou et al. (1992) *Plant. J.* 2: 275-281
Ciarapica et al. (2003) *J. Biol. Chem.* 278: 12182-12190
Corona et al. (1996) *Plant J.* 9: 505-512
Costa and Dolan (2003) *Development* 130: 2893-2901
Coupland (1995) *Nature* 377: 482-483
Coustry et al. (1995) *J. Biol. Chem.* 270: 468-475
Coustry et al. (1996) *J. Biol. Chem.* 271: 14485-14491
Coustry et al. (1998) *Biochem J.* 331(Pt 1): 291-297
Coustry et al. (2001) *J. Biol. Chem.* 276: 40621-40630.
Crawford et al. (2004) *Plant Physiol.* 135: 244-253
Crozatier et al. (1996) *Curr. Biol.* 6: 707-718
Currie (1997) *J. Biol. Chem.* 272: 30880-30888
Daly et al. (2001) *Plant Physiol.* 127: 1328-1333
Dang et al. (1992) *Proc. Natl. Acad. Sci. USA* 89: 599-602
Dang et al. (1996) *J. Bacteriol.* 178: 1842-1849
Dayhoff et al. (1978) "A model of evolutionary change in proteins," in "Atlas of Protein Sequence and Structure," Vol. 5, Suppl. 3 (ed. M. O. Dayhoff), pp. 345-352. Natl. Biomed. Res. Found., Washington, D.C.
de Pater et al. (1996) *Nucleic Acids Res.* 24: 4624-4631
Dellagi et al. (2000) *Mol. Plant Microbe Interact.* 13: 1092-110
Deshayes et al. (1985) *EMBO J.:* 4: 2731-2737
D'Halluin et al. (1992) *Plant Cell* 4: 1495-1505
Di Cristina et al. (1996) *Plant J.* 10: 393-402
Doebley and Lukens (1998) *Plant Cell* 10: 1075-1082
Donn et al. (1990) in *Abstracts of VIIth International Congress on Plant Cell and Tissue Culture IAPTC*, A2-38: 53
Doolittle, ed. (1996) Methods in Enzymology, vol. 266: "Computer Methods for Macromolecular Sequence Analysis" Academic Press, Inc., San Diego, Calif., USA
Draper et al. (1982) *Plant Cell Physiol.* 23: 451-458
Du and Chen (2000) *Plant J.* 24: 837-847
Duboule (1994), (ed.) *Guidebook to the homeobox genes* Oxford University Press, Oxford
Duckett et al. (1994) *Development* 120: 3247-3255
Eddy (1996) *Curr. Opin. Str. Biol.* 6: 361-365
Edwards et al. (1998) *Plant Physiol.* 117: 1015-1022.
Eimert et al. (1995) *Plant Cell* 7: 1703-1712
Ellenberger et al. (1994) *Genes Dev.* 8: 970-980
Eulgem et al. (1999) *EMBO J.* 18: 4689-4699
Eulgem (2000) *Trends Plant Sci.* 5: 199-206.
Ezcurra et al. (2000) *Plant J.* 24: 57-66
Fairchild et al. (2000) *Genes Dev.* 14: 2377-2391
Fairman et al. (1993) *Proc. Natl. Acad. Sci. USA* 90: 10429-10433
Falvo et al. (1995) *Cell* 83: 1101-1111
Feng and Doolittle (1987) *J. Mol. Evol.* 25: 351-360
Ferre-D'Amare et al. (1994) *EMBO J.* 13: 180-189
Finkelstein et al. (1998) *Plant Cell* 10: 1043-1054
Fischer and Droge-Laser (2004) *Mol. Plant Microbe Interact.* 17: 1162-1171
Fisher and Goding (1992) *EMBO J.* 11: 4103-4109
Fisher and Caudy (1998) *Bioessays* 20: 298-306
Forsburg and Guarente (1988) *Genes Dev.* 3: 1166-117
Forzani et al. (2001) *J. Biol. Chem.* 276: 16731-16738
Fowler et al. (2002) *Plant Cell* 14: 1675-1679
Fowler and Thomashow (2002) *Plant Cell* 14: 1675-1690
Frampton et al. (1991) *Protein Eng.* 4: 891-901
Frank et al. (2000) *Plant Cell* 12: 111-124.
Freeling and Hake (1985) *Genetics* 111: 617-634
Friedrichsen et al. (2002) *Genetics* 162: 1445-1456
Fromm et al. (1990) *Bio/Technol.* 8: 833-839
Fu et al. (2001) *Plant Cell* 13: 1791-1802
Fuji et al. (2000) *Nat. Struct. Biol.* 7: 889-893
Fujimoto et al. (2000) *Plant Cell* 12: 393-404
Fujimoto et al. (2004) *Plant Mol. Biol.* 56: 225-239
Galigniana et al. (1998) *Mol. Endocrinol.* 12:1903-1913
Galway et al. (1994) *Dev. Biol.* 166: 740-754
Gampala et al. (2004). International Conference on *Arabidopsis* Research. Berlin. Abstract # T04-085
Gancedo (1998) *Microbiol. Mol. Biol. Rev.* 62: 334-361.
Gaxiola et al. (2001) *Proc. Natl. Acad. Sci. USA* 98: 11444-11449.
Gelinas et al. (1985) *Prog. Clin. Biol. Res.* 191: 125-139
Gelvin et al. (1990) *Plant Molecular Biology Manual*, Kluwer Academic Publishers
Gilmour et al. (1998) *Plant J.* 16: 433-442
Giraudat et al. (1992) *Plant Cell* 4: 1251-1261
Glick and Thompson, eds. (1993) *Methods in Plant Molecular Biology and Biotechnology.* CRC Press., Boca Raton, Fla.
Goff et al. (1992) *Genes Dev.* 6: 864-875
Good and Chen (1996) *Biol Signals* 5: 163-169
Goodrich et al. (1993) *Cell* 75: 519-530
Gordon-Kamm et al. (1990) *Plant Cell* 2: 603-618
Graf (1992) *Curr. Opin. Genet. Dev.* 2: 249-255.
Grandori et al. (2000) *Ann. Rev. Cell. Dev. Biol.* 16: 653-699
Grant et al. (2003) *Mol. Plant Microbe Interact.* 16: 669-680.
Grasser (1995) *Plant J.* 7: 185-192
Grasser (2003) *Plant Mol. Biol.* 53: 281-295
Gruber et al. ((1993) in *Methods in Plant Molecular Biology and Biotechnology*, p. 89-119
Gu et al. (2000) *Plant Cell* 12: 771-786
Gu et al. (2002) *Plant Cell* 14: 817-831
Guiltinan et al. (1990) *Science* 250: 267-271
Guo et al. (2004) *Plant Mol. Biol.* 55: 607-618.
Gupta et al (1997a) *Plant Mol. Biol.* 35: 987-992
Gupta et al. (1997b) *Plant Mol. Biol.* 34: 529-536
Gusmaroli et al. (2001) *Gene* 264: 173-185
Gusmaroli et al. (2002) *Gene* 283: 41-48
Haake et al. (2002) *Plant Physiol.* 130: 639-648
Hain et al. (1985) *Mol. Gen. Genet.* 199: 161-168
Hall et al. (2000) *Plant Physiol.* 123: 1449-1458.
Halliday et al. (1999) *Proc. Natl. Acad. Sci. USA* 96: 5832-5837

Haymes et al. "Nucleic Acid Hybridization: A Practical Approach", IRL Press, Washington, D.C. (1985)
Hanes and Brent (1989) Cell 57: 1275-1283
Hanes and Brent (1991) Science 251: 426-430
Hao et al. (1998) J. Biol. Chem. 273: 26857-26861
Hao (2002) Biochemistry 41: 4202-4208
Harper (2002) WO0216655
Hasegawa et al. (2000) Annu. Rev. Plant Mol. Plant Physiol. 51: 463-499.
Hatch (1987) Biochim. Biophys. Acta 895: 81-106
Hattori et al. (1992) Genes Dev. 6: 609-618
Hayashi and Scott (1990) Cell 63: 883-894
He et al. (2000) Transgenic Res. 9: 223-227
He et al. (2001) Mol. Plant Microbe Interact. 14: 1453-1457
Heim et al. (2003) Mol. Biol. Evol. 20: 735-747
Hein (1990) Methods Enzymol. 183: 626-645
Heisler et al. (2001) Development 128: 1089-1098
Hempel (1997) Development 124: 3845-3853
Henikoff and Henikoff (1991) Nucleic Acids Res. 19: 6565-6572
Henikoff and Henikoff (1992) Proc. Natl. Acad. Sci. USA 89:10915)
Herrera-Estrella et al. (1983) Nature 303: 209
Hiei et al. (1994) Plant J. 6:271-282
Hiei et al. (1997) Plant Mol. Biol. 35:205-218
Higgins and Sharp (1988) Gene 73: 237-244
Higgins et al. (1996) Methods Enzymol. 266: 383-402
Hirano et al. (2002) Gene 290: 107-114
Hobo et al. (1999) Proc. Natl. Acad. Sci. USA 96: 15348-15353
Hoecker et al. (1995) Genes Dev. 9: 2459-2469
Hsieh et al. (1998) Proc. Natl. Acad. Sci. USA 95: 13965-13970
Hu et al. (2004) Cell Res. 14: 8-15
Hung et al. (1998) Plant Physiol. 117: 73-84
Huq and Quail (2002) EMBO J. 21: 2441-2450
Huth et al. (1997) Nat. Struct. Biol. 4: 657-665
Hwang and Goodman (1995) Plant J. 8: 37-43
Ishida (1990) Nature Biotechnol. 14:745-750
Ishiguro and Nakamura (1994) Mol. Gen. Genet. 244: 563-571
Ito et al. (1995) Plant Cell Physiol. 36: 1281-1289
Jaglo et al. (2001) Plant Physiol. 127: 910-917
Jaglo-Ottosen et al. (1998) Science. 280:104-106
Jakoby et al. (2002) Trends Plant Sci. 7: 106-111
Jaglo et al. (2001) Plant Physiol. 127: 910-917
Jang et al. (1997) Plant Cell 9: 5-19
Jofuku et al. (1994) Plant Cell 6: 1211-1225
Johnson and McKnight (1989) Ann. Rev. Biochem. 58: 799-839
Johnson et al. (2002) Plant Cell 14: 1359-1375
Kagaya et al. (1999) Nucleic Acids Res. 27: 470-478
Kaiser et al. (1998) Science 281: 1202-1206
Kashima et al. (1985) Nature 313: 402-404
Kasuga et al. (1999) Nature Biotechnol. 17: 287-291
Kehoe et al. (1994) Plant Cell 6: 1123-1134
Keith et al. (1994) Plant Cell 6: 589-600
Kerstetter et al. (1994) Plant Cell 6: 1877-1887
Kerstetter et al. (1997) Development 124: 3045-3054
Kim and Sheffrey (1990) J. Biol. Chem. 265: 13362-13369
Kim et al. (1996) Mol. Cell. Biol. 16: 4003-4013
Kim et al. (2001) Plant J. 25: 247-259
Kim (2004) Plant Mol. Biol. 55: 883-904
Kimmel (1987) Methods Enzymol. 152: 507-511
Kirik et al. (2004a) Dev. Biol. 268: 506-513
Kirik et al. (2004b) Plant Mol. Biol. 55: 389-398
Kissinger et al. (1990) Cell 63: 579-590
Klee (1985) Bio/Technology 3: 637-642
Klein et al. (1987) Nature 327: 70-73
Knight (2000a) Int. Rev. Cytol. 195: 269-324.
Koornneef et al (1986) In Tomato Biotechnology: Alan R. Liss, Inc., 169-178
Ku et al. (2000) Proc. Natl. Acad. Sci. USA 97: 9121-9126
Kunst et al. (2000) Biochem Soc. Trans. 28: 651-654.
Kusnetsov et al. (1999) J. Biol. Chem. 274: 36009-36014
Kwak et al. (2005) Science 307: 1111-1113
Kwong (2003) Plant Cell 15: 5-18
Kyozuka and Shimamoto (2002) Plant Cell Physiol. 43: 130-135
Lapik and Kaufman (2003) Plant Cell 15: 1578-1590
Larkin et al. (2003) Ann. Rev. Plant Biol. 54: 403-430
Lebel et al. (1998) Plant J. 16: 223-233
Ledent and Vervoort (2001) Genome Res. 11: 754-770
Lee and Schiefelbein (1999) Cell 99: 473-483
Lee et al. (2002) Genome Res. 12: 493-502
Lee and Schiefelbein (2002) Plant Cell 14: 611-618
Lee et al. (2003) Proc. Natl. Acad. Sci. USA 100: 2152-2156.
Lee et al. (2004) Plant Mol. Biol. 55: 61-81.
Lefstin and Yamamoto (1998) Nature 392: 885-888
Leon-Kloosterziel et al. (1996) Plant Physiol. 110: 233-240
Levens (2003) Genes Dev. 17: 1071-1077
Li et al. (1992) Nucleic Acids Res. 20: 1087-1091
Li et al. (1998) EMBO J. 17: 6300-6315
Lin et al. (1991) Nature 353: 569-571
Lincoln et al. (1990) Plant Cell 2: 1071-1080
Liscum and Reed (2002) Plant Mol. Biol. 49: 387-400
Littlewood and Evan (1998) Helix-Loop-Helix Transcription Factors (New York: Oxford University Press)
Liu and Zhu (1997) Proc. Natl. Acad. Sci. USA 94: 14960-14964
Liu et al. (1999) Eur. J. Biochem. 262: 247-257
Livingston et al. (2004) Economic and policy implications of wind-borne entry of Asian soybean rust into the United States. www.ers.usda.gov/Features/SoyBeanRust/Long
Long et al. (1996) Nature 379: 66-69
Long and Barton (2000) Dev. Biol. 218: 341-353
Lorenzo et al. (2003) Plant Cell 15: 165-178
Lorenzo et al. (2004) Plant Cell 16: 1938-1950
Lotan et al. (1998) Cell 93: 1195-1205.
Loulergue et al. (1998) Gene 225: 47-57
Ludwig et al. (1989) Proc. Natl. Acad. Sci. USA 86: 7092-7096
Ludwig et al. (1990) Cell 62: 849-851
Luerssen et al. (1998) Plant J. 15: 755-764
Luger et al. (1997) Nature 389: 251-260
Lynch et al. (2002) Phytopathol. 92: S33.
Ma et al. (1994) Cell 77: 451-459
Mackay and Crossley (1998) Trends Biochem. Sci. 23: 1-4
Maity and de Crombrugghe (1998) Trends Biochem. Sci. 23: 174-178
Maleck (2000) Nat. Genet. 26: 403-410
Mandel (1992) Nature 360: 273-277
Mandel et al. (1992) Cell 71-133-143
Mantovani (1998) Nucleic Acids Res. 26: 1135-1143
Mantovani (1999) Gene 239: 15-27.
Mare et al. (2004) Plant Mol. Biol. 55: 399-416
Martin and Paz-Ares (1997) Trends Genet. 13: 67-73
Martinez-Garcia and Quail (1999) Plant J. 18: 173-183
Martinez-Garcia et al. (2000) Science 288: 859-863
Masiero et al. (2002) J. Biol. Chem. 277: 26429-26435
Massari and Murre (2000) Mol. Cell. Biol. 20: 429-440
Masucci J. et al. (1996) Development 122: 1253-1260
Mazon et al. (1982) Eur. J. Biochem. 127: 605-608
McCarty et al. (1989) Plant Cell 1: 523-532

McCarty et al. (1991) *Cell* 66: 895-905
McCue and Hanson (1990) *Trends Biotechnol.* 8: 358-362
McNabb et al. (1995) *Genes Dev.* 9: 47-58
McNabb et al. (1997) *Mol. Cell. Biol.* 17: 7008-7018
Meijer et al. (1996) *Plant Mol. Biol.* 31: 607-618
Meinke (1992) *Science* 258: 1647-1650
Meinke et al. (1994) *Plant Cell* 6: 1049-1064
Merlot et al. (2001) *Plant J.* 25: 295-303.
Mewes et al. (2002) *Nucleic Acids Res.* 30: 31-34
Meyers (1995) *Molecular Biology and Biotechnology*, Wiley VCH, New York, N.Y., p 856-853
Mild et al. (1993) in *Methods in Plant Molecular Biology and Biotechnology*, p. 67-88, Glick and Thompson, eds., CRC Press, Inc., Boca Raton
Miles et al. (2003) Soybean rust: is the U.S. soybean crop at risk? www.apsnet.org/online/feature/rust/Miyoshi et al. (2003) *Plant J.* 36: 532-540
Mizukami (2001) *Curr Opinion Plant Biol.* 4: 533-539
Mohr and Cahill (2003) *Functional Plant Biology* 30: 461-469
Montgomery et al. (1993) *Plant Cell* 5: 1049-1062
Mount (2001), in Bioinformatics: Sequence and Genome Analysis, Cold Spring Harbor Laboratory Press, Cold Spring Harbor, N.Y., page 543
Müller et al. (2001) *Plant J.* 28: 169-179
Munkvold (2003) *Annu. Rev. Phytopathol.* 41: 99-116.
Murre et al. (1989) *Cell* 56: 777-783
Myers et al. (1986) *Science* 232: 613-618
Nair and Burley (2000) *Nature* 404: 715: 717-718
Nakshatri (1996) *J. Biol. Chem.* 271: 28784-28791.
Nambara et al. (1995) *Development* 121: 629-636
Nandi et al. (2000) *Curr. Biol.* 10: 215-218
Nesi et al. (2000) *Plant Cell* 12: 1863-1878
Ni et al. (1998) *Cell* 95: 657-667
Nicholass et al. (1995) *Plant Mol. Biol.* 28: 423-435
Nieto-Sotelo and Quail (1994) *Biochem. Soc. Symp.* 60: 265-275
Nieto-Sotelo, Ichida and Quail (1994) *Plant Cell* 6: 287-301
North Dakota State University Extension Service. (2002). Managing Row Crop Diseases in Drought Years. www.ag.ndsu.nodak.edu/drought/ds-10-97.htm
North Dakota State University Extension Service. (2004). Small Grain Diseases: Management of Those More Common and Severe in Dry Years. www.ag.ndsu.nodak.edu/drought/ds-01-02.htm
Novillo et al. (2004) *Proc. Natl. Acad. Sci. USA* 101: 3985-3990
Odell (1985) *Nature* 313: 810-812
Ohme-Takagi and Shinshi (1995) *Plant Cell* 7: 173-182
Ohta et al. (2001) *Plant Cell* 13: 1959-1968
Okamuro et al. (1997) *Proc. Natl. Acad. Sci. USA* 94: 7076-7081
Olesen and Guarente (1990) *Genes Dev.* 4: 1714-1729
Onate et al. (1994) *Mol. Cell. Biol.* 14: 3376-3391
Onate-Sanchez and Singh (2002) *Plant Physiol.* 128: 1313-1322
Ooms et al. (1993) *Plant Physiol.* 102: 1185-1191
Parcy and Giraudat (1997) *Plant J.* 11: 693-702
Parcy et al. (1997) *Plant Cell* 9: 1265-1277
Park (2001) *Plant Cell* 13: 1035-1046.
Payne et al. (2000) *Genetics* 156: 1349-1362
Peng et al. (1997) *Genes Development* 11: 3194-3205)
Peng et al. (1999) *Nature:* 400: 256-261
Pinkham and Guarente (1985) *Mol. Cell Biol.* 5: 3410-3416.
Pnueli et al. (2002) *Plant J.* 31: 319-330
Porra et al. (1989) *Biochim. Biophys. Acta* 975: 384-394
Pourtau et al. (2004) *Planta* 219: 765-772
Putterill et al (1995) *Cell* 80: 847-857
Rajani and Sundaresan (2001) *Curr. Biol.* 11: 1914-1922
Ratcliffe et al. (2001) *Plant Physiol.* 126: 122-132
Reeves and Nissen (1990) *J. Biol. Chem.* 265: 8573-8582
Reeves (2001) *Gene* 277: 63-81.
Reeves and Beckerbauer (2001) *Biochim Biophys Acta* 1519: 13-29.
Reidt et al. (2000) *Plant J.* 21: 401-408
Remm et al. (2001) *J. Mol. Biol.* 314: 1041-1052
Reuber (1998) *Plant J.* 16: 473-485.
Riechmann and Meyerowitz (1998) *Biol. Chem.* 379: 633-646
Riechmann et al. (2000a) *Science* 290: 2105-2110
Riechmann and Ratcliffe (2000b) *Curr. Opin. Plant Biol.* 3: 423-434
Rieger et al. (1976) *Glossary of Genetics and Cytogenetics: Classical and Molecular*, 4th ed., Springer Verlag, Berlin
Rieping and Schoffl (1992) *Mol. Gen. Genet.* 231: 226-232
Rigaut et al. (1999) *Nat. Biotechnol.* 17: 1030-1032
Robatzek and Somssich (2002) *Genes Dev.* 16: 1139-1149
Robinson et al. (2000) *Nucleic Acids Res.* 28: 4460-4466
Robson et al. (2001) *Plant J.* 28: 619-631
Rohila et al. (2004) *Plant J.* 38: 172-181
Romier et al. (2003) *J. Biol. Chem.* 278: 1336-1345
Rushton et al. (1995) *Plant Mol. Biol.* 29: 691-702
Rushton et al. (1996) *EMBO J.* 15: 5690-5700
Sadowski et al. (1988) *Nature* 335: 563-564
Saijo et al. (2000) *Plant J.* 23: 319-327.
Sakuma et al. (2002) *Biochem. Biophys. Res. Comm.* 290: 998-1009
Saleki et al. (1993) *Plant Physiol.* 101: 839-845
Salsi et al. (2003) *J. Biol. Chem.* 278: 6642-6650
Sambrook et al. (1989) *Molecular Cloning: A Laboratory Manual*, 2nd Ed., Cold Spring Harbor Laboratory, Cold Spring Harbor, N.Y.
Sanchez and Cejudo (2003) *Plant Physiol.* 132: 949-957
Sanders et al. (1999) *Plant Cell* 11: 691-706
Sanford et al. (1987) *Part. Sci. Technol.* 5:27-37
Sanford (1993) *Methods Enzymol.* 217: 483-509
Schaffer et al. (1998) *Cell* 93: 1219-1229
Schellmann et al. (2002) *EMBO J.* 21: 5036-5046
Schindler et al. (1993) *Plant J.* 4: 137-150
Schnittger et al. (1998) *Development* 125: 2283-2289
Schnittger et al. (1999) *Plant Cell* 11: 1105-1116
Schoof et al. (2000) *Cell* 100: 635-644
Sessa et al. (1994) *Molecular genetic analysis of plant development and metabolism.* (Berlin: Springer Verlag).
Sharp and LeNoble (2002) *J. Exp. Bot.* 53: 33-37.
Sheen (1999) *Ann. Rev. Plant Physiol. Plant Mol. Biol.* 50: 187-217
Shimizu et al. (1997) *EMBO J.* 16: 4689-4697
Shin et al. (2002) *Mol Plant Microbe Interact* 15: 983-989.
Shirakata et al. (1993) *Genes Dev.* 7: 2456-2470
Shpaer (1997) *Methods Mol. Biol.* 70: 173-187
Silver et al. (2003) *Mol. Cell. Biol.* 23: 5989-5999
Sinha et al. (1996) *Mol. Cell. Biol.* 16: 328-337
Sivamani et al. (2000) *Plant Science* 155: 1-9
Sjodahl et al. (1995) *Planta* 197: 264-271
Smalle et al (1998) *Proc. Natl. Acad. Sci. USA.* 95:3318-3322
Smeekens (1998) *Curr. Opin. Plant Biol.* 1: 230-234
Smith et al. (1992) *Protein Engineering* 5: 35-51
Smolen et al. (2002) *Genetics* 161: 1235-1246
Soltis et al. (1997) *Ann. Missouri Bot. Gard.* 84: 1-49
Solano et al. (1998) *Genes Dev.* 12: 3703-3714
Sonnhammer et al. (1997) *Proteins* 28: 405-420
Sorensen et al. (2003) *Plant J.* 33: 413-423

Spencer et al. (1994) *Plant Mol. Biol.* 24: 51-61
Spollen et al. (2000) *Plant Physiol.* 122: 967-976.
Stockinger et al. (1997) *Proc. Natl. Acad. Sci. USA* 94: 1035-1040
Stone et al. (2001) *Proc. Natl. Acad. Sci. USA* 98: 11806-11811
Surpin et al. (2002) *Plant Cell* 14 Suppl: S327-S338
Suzuki et al. (1997) *Plant Cell* 9: 799-807
Suzuki et al. (2001) *Plant J.* 28: 409-418
Suzuki et al. (2003) *Plant Physiol.* 132: 1664-1677
Svensson et al. (2003) *Arch. Biochem. Biophys.* 414: 180-188
Tahtiharju and Palva (2001) Plant J 26: 461-470.
Tamminen et al. (2001) *Plant J.* 25: 1-8
Tanimoto et al. (1995) *Plant J.* 8: 943-948
Tasanen et al. (1992) *J. Biol. Chem.* 267: 11513-11519
Taylor and Scheuring (1994) *Mol. Gen. Genet.* 243: 148-157
Tepperman et al. (2001) *Proc. Natl. Acad. Sci. USA* 98: 9437-9442
Thaler and Bostock (2003) *Ecology* 85: 48-58.
Thoma (1994) *Plant Physiol.* 105: 35-45
Thompson et al. (1994) *Nucleic Acids Res.* 22: 4673-4680
Tiwari et al. (2001) *Plant Cell* 13: 2809-2822
Tiwari et al. (2003) *Plant Cell* 15: 533-543
Toledo-Ortiz et al. (2003) *Plant Cell* 15: 1749-1770
Tournier et al. (2003) *FEBS Lett.* 550: 149-154
Toyama et al. (1999) *Plant Cell Physiol.* 40: 1087-1092
Truernit and Sauer (1995) *Planta* 196: 564-570
Tudge (2000) in *The Variety of Life*, Oxford University Press, New York, N.Y. pp. 547-606
Ulmasov et al. (1997) *Science* 276: 1865-1868
Vasil et al. (1992) *Bio/Technol.* 10:667-674
Vasil et al. (1993) *Bio/Technol.* 11:1553-1558
Vasil (1994) *Plant Mol. Biol.* 25: 925-937
Verslues and Sharp (1999) *Plant Physiol.* 119: 1349-1360
Vicient et al. (2000) *J. Exp. Bot.* 51: 995-1003
Vollbrecht et al. (1991) *Nature* 350: 241-243
Wada et al. (1997) *Science* 277: 1113-1116
Wada et. al. (2002) *Development* 129: 5409-5419
Wahl and Berger (1987) *Methods Enzymol.* 152: 399-407
Wan and Lemeaux (1994) *Plant Physiol.* 104: 37-48
Wang et al. (1997) *Plant Cell* 9: 491-507
Wang (1998) *Plant J.* 16: 515-522
Wanner and Gruissem (1991) *Plant Cell* 3: 1289-1303
Waterhouse et al. (2001) *Trends Plant Sci.* 6: 297-301
Waterston et al. (2002) *Nature* 420: 520-562
Weeks et al. (1993) *Plant Physiol.* 102:1077-1084
Weigel et al. (1992) *Cell* 69: 843-859
Weigel (1995) *Plant Cell* 7: 388-389
Weigel et al. (2000) *Plant Physiol.* 122: 1003-1013
Weigel and Nilsson (1995) *Nature* 377: 482-500
Weissbach and Weissbach (1989) *Methods for Plant Molecular Biology*, Academic Press
Wendler et al. (1997) *J. Biol. Chem.* 272: 8482-8489
Wesley et al. (2001) *Plant J.* 27: 581-590
West et al. (1994) *Plant Cell* 6: 1731-1745
Westhoff and Gowik (2004) *Ann. Bot.* (London) 93: 13-23
Windhovel (2001) *Plant Mol. Biol.* 45: 201-214.
Wobus and Weber (1999) *Curr. Opin. Plant Biol.* 2: 33-38
Wolberger et al. (1991) *Cell* 67: 517-528
Wrather and Sweets (2004) Aflatoxin in Corn. website: aes.missouri.edu/delta/croppest/aflacorn.stm
Wu et al. (1996) *Plant Cell* 8: 617-627
Xin and Browse (1998) *Proc. Natl. Acad. Sci. USA* 95: 7799-7804
Xing et al. (1993) *EMBO J.* 12: 4647-4655
Xiong et al. (2001a) *Genes Dev.* 15: 1971-1984.
Xiong and Zhu (2002) *Plant Cell Environ.* 25: 131-139.
Xiong and Yang (2003) *Plant Cell* 15: 745-759.
Xu et al. (1996) *Plant Physiol.* 110: 249-257
Xu et al. (2001) *Proc. Natl. Acad. Sci USA* 98: 15089-15094
Yamada et al. (1999a) *FEBS Lett.* 460: 41-45
Yamada et al. (1999b) *Biochem. Biophys. Res. Commun.* 261: 614-621
Yamada et al. (2003) *Biochem J.* 373: 167-178
Yamaguchi-Shinozaki and Shinozaki (1993) *Mol. Gen. Genet.* 236: 331-340
Yamasaki et al. (2005) *Plant Cell* 17: 944-956
Yang et al. (1999) *Plant J.* 18: 141-149
Yi et al. (2004) *Plant Physiol.* 136: 2862-2874
Yu et al. (2001) *Plant Cell* 13: 1527-1540
Yun et al. (2003) *J. Biol. Chem.* 278: 36966-36972
Zhang et al. (1991) *Bio/Technology* 9: 996-997
Zhang et al. (2002) *Planta* 215: 191-194
Zhang et al. (2003) *Development* 130: 4859-4869
Zhang and Wang (2005) *BMC Evol. Biol.* 5: 1
Zhou et al. (1995a) *Nature* 376: 771-774
Zhou et al. (1995b) *Cell* 83: 925-935
Zhou et al. (1997) *EMBO J.* 16: 3207-3218
Zhou and Lee (1998) *J. Natl. Cancer Inst.* 90: 381-388
Zhu et al. (1998) *Plant Cell* 10: 1181-1191
Zou et al. (2004) *J. Biol. Chem.* 279: 55770-5577

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the appended claims. Modifications that become apparent from the foregoing description and accompanying figures fall within the scope of the claims.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10597667B2). An electronic copy of the "Sequence Listing" will also be available from the USPTO upon request and payment of the fee set forth in 37 CFR 1.19(b)(3).

What is claimed is:

1. A recombinant host cell comprising a recombinant nucleic acid construct comprising a heterologous promoter operably linked to a nucleic acid molecule encoding a polypeptide; wherein the nucleic acid molecule comprises a nucleotide sequence that has at least 95% sequence identity to the nucleotide sequence of SEQ ID NO:669, or wherein the polypeptide comprises an amino acid sequence that has at least 95% sequence identity to the amino acid sequence of SEQ ID NO:670.

2. A transgenic plant having an altered trait as compared to a control plant, wherein the transgenic plant comprises a recombinant nucleic acid construct comprising a heterologous promoter operably linked to a nucleic acid molecule encoding a polypeptide; wherein the nucleic acid molecule comprises a nucleotide sequence that has at least 95% sequence identity to the nucleotide sequence of SEQ ID NO:669, or wherein the polypeptide comprises an amino acid sequence that has at least 95% sequence identity to the amino acid sequence of SEQ ID NO:670.

3. The transgenic plant of claim 2, wherein the transgenic plant is a eudicot.

4. The transgenic plant of claim 2, wherein the transgenic plant is a legume.

5. The transgenic plant of claim 2, wherein the transgenic plant is a monocot.

6. The transgenic plant of claim 2, wherein the transgenic plant is a transgenic seed comprising the recombinant nucleic acid construct.

7. A method for conferring to a plant an altered trait as compared to a control plant, the method comprising:
  (a) providing the recombinant nucleic acid construct comprising a heterologous promoter operably linked to a nucleic acid molecule encoding a polypeptide; wherein the nucleic acid molecule comprises a nucleotide sequence that has at least 95% sequence identity to the nucleotide sequence of SEQ ID NO:669, or wherein the polypeptide comprises an amino acid sequence that has at least 95% sequence identity to the amino acid sequence of SEQ ID NO:670; and
  (b) transforming a target plant with the recombinant nucleic acid construct to produce a transgenic plant having the altered trait as compared to the control plant.

8. The method of claim 7, wherein the method further comprises the step of:
  (c) selecting a transgenic plant that ectopically expresses the polypeptide.

9. The method of claim 7, wherein the method further comprises the step of:
  (c) selfing or crossing the transgenic plant with itself or another plant, respectively, to produce a transgenic seed.

10. The recombinant host cell of claim 1, wherein the nucleic acid molecule comprises a nucleotide sequence that has at least 95% sequence identity to the nucleotide sequence of SEQ ID NO: 669.

11. A recombinant nucleic acid construct comprising a heterologous promoter operably linked to a nucleic acid molecule encoding a polypeptide, wherein the nucleic acid molecule comprises the nucleotide sequence of SEQ ID NO: 669.

12. The recombinant host cell of claim 1, wherein the polypeptide comprises an amino acid sequence that has at least 95% sequence identity with the amino acid sequence of SEQ ID NO:670.

13. A recombinant nucleic acid construct comprising a heterologous promoter operably linked to a nucleic acid molecule encoding a polypeptide, wherein the polypeptide comprises the amino acid sequence of SEQ ID NO:670.

14. The transgenic plant of claim 2, wherein the polypeptide comprises an amino acid sequence that has at least 95% sequence identity with the amino acid sequence of SEQ ID NO:670.

15. The transgenic plant of claim 2, wherein the nucleic acid molecule comprises the nucleotide sequence of SEQ ID NO: 669.

16. The transgenic plant of claim 2, wherein the polypeptide comprises the amino acid sequence of SEQ ID NO:670.

* * * * *